US010048208B2

(12) United States Patent
Rothberg et al.

(10) Patent No.: US 10,048,208 B2
(45) Date of Patent: Aug. 14, 2018

(54) INTEGRATED DEVICE WITH EXTERNAL LIGHT SOURCE FOR PROBING DETECTING AND ANALYZING MOLECULES

(71) Applicant: Quantum-Si Incorporated, Guilford, CT (US)

(72) Inventors: Jonathan M. Rothberg, Guilford, CT (US); Ali Kabiri, Madison, CT (US); Jason W. Sickler, Madison, CT (US); Brett J. Gyarfas, Guilford, CT (US); Jeremy Lackey, Guilford, CT (US); Gerard Schmid, Guilford, CT (US); Benjamin Cipriany, Branford, CT (US); Jack Jewell, Boulder, CO (US); Lawrence West, San Jose, CA (US); Michael Ferrigno, Farmington, CT (US); Paul E. Glenn, Wellesley, MA (US); Anthony Bellofiore, Glastonbury, CT (US)

(73) Assignee: Quantum-Si Incorporated, Guilford, CT (US)

( * ) Notice: Subject to any disclaimer, the term of this patent is extended or adjusted under 35 U.S.C. 154(b) by 701 days.

(21) Appl. No.: 14/543,865

(22) Filed: Nov. 17, 2014

(65) Prior Publication Data

US 2015/0141267 A1    May 21, 2015

Related U.S. Application Data

(60) Provisional application No. 61/941,916, filed on Feb. 19, 2014, provisional application No. 61/917,926, (Continued)

(51) Int. Cl.
*G01N 21/00* (2006.01)
*G01N 21/64* (2006.01)
(Continued)

(52) U.S. Cl.
CPC ....... *G01N 21/6486* (2013.01); *C12Q 1/6869* (2013.01); *C12Q 1/6874* (2013.01);
(Continued)

(58) Field of Classification Search
None
See application file for complete search history.

(56) References Cited

U.S. PATENT DOCUMENTS 5,198,543 A    3/1993 Blanco et al.
5,302,509 A    4/1994 Cheeseman
(Continued)

FOREIGN PATENT DOCUMENTS

CA    2283789 A1    9/1998
CA    2330673 C    11/1999
(Continued)

OTHER PUBLICATIONS

International Preliminary Report on Patentability for International Application No. PCT/US2014/066014 dated May 26, 2016.
(Continued)

*Primary Examiner* — Jill A Warden
*Assistant Examiner* — Brittany I Fisher
(74) *Attorney, Agent, or Firm* — Wolf, Greenfield & Sacks, P.C.

(57) ABSTRACT

Apparatus and methods for analyzing single molecule and performing nucleic acid sequencing. An integrated device includes multiple pixels with sample wells configured to receive a sample, which, when excited, emits radiation; at least one element for directing the emission radiation in a particular direction; and a light path along which the emission radiation travels from the sample well toward a sensor. The apparatus also includes an instrument that interfaces with the integrated device. Each sensor may detect emission radiation from a sample in a respective sample well. The
(Continued)

instrument includes an excitation light source for exciting the sample in each sample well.

22 Claims, 61 Drawing Sheets

Related U.S. Application Data filed on Dec. 18, 2013, provisional application No. 61/905,282, filed on Nov. 17, 2013.

(51) Int. Cl.
*C12Q 1/6874* (2018.01)
*G01N 21/77* (2006.01)
*C12Q 1/6869* (2018.01)

(52) U.S. Cl.
CPC ........... *G01N 21/64* (2013.01); *G01N 21/645* (2013.01); *G01N 21/648* (2013.01); *G01N 21/6452* (2013.01); *G01N 21/7743* (2013.01); *G01N 21/7746* (2013.01); *G01N 2021/6419* (2013.01); *G01N 2021/6441* (2013.01); *G01N 2021/6478* (2013.01); *G01N 2201/02* (2013.01); *G01N 2201/062* (2013.01); *G01N 2201/068* (2013.01); *G01N 2201/0612* (2013.01); *G01N 2201/06113* (2013.01); *G01N 2201/125* (2013.01); *Y10T 29/49016* (2015.01)

(56) References Cited

U.S. PATENT DOCUMENTS

| | | | |
|---|---|---|---|
| 5,471,515 A | 11/1995 | Fossum et al. | |
| 5,495,462 A * | 2/1996 | Nishiwaki | G02B 6/14 369/112.27 |
| 5,576,204 A | 11/1996 | Blanco et al. | |
| 5,674,743 A | 10/1997 | Ulmer | |
| 5,822,472 A | 10/1998 | Burkhard et al. | |
| 5,912,155 A | 6/1999 | Chatterjee et al. | |
| 5,939,301 A | 8/1999 | Hughes, Jr. et al. | |
| 5,990,506 A | 11/1999 | Fossum et al. | |
| 6,137,117 A | 10/2000 | Feldstein et al. | |
| 6,198,869 B1 | 3/2001 | Kraus et al. | |
| 6,210,896 B1 | 4/2001 | Chan | |
| 6,232,103 B1 | 5/2001 | Short | |
| 6,255,083 B1 | 7/2001 | Williams | |
| 6,261,797 B1 | 7/2001 | Sorge et al. | |
| 6,265,193 B1 | 7/2001 | Brandis et al. | |
| 6,280,939 B1 | 8/2001 | Allen | |
| 6,327,410 B1 | 12/2001 | Walt et al. | |
| 6,355,420 B1 | 3/2002 | Chan | |
| 6,384,912 B2 | 5/2002 | Kraus et al. | |
| 6,399,320 B1 | 6/2002 | Markau et al. | |
| 6,399,335 B1 | 6/2002 | Kao et al. | |
| 6,437,345 B1 | 8/2002 | Bruno-Raimondi et al. | |
| 6,456,326 B2 | 9/2002 | Fossum et al. | |
| 6,549,235 B1 | 4/2003 | Fossum et al. | |
| 6,555,842 B1 | 4/2003 | Fossum et al. | |
| 6,570,617 B2 | 5/2003 | Fossum et al. | |
| 6,607,883 B1 | 8/2003 | Frey et al. | |
| 6,716,394 B2 | 4/2004 | Jensen et al. | |
| 6,744,068 B2 | 6/2004 | Fossum et al. | |
| 6,762,048 B2 | 7/2004 | Williams | |
| 6,794,177 B2 | 9/2004 | Markau et al. | |
| 6,825,921 B1 * | 11/2004 | Modlin | G01N 21/255 235/454 |
| 6,936,702 B2 | 8/2005 | Williams et al. | |
| 7,033,762 B2 | 4/2006 | Nelson et al. | |
| 7,041,812 B2 | 5/2006 | Kumar et al. | |
| 7,052,839 B2 | 5/2006 | Nelson et al. | |
| 7,052,847 B2 | 5/2006 | Korlach et al. | |
| 7,056,661 B2 | 6/2006 | Korlach et al. | |
| 7,057,026 B2 | 6/2006 | Barnes et al. | |
| 7,153,672 B1 | 12/2006 | Eickbush et al. | |
| 7,158,224 B2 | 1/2007 | Montagu | |
| 7,170,050 B2 | 1/2007 | Turner et al. | |
| 7,179,654 B2 | 2/2007 | Verdonk et al. | |
| 7,223,541 B2 | 5/2007 | Fuller et al. | |
| 7,229,799 B2 | 6/2007 | Williams | |
| 7,244,566 B2 | 7/2007 | Sood et al. | |
| 7,244,602 B2 | 7/2007 | Frey et al. | |
| 7,270,951 B1 | 9/2007 | Stemple et al. | |
| 7,313,308 B2 | 12/2007 | Turner et al. | |
| 7,315,019 B2 | 1/2008 | Turner et al. | |
| 7,345,764 B2 | 3/2008 | Bulovic et al. | |
| 7,361,466 B2 | 4/2008 | Korlach et al. | |
| 7,393,640 B2 | 7/2008 | Kumar et al. | |
| 7,405,281 B2 | 7/2008 | Xu et al. | |
| 7,452,698 B2 | 11/2008 | Sood et al. | |
| 7,462,452 B2 | 12/2008 | Williams et al. | |
| 7,476,503 B2 | 1/2009 | Turner et al. | |
| 7,595,883 B1 | 9/2009 | El Gamal et al. | |
| 7,625,701 B2 | 12/2009 | Williams et al. | |
| 7,630,073 B2 | 12/2009 | Lundquist et al. | |
| 7,727,722 B2 | 6/2010 | Nelson et al. | |
| 7,738,086 B2 | 6/2010 | Shepard et al. | |
| 7,745,116 B2 | 6/2010 | Williams | |
| 7,777,013 B2 | 8/2010 | Xu et al. | |
| 7,820,983 B2 | 10/2010 | Lundquist et al. | |
| 7,858,311 B2 | 12/2010 | Williams | |
| 7,871,777 B2 | 1/2011 | Schneider et al. | |
| 7,873,085 B2 | 1/2011 | Babushkin et al. | |
| 7,875,440 B2 | 1/2011 | Williams et al. | |
| 7,897,738 B2 | 3/2011 | Brandis et al. | |
| 7,939,256 B2 | 5/2011 | Williams | |
| 7,968,702 B2 | 6/2011 | Wegener et al. | |
| 7,973,146 B2 | 7/2011 | Shen et al. | |
| 7,981,604 B2 | 7/2011 | Quake | |
| 7,995,202 B2 | 8/2011 | Lundquist et al. | |
| 8,023,113 B2 | 9/2011 | El Gamal et al. | |
| 8,053,742 B2 | 11/2011 | Lundquist et al. | |
| 8,058,030 B2 | 11/2011 | Smith et al. | |
| 8,058,031 B2 | 11/2011 | Xu et al. | |
| 8,133,672 B2 | 3/2012 | Bjornson et al. | |
| 8,133,702 B2 | 3/2012 | Shen et al. | |
| 8,148,516 B2 | 4/2012 | Williams et al. | |
| 8,153,375 B2 | 4/2012 | Travers et al. | |
| 8,168,380 B2 | 5/2012 | Chan | |
| 8,174,696 B2 | 5/2012 | Ebbesen et al. | |
| 8,192,961 B2 | 6/2012 | Williams | |
| 8,252,911 B2 | 8/2012 | Bjornson et al. | |
| 8,257,954 B2 | 9/2012 | Clark et al. | |
| 8,274,034 B2 | 9/2012 | Vogel et al. | |
| 8,274,040 B2 | 9/2012 | Zhong et al. | |
| 8,278,728 B2 | 10/2012 | Murshid | |
| 8,323,939 B2 | 12/2012 | Hanzel et al. | |
| 8,343,746 B2 | 1/2013 | Rank et al. | |
| 8,354,252 B2 | 1/2013 | Wegener et al. | |
| 8,383,369 B2 | 2/2013 | Maxham et al. | |
| 8,420,366 B2 | 4/2013 | Clark et al. | |
| 8,465,699 B2 | 6/2013 | Fehr et al. | |
| 8,467,061 B2 | 6/2013 | McCaffrey et al. | |
| 8,471,219 B2 | 6/2013 | Lundquist et al. | |
| 8,471,230 B2 | 6/2013 | Zhong et al. | |
| 8,481,264 B2 | 7/2013 | Bjornson et al. | |
| 8,501,406 B1 | 8/2013 | Gray et al. | |
| 8,501,922 B2 | 8/2013 | Otto et al. | |
| 8,502,169 B2 | 8/2013 | Rigneault et al. | |
| 8,530,154 B2 | 9/2013 | Williams | |
| 8,530,164 B2 | 9/2013 | Patel et al. | |
| 8,535,886 B2 | 9/2013 | Patel et al. | |
| 8,580,539 B2 | 11/2013 | Korlach | |
| 8,592,148 B2 | 11/2013 | Williams et al. | |
| 8,618,507 B1 | 12/2013 | Lundquist et al. | |
| 8,649,011 B2 | 2/2014 | McCaffrey et al. | |
| 8,652,781 B2 | 2/2014 | Korlach | |
| 8,658,365 B2 | 2/2014 | Bjornson et al. | |
| 8,865,077 B2 | 10/2014 | Chiou et al. | |
| 8,865,078 B2 | 10/2014 | Chiou et al. | |
| 8,867,038 B2 | 10/2014 | McCaffrey et al. | |
| 8,906,614 B2 | 12/2014 | Wegener et al. | |
| 8,921,046 B2 | 12/2014 | Bjornson et al. | |
| 8,921,086 B2 | 12/2014 | Hanzel et al. | |

(56) References Cited

U.S. PATENT DOCUMENTS

| | | |
|---|---|---|
| 8,936,926 B2 | 1/2015 | Hanzel et al. |
| 8,980,584 B2 | 3/2015 | Williams |
| 8,999,676 B2 | 4/2015 | Emig et al. |
| 9,012,144 B2 | 4/2015 | Lapidus et al. |
| 9,045,798 B1 | 6/2015 | Williams et al. |
| 9,062,091 B2 | 6/2015 | Bjornson et al. |
| 9,096,898 B2 | 8/2015 | Williams et al. |
| 9,127,259 B2 | 9/2015 | Bjornson et al. |
| 2002/0031836 A1 | 3/2002 | Feldstein |
| 2003/0138809 A1 | 7/2003 | Williams et al. |
| 2004/0169842 A1 | 9/2004 | Dosluoglu et al. |
| 2004/0259082 A1 | 12/2004 | Williams |
| 2006/0060766 A1 | 3/2006 | Turner et al. |
| 2007/0196846 A1 | 8/2007 | Hanzel et al. |
| 2007/0281288 A1 | 12/2007 | Belkin et al. |
| 2008/0030628 A1 | 2/2008 | Lundquist et al. |
| 2008/0050747 A1 | 2/2008 | Korlach et al. |
| 2010/0009872 A1 | 1/2010 | Eid et al. |
| 2010/0047802 A1 | 2/2010 | Bjorson et al. |
| 2010/0075328 A1 | 3/2010 | Bjornson et al. |
| 2010/0075332 A1 | 3/2010 | Patel et al. |
| 2010/0093068 A1 | 4/2010 | Williams |
| 2010/0093555 A1 | 4/2010 | Bjornson et al. |
| 2010/0112645 A1 | 5/2010 | Clark et al. |
| 2010/0140460 A1 | 6/2010 | Rigneault et al. |
| 2010/0173394 A1 | 7/2010 | Colston et al. |
| 2010/0255487 A1 | 10/2010 | Beechem |
| 2010/0261247 A1 | 10/2010 | Hanzel et al. |
| 2010/0323406 A1 | 12/2010 | Vatta et al. |
| 2011/0136201 A1 | 6/2011 | Mao et al. |
| 2011/0165652 A1 | 7/2011 | Hardin et al. |
| 2011/0183321 A1 | 7/2011 | Williams et al. |
| 2011/0189659 A1 | 8/2011 | Clark et al. |
| 2011/0223590 A1* | 9/2011 | Chiou ............... C12Q 1/6869 435/6.1 |
| 2011/0236983 A1 | 9/2011 | Beechem et al. |
| 2011/0244447 A1 | 10/2011 | Korlach |
| 2011/0294115 A1 | 12/2011 | Williams et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0034602 A1 | 2/2012 | Emig et al. |
| 2012/0094332 A1 | 4/2012 | Lee et al. |
| 2012/0115736 A1 | 5/2012 | Bjornson et al. |
| 2012/0322692 A1 | 12/2012 | Pham et al. |
| 2013/0023039 A1 | 1/2013 | Zaccarin et al. |
| 2013/0040363 A1 | 2/2013 | Nikiforov |
| 2013/0071849 A1 | 3/2013 | Kong et al. |
| 2013/0130363 A1 | 5/2013 | Lundquist et al. |
| 2013/0143206 A1 | 6/2013 | McCaffrey et al. |
| 2013/0183663 A1 | 7/2013 | Wegener et al. |
| 2013/0217007 A1 | 8/2013 | Kamtekar et al. |
| 2013/0295560 A1 | 11/2013 | Williams et al. |
| 2013/0296195 A1 | 11/2013 | Gray et al. |
| 2013/0316912 A1 | 11/2013 | Bjornson et al. |
| 2013/0338013 A1 | 12/2013 | Zhong et al. |
| 2014/0206550 A1 | 7/2014 | Bjornson et al. |
| 2015/0057194 A1 | 2/2015 | McCaffrey et al. |
| 2015/0086994 A1 | 3/2015 | Williams et al. |
| 2015/0141268 A1 | 5/2015 | Rothberg et al. |
| 2015/0177150 A1 | 6/2015 | Rothberg et al. |
| 2015/0218632 A1 | 8/2015 | Williams |
| 2015/0330987 A1 | 11/2015 | Bjornson et al. |
| 2016/0041095 A1 | 2/2016 | Rothberg et al. |
| 2016/0084761 A1 | 3/2016 | Rothberg et al. |
| 2016/0133668 A1 | 5/2016 | Rothberg et al. |

FOREIGN PATENT DOCUMENTS

| | | |
|---|---|---|
| CA | 2343377 A1 | 3/2000 |
| CA | 2373385 C | 11/2000 |
| CA | 2457513 A1 | 3/2003 |
| CA | 2579150 A1 | 4/2006 |
| CN | 101199241 A | 6/2008 |
| CN | 101365807 A | 2/2009 |
| CN | 101421598 A | 4/2009 |
| CN | 101914620 A | 12/2010 |
| CN | 102084001 A | 6/2011 |
| CN | 102212515 A | 10/2011 |
| CN | 102224408 A | 10/2011 |
| CN | 102985803 A | 3/2013 |
| CN | 104624258 A | 5/2015 |
| EP | 1311824 | 5/2003 |
| EP | 1141409 B1 | 3/2006 |
| EP | 1681356 A1 | 7/2006 |
| EP | 1790202 | 5/2007 |
| EP | 1963530 | 9/2008 |
| EP | 1963536 A2 | 9/2008 |
| EP | 1984712 A2 | 10/2008 |
| EP | 2064488 A2 | 6/2009 |
| EP | 1421213 B1 | 2/2010 |
| EP | 1179085 B1 | 5/2010 |
| EP | 2182523 A1 | 5/2010 |
| EP | 2226330 A1 | 9/2010 |
| EP | 2263087 A1 | 12/2010 |
| EP | 2271751 | 1/2011 |
| EP | 2274449 | 1/2011 |
| EP | 2331934 | 6/2011 |
| EP | 2339632 A1 | 6/2011 |
| EP | 2365093 A2 | 9/2011 |
| EP | 2391639 | 12/2011 |
| EP | 2002019 B1 | 2/2012 |
| EP | 2134871 B1 | 3/2012 |
| EP | 2537010 | 12/2012 |
| EP | 2537019 | 12/2012 |
| EP | 2537053 | 12/2012 |
| EP | 1984670 B1 | 7/2014 |
| EP | 2814953 | 12/2014 |
| WO | WO 91/06678 A1 | 5/1991 |
| WO | WO 00/70073 A1 | 11/2000 |
| WO | WO 2001/094609 A1 | 12/2001 |
| WO | WO 2003/020891 A2 | 3/2003 |
| WO | WO 2003/020984 A2 | 3/2003 |
| WO | WO 2004/072238 A2 | 8/2004 |
| WO | WO 2004/072297 A2 | 8/2004 |
| WO | WO 2004/092331 A2 | 10/2004 |
| WO | WO 2005/073407 A1 | 8/2005 |
| WO | WO 2005073407 A1 * | 8/2005 | ......... G01N 21/6408 |
| WO | WO 2006/044078 A2 | 4/2006 |
| WO | WO 2007/015168 A2 | 2/2007 |
| WO | WO 2007/041342 A2 | 4/2007 |
| WO | WO 2007/076057 A2 | 7/2007 |
| WO | WO 2008/028160 A2 | 3/2008 |
| WO | WO 2008/051530 A2 | 5/2008 |
| WO | WO 2008/085652 A1 | 7/2008 |
| WO | WO 2009/102470 A2 | 8/2009 |
| WO | WO 2009/120372 A2 | 10/2009 |
| WO | WO 2009/145820 A2 | 12/2009 |
| WO | WO 2009/145828 A2 | 12/2009 |
| WO | WO 2010/027484 A2 | 3/2010 |
| WO | WO 2010/033193 A2 | 3/2010 |
| WO | WO 2011/040971 A2 | 4/2011 |
| WO | WO 2011/103497 A1 | 8/2011 |
| WO | WO 2011/103504 A1 | 8/2011 |
| WO | WO 2013/171197 A1 | 11/2013 |
| WO | WO 2015/074001 A1 | 5/2015 |
| WO | WO 2015/074004 A1 | 5/2015 |

OTHER PUBLICATIONS

Invitation to Pay Additional Fees for International Application No. PCT/US2015/044360 dated Nov. 20, 2015.
International Search Report and Written Opinion for International Application No. PCT/US2015/044360 dated Feb. 3, 2016.
Invitation to Pay Additional Fees for International Application No. PCT/US2015/044378 dated Oct. 30, 2015.
International Search Report and Written Opinion for International Application No. PCT/US2015/044378 dated Jan. 15, 2016.
Invitation to Pay Additional Fees for International Application No. PCT/US2015/044379 dated Nov. 2, 2015.
International Search Report and Written Opinion for International Application No. PCT/US2015/044379 dated Jan. 15, 2016.

(56) References Cited

OTHER PUBLICATIONS

International Preliminary Report on Patentability for International Application No. PCT/US2014/066013 dated May 26, 2016.
International Preliminary Report on Patentability for International Application No. PCT/US2014/066010 dated May 26, 2016.
Taitt et al., Evanescent wave fluorescence biosensors. Biosens Bioelectron. Jun 2005;20(12):2470-87. Epub Dec 8, 2004.
U.S. Appl. No. 14/821,656, filed Aug. 7, 2015, Rothberg et al.
U.S. Appl. No. 14/821,686, filed Aug. 7, 2015, Rothberg et al.
U.S. Appl. No. 14/821,688, filed Aug. 7, 2015, Rothberg et al.
PCT/US2014/066014, dated May 26, 2016, International Preliminary Report on Patentability.
PCT/US2015/044360, dated Nov. 20, 2015, Invitation to Pay Additional Fees.
PCT/US2015/044360, dated Feb. 3, 2016, International Search Report and Written Opinion.
PCT/US2015/044378, dated Oct. 30, 2015, Invitation to Pay Additional Fees.
PCT/US2015/044378, dated Jan. 15, 2016, International Searh Report and Written Opinion.
PCT/US2015/044379, dated Nov. 2, 2015, Invitation to Pay Additional Fees.
PCT/US2015/044379, dated Jan. 15, 2016, International Search Report and Written Opinion.
PCT/US2014/066013, dated May 26, 2016, International Preliminary Report on Patentability.
PCT/US2014/066010, dated May 26, 2016, International Preliminary Report on Patentability.
U.S. Appl. No. 14/543,888, filed Nov. 17, 2014, Rothberg et al.
U.S. Appl. No. 14/543,867, filed Nov. 17, 2014, Rothberg et al.
PCT/US2014/066014, dated Jan. 28, 3015, Invitation to Pay Additional Fees.
PCT/US2014/066014, dated Apr. 7, 2015, International Search Report and Written Opinion.
PCT/US2014/066013, dated Jan. 28, 2015, Invitation to Pay Additional Fees.
PCT/US2014/066013, dated Apr. 7, 2015, International Search Report.
PCT/US2014/066010, dated Jan. 28, 2015, Invitation to Pay Additional Fees.
PCT/US2014/066010, dated Apr. 7, 2015, International Search Report and Written Opinion.
Invitation to Pay Additional Fees for Application No. PCT/US2014/066014 dated Jan. 28, 2015.
Invitation to Pay Additional Fees for Application No. PCT/US2014/066013 dated Jan. 28, 2015.
Invitation to Pay Additional Fees for Application No. PCT/US2014/066010 dated Jan. 28, 2015.
International Search Report and Written Opinion for Application No. PCT/US2014/066014 dated Apr. 7, 2015.
International Search Report and Written Opinion for Application No. PCT/US2014/066013 dated Apr. 7, 2015.
International Search Report and Written Opinion for Application No. PCT/US2014/066010 dated Apr. 7, 2015.
[No Author Listed] 5.2 Megapixels, 1-inch, 250fps, global-shutter CMOS image sensor, Anafocus, Oct. 2012, 4 pages, Sevilla, Spain.
[No Author Listed] Description of our technology, CrackerBio, 4 pages, Taiwan.
[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].
[No Author Listed] ICCD camera applications in the field of Life Science, Stanford Computer Optics, 2013, 2 pages, http://www.stanfordcomputeroptics.com/applications/life-science.html [last accessed 9 May 2014].
[No Author Listed] OLED-on-CMOS for Sensors and Microdisplays, IPMS Fraunhofer Institut Photonische Mikrosysteme, 2 pages, Dresden, Germany.

Achermann, Exciton—Plasmon Interactions in Metal—Semiconductor Nanostructures, The Journal Physical Chemistry Letters, Sep. 13, 2010, 1(19):2837-43.
Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.
Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.
Aouani et al., Bright unidirectional fluorescence emission of molecules in a nanoaperture with plasmonic corrugations. Nano Lett. Feb. 9, 2011;11(2):637-44. doi: 10.1021/n1103738d. Epub Jan. 19, 2011.
Aouani et al., Supporting Information for Bright unidirectional fluorescence emission of molecules in a nanoaperture with plasmonic corrugations. Nano Lett. Feb. 9, 2011;11(2):19 pages.
Aouani et al., Plasmonic Antennas for Directional Sorting of Fluorescence Emission, Nano Letters, May 18, 2011, 11(6):2400-6.
Aouani et al., Supporting Information for Plasmonic Antennas for Directional Sorting of Fluorescence Emission, Nano Letters, May 18, 2011, 11(6):9 pages.
Aouani et al., Saturated excitation of fluorescence to quantify excitation enhancement in aperture antennas, Optics Express, Jul. 30, 2012, 20(16):18085-90.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.
Chanyawadee et al., Nonradiative exciton energy transfer in hybrid organic-inorganic heterostructures, Phys. Rev. B., May 14, 2008, 77(19): 193402-1-4.
Daldosso et al., Fabrication and optical characterization of thin two-dimensional $Si_3N_4$ waveguides, Materials Science in Semiconductor Processing, Oct. 18, 2004, 7(4-6): 453-8.
Davies et al., Plasmonic Nanogap Tilings: Light-Concentrating Surfaces for Low-Loss Photonic Integration, ACS Nano, Jul. 4, 2013, 7(8):7093-100, arXiv:1305.2839v2, http://arxiv.orhtbs/1305.2839v2.
Deshpande et al., Electrically driven polarized single-photon emission from an InGaN quantum dot in a GaN nanowire, Nature Communcations, Apr. 9, 2013, 8 pages.
Deutsch et al., Luminescence upconversion in colloidal double quantum dots, Nature Nanotechnology Letter, Sep. 2013, 8(9):649-53.
Edel et al., Accurate Single Molecule FRET Efficiency Determination for Surface Immobilized DNA Using Maximum Likelihood Calculated Lifetimes, J. Phys. Chem, Mar. 22, 2007, 111(11):2986-90.
Eid et al., Real-time DNA sequencing from single polymerase molecules. Science. Jan. 2, 2009;323(5910):133-8. doi:10.1126/science.1162986. Epub Nov. 20, 2008.
Eid et al., Supporting Online Material for Real-time DNA sequencing from single polymerase molecules. Science. Jan. 2, 2009;323(5910):21 pages.
Feldman et al., Wafer-Level Camera Technologies Shrink Camera Phone Handsets, Photonics.com, Aug. 1, 2007, 3 pages, http://www.photonics.com/Article.aspx?AID=30459 . [last accessed Dec. 17, 2013].
Fu et al., A microfabricated fluorescence-activated cell sorter. Nature Biotechnology. Nov. 1999; 17(11): 1109-1111.
Gorin et al., Fabrication of silicon nitride waveguides for visible-light using PECVD: a study of the effect of plasma frequency on optical properties, Optics Express, Sep. 1, 2008, 16(18):13509-16.

(56) References Cited

OTHER PUBLICATIONS

Gryczynski et al., Two-photon excitation by the evanescent wave from total internal reflection. Anal Biochem., Apr. 5, 1997;247(1):69-76.

Haase et al., Upconverting Nanoparticles, Angewandte Chemie International Edition, Jun. 20, 2011, 50(26):5808-29.

Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.

Hansard et al., Time-of-Flight Cameras: Principles, Methods and Applications, Nov. 2012, 102 pages, Springer-Verlag, London, UK.

He et al., DNA Sequencing by Capillary Electrophoresis with Four-Decay Fluorescence Detection, Anal. Chem., Dec. 15, 2000, 72(24):5865-73.

Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.

Heucke et al., Placing Individual Molecules in the Center of Nanoapertures, Nano Letters, Feb. 12, 2014, 14(2):391-5.

Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.

Ishii et al., Self-matched high-voltage rectangular wave pulse generator, Rev. Sci. Instrum, Nov. 1985, 56(11):2116-8.

Jun et al., Plasmonic beaming and active control over fluorescent emission, Nature Communications, Apr. 19, 2011, 6 pages.

Juodawlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.

Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.

Kano et al., Two-photon-excited fluorescence enhanced by a surface plasmon. Opt Lett. Nov. 15, 1996;21(22):1848-50.

Karow, PacBio Aims to Boost Throughput of SMRT Technology with Microchip Co-development Deal, in Sequence and Clinical Sequencing News, Jul. 24, 2012, 3 pages, GenomeWeb.

Klein et al., Controlling plasmonic hot spots by interfering Airy beams, Optics Letters, Aug. 15, 2012, 37(16): 3402-4.

Korlach et al., Real-time DNA sequencing from single polymerase molecules. Methods Enzymol. May 2010;472:431-55. doi:10.1016/S0076-6879(10)72001-2.

Kreye et al, P-200: Evaluation of different OLED-Stacks for Active-Matrix OLED Microdisplays on CMOS-Substrates, SID 06 Digest, Jun. 2006, 37(1); 979-81.

Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.

Lenne et al., Fluorescence fluctuations analysis in nanoapertures: physical concepts and biological applications, Histochem Cell Biol, Sep. 2008, 130:795-805.

Leslie et al., Convex Lens-Induced Confinement for Imaging Single Molecules, Anal. Chem., Jul. 15, 2010, 82(14):6224-9.

Levy et al., An 852x600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.

Lezec et al., Beaming Light from a Subwavelength Aperture, Science, Aug. 2, 2002, 297(5582):820-2.

Li et al., Employing~100% Excitons in OLEDs by Utilizing a Fluorescent Molecule with Hybridized Local and Charge-Transfer Excited State, Advanced Functional Materials, Mar. 19, 2014, 24(11):1609-14.

Lin et al., Cosine-Gauss Plasmon Beam: A Localized Long-Range Nondiffracting Surface Wave, Physical Review Letters, Aug. 31, 2012, 109(9):093904-1-5.

McGinty et al., Wide-field fluorescence lifetime imaging of cancer, Biomedical Optics Express, Sep. 1, 2010, 1(2): 627-40.

Misra et al., White organic LEDs and their recent advancements, Semiconductor Science and Technology, Apr. 25, 2006, 21(7):R35-47.

Mitchell et al., Nanosecond Fluorescence Lifetime Imaging with gated CCD detection and pulsed laser excitation, Photonic Research Systems Ltd., May 1, 2013, 13 pages, Newhaven East Sussex UK.

Murshid et al., Array of concentric CMOS photodiodes for detection and de-multiplexing of spatially modulated optical channels, Optics & Laser Technology, Sep. 2009, 41(6):764-9.

Murshid et al., CMOS Detectors: Concentric photodiode array enables spatial-domain multiplexing, Laser Focus World, Apr. 1, 2009, 10 pages, http://www.laserfocusworld.com/articles/print/volume-45/issue-4/features/cmos-detectors-concentric-photodiode-array-enables-spatial-domain-multiplexing.html, [last accessed Dec. 12, 2013].

Murshid et al., Concentric octagonal CMOS photodiodes for direct detection of spatially multiplexed optical fiber channels, Optical Society of America, Oct. 2008, 1 page.

Nozik, Multiple exciton generation in semiconductor quantum dots, Chemical Physics Letters, May 20, 2008, 457(1-3):3-11.

Park et al., A dual-modality optical coherence tomography and fluorescence lifetime imaging microscopy system for simultaneous morphological and biochemical tissue characterization, Biochemical Optics Express, Aug. 2, 2010, 1(1):186-200.

Pfeifer et al., Improved optical outcoupling of OLED microdisplays by nanostructured substrates, IEEE Semiconductor Conference Dresden, Sep. 27-18, 2011, 4 pages, Dresden, Germany.

Poddubny et al., Photonic quasicrystalline and aperiodic structures, Physica E: Low-dimensional Systems and Nanostructures, May 2010, 42(7): 1871-95.

Pons et al., Solution-phase single quantum dot fluorescence resonance energy transfer. J Am Chem Soc., Nov. 29, 2006;128(47):15324-31.

Pudavar, Fluorescence Lifetime Imaging (FILM), Leica Microsystems Inc., Oct. 25, 2009, 60 pages, Exton, PA.

Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.

Ramuz et al., Coupling light from an organic light emitting diode (OLED) into a single-mode waveguide: Toward monolithically integrated optical sensors, Journal of Applied Physics, Apr. 2009, 105(8):084508-1-7.

Ran et al., Design of a 16 gray scales 320 x 240 pixels OLED-on-silicon driving circuit, Journal of Semiconductors, Jan. 2009, 30(1):015010-1-4.

Reckziegel et al., Optical sensors based on monlithic integrated organic light-emitting diodes (OLEDs), Proceedings of SPIE Optical Sensors, Apr. 28, 2008, vol. 7003: 8 pages.

Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.

Richter et al., OLED-on-CMOS based bidirectional microdisplay for near-to-eye and sensor applications, IEEE Semiconductor Conference Dresden, Sep. 27-28, 2011, 3 pages, Dresden, Germany.

Rigneault et al., Enhancement of Single-Molecule Fluorescence Detection in Subwavelength Apertures, Physical Review Letters, Sep. 9, 2005, 95(11): 117401-1-4.

Romero-Garcia et al., Silicon nitride back-end optics for biosensor applications, Proc. of SPIE Integrated Optics: Physics and Simulations, May 7, 2013, vol. 8781: 87810W-1-11.

Romero-Garcia et al., Visible wavelength silicon nitride focusing grating coupler with AlCu/TiN reflector. Optics Letters. Jul. 15, 2013, 38(14):2521-3.

(56) References Cited

OTHER PUBLICATIONS

Rui et al., Demonstration of beam steering via dipole-coupled plasmonic spiral antenna, Scientific Reports, Jul. 19, 2013, 7 pages.
Sakadzic et al., Multi-photon microscopy with a low-cost and highly efficient Cr:LiCAF laser, Optics Express, Dec. 8, 2008, 16(25):20848-63.
Salthouse et al., Development of a Time Domain Fluorimeter for Fluorescent LifetimeMultiplexing Analysis, IEEE Biomed Circuits Syst., Sep. 1, 2008, 2(3): 204-11.
Schalberger et al., 60.4: Distinguished Paper: A Fully Integrated 1 AMOLED Display Using Current Feedback Based on a Five Mask LTPS CMOS Process, SID 10 Digest, May 2010, 41(1): 905-8.
Schmidt, Direct Encapsulation of OLED on CMOS, Bio and Nano Packaging Techniques for Electron Devices, Jul. 17, 2012, Chapter 29, 581-99, Springer-Verlag Berling Heidelberg.
Siegfried et al., Gap Plasmons and Near-Field Enhancement in Closely Packed Sub-10 nm Gap Resonators, Nano Lett., Oct. 10, 2013, 13(11):5449-53.
Sorokina et al., Fluorescent Lifetime Trajectories of a Single Fluorophore Reveal Reaction Intermediates During Transcription Initiation, J. Am. Chem. Soc., Jul. 22, 2009, 131(28):9630-31.
Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.
Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html , [last accessed May 9, 2014].
Takkellapati et al., Synthesis of aminomethyl- and bis-aminomethyl-fluorescein energy transfer terminators. Nucleosides Nucleotides Nucleic Acids. Dec. 2007;26(10-12):1467-70.
Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.
Toma et al., Compact surface plasmon-enhanced fluorescence biochip, Opt. Express Apr. 22, 2013 21(8): 10121-10132.
Toma et al., Surface plasmon-coupled emission on plasmonic Bragg gratings, Optics Express, Jun. 18, 2012, 20(13):14042-53.
Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.
Unfricht et al., Grating-coupled surface plasmon resonance: a cell and protein microarray platform. Proteomics. Nov. 2005;5(17):4432-42.
Vogel et al., OLED-on-CMOS Integration for Optoelectronic Sensor Applications, Proc. of SPIE Silicon Photonics II, Mar. 1, 2007, vol. 6477:8 pages.
Vogel et al., Optoelectronic Sensors based on OLED-on-CMOS, 2008 $2^{nd}$ European Conference & Exhibition on Integration Issues of Minaturized Systems—MOMS, MOEMS, ICS, and Electronic Components (SSI), Apr. 9-10, 2008, 3 pages, Barcelona, Spain.
Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.
Walpole, Slab-coupled optical waveguide lasers: a review, Proc. SPIE Novel In-Plane Semiconductor Lasers III, May 11, 2004, vol. 5365, 124-32.
Wenger et al., Emission and excitation contributions to enhanced single molecule fluorescence by gold nanometric apertures, Optics Express, Mar. 3, 2008, 16(5):3008-20.
Wenger et al., Enhanced fluorescence from metal nanoapertures: physical characterizations and biophotonic applications, Proc. SPIE Plasmonics in Biology and Medicine VII, Feb. 16, 2010, 8 pages.
Wenger, Aperture optical antennas, Optical Antennas, Feb. 2013, 25pages, Cambridge University Press, Cambridge, UK.
Willoughby, Elastically Averaged Precision Alignment, Massachusetts Institute of Technology, Jun. 2005, 158 pages, Cambridge, MA.
Xiong et al., Aluminum nitrade as a new material for chip-scale optomechanics and nonlinear optics, New Journal of Physics, Sep. 17, 2012, 14: 21 pages.
Yan-Yan et al., OLED-on-silicon chip with new pixel circuit, J. Cent. South Univ., May 2012 19(5):1276-82.
Yu et al., Light Propagation with Phase Discontinuities: Generalized Laws of Reflection and Refraction, Science, Oct. 21, 2011, 334 (6054):333-7.
Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2012.
Zhang et al., Continuous metal plasmonic frequency selective surfaces, Optics Express, Nov. 7, 2011, 19(23):23279-85.
Zhao et al., Plasmonic demultiplexer and guiding. ACS Nano. Nov. 23, 2010;4(11):6433-8. doi: 10.1021/nn101334a. Epub Oct. 6, 2010.
Zhu et al., Zero-Mode Waveguides for Single-Molecule Analysis, Annu. Rev. Biophys., Jun. 2012, 41:269-93.
Zong et al., Equivalent Circuit Model of Top-emitting OLED for the Designing of OLED-on-Silicon Microdisplay, Advanced Materials Research, Nov. 2011, 383-90:7037-42.

\* cited by examiner

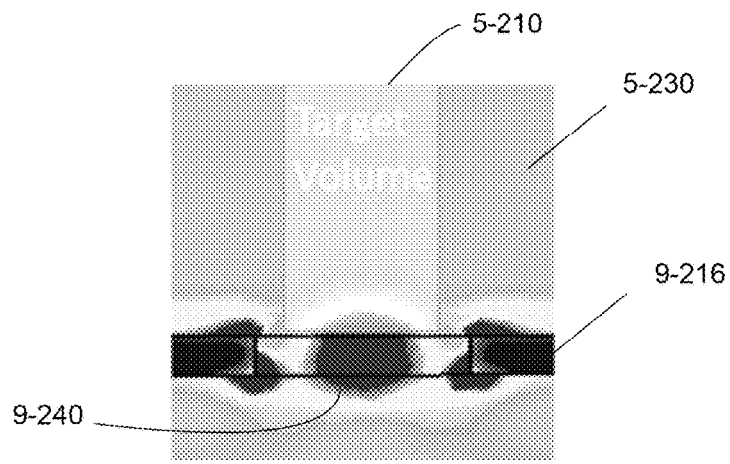
FIG. 9-2D
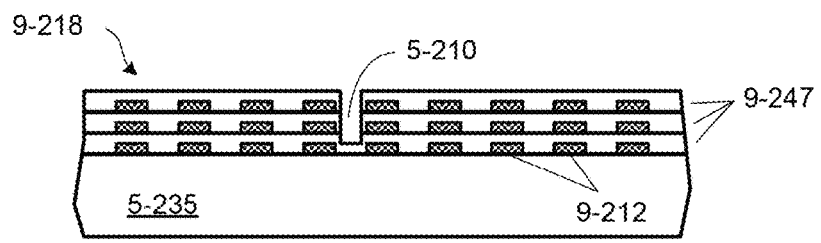
FIG. 9-2E
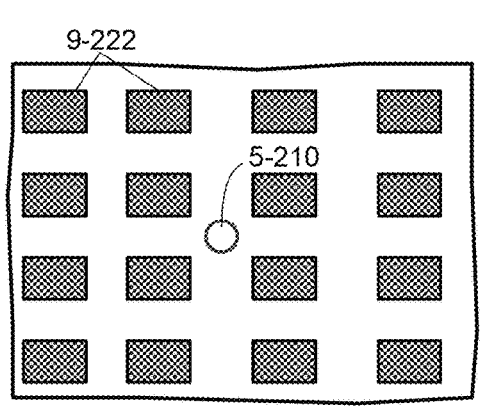 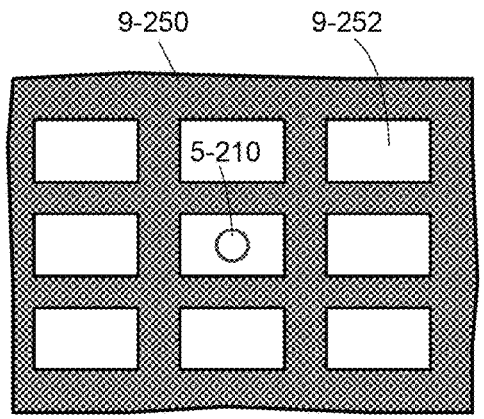
FIG. 9-2F  FIG. 9-2G

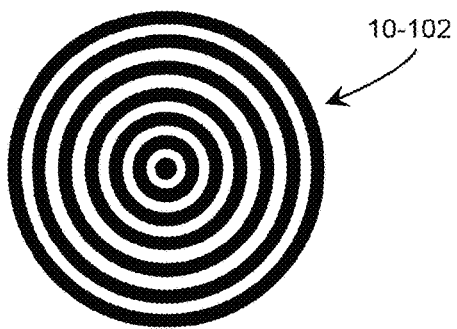
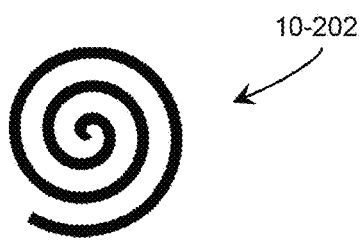
FIG. 10-1  FIG. 10-2
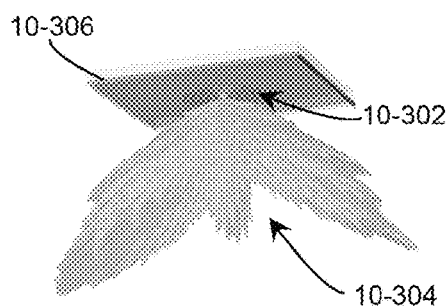
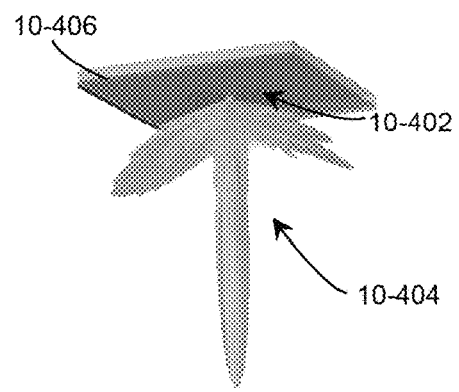
FIG. 10-3  FIG. 10-4
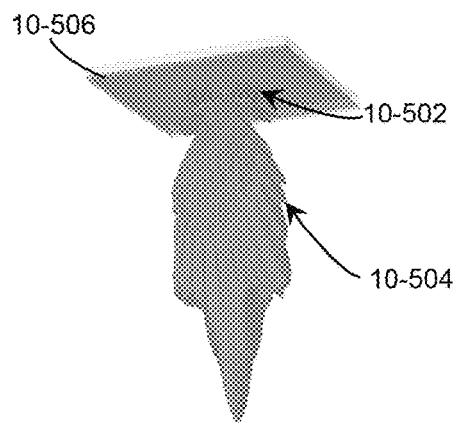
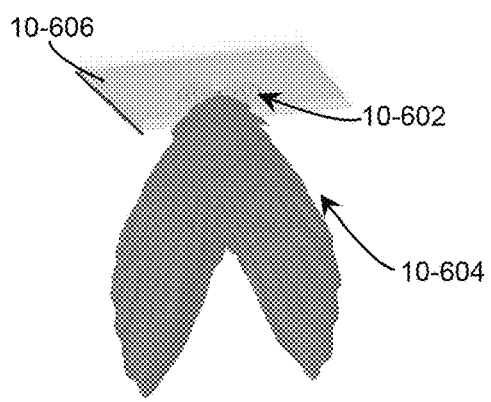
FIG. 10-5  FIG. 10-6

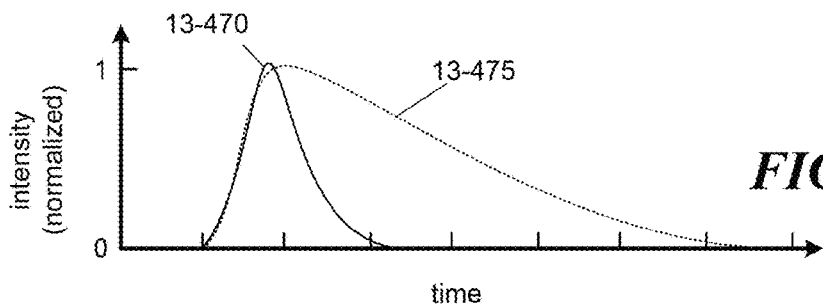
*FIG. 13-4D*
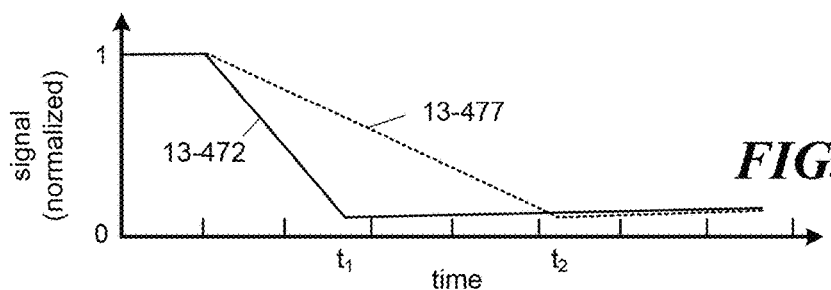
*FIG. 13-4E*
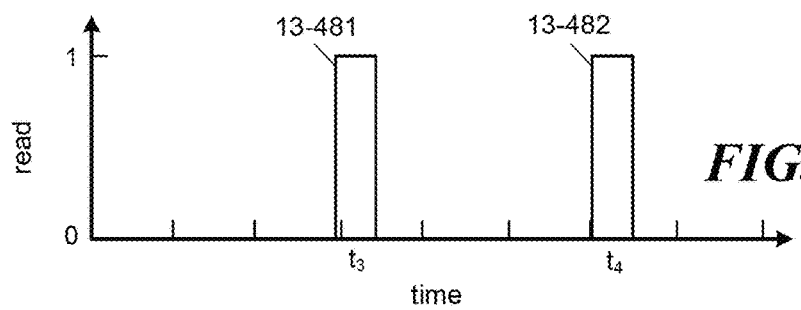
*FIG. 13-4F*
*FIG. 13-4G*          *FIG. 13-4H*

INTEGRATED DEVICE WITH EXTERNAL LIGHT SOURCE FOR PROBING DETECTING AND ANALYZING MOLECULES

RELATED APPLICATIONS

This application claims the benefit under 35 U.S.C. § 119(e) of U.S. Provisional Patent Application 61/905,282, entitled "Integrated Device for Probing, Detecting and Analyzing Molecules," filed Nov. 17, 2013; U.S. Provisional Patent Application 61/917,926, entitled "Integrated Device for Probing, Detecting and Analyzing Molecules," filed Dec. 18, 2013; U.S. Provisional Patent Application 61/941,916, entitled "Integrated Device for Probing, Detecting and Analyzing Molecules," filed Feb. 19, 2014, all of which are incorporated by reference in their entirety.

FIELD

The present application is directed to devices and methods for analyses of biological and chemical specimens and reactions involving biological and chemical samples, and methods of fabricating said devices.

BACKGROUND

Analyses of biological and chemical specimens may be performed conventionally using large, expensive laboratory equipment requiring skilled scientists trained to operate the equipment and interpret the results. In some cases, detection and analysis of biological samples may be performed using biological assays ("bioassays"). Bioassays are conventionally performed in bulk such that a large amount of a particular type of sample is necessary for detection and quantitation.

Some bioassays are performed by tagging samples with luminescent tags that emit light of a particular wavelength. The tags are illuminated with an excitation light source to cause luminescence, and the luminescent light is detected with a photodetector to quantify the amount of luminescent light emitted by the tags. Bioassays using luminescent tags conventionally involve expensive laser light sources to illuminate samples and complicated, bulky luminescent detection optics and electronics to collect the luminescence from the illuminated samples.

Because conventional analytical equipment is typically expensive and requires a skilled operator, specimens to be analyzed may need to be sent to an on-site or off-site facility for processing. This can introduce appreciable delay and cost associated with even routine analysis of a specimen. For example, a patient may have to wait several days and schedule a return visit to a doctor's office to learn about the results of a laboratory test on a specimen provided by the patient.

SUMMARY

The technology described herein relates to apparatus and methods for analyzing specimens rapidly using an active-source-pixel, integrated device that can be interfaced with a mobile computing instrument. The integrated device may be in the form of a disposable or recyclable lab-on-chip or a packaged module that is configured to receive a small amount of a specimen and execute, in parallel, a large number of analyses of samples within the specimen. The integrated device may be used to detect the presence of particular chemical or biological analytes in some embodiments, to evaluate a chemical or biological reactions in some embodiments, and to determine genetic sequences in some embodiments. According to some implementations, the integrated device may be used for single-molecule gene sequencing.

According to some implementations, a user deposits a specimen in a chamber on the integrated device, and inserts the integrated device into a receiving instrument. The receiving instrument, alone or in communication with a computer, automatically interfaces with the integrated device, receives data from the integrated device, processes the received data, and provides results of the analysis to the user. As may be appreciated, integration and computing intelligence on the chip, receiving instrument, and or computer reduce the skill level required from the user.

According to some embodiments of the present application, an integrated device is provided, comprising a pixel region comprising a plurality of pixels. Each pixel of the plurality of pixels has a sample well on a surface of the integrated device, wherein the sample well is configured to receive a sample, at least one component configured to generate a radiation pattern based on emission energy emitted from the sample in the sample well in response to the excitation energy, and at least one sensor configured to detect a spatial distribution of at least a portion of the radiation pattern. The integrated device further comprises at least one waveguide configured to deliver excitation energy to at least a portion of the plurality of pixels.

According to some embodiments of the present application, an integrated device is provided, comprising a sample well configured to receive a sample labeled with one of a plurality of markers. Each of the plurality of markers emit emission energy within one of a plurality of spectral ranges in response to excitation energy illuminating the sample. The integrated device further comprises an emission-energy coupling structure located in a vicinity of the sample well for generating a radiation pattern for each spectral range of the plurality of spectral ranges when emission energy is emitted from the sample well. The integrated device further comprises a plurality of sensors configured to receive at least a portion of the emission energy and detect a spatial distribution of the radiation pattern for each spectral range of the plurality of spectral ranges.

According to some embodiments of the present application, a method of forming an integrated device is provided, comprising forming a plurality of sensor regions and forming a plurality of sample wells. Each sensor region of the plurality of sensor regions includes a plurality of sensors. Each sample well of the plurality of sample wells aligns with a corresponding one of the plurality of sensor regions. The method further comprises forming at least one waveguide configured to couple excitation energy separate from the plurality of sample wells and direct excitation energy to at least one sample well and forming a plurality of surface-energy coupling elements, wherein each surface-energy coupling element is configured to form a radiation pattern on one of the plurality of sensor regions. The radiation pattern is based on emission energy from a corresponding one of the plurality of sample wells.

According to some embodiments of the present application, an instrument is provided, comprising at least one excitation source for providing at least one excitation energy, an excitation source positioning system for aligning the at least one excitation energy emitted by the excitation source to a coupling region of an integrated device, and readout circuitry configured to receive at least one readout signal representative of emission energy detected by a sensor on the integrated device.

According to some embodiments of the present application a system is provided, comprising an instrument and an integrated device. The instrument includes an excitation energy source configured to emit at least one excitation energy, and at least one alignment component. The integrated device includes a pixel region having a plurality of pixels. Each pixel has a sample well and at least one sensor. The sample well is configured to receive a sample which, when coupled to the at least one excitation energy emits emission energy having a spectral range. Each pixel further includes at least one waveguide configured to direct excitation energy to the sample well, at least one element for generating a radiation pattern based on the spectral range of the emission energy, at least one sensor configured to detect a spatial distribution of at least a portion of the radiation pattern. The integrated device further includes an excitation source coupling region for receiving excitation energy from the excitation energy source and coupling the excitation energy into the at least one waveguide. The at least one alignment component is configured to align the integrated device to the instrument such that the at least one excitation energy couples to at least a portion of the excitation source coupling region.

According to some embodiments, a method of analyzing a specimen comprises depositing the specimen on a surface of an integrated device having a plurality of pixels. Each pixel has a sample well configured to receive a sample labeled with a first marker of a plurality of markers and a sensor region having a plurality of sensors. The method further comprises aligning the integrated device with an instrument having at least one excitation energy source for coupling excitation energy to a sample well of a first pixel and readout circuitry for receiving readout signals from the plurality of sensors of the sensor region of the first pixel. The method further comprises illuminating the first marker with excitation energy and detecting, from the readout signals from the plurality of sensors of the sensor region of the first pixel, a spatial distribution of emission energy generated by the first marker.

According to some embodiments, a method for sequencing a target nucleic acid molecule comprises providing an integrated device that includes a sample well containing the target nucleic acid molecule, a polymerizing enzyme and a plurality of types of nucleotides or nucleotide analogs. Each type of nucleotide or nucleotide analog of the plurality of types of nucleotides or nucleotide analogs is labeled with one of a plurality of markers. The method further comprises providing at least one excitation source configured to direct excitation energy to the sample well. The method further comprises performing an extension reaction at a priming location of the target nucleic acid molecule in the presence of the polymerizing enzyme to sequentially incorporate a portion of the plurality of types of nucleotides or nucleotide analogs into a growing strand that is complementary to the target nucleic acid molecule, wherein upon excitation by excitation energy, the marker labelling one type of nucleotide or nucleotide analog produce emissions from the sample well while the one type of nucleotide or nucleotide analog is incorporated into the growing strand. The method further comprises detecting at least a portion of the emissions at a sensor that is configured to receive the emissions from the sample well and receiving signal sets from the sensor for each detected emission, wherein the signal sets are representative of spatial distribution of the detected emissions and distinguish among the plurality of types of nucleotides or nucleotide analogs. The method further comprises identifying the types of nucleotides or nucleotide analogs based on the received signal sets, thereby sequencing the target nucleic acid molecule.

According to some embodiments of the present application, a method for nucleic acid sequencing comprises providing an integrated device comprising a plurality of sample wells and an excitation energy source that is operatively coupled to the plurality of sample wells. An individual sample well of the plurality of sample wells comprises a target nucleic molecule, a polymerizing enzyme and nucleotides or nucleotide analogs. The method further comprises subjecting the target nucleic acid molecule to a polymerization reaction to yield a growing strand that is complementary to the target nucleic acid molecule in the presence of the nucleotides or nucleotide analogs and the polymerizing enzyme. One marker of a plurality of markers labels each of the nucleotides or nucleotide analogs and the plurality of markers emit emissions upon excitation by excitation energy from the excitation source while the corresponding nucleotide or nucleotide analog is incorporated into the growing strand. The method further comprises detecting spatial distribution patterns of the emissions while performing the extension reaction, wherein the spatial distribution patterns of the emissions are distinguishable for the plurality of markers and identifying a sequence of the target nucleic acid molecule based on the spatial distribution patterns of the emissions.

The term "pixel" may be used in the present disclosure to refer to a unit cell of an integrated device. The unit cell may include a sample well and a sensor. The unit cell may further include an excitation source. The unit cell may further include at least one excitation-coupling optical structure (which may be referred to as a "first structure") that is configured to enhance coupling of excitation energy from the excitation source to the sample well. The unit cell may further include at least one emission-coupling structure that is configured to enhance coupling of emission from the sample well to the sensor. The unit cell may further include integrated electronic devices (e.g., CMOS devices). There may be a plurality of pixels arranged in an array on an integrated device.

The term "optical" may be used in the present disclosure to refer to visible, near infrared, and short-wavelength infrared spectral bands.

The term "tag" may be used in the present disclosure to refer to a tag, probe, marker, or reporter attached to a sample to be analyzed or attached to a reactant that may be reacted with a sample.

The phrase "excitation energy" may be used in the present disclosure to refer to any form of energy (e.g., radiative or non-radiative) delivered to a sample and/or tag within the sample well. Radiative excitation energy may comprise optical radiation at one or more characteristic wavelengths.

The phrase "characteristic wavelength" may be used in the present disclosure to refer to a central or predominant wavelength within a limited bandwidth of radiation. In some cases, it may refer to a peak wavelength of a bandwidth of radiation. Examples of characteristic wavelengths of fluorophores are 563 nm, 595 nm, 662 nm, and 687 nm.

The phrase "characteristic energy" may be used in the present disclosure to refer to an energy associated with a characteristic wavelength.

The term "emission" may be used in the present disclosure to refer to emission from a tag and/or sample. This may include radiative emission (e.g., optical emission) or non-radiative energy transfer (e.g., Dexter energy transfer or Förster resonant energy transfer). Emission results from excitation of a sample and/or tag within the sample well.

The phrase "emission from a sample well" or "emission from a sample" may be used in the present disclosure to refer to emission from a tag and/or sample within a sample well.

The term "self-aligned" may be used in the present disclosure to refer to a microfabrication process in which at least two distinct elements (e.g., a sample well and an emission-coupling structure, a sample well and an excitation-source) may be fabricated and aligned to each other without using two separate lithographic patterning steps in which a first lithographic patterning step (e.g., photolithography, ion-beam lithography, EUV lithography) prints a pattern of a first element and a second lithographic patterning step is aligned to the first lithographic patterning step and prints a pattern of the second element. A self-aligned process may comprise including the pattern of both the first and second element in a single lithographic patterning step, or may comprise forming the second element using features of a fabricated structure of the first element.

The term "sensor" may be used in the present disclosure to refer to one or more integrated circuit devices configured to sense emission from the sample well and produce at least one electrical signal representative of the sensed emission.

The term "nano-scale" may be used in the present disclosure to refer to a structure having at least one dimension or minimum feature size on the order of 150 nanometers (nm) or less, but not greater than approximately 500 nm.

The term "micro-scale" may be used in the present disclosure to refer to a structure having at least one dimension or minimum feature size between approximately 500 nm and approximately 100 microns.

The phrase "enhance excitation energy" may be used in the present disclosure to refer to increasing an intensity of excitation energy at an excitation region of a sample well. The intensity may be increased by concentrating and/or resonating excitation energy incident on the sample well, for example. In some cases, the intensity may be increased by anti-reflective coatings or lossy layers that allow the excitation energy to penetrate further into the excitation region of a sample well. An enhancement of excitation energy may be a comparative reference to an embodiment that does not include structures to enhance the excitation energy at an excitation region of a sample well.

The terms "about," "approximately," and "substantially" may be used in the present disclosure to refer to a value, and are intended to encompass the referenced value plus and minus acceptable variations. The amount of variation could be less than 5% in some embodiments, less than 10% in some embodiments, and yet less than 20% in some embodiments. In embodiments where an apparatus may function properly over a large range of values, e.g., a range including one or more orders of magnitude, the amount of variation could be a factor of two. For example, if an apparatus functions properly for a value ranging from 20 to 350, "approximately 80" may encompass values between 40 and 160.

The term "adjacent" may be used in the present disclosure to refer to two elements arranged within close proximity to one another (e.g., within a distance that is less than about one-fifth of a transverse or vertical dimension of a pixel). In some cases there may be intervening structures or layers between adjacent elements. In some cases adjacent elements may be immediately adjacent to one another with no intervening structures or elements.

The term "detect" may be used in the present disclosure to refer to receiving an emission at a sensor from a sample well and producing at least one electrical signal representative of or associated with the emission. The term "detect" may also be used in the present disclosure to refer to determining the presence of, or identifying a property of, a particular sample or tag in the sample well based upon emission from the sample well.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-2A depicts absorption wavelength spectra, according to some embodiments.

FIG. 1-2B depicts emission wavelength spectra, according to some embodiments.

FIG. 2-1A is a block diagram representation of an apparatus that may be used for rapid, mobile analysis of biological and chemical specimens, according to some embodiments.

FIG. 2-1B is a block diagram of an integrated device and an instrument, according to some embodiments.

FIG. 2-2 depicts and integrated device, according to some embodiments.

FIG. 3-1A depicts a row of pixels of an integrated device, according to some embodiments.

FIG. 3-1B depicts excitation energy coupling to sample wells in a row of pixels and emission energy from each sample well directed towards sensors, according to some embodiments.

FIG. 4-1A depicts edge-coupling of an excitation source to a waveguide, according to some embodiments.

FIG. 4-1B depicts a grating coupler for coupling an integrated device to an excitation source, according to some embodiments.

FIG. 4-2 depicts waveguides arranged in an integrated device, according to some embodiments.

FIG. 4-3A depicts a cross sectional view of an excitation source area of an integrated device, according to some embodiments.

FIG. 4-3B depicts a cross-sectional view of a pixel array area of an integrated device, according to some embodiments.

FIG. 4-4 depicts coupling multiple excitation sources to multiple pixels via waveguides, according to some embodiments.

FIGS. 4-5A and 4-5B depict a numerical simulation of excitation radiation through a waveguide coupling to a sample well, according to some embodiments.

FIG. 5-1 depicts a sample well formed in a pixel region of an integrated device, according to one embodiment.

FIG. 5-2 depicts excitation energy incident on a sample well, according to some embodiments.

FIG. 5-3 illustrates attenuation of excitation energy along a sample well that is formed as a zero-mode waveguide, according to some embodiments.

FIG. 5-4 depicts a sample well that includes a divot, which increases excitation energy at an excitation region associated with the sample well in some embodiments.

FIG. 5-5 compares excitation intensities for sample wells with and without a divot, according to one embodiment.

FIG. 5-6 depicts a sample well and divot formed at a protrusion, according to some embodiments.

FIG. 5-7A depicts a sample well having tapered sidewalls, according to some embodiments.

FIG. 5-7B depicts a sample well having curved sidewalls and a divot with a smaller transverse dimension, according to some embodiments.

FIG. 5-7C and FIG. 5-7D depict a sample well formed from surface plasmonic structures.

FIG. 5-7E depicts a sample well that includes an excitation-energy-enhancing structure formed along sidewalls of the sample well, according to some embodiments.

FIG. 5-7F depicts a sample well formed in a multi-layer stack, according to some embodiments.

FIG. 5-8 illustrates surface coating formed on surfaces of a sample well, according to some embodiments.

FIG. 5-9A through FIG. 5-9E depict structures associated with a lift-off process of forming a sample well, according to some embodiments.

FIG. 5-9F depicts a structure associated with an alternative lift-off process of forming a sample well, according to some embodiments.

FIG. 5-10A through FIG. 5-10D depict structures associated with a direct etching process of forming a sample well, according to some embodiments.

FIG. 5-11 depicts a sample well that may be formed in multiple layers using a lift-off process or a direct etching process, according to some embodiments.

FIG. 5-12 depicts a structure associated with an etching process that may be used to form a divot, according to some embodiments.

FIG. 5-13A through FIG. 5-13C depict structures associated with an alternative process of forming a divot, according to some embodiments.

FIG. 5-14A through FIG. 5-14D depict structures associated with a process for depositing an adherent and passivating layers, according to some embodiments.

FIG. 5-15 depicts a structure associated with a process for depositing an adherent centrally within a sample well, according to some embodiments.

FIG. 6-1 depicts a linear resonator, according to some embodiments.

FIG. 6-2 depicts a ring resonator, according to some embodiments.

FIG. 6-3A through FIG. 6-3F depict examples of plasmonic ring resonators, according to some embodiments.

FIG. 6-4 depicts a cavity in a photonic crystal, according to some embodiments.

FIG. 7-1A through FIG. 7-1D depict a pixel waveguide that couples to a bus waveguide, according to some embodiments.

FIG. 7-2A and FIG. 7-2B depict a multiple waveguide layer design, according to some embodiments.

FIG. 8-1A and FIG. 8-1B depict a diffractive optical element to direct excitation light towards multiple sample wells, according to some embodiments.

FIG. 9-1A and FIG. 9-1B depict a surface-plasmon structure, according to just one embodiment.

FIG. 9-1C depicts a surface-plasmon structure formed adjacent a sample well, according to some embodiments.

FIG. 9-1D and FIG. 9-1E depict surface-plasmon structures formed in a sample well, according to some embodiments.

FIG. 9-2A through FIG. 9-2C depict examples of periodic surface-plasmon structures, according to some embodiments.

FIG. 9-2D depicts a numerical simulation of excitation radiation at a sample well-formed adjacent a periodic surface-plasmon structure, according to some embodiments.

FIG. 9-2E through FIG. 9-2G depict periodic surface-plasmon structures, according to some embodiments.

FIG. 9-2H and FIG. 9-2I depict a nano-antenna comprising surface-plasmon structures, according to some embodiments.

FIG. 9-3A through FIG. 9-3E depict structures associated with process steps for forming a surface-plasmon structure, according to some embodiments.

FIG. 9-4A through FIG. 9-4G depict structures associated with process steps for forming a surface-plasmon structure and self-aligned sample well, according to some embodiments.

FIG. 9-5A through FIG. 9-5E depict structures associated with process steps for forming a surface-plasmon structure and self-aligned sample well, according to some embodiments.

FIG. 9-6A depicts a thin lossy film formed adjacent a sample well, according to some embodiments.

FIG. 9-6B and FIG. 9-6C depict results from numerical simulations of excitation radiation in the vicinity of a sample well and thin lossy film, according to some embodiments.

FIG. 9-6D depicts a thin lossy film spaced from a sample well, according to some embodiments.

FIG. 9-6E depicts a thin lossy film stack formed adjacent a sample well, according to some embodiments.

FIG. 9-7A illustrates a reflective stack that may be used to form a resonant cavity adjacent a sample well, according to some embodiments.

FIG. 9-7B depicts a dielectric structure that may be used to concentrate excitation radiation at a sample well, according to some embodiments.

FIG. 9-7C and FIG. 9-7D depict a photonic bandgap structure that may be patterned adjacent a sample well, according to some embodiments.

FIG. 9-8A through FIG. 9-8G depict structures associated with process steps for forming dielectric structures and a self-aligned sample well, according to some embodiments.

FIG. 9-9A and FIG. 9-9B depict structures for coupling excitation energy to a sample via a non-radiative process, according to some embodiments.

FIG. 9-9C depicts a structure for coupling excitation energy to a sample by multiple non-radiative processes, according to some embodiments.

FIG. 9-9D depicts a structure that incorporates one or more energy-converting particles to couple excitation energy to a sample via a radiative or non-radiative process, according to some embodiments.

FIG. 9-9E depicts spectra associated with down conversion of excitation energy to a sample, according to some embodiments.

FIG. 9-9F depicts spectra associated with up conversion of excitation energy to a sample, according to some embodiments.

FIG. 10-1 depicts a concentric circular grating, according to some embodiments.

FIG. 10-2 depicts a spiral grating, according to some embodiments.

FIG. 10-3 through FIG. 10-6 depict emission spatial distribution patterns from a concentric circular grating for various emission wavelengths, according to some embodiments.

FIG. 11-1A through FIG. 11-2B depict nano-antennas, according to some embodiments.

FIG. 11-3 depicts a pattern for a spiral nano-antenna, according to some embodiments.

FIG. 11-4 depicts results from a numerical simulation of electromagnetic field in the vicinity of the spiral, nano-antenna of FIG. 11-3, according to some embodiments.

FIG. 11-5 through FIG. 11-7 illustrate various configurations of nano-antennas, according to some embodiments.

FIG. 11-8 through FIG. 11-11 depicts results from numerical simulations of spatial distribution patterns associated with different wavelengths that emit from a sample well surrounded by a nano-antenna, according to some embodiments.

FIG. 12-1A and FIG. 12-1B depicts far-field spectral sorting optics, according to some embodiments.

FIG. 12-2A and FIG. 12-2B depicts far-field spectral filtering optics, according to some embodiments.

FIG. 13-1A depicts, in elevation view, a sensor 2-260 within a pixel, according to some embodiments.

FIG. 13-1B depicts a bulls-eye sensor having two separate and concentric active areas, according to some embodiments.

FIG. 13-1C depicts a stripe sensor having four separate active areas, according to some embodiments.

FIG. 13-1D depicts a quad sensor having four separate active areas, according to some embodiments.

FIG. 13-1E depicts an arc-segment sensor having four separate active areas, according to some embodiments.

FIG. 13-1F depicts a stacked-segment sensor, according to some embodiments.

FIG. 13-2A depicts an emission distribution from a sample well for radiation emitted at a first wavelength, according to some embodiments.

FIG. 13-2B depicts a radiation pattern received by a bulls-eye sensor corresponding to the emission distribution depicted in FIG. 13-2A, according to some embodiments.

FIG. 13-2C depicts an emission distribution from a sample well for radiation emitted at a second wavelength, according to some embodiments.

FIG. 13-2D depicts a radiation pattern received by a bulls-eye sensor corresponding to the emission distribution depicted in FIG. 13-2C, according to some embodiments.

FIG. 13-2E represents results from a numerical simulation of signal detection for a bulls-eye sensor having two active areas for a first emission wavelength from a sample, according to some embodiments.

FIG. 13-2F represents results from a numerical simulation of signal detection for the bulls-eye sensor associated with FIG. 13-2E for a second emission wavelength from a sample, according to some embodiments.

FIG. 13-2G represents results from a numerical simulation of signal detection for the bulls-eye sensor associated with FIG. 13-2E for a third emission wavelength from a sample, according to some embodiments.

FIG. 13-2H represents results from a numerical simulation of signal detection for the bulls-eye sensor associated with FIG. 13-2E for a fourth emission wavelength from a sample, according to some embodiments.

FIG. 13-2I represents results from a numerical simulation of signal detection for a bulls-eye sensor having four active areas for a first emission wavelength from a sample, according to some embodiments.

FIG. 13-2J represents results from a numerical simulation of signal detection for the bulls-eye sensor associated with FIG. 13-2I for a second emission wavelength from a sample, according to some embodiments.

FIG. 13-3A depicts circuitry on an integrated device that may be used to read signals from a sensor comprising two active areas, according to some embodiments.

FIG. 13-3B depicts a three-transistor circuit that may be included at a sensor segment for signal accumulation and read-out, according to some embodiments.

FIG. 13-3C depicts circuitry on an integrated device that may be used to read signals from a sensor comprising four active areas, according to some embodiments.

FIG. 13-4A depicts temporal emission characteristics for two different emitters that may be used for sample analysis, according to some embodiments.

FIG. 13-4B depicts temporal evolution of an excitation source and luminescence from a sample, according to some embodiments.

FIG. 13-4C illustrates time-delay sampling, according to some embodiments.

FIG. 13-4D depicts temporal emission characteristics for two different emitters, according to some embodiments.

FIG. 13-4E depicts voltage dynamics at a charge-accumulation node of a sensor, according to some embodiments.

FIG. 13-4F depicts a double read of a sensor segment without reset, according to some embodiments.

FIG. 13-4G and FIG. 13-4H illustrate first and second read signal levels associated with two emitters having temporally-distinct emission characteristics, according to some embodiments.

FIG. 14-1 depicts a method of operation of a compact apparatus that may be used for rapid, mobile analysis of biological and chemical specimens, according to some embodiments.

FIG. 14-2 depicts a calibration procedure, according to some embodiments.

FIG. 14-3 depicts a data-analysis procedure, according to some embodiments.

FIG. 15-1 depicts an embodiment of a computing system, according to some embodiments.

Figure 1:
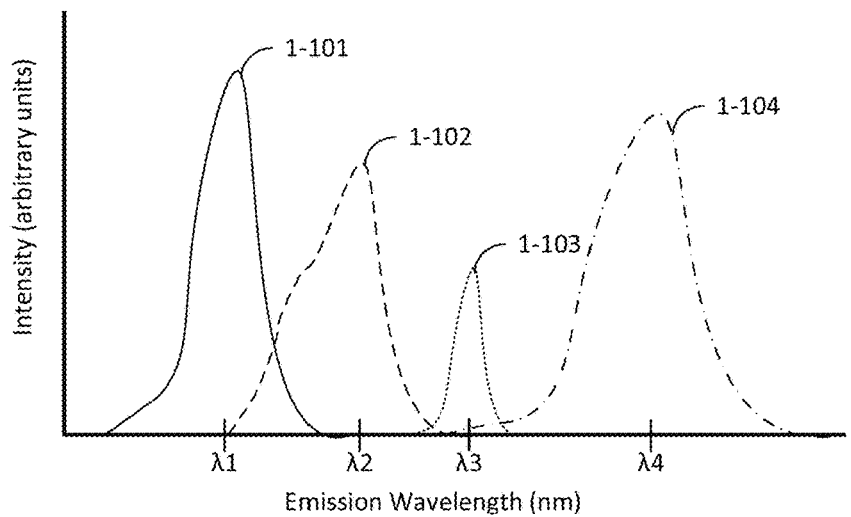
FIG. 1-1 depicts emission wavelength spectra, according to some embodiments.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used.

Such references are intended merely as an aid to the reader viewing the drawings in a normal orientation. These directional references are not intended to describe a preferred or only orientation of an embodied device. A device may be embodied in other orientations.

DETAILED DESCRIPTION

I. Inventor's Recognition of the Problem and Solution Thereto

The inventors have recognized and appreciated that conventional apparatuses for performing bioassays are large, expensive and may require advanced laboratory techniques to perform. Many types of bioassays depend on the detection of single molecules in a specimen. Single molecule detection may require large, bulky laser systems used to generate high intensity light needed for excition of molecules. In addition, bulky optical components may be used to direct the laser light to the specimen and additional optical components may be used to direct luminescent light from the specimen to a sensor. These conventional optical components may require precise alignment and stabilization. The conventional laboratory equipment and training required to use this conventional equipment may result in complex, expensive bioassays.

The inventors have recognized and appreciated that there is a need for a device that can simply and inexpensively analyze biological and/or chemical specimens to determine the identity of its constituent parts. An application of such device may be for sequencing a biomolecule, such as a nucleic acid or a polypeptide (e.g. protein) having a plurality of amino acids. A compact, high-speed apparatus for performing detection and quantitation of single molecules or particles could reduce the cost of performing complex quantitative measurements of biological and/or chemical samples and rapidly advance the rate of biochemical technological discoveries. Moreover, a cost-effective device that is readily transportable could transform not only the way bioassays are performed in the developed world, but provide people in developing regions, for the first time, ready access to essential diagnostic tests that could dramatically improve their health and well-being. For example, in some embodiments, an apparatus for performing bioassays is used to perform diagnostic tests of biological samples, such as blood, urine and/or saliva that may be used by individuals in their home, by a doctor in a remote clinic in developing countries or any other location, such as rural doctors' offices. Such diagnostic tests can include the detection of biomolecules in a biological sample of a subject, such as a nucleic acid molecule or a protein. In some examples, diagnostic tests include sequencing a nucleic acid molecule in a biological sample of a subject, such as sequencing of cell free deoxyribonucleic acid molecules or expression products in a biological sample of the subject.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

A nucleotide generally includes a nucleoside and at least 1, 2, 3, 4, 5, 6, 7, 8, 9, 10, or more phosphate (PO3) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable tags, such as luminescent tags or markers (e.g., fluorophores).

A nucleoside polyphosphate can have 'n' phosphate groups, where 'n' is a number that is greater than or equal to 2, 3, 4, 5, 6, 7, 8, 9, or 10. Examples of nucleoside polyphosphates include nucleoside diphosphate and nucleoside triphosphate. A nucleotide can be a terminal phosphate labeled nucleoside, such as a terminal phosphate labeled nucleoside polyphosphate. Such label can be a luminescent (e.g., fluorescent or chemiluminescent) label, a fluorogenic label, a colored label, a chromogenic label, a mass tag, an electrostatic label, or an electrochemical label. A label (or marker) can be coupled to a terminal phosphate through a linker. The linker can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker can be cleavable so as to separate a label from the terminal phosphate, such as with the aid of a polymerization enzyme. Examples of nucleotides and linkers are provided in U.S. Pat. No. 7,041,812, which is entirely incorporated herein by reference.

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome.

The present disclosure provides devices, systems and methods for detecting biomolecules or subunits thereof, such as nucleic acid molecules. Such detection can include sequencing. A biomolecule may be extracted from a biological sample obtained from a subject. The biological sample may be extracted from a bodily fluid or tissue of the subject, such as breath, saliva, urine or blood (e.g., whole blood or plasma). The subject may be suspected of having a health condition, such as a disease (e.g., cancer). In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified form a bodily fluid or tissue of the subject, and amplified through nucleic acid amplification, such as polymerase chain reaction (PCR). Then, the one or more nucleic acids molecules or subunits thereof can be identified, such as through sequencing.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (i.e., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30 base pairs (bp)) that can be used to identify a larger sequence or region, e.g., that can be aligned to a location on a chromosome or genomic region or gene.

Sequence reads can be used to reconstruct a longer region of a genome of a subject (alignment). Reads can be used to reconstruct chromosomal regions, whole chromosomes, or the whole genome. Sequence reads or a larger sequence generated from such reads can be used to analyze a genome of a subject, such as identify variants or polymorphisms. Examples of variants include, but are not limited to, single nucleotide polymorphisms (SNPs) including tandem SNPs, small-scale multi-base deletions or insertions, also referred to as indels or deletion insertion polymorphisms or DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

Individual subunits of biomolecules may be identified using markers. In some examples, luminescent markers are used to identified individual subunits of biomolecules. Luminescent markers (also referred to herein as "markers") may be exogenous or endogenous markers. Exogenous markers may be external luminescent markers used as a reporter and/or tag for luminescent labeling. Examples of exogenous markers may include, but are not limited to, fluorescent molecules, fluorophores, fluorescent dyes, fluorescent stains, organic dyes, fluorescent proteins, enzymes, species that participate in fluorescence resonance energy transfer (FRET), enzymes, and/or quantum dots. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acid (e.g. DNA, RNA) molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

Although the present disclosure makes reference to luminescent markers, other types of markers may be used with devices, systems and methods provided herein. Such markers may be mass tags or electrostatic tags.

While exogenous markers may be added to a sample, endogenous markers may be already part of the sample. Endogenous markers may include any luminescent marker present that may luminesce or "autofluoresce" in the presence of excitation energy. Autofluorescence of endogenous fluorophores may provide for label-free and noninvasive labeling without requiring the introduction of exogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

While some embodiments may be directed to diagnostic testing by detecting single molecules in a specimen, the inventors have also recognized that some embodiments may use the single molecule detection capabilities to perform nucleic acid (e.g. DNA, RNA) sequencing of one or more nucleic acid segments such as, for example, genes, or polypeptides. Nucleic acid sequencing allows for the determination of the order and position of nucleotides in a target nucleic acid molecule. Nucleic acid sequencing technologies may vary in the methods used to determine the nucleic acid sequence as well as in the rate, read length, and incidence of errors in the sequencing process. For example, some nucleic acid sequencing methods are based on sequencing by synthesis, in which the identity of a nucleotide is determined as the nucleotide is incorporated into a newly synthesized strand of nucleic acid that is complementary to the target nucleic acid molecule. Some sequencing by synthesis methods require the presence of a population of target nucleic acid molecules (e.g, copies of a target nucleic acid) or a step of amplification of the target nucleic acid to achieve a population of target nucleic acids.

During sequencing, a polymerizing enzyme may couple (e.g., attach) to a priming location of a target nucleic acid molecule. The priming location can be a primer that is complementary to the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support, such as a sample well. In some embodiments, a sequencing primer may be immobilized to a solid support and hybridization of the target nucleic acid molecule also immobilizes the target nucleic acid molecule to the solid support. Via the action of an enzyme (e.g., a polymerase) capable of adding or incorporating a nucleotide to the primer, nucleotides can be added to the primer in 5' to 3', template bound fashion. Such incorporation of nucleotides to a primer (e.g., via the action of a polymerase) can generally be referred to as a primer extension reaction. Each nucleotide can be associated with a detectable tag that can be detected and used to determine each nucleotide incorporated into the primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). Moreover, some sequencing by synthesis methods can include the presence of a population of target nucleic acid molecules (e.g, copies of a target nucleic acid) and/or a step of amplification of the target nucleic acid to achieve a population of target nucleic acids.

Embodiments are capable of sequencing single nucleic acid molecules with high accuracy and long read length. In some embodiments, the target nucleic acid molecule used in single molecule sequencing is a single-stranded target nucleic acid (e.g. deoxyribonucleic acid (DNA), DNA derivatives, ribonucleic acid (RNA), RNA derivatives) template that is added or immobilized to a sample well containing at least one additional component of a sequencing reaction (e.g., a polymerase such as, a DNA polymerase, a sequencing primer) immobilized or attached to a solid support such as the bottom of the sample well. The target nucleic acid molecule or the polymerase can be attached to a sample wall, such as at the bottom of the sample well directly or through a linker. The sample well can also contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent tags, such as fluorophores. Each class of dNTPs (e.g. adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a distinct luminescent tag such that detection of light emitted from the tag indicates the identity of the dNTP that was incorporated into the newly synthesized nucleic acid. Emitted light from the luminescent tag can be detected and attributed to its appropriate luminescent tag (and, thus, associated dNTP) via any suitable device and/or method, including such devices and methods for detection described elsewhere herein. The luminescent tag may be conjugated to the dNTP at any position such that the presence of the luminescent tag does not inhibit the incorporation of the dNTP into the newly synthesized nucleic acid strand or the activity of the polymerase. In some embodiments, the luminescent tag is conjugated to the terminal phosphate (the gamma phosphate) of the dNTP.

The single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

The sequencing primer anneals to the single-stranded target nucleic acid template and the polymerase consecutively incorporates the dNTPs (or other deoxyribonucleoside polyphosphate) to the primer via the single-stranded target nucleic acid template. The unique luminescent tag associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light can be attributed to a particular dNTP incorporated. The sequence obtained from the collection of detected luminescent tags can then be used to determine the sequence of the single-stranded target nucleic acid template via sequence complementarity.

While the present disclosure makes reference to dNTPs, devices, systems and methods provided herein may be used with various types of nucleotides, such as ribonucleotides and deoxyribonucleotides (e.g., deoxyribonucleoside polyphophates with at least 4, 5, 6, 7, 8, 9, or 10 phosphate groups). Such ribonucleotides and deoxyribonucleotides can include various types of tags (or markers) and linkers.

Signals emitted upon the incorporation of nucleosides can be stored in memory and processed at a later point in time to determine the sequence of the target nucleic acid template. This may include comparing the signals to a reference signals to determine the identities of the incorporated nucleosides as a function of time. Alternative or in addition to, signal emitted upon the incorporation of nucleoside can be collected and processed in real time (i.e., upon nucleoside incorporation) to determine the sequence of the target nucleic acid template in real time.

Nucleic acid sequencing of a plurality of single-stranded target nucleic acid templates may be completed where multiple sample wells are available, as is the case in devices described elsewhere herein. Each sample well can be provided with a single-stranded target nucleic acid template and a sequencing reaction can be completed in each sample well. Each of the sample wells may be contacted with the appropriate reagents (e.g., dNTPs, sequencing primers, polymerase, co-factors, appropriate buffers, etc.) necessary for nucleic acid synthesis during a primer extension reaction and the sequencing reaction can proceed in each sample well. In some embodiments, the multiple sample wells are contacted with all appropriate dNTPs simultaneously. In other embodiments, the multiple sample wells are contacted with each appropriate dNTP separately and each washed in between contact with different dNTPs. Incorporated dNTPs can be detected in each sample well and a sequence determined for the single-stranded target nucleic acid in each sample well as is described above.

Embodiments directed towards single molecule nucleic acid sequencing may use any polymerase that is capable of synthesizing a nucleic acid complementary to a target nucleic acid. Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase φ29 (psi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity and variants, modified products and derivatives thereof. In some embodiments, the polymerase is a single subunit polymerase. In some embodiments, the polymerase is a polymerase with high processivity. Polymerase processivity generally refers to the capability of a polymerase to consecutively incorporate dNTPs into a nucleic acid template without releasing the nucleic acid template. Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the luminescent tag conjugated to the dNTP is a fluorophore, its presence is signaled by excitation and a pulse of emission is detected during the step of incorporation. For detection labels that are conjugated to the terminal (gamma) phosphate of the dNTP, incorporation of the dNTP into the newly synthesized strand results in release of the beta and gamma phosphates and the detection label, which is free to diffuse in the sample well, resulting in a decrease in emission detected from the fluorophore.

Embodiments directed toward single molecule RNA sequencing may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined as described above. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

Having recognized the need for simple, less complex apparatuses for performing single molecule detection and/or nucleic acid sequencing, the inventors have conceived of a technique for detecting single molecules using sets of tags, such as optical (e.g., luminescent) tags, to label different molecules. Such single molecules may be nucleotides or amino acids having tags. Tags may be detected while bound to single molecules, upon release from the single molecules, or while bound to and upon release from the single molecules. In some examples, tags are luminescent tags. Each luminescent tag in a selected set is associated with a respective molecule. For example, a set of four tags may be used to "label" the nucleobases present in DNA—each tag of the set being associated with a different nucleobase, e.g., a first tag being associated with adenine (A), a second tag being associated with cytosine (C), a third tag being associated with guanine (G), and a fourth tag being associated with thymine (T). Moreover, each of the luminescent tags in the set of tags has different properties that may be used to distinguish a first tag of the set from the other tags in the set. In this way, each tag is uniquely identifiable using one or more of these distinguishing characteristics. By way of example and not limitation, the characteristics of the tags that may be used to distinguish one tag from another may include the emission energy and/or wavelength of the light that is emitted by the tag in response to excitation and/or the wavelength and/or energy of the excitation light that excites a particular tag.

Embodiments may use any suitable combination of tag characteristics to distinguish a first tag in a set of tags from the other tags in the same set. For example, some embodiments may use only the wavelength of the emission light from the tags to identify the tags. In such embodiments, each tag in a selected set of tags has a different peak emission wavelength from the other tags in the set and the luminescent tags are all excited by light from a single excitation source. FIG. 1-1 illustrates the emission spectra from four luminescent tags according to an embodiment where the four tags exhibit their respective intensity peak at different emission wavelengths, referred to herein as the tag's "peak emission wavelength." A first emission spectrum 1-101 from a first luminescent tag has a peak emission wavelength at $\lambda 1$, a second emission spectrum 1-102 from a second luminescent tag has a peak emission wavelength at $\lambda 2$, a third emission spectrum 1-103 from a third luminescent tag has a peak emission wavelength at $\lambda 3$, and a fourth emission spectrum 1-104 from a fourth luminescent tag has a peak emission wavelength at $\lambda 4$. In this embodiment, the emission peaks of the four luminescent tags may have any suitable values that satisfy the relation $\lambda 1 < \lambda 2 < \lambda 3 < \lambda 4$. The four emission spectra may or may not overlap. However, if the emission spectra of two or more tags overlap, it is desirable to select a luminescent tag set such that one tag emits substantially more light than any other tag at each respective peak wavelength. In this embodiment, the excitation wavelength at which each of the four tags maximally absorbs light from the excitation source is substantially equal, but that need not be the case. Using the above tag set, four different molecules may be labeled with a respective tag from the tag set, the tags may be excited using a single excitation source, and the tags can be distinguished from one another by detecting the emission wavelength of the tags using an optical system and sensors. While FIG. 1-1 illustrates four different tags, it should be appreciated that any suitable number of tags may be used.

Figures 1, 2, 2A:
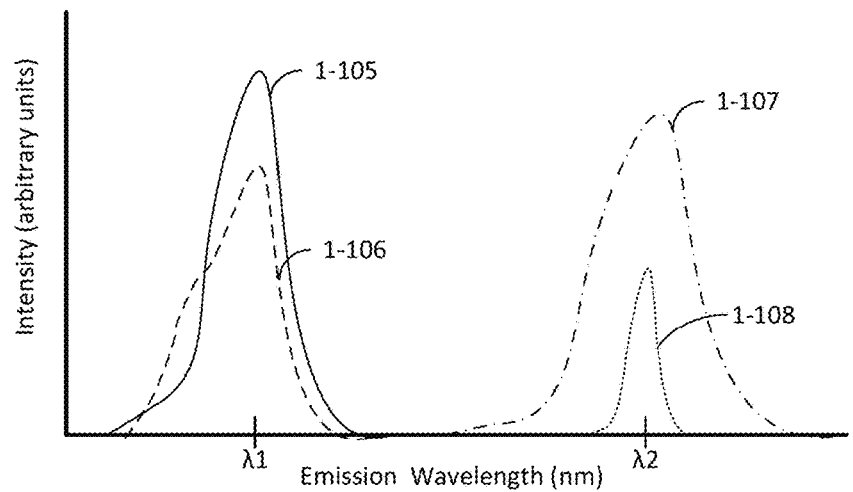
Figures 1, 2, 2B:
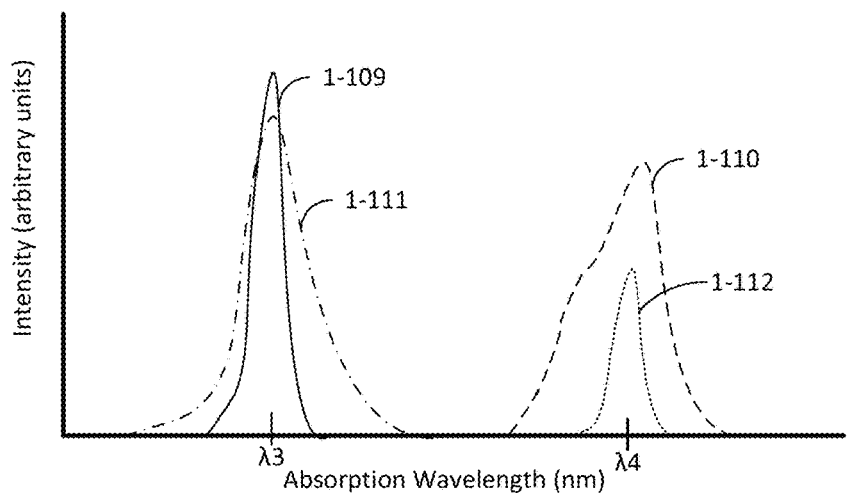

Other embodiments may use both the wavelength of the emission light from the tags and the wavelength at which the tags absorb excitation light to identify the tags. In such embodiments, each tag in a selected set of tags has a different combination of emission wavelength and excitation wavelength from the other tags in the set. Thus, some tags within a selected tag set may have the same emission wavelength, but be excited by light of different wavelengths. Conversely, some tags within a selected tag set may have the same excitation wavelength, but emit light at different wavelengths. FIG. 1-2a illustrates the emission spectra from four luminescent tags according to an embodiment where two of the tags have a first peak emission wavelength and the other two tags have a second peak emission wavelength. A first emission spectrum 1-105 from a first luminescent tag has a peak emission wavelength at $\lambda 1$, a second emission spectrum 1-106 from a second luminescent tag also has a peak emission wavelength at $\lambda 1$, a third emission spectrum 1-107 from a third luminescent tag has a peak emission wavelength at $\lambda 2$, and a fourth emission spectrum 1-108 from a fourth luminescent tag also has a peak emission wavelength at $\lambda 2$. In this embodiment, the emission peaks of the four luminescent tags may have any suitable values that satisfy the relation $\lambda 1 < \lambda 2$. FIG. 1-2b illustrates the absorption spectra from the four luminescent tags, where two of the tags have a first peak absorption wavelength and the other two tags have a second peak absorption wavelength. A first absorption spectrum 1-109 for the first luminescent tag has a peak absorption wavelength at $\lambda 3$, a second absorption spectrum 1-110 for the second luminescent tag has a peak absorption wavelength at $\lambda 4$, a third absorption spectrum 1-111 for the third luminescent tag has a peak absorption wavelength at $\lambda 3$, and a fourth absorption spectrum 1-112 for the fourth luminescent tag has a peak absorption wavelength at $\lambda 4$. Note that the tags that share an emission peak wavelength in FIG. 1-2a do not share an absorption peak wavelength in FIG. 1-2b. Using such a tag set allows distinguishing between four tags even when there are only two emission wavelengths for the four dyes. This is possible using two excitation sources that emit at different wavelengths or a single excitation source capable of emitting at multiple wavelengths. If the wavelength of the excitation light is known for each detected emission event, then it can be determined which tag was present. The excitation source(s) may alternate between a first excitation wavelength and a second excitation wavelength, which is referred to as interleaving. Alternatively, two or more pulses of the first excitation wavelength may be used followed by two or more pulses of the second excitation wavelength.

While not illustrated in the figures, other embodiments may determine the identity of a luminescent tag based on the absorption frequency alone. Such embodiments are possible if the excitation light can be tuned to specific wavelengths that match the absorption spectrum of the tags in a tag set. In such embodiments, the optical system and sensor used to direct and detect the light emitted from each tag does not need to be capable of detecting the wavelength of the emitted light. This may be advantageous in some embodiments because it reduces the complexity of the optical system and sensors because detecting the emission wavelength is not required in such embodiments.

As discussed above, the inventors have recognized and appreciated the need for being able to distinguish different luminescent tags from one another using various characteristics of the tags. The type of characteristics used to determine the identity of a tag impacts the physical device used to perform this analysis. The present application discloses several embodiments of an apparatus, device, instrument and methods for performing these different experiments.

Briefly, the inventors have recognized and appreciated that a pixelated sensor device with a relatively large number of pixels (e.g., hundreds, thousands, millions or more) that allows for the detection of a plurality of individual molecules or particles in parallel. At least some, a subset or all of the pixels can be independently addressable. The molecules may be, by way of example and not limitation, proteins and/or nucleic acids (e.g. DNA, RNA). Moreover, a high-speed device that can acquire data at more than one hundred frames per second allows for the detection and analysis of dynamic processes or changes that occur over time within the sample being analyzed.

The inventors have recognized and appreciated that a low-cost, single-use disposable integrated device that includes optics and sensors may be used in connection with an instrument that includes an excitation source to measure luminescent light emitted from biological samples. Using a low-cost integrated device reduces the cost of performing a given bioassay. A biological sample is placed onto the integrated device and, upon completion of the bioassay, may be discarded. The integrated device interfaces with the more expensive, multi-use instrument, which may be used repeatedly with many different disposable integrated devices. A low-cost integrated device that interfaces with a compact, portable instrument may be used anywhere in the world, without the constraint of high-cost biological laboratories requiring laboratory expertise to analyze samples. Thus, automated bioanalytics may be brought to regions of the world that previously could not perform quantitative analysis of biological samples. For example, blood tests for infants may be performed by placing a blood sample on a disposable integrated device, placing the disposable integrated device into the small, portable instrument for analysis, and processing the results by a computer that connects to the instrument for immediate review by a user. The data may also be transmitted over a data network to a remote location to be analyzed, and/or archived for subsequent clinical analyses. Alternatively, the instrument may include one or more processors for analyzing the data obtained from the sensors of the integrated device.

Various embodiments are described in more detail below.

II. Overview of the System

The system includes an integrated device and an instrument configured to interface with the integrated device. The integrated device includes an array of pixels, where each pixel includes a sample well and at least one sensor. A surface of the integrated device has a plurality of sample wells which are openings configured to receive a sample from within a specimen placed on the surface of the integrated device. Multiple samples may be included in a specimen and the sample well may be designed to receive one sample such that each sample well contains a different sample. For example, a specimen containing many single-stranded DNA templates is placed on a surface of the integrated device and each sample well may receive a single-stranded DNA template. The specimen may also contain tagged dNTPs which then enter in the sample well for identifying a nucleotide as it is incorporated into a complementary strand of DNA. In such an example, the "sample" may refer to both the single-stranded DNA and the tagged dNTP currently being incorporated by a polymerase.

Excitation energy is provided from a source located away from the pixels of the integrated device. The excitation energy is directed at least in part by elements of the integrated device towards one or more pixels to illuminate an illumination region within the sample well. A marker or tag may then emit emission energy when located within the illumination region and in response to being illuminated by excitation energy. In some embodiments, one or more excitation sources are part of the instrument of the system where components of the instrument and the integrated device are configured to direct the excitation energy towards one or more pixels. In other embodiments, one or more excitation sources are located on the integrated device but are located in a separate region from the array of pixels, and components in the integrated device are configured to direct excitation energy from the excitation source region to one or more pixels.

Emission energy emitted by a sample may then be detected by one or more sensor within a pixel of the integrated device. In some embodiments, a plurality of sensors may be sized and arranged to capture a spatial distribution of the emission energy. Output signals from the one or more sensors may then be used to distinguish a marker from among a plurality of markers, where the plurality of markers may be used identify a sample within the specimen.

Figures 1A, 2:
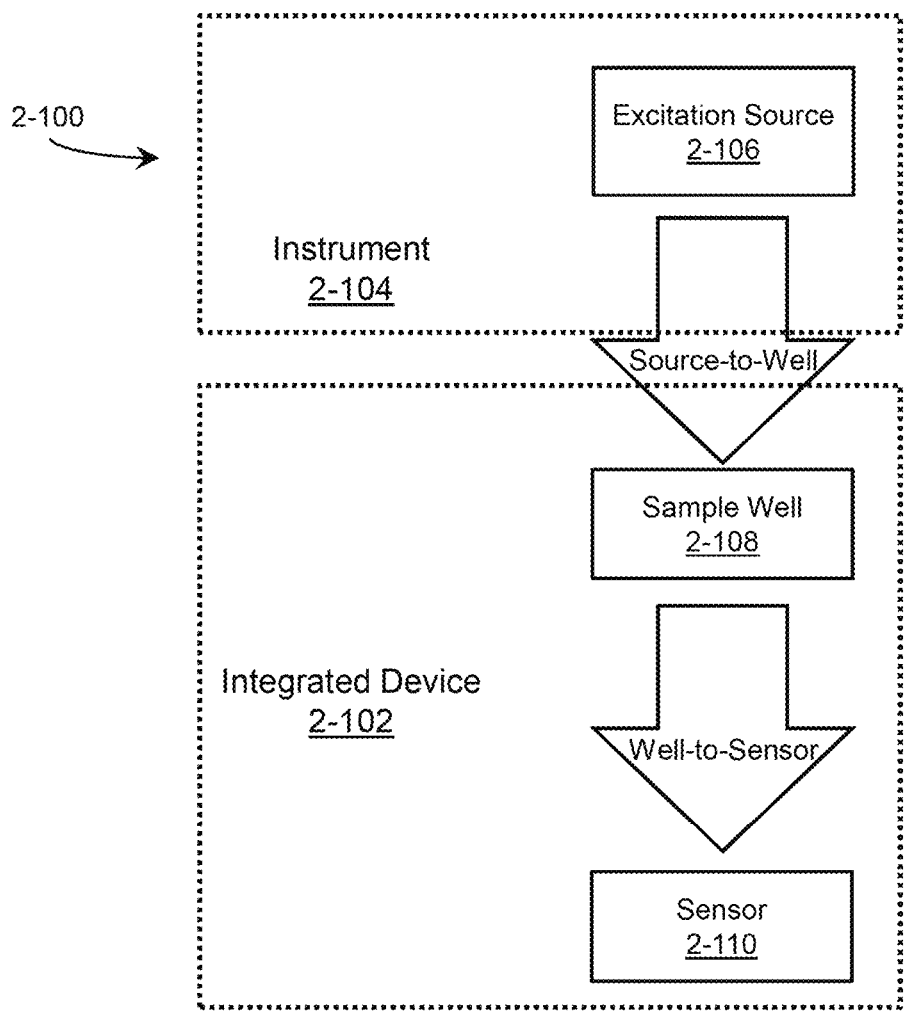
Figures 1B, 2:
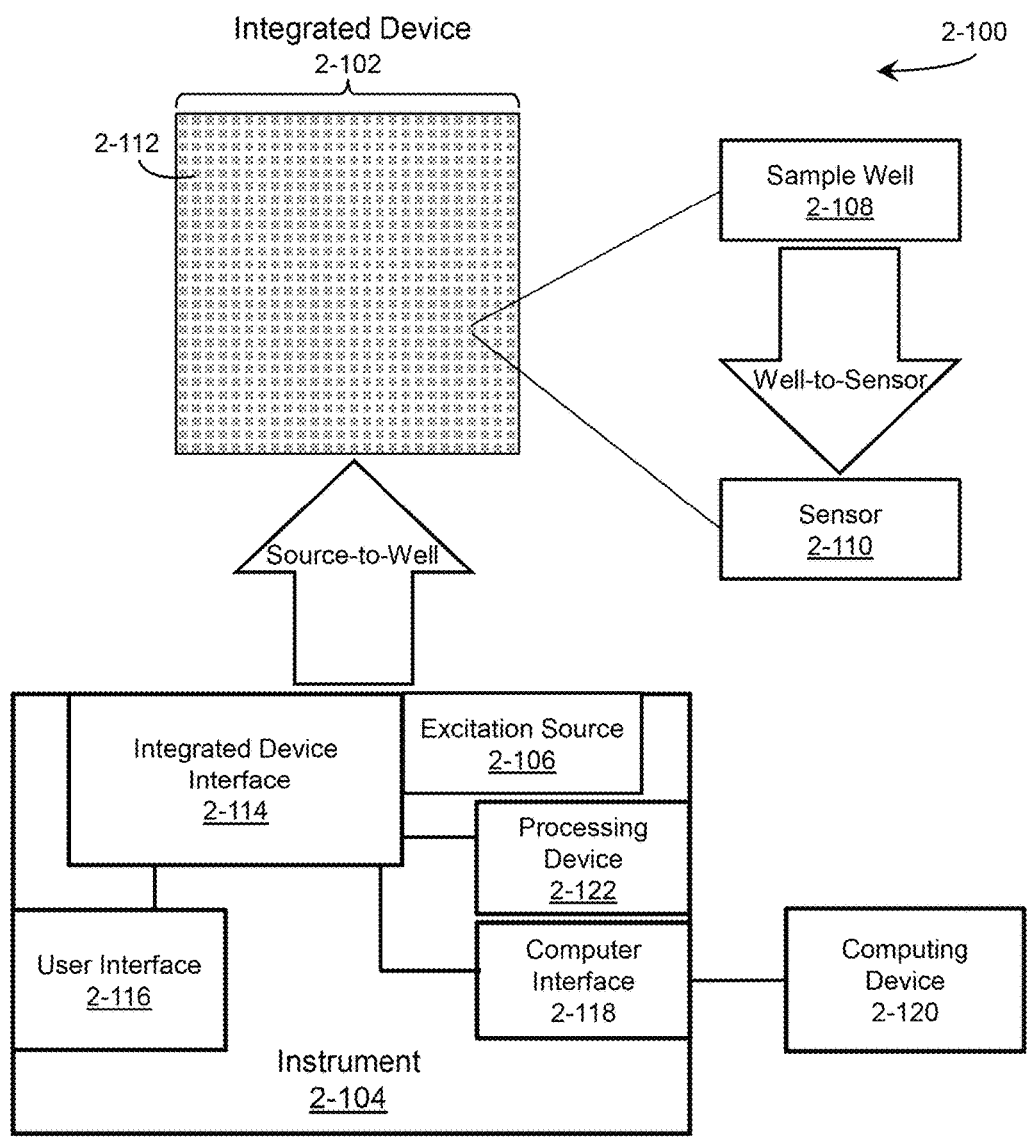
Figure 2:
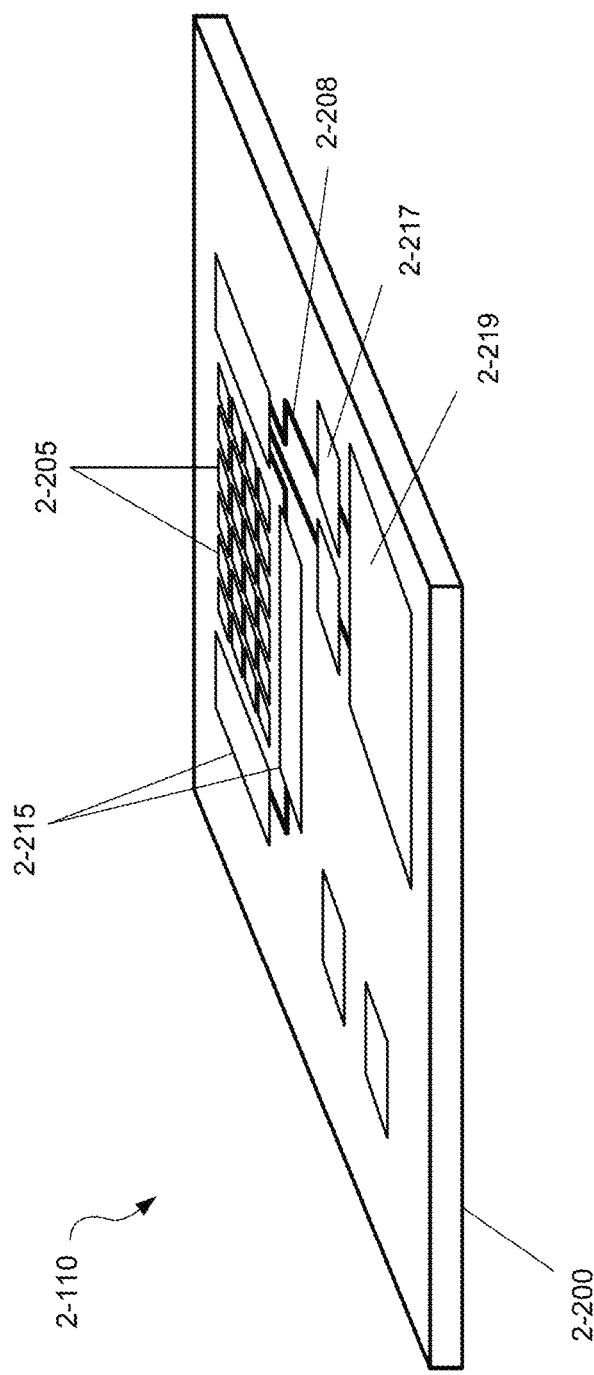

A schematic overview of the system 2-100 is illustrated in FIGS. 2-1A and 2-1B. The system comprises both an integrated device 2-102 that interfaces with an instrument 2-104 having an excitation source 2-106. The integrated device interfaces with the instrument using any suitable socket for receiving the integrated device and holding it in precise optical alignment with the excitation source. The external excitation source 2-106 in the instrument 2-104 is configured to provide excitation energy to the integrated device 2-102. Although the excitation source is shown to be located on the instrument, the excitation source may be located on the integrated device in a region separate from the pixels in some instances. As illustrated schematically in FIG. 2-1B, the integrated device 2-102 has multiple pixels, where each pixel 2-112 is capable of independent analysis of a sample. Such pixels may be referred to as "passive source pixels" since a pixel receives excitation energy from a source separate from the pixel, where the source excites a plurality of pixels. Each pixel 2-112 has a sample well 2-108 for retaining and analyzing a sample and a sensor 2-110 for detecting emission energy emitted by the sample in response to illuminating the sample with excitation energy provided by the excitation source 2-106. In some embodiments, each sensor may include multiple sub-sensors, each sub-sensor configured to detect a different wavelength of emission energy from the sample.

Optical elements for guiding and coupling excitation energy to the sample well 2-108 are located both on the integrated device 2-102 and the instrument 2-104. Such source-to-well elements may include a grating coupler located on the integrated device to couple excitation energy to the integrated device, waveguides to deliver excitation energy to each pixel, and lenses, plasmonic elements and dielectric coatings on the integrated device to direct excitation energy received from the instrument to the sample well. Additionally, optical elements located on the integrated device direct emission energy from the sample well towards the sensor. Such well-to-sample elements may include components that direct the emission energy into a radiation pattern where the radiation pattern depends on the emission energy emitted by a sample in a sample well. The sample well, a portion of the excitation source-to-well optics, and the sample well-to-sensor optics are located on the integrated device. The excitation source and a portion of the source-to-well components are located in the instrument 2-104 containing an excitation source 2-106. In some embodiments, a single component may play a role in both coupling excitation energy to a sample well and delivering emission energy from the sample well to the sensor.

As illustrated in FIG. 2-1B, the integrated device comprises a plurality of pixels, each pixel 2-112 associated with its own individual sample well 2-108 and sensor 2-110. The plurality of pixels may be arranged in an array, and there may be any suitable number of pixels. For example, the integrated device may include between 100 and 1,000 pixels according to some embodiments, between 1,000 and 10,000 pixels according to some embodiments, between 10,000 and 100,000 pixels according to some embodiments, between 100,000 and 1,000,000 pixels according to some embodiments, and yet between 1,000,000 and 10,000,000 pixels according to some embodiments. In some implementations, there may be fewer or more pixels on an integrated device. The integrated device 2-112 and instrument 2-104 may include multi-channel, high-speed communication links for handling data associated with large pixel arrays (e.g., more than 1000 pixels).

The instrument interfaces with the integrated device through an integrated device interface 2-114. The integrated device interface 2-114 may include components to position and/or align the integrated device to the instrument to improve coupling of excitation energy from the excitation source to the integrated device. In some embodiments, excitation source 2-106 includes multiple excitation sources that are combined to deliver excitation energy to the integrated device 2-112. The multiple excitation sources may be configured to produce multiple excitation energies or wavelengths. The integrated device interface 2-114 may receive readout signals from the sensors in the pixels located on the integrated device. Additionally, the integrated device interface 2-114 may be designed such that the integrated device attaches to the instrument by securing the integrated device to the integrated device interface 2-114.

The instrument 2-104 includes a user interface 2-116 for controlling the operation of the instrument. The user interface 2-116 is configured to allow a user to input information into the instrument, such as commands and/or settings used to control the functioning of the instrument. In some embodiments, the user interface 2-116 may include buttons, switches, dials, and a microphone for voice commands. Additionally, the user interface 2-116 may allow a user to receive feedback on the performance of the instrument and/or integrated device, such as proper alignment and/or information obtained by readout signals from the sensors on the integrated device. In some embodiments, the user interface 2-116 may provide feedback using a speaker to provide audible feedback, and indicator lights and/or display screen for providing visual feedback. In some embodiments, the instrument 2-104 includes a computer interface 2-118 used to connect with a computing device 2-120. Any suitable computer interface 2-118 and computing device 2-120 may be used. For example, the computer interface 2-118 may be a USB interface or a FireWire interface. The computing device 2-120 may be any general purpose computer, such as a laptop or desktop computer. The computer interface 2-118 facilitates communication of information between the instrument 2-104 and the computing device 2-120. Input information for controlling and/or configuring the instrument 2-104 may be provided through the computing device 2-120 connected to the computer interface 2-118 of the instrument. Additionally, output information may be received by the computing device 2-120 through the computer interface 2-118. Such output information may include feedback about performance of the instrument 2-104 and/or or integrated device 2-112 and information from the readout signals of the sensor 2-110. The instrument 2-104 may also include a processing device 2-122 for analyzing data received from the sensor 2-110 and/or sending control signals to the excitation source 2-106. In some embodiments, the processing device 2-122 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 2-110 may be performed by both the processing device 2-122 and the external computing device 2-120. In other embodiments, the computing device 2-120 may be omitted and processing of data from the sensor 2-110 may be performed solely by processing device 2-122.

Figures 1A, 3:
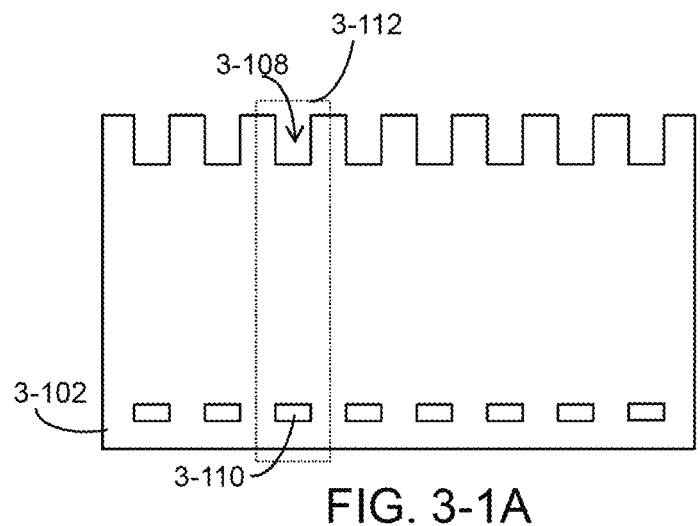
Figures 1B, 3:
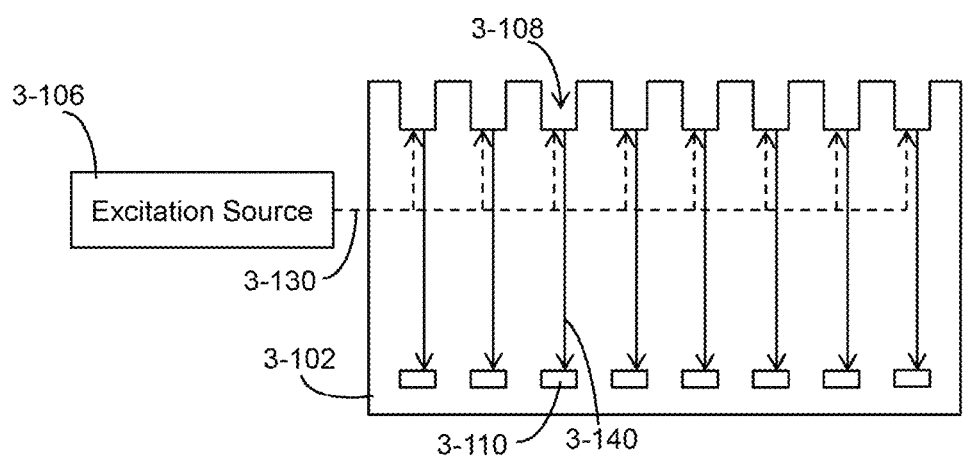

A cross-sectional schematic of the integrated device 3-102 illustrating a row of pixels is shown in FIG. 3-1A. Each pixel 3-112 includes a sample well 3-108 and a sensor 3-110. The sensor 3-110 may be aligned and positioned to the sample well 3-112. When an excitation source is coupled to the integrated device, excitation energy is provided to one or more pixels. FIG. 3-1B is a schematic illustrating coupling an excitation source 3-106 to integrated device 3-102. Excitation source 3-106 provides excitation energy 3-130 (shown in dotted lines) in the integrated device 3-102. FIG. 3-1B illustrates the path of excitation emicnergy from excitation energy source 3-106 to a sample well 3-108 in pixel 3-112. Components located off of the integrated device may be used to position and align the excitation source 3-106 to the integrated device. Such components may include optical components including lenses, minors, prisms, apertures, attenuators, and/or optical fibers. Additional mechanical components may be included in the instrument configured to allow control of one or more alignment components. Such mechanical components may include actuators, stepper motors, and/or knobs. The integrated device includes components that direct the excitation energy 3-130 towards pixels in the integrated device. Within each pixel 3-112, excitation energy is coupled to the sample well 3-108 associated with a pixel. Although FIG. 3-1B illustrates excitation energy coupling to each sample well in a row of pixels, in some embodiments, excitation energy may not couple to all of the pixels in a row. In some embodiments, excitation energy may couple to a portion of pixels or sample wells in a row of pixels of the integrated device. Excitation energy may illuminate a sample located within a sample well. The sample may reach an excited state in response to being illuminated by the excitation energy. When a sample is in an excited state, the sample may emit emission energy and the emission energy may be detected by a sensor. FIG. 3-1B schematically illustrates the path of emission energy 3-140 (shown as solid lines) from the sample well 3-108 to the sensor 3-110 of a pixel 3-112. The sensor 3-110 in a pixel 3-112 may be configured and positioned to detect emission energy from sample well 3-108. In some embodiments, the sensor 3-110 may include one or more sub-sensors.

When a specimen containing multiple samples is labeled with multiple markers and the multiple markers are identifiable by the emission energy, the path in a pixel between the sample well and the sensor may include one or more components that aid in identifying the multiple markers based on emission energy. Components may focus emission energy towards the sensor and may additionally or alternatively spatially separate emission energies that have characteristic energies or wavelengths. In some embodiments, the integrated device may include components that direct emission energy into a radiation pattern that is dependent on the spectral range of the emission energy. The sensor or sensor region containing multiple sub-sensors may detect a spatial distribution of the emission energy that depends on the radiation pattern. Markers that emit different emission energies and/or spectral ranges may form different radiation patterns. The sensor or sensor region may detect information about the spatial distribution of the emission energy that can be used to identify a marker among the multiple markers.

The emission energy or energies may be detected by the sensor and converted to at least one electrical signal. The electrical signals may be transmitted along conducting lines in the circuitry of the integrated device connected to the instrument through the integrated device interface, such as integrated device interface 2-114 of instrument 2-104 shown in FIG. 2-1B. The electrical signals may be subsequently processed and/or analyzed. Processing or analyzing of electrical signals may occur on a suitable computing device either located on the instrument 2-104 or off instrument, such as computing device 2-120 shown in FIG. 2-1B.

An integrated device may appear as depicted in FIG. 2-2. Electronic, optical, and related structures may all be incorporated onto a single substrate 2-200. The integrated device may include an array of active-source pixels 2-205 and integrated electronic circuitry. The integrated electronic circuitry may include drive and read-out circuitry 2-215 coupled to the sensors of the pixel array, and signal processing circuitry. The signal processing circuitry may include analog-to-digital converters 2-217 and one or more field-programmable gate arrays and/or digital signal processors 2-219. Some embodiments may have more circuit components, and some embodiments may have fewer circuit components integrated on the substrate. Although the components of the integrated device are depicted on a single level in FIG. 2-2, the components may be fabricated on multiple levels on the substrate 2-200.

In some embodiments, there may be optical elements (not shown) located on the integrated device that are arranged for guiding and coupling excitation energy from one or more excitation sources to the sample wells. Such source-to-well elements may include plasmonic structures and other microfabricated structures located adjacent the sample wells. Additionally, in some embodiments, there may be optical elements located on the integrated device that are configured for guiding emission energy from the sample wells to corresponding sensors. Such well-to-sample elements may include may include plasmonic structures and other microfabricated structures located adjacent the sample wells. In some embodiments, a single component may play a role in both in coupling excitation energy to a sample well and delivering emission energy from the sample well to a corresponding sensor.

In some implementations, an integrated device may include more than one type of excitation source that is used to excite samples at a sample well. For example, there may be multiple excitation sources configured to produce multiple excitation energies or wavelengths for exciting a sample. In some embodiments, a single excitation source may be configured to emit multiple wavelengths that are used to excite samples in the sample wells. In some embodiments, each sensor at a pixel of the integrated device may include multiple sub-sensors configured to detect different emission energy characteristics from the sample.

In operation, parallel analyses of samples within the sample wells are carried out by exciting the samples within the wells using the excitation source and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

When an excitation source delivers excitation energy to a sample well, at least one sample within the well may luminesce, and the resulting emission may be detected by a sensor. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

In some embodiments, samples may be labeled with one or more tags, and emission associated with the tags is discernable by the instrument. For example, components of the integrated device may affect the emission from a sample well to produce a spatial emission distribution pattern that is dependent on the emission wavelength. A corresponding sensor for the sample well may be configured to detect the spatial distribution patterns from a sample well and produce signals that differentiate between the different emission wavelengths, as described in further detail below.

III. Integrated Device

The integrated device may be configured to receive excitation energy from an external excitation energy source. In some embodiments, a region of the device may be used to couple to an excitation energy source located off the integrated device. Components of the integrated device may guide excitation energy from the excitation source coupling region to at least one pixel. In some embodiments, at least one waveguide may be configured to deliver excitation energy to at least one pixel having a sample well. A sample located within the sample well may emit emission energy in response to being illuminated with excitation energy. One or more sensors located within the pixel are configured to receive the emission energy.

A. Excitation Source Coupling Region

In some embodiments, the integrated device has an excitation source coupling region configured to couple with an external excitation energy source and guide excitation towards at least one pixel in a pixel area of the integrated device. Any suitable mechanism for coupling excitation energy into a waveguide may be used. Excitation energy from an external excitation source may be coupled to a waveguide through edge-coupling. As an example illustrated in FIG. 4-1A, an optical fiber 4-106, configured to propagate excitation energy, is positioned to couple with a waveguide 4-104 on integrated device 4-102. Alignment of the optical fiber 4-106 to the waveguide 4-104 may be monitored in order to achieve coupling of excitation energy provided by the optical fiber to the waveguide.

Additionally or alternatively, the excitation source coupling region may include structural components configured to couple with an external excitation source. Such structural components may include a grating coupler and a waveguide with a tapered region. In such embodiments, the excitation source may be positioned to couple excitation energy via the grating coupler to the tapered waveguide. Features of the grating coupler, such as the size, shape, and/or grating configurations may be formed to improve coupling of the excitation energy from the excitation source to the waveguide. Additionally, the taper in the waveguide may be formed to improve propagation of excitation energy into the waveguide. Such a combination of grating coupler and waveguide taper may allow for more tolerance in the alignment and positioning of the excitation source to the integrated device. As an example illustrated in FIG. 4-1B, integrated device 4-112 may include a grating coupler 4-116 and a waveguide having a taper 4-114 located in an excitation source coupling region. The optical fiber 4-120 may be positioned and aligned to the grating coupler 4-116 in order to couple excitation energy to the waveguide.

Figures 1A, 4:
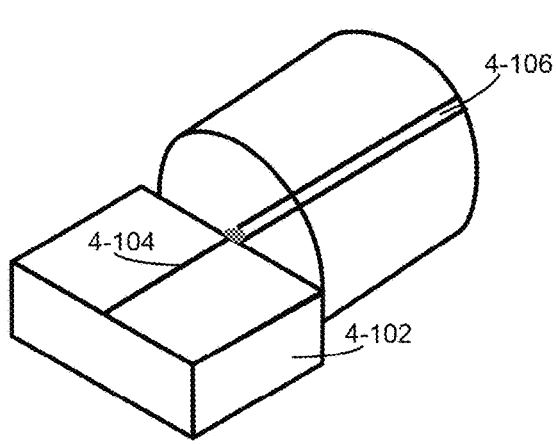
Figures 1B, 4:
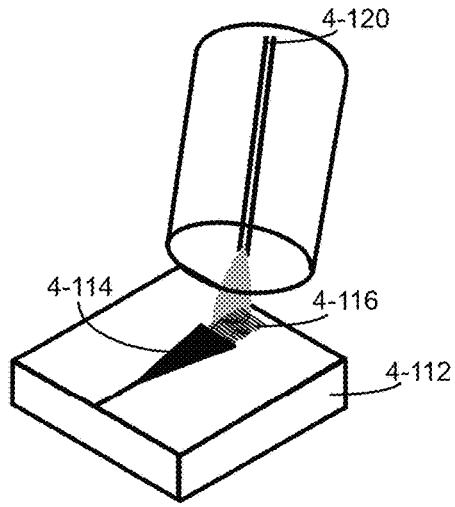
Figures 2, 4:
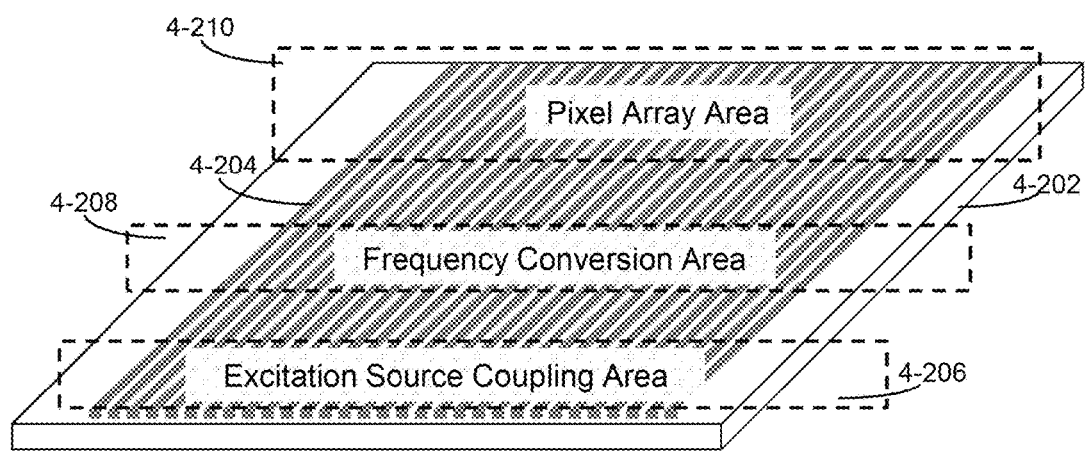

An excitation source may be formed on an excitation source coupling region of the integrated device. The excitation source coupling region may be separate and/or laterally displaced from the pixels of the integrated device in a pixel array area. The pixel array area comprises a plurality of pixels, each pixel being associated with at least one waveguide from which it will receive excitation light. Waveguides in the integrated device may couple with the excitation source and be configured to deliver excitation energy to at least one sample well in the pixel array. Optionally, the waveguides may include a frequency conversion area for performing second harmonic generation, third harmonic generation, or sum frequency generation to convert the wavelength of the light emitted from the excitation source. As illustrated in FIG. 4-2, integrated device 4-202 includes an excitation source coupling area 4-206 and a pixel array area 4-210. A plurality of pixels is located within the pixel array area of the integrated device. Waveguides 4-204 are formed to connect the excitation source coupling area 4-206 to the pixel array area 4-210. An excitation source positioned on the excitation source coupling area may couple excitation energy to at least one waveguide which is positioned to deliver excitation energy into one or more sample wells located in the pixel array area. In some embodiments, a frequency conversion area 4-208 may be located between the excitation source coupling area 4-206 and the pixel array area 4-210. The frequency conversion area 4-208 may convert the wavelength of the light emitted by the excitation source to another wavelength.

Figures 3A, 4:
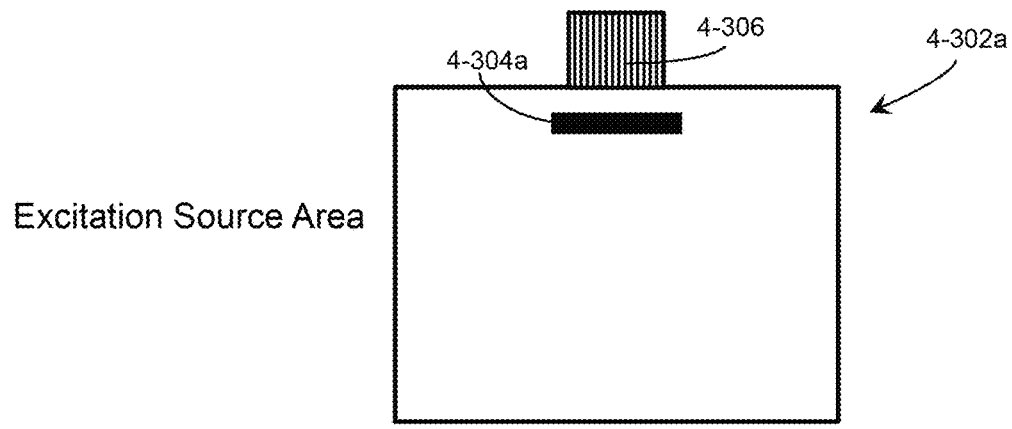

FIG. 4-3A is an example of a cross-sectional schematic of the excitation source area of an integrated device 4-302a. In this example, an excitation source 4-306 is positioned over a portion of a waveguide 4-304a in the integrated device 4-302a. The relative positioning and alignment of the excitation source 4-306 to the waveguide 4-304a allows for coupling of excitation energy emitted by the excitation source to the waveguide. The waveguide may be configured to guide excitation energy towards at least one pixel on the integrated device. Although, FIG. 4-3a illustrates a single excitation source coupling to a single waveguide, any suitable number and arrangement of excitation sources and/or waveguides may be provided in the excitation source coupling area. For example, one excitation source may couple to a plurality of waveguides. Additionally or alternatively, a plurality of excitation sources may couple to one or more waveguides. A plurality of excitation sources may be used to excite one or more markers or samples.

Figures 3B, 4:
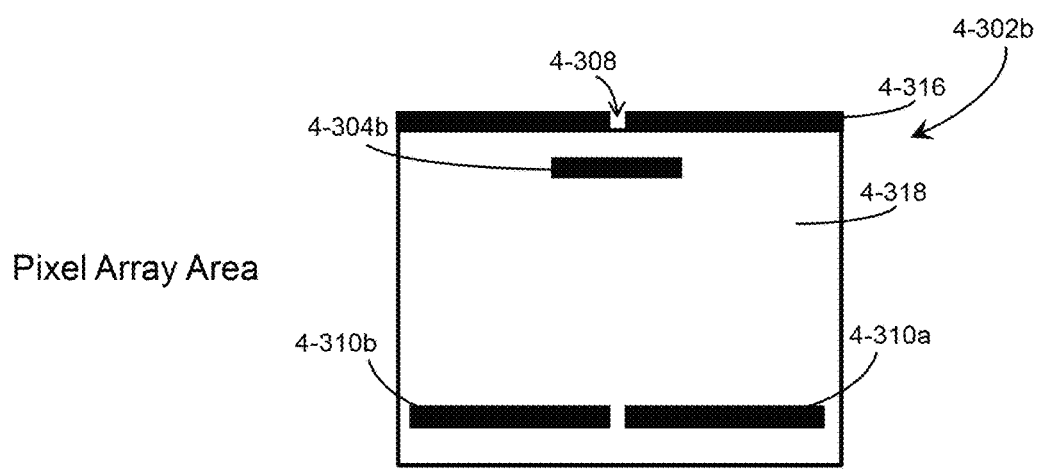
Figure 4:
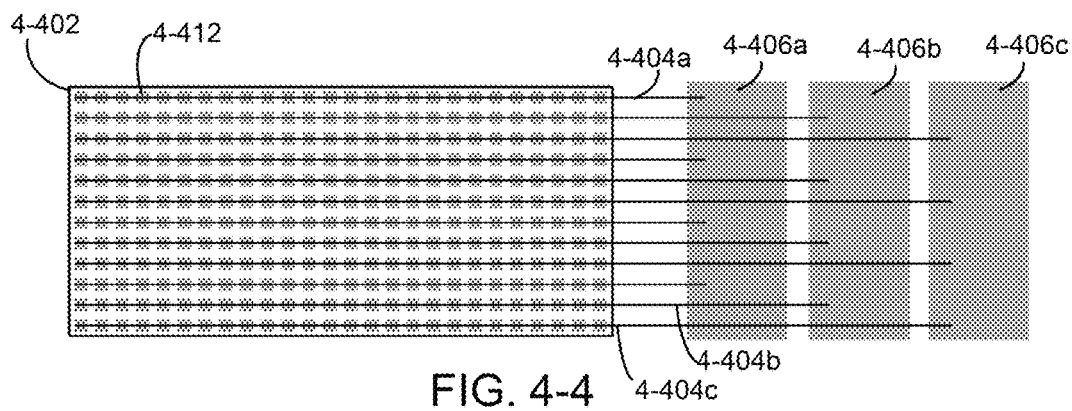

FIG. 4-3B illustrates an exemplary cross-sectional view of a pixel region in a pixel array area of an integrated device 4-302b. The pixel shown in FIG. 4-3B includes a sample well 4-308 formed in a sample well material layer 4-316 and sensors 4-310a and 4-310b. A waveguide 4-304b is positioned in proximity to the sample well 4-308 to couple excitation energy provided by an excitation source located in the excitation source coupling area to the sample well 4-308. Sensors 4-310b and 4-310a are positioned within the pixel region aligned to the sample well 4-308 to receive emission energy emitted by a sample located in the sample well 4-308. Although two sensors are shown in this example, as will be further discussed, any suitable number and arrangement of sensors may be positioned within a pixel region. Additionally or alternatively, there may be more than one waveguide configured to deliver excitation energy to a sample well within a pixel.

As an example, vertical-cavity surface-emitting lasers (VCSELs), as the excitation source, may be formed on the excitation source coupling area. The excitation source area includes a plurality of VCSELs positioned above a corresponding waveguide. The VCSELs emit excitation light, which is then coupled to a waveguide and the waveguide directs the excitation light towards the pixel array area, where each waveguide couples a portion of the excitation light to each pixel associated with the waveguide. The waveguide is positioned to direct the excitation light towards at least one sample well. In some embodiments, a row or a column of pixels is associated with a single waveguide. In some instances, a frequency conversion area may create light of a different wavelength than the light emitted from the VCSELs. For example, the frequency conversion area may convert light emitted by the VCSELs to light of a shorter wavelength. In other embodiments, the frequency conversion area may convert light emitted from the VCSELs to light having a longer wavelength A plurality of excitation sources may be used to provide excitation energy to pixels located on an integrated device. In some embodiments, each row of pixels may be illuminated by a waveguide coupled to one of the plurality of excitation sources. As illustrated in FIG. 4-4, multiple excitation sources 4-406a, 4-406b, and 4-406c may couple to waveguides configured to carry excitation energy towards the pixels 4-412 located on an integrated device 4-402. Any suitable configuration for excitation sources, waveguides, and arrangement of pixels may be used. An exemplary configuration shown in FIG. 4-4 alternates the excitation source used to illuminate each row of pixels. For example, excitation source 4-406a couples to the first row of pixels through waveguide 4-404a as well as the fourth row of pixels, the seventh row of pixels, and the tenth row of pixels through additional waveguides. Similarly, excitation source 4-406b couples to second, fifth, eighth, and eleventh rows of pixels, such as through waveguide 4-404b which connects to the eleventh rows of pixels. Excitation source 4-406c couples to the third, sixth, ninth, and twelfth rows of pixels. In some embodiments, excitation sources 4-406a, 4-406b, and 4-406c may comprise multiple excitation sources. For example, in some embodiments with VCSEL light sources, a plurality of columns of VCSELs may be used such that each VCSEL overlaps vertically with at least one VCSEL from another column. Each row of pixels is illuminated by a separate VCSEL and the column of VCSELs alternates for each row of pixels, such as in the example configuration shown in FIG. 4-4.

B. Waveguide

In embodiments of the integrated device with waveguides, the waveguides may be designed in any suitable way to deliver excitation energy to one or more sample wells. The waveguide may act as a bus, coupling excitation energy to a plurality of pixels. As excitation energy propagates along a waveguide associated with one or more sample wells, a portion of the excitation energy may be delivered to the sample well(s). A single waveguide may deliver excitation energy to a row or column of pixels in the integrated device. A waveguide may carry an optical mode having an evanescent tail extending into a sample well and/or in a region near the sample well. Additional energy-coupling structures located near the sample well may couple energy from the evanescent tail into the sample well. Alternatively or additionally, structures may be included to direct energy from the waveguide toward the vicinity of the sample well.

The position and arrangement of the waveguide with respect to other components in a pixel of the integrated devices may be configured to improve coupling of excitation energy towards the sample well, improve collection of emission energy by the sensor, and/or reduce signal noise introduced by excitation energy. A waveguide may be sized and located adjacent to a sample well so as to reduce interference with emission energy emitted from the sample well. For example, the width of the waveguide may be increased so that emission from a sample well equally passes through the same materials as it propagates to the sensor of the pixel. In some implementations, the distance between the sample well and waveguide and waveguide thickness may be selected to minimize reflections from the waveguide material interfaces. The distance and thickness will depend upon the refractive indices of the waveguide and surrounding material. In some embodiments, the waveguide layer is composed of silicon nitride with a refractive index of approximately 1.90 and a thickness of approximately 100 nm, and the surrounding material is silicon dioxide with a refractive index of approximately 1.46. According to some embodiments, the reflection of emission energy by the waveguide may be reduced to less than about 5% in some embodiments, less than about 2% in some embodiments, and yet less than about 1% in some embodiments.

A waveguide may pass through a pixel and be located between the sample well and sensor, as shown in the exemplary integrated device of FIG. 4-3B. However, in some embodiments, the sample well may be located between the waveguide and sensor. A waveguide may be aligned, for example, center-to-center with the sensor such that the center of the waveguide is substantially aligned with the center of the sample well. In some embodiments, the waveguide may be displaced from a center-to-center alignment with the sample well. In some embodiments, two substantially parallel waveguides may deliver excitation energy of a same wavelength or different wavelengths to a pixel, and the sample well may be located between the two waveguides. In some embodiments, a plurality of waveguides at different levels within the integrated device may direct excitation energy towards the vicinity of one or more sample wells located on the integrated device.

A waveguide may be dimensioned to support a single transverse radiation mode or may be dimensioned to support multi-transverse radiation modes. In some implementations, a waveguide may have highly reflective sections formed on its ends, so that it supports a longitudinal standing mode within the waveguide. In some embodiments, the highly reflective sections comprise a single, highly reflective surface. In other embodiments, the highly reflective sections comprise multiple reflective structures that, in aggregate, result in a high reflectance. Waveguides may be configured to split excitation energy from a single excitation source having a higher output intensity using waveguide beam splitters to create a plurality of excitation energy beams from a single excitation source. Such beam splitters may include evanescent coupling mechanisms.

One or more parameters of the waveguide may be selected to propagate one or more wavelengths of excitation energy. The material of both the waveguide and the surrounding material may be selected for improving propagation of excitation energy through the waveguide. Examples of a waveguide 4-304b and surrounding material 4-318 are shown in FIG. 4-3B. Material for either the waveguide or the surrounding material may be selected for particular indices of refraction or combination of indices of refraction. Example waveguide materials include silicon nitride ($Si_xN_y$), silicon oxynitride, silicon carbide, tantalum oxide ($TaO_2$), aluminum dioxide. Example waveguide surrounding materials include silicon dioxide ($SiO_2$) and silicon oxide. A combination of materials may be selected for either the waveguide and/or the material surrounding the waveguide. In some embodiments, waveguides are made of silicon nitride surrounded by silicon dioxide.

Additionally, the dimensions of the waveguide may be selected to improve propagation of excitation energy. As an exemplary embodiment, a waveguide may have a cross-sectional width of approximately 0.5 μm and a cross-sectional height of approximately 0.1 μm, and be positioned approximately 0.5 µm below the sample well layer. In some instances, a waveguide may be positioned approximately 0.5 µm below the sample well layer. In another exemplary embodiment, a waveguide may have a cross-sectional width of approximately 1 µm and a cross-sectional height of 0.18 µm, and be positioned 0.3 µm below the sample well layer.

C. Sample Well

Figures 4, 5, 5A:
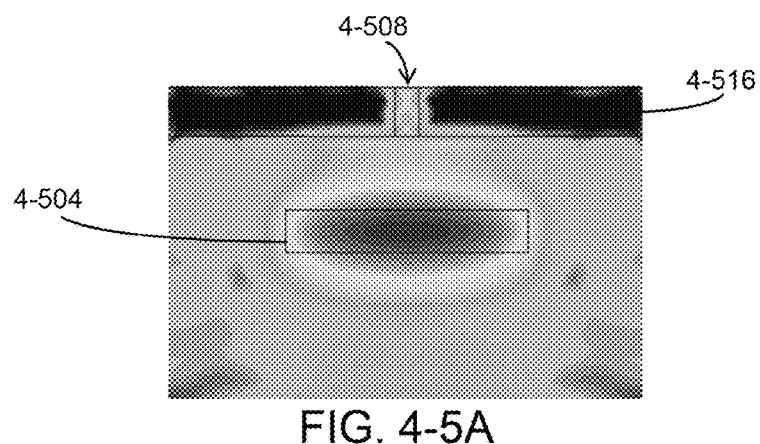

According to some embodiments, a sample well 5-210 may be formed at one or more pixels of an integrated device. A sample well may comprise a small volume or region formed at a surface of a substrate 5-105 and arranged such that samples 5-101 may diffuse into and out of the sample well from a specimen deposited on the surface of the substrate, as depicted in FIG. 5-1. In various embodiments, a sample well 5-210 may be arranged to receive excitation energy from an excitation source 5-240. Samples 5-101 that diffuse into the sample well may be retained, temporarily or permanently, within an excitation region 5-215 of the sample well by an adherent 5-211. In the excitation region, a sample may be excited by excitation energy (e.g., excitation radiation 5-247), and subsequently emit radiation that may be observed and evaluated to characterize the sample.

In further detail of operation, at least one sample 5-101 to be analyzed may be introduced into a sample well 5-210, e.g., from a specimen (not shown) containing a fluid suspension of samples. Energy from an excitation source 5-240 on the substrate may excite the sample or at least one tag (also referred to as a biological marker, reporter, or probe) attached to the sample or otherwise associated with the sample while it is within an excitation region 5-215 within the sample well. According to some embodiments, a tag may be a luminescent molecule (e.g., a luminescent tag or probe) or quantum dot. In some implementations, there may be more than one tag that is used to analyze a sample (e.g., distinct tags that are used for single-molecule genetic sequencing as described in "Real-Time DNA Sequencing from Single Polymerase Molecules," by J. Eid, et al., *Science* 323, p. 133 (2009), which is incorporated by reference). During and/or after excitation, the sample or tag may emit emission energy. When multiple tags are used, they may emit at different characteristic energies and/or emit with different temporal characteristics. The emissions from the sample well may radiate or otherwise travel to a sensor 5-260 where they are detected and converted into electrical signals that can be used to characterize the sample.

According to some embodiments, a sample well 5-210 may be a partially enclosed structure, as depicted in FIG. 5-2. In some implementations, a sample well 5-210 comprises a sub-micron-sized hole or opening (characterized by at least one transverse dimension $D_{sw}$) formed in at least one layer of material 5-230. In some cases, the hole may be referred to as a "nanoaperture." The transverse dimension of the sample well may be between approximately 20 nanometers and approximately 1 micron, according to some embodiments, though larger and smaller sizes may be used in some implementations. A volume of the sample well 5-210 may be between about $10^{-21}$ liters and about $10^{-15}$ liters, in some implementations. A sample well may be formed as a waveguide that may, or may not, support a propagating mode. In some embodiments, a sample well may be formed as a nanoaperture having a cylindrical shape (or other shape) with a diameter (or largest transverse dimension) $D_{sw}$. When the sample well is a waveguide structure that does not support a propagating mode for a selected wavelength of radiation incident on the waveguide structure, then the sample well. In such instances, the sample well may act as a zero-mode waveguide (ZMW) when the sample well. A ZMW may be formed in a single metal layer as a nano-scale hole that does not support a propagating optical mode through the hole.

Because the sample well 5-210 has a small volume, detection of single-sample events (e.g., single-molecule events) at each pixel may be possible even though samples may be concentrated in an examined specimen at concentrations that are similar to those found in natural environments. For example, micromolar concentrations of the sample may be present in a specimen that is placed in contact with the integrated device, but at the pixel level only about one sample (or single molecule event) may be within a sample well at any given time. Statistically, some sample wells may contain no samples and some may contain more than one sample. However, an appreciable number of sample wells may contain a single sample, so that single-molecule analysis can be carried out in parallel for a large number of pixels. Sample wells of the integrated device are sized such that statistically they most likely contain no sample or one sample, so that single molecule analysis may be performed. However, sample wells may contain more than one sample. Because single-molecule or single-sample events may be analyzed at each pixel, the integrated device makes it possible to detect rare events that may otherwise go unnoticed in ensemble averages.

A transverse dimension $D_{sw}$ of a sample well may be between about 500 nanometers (nm) and about one micron in some embodiments, between about 250 nm and about 500 nm in some embodiments, between about 100 nm and about 250 nm in some embodiments, and yet between about 20 nm and about 100 nm in some embodiments. According to some implementations, a transverse dimension of a sample well is between approximately 80 nm and approximately 180 nm, or between approximately one-quarter and one-eighth of the excitation wavelength or emission wavelength. According to other implementations, a transverse dimension of a sample well is between approximately 120 nm and approximately 170 nm. In some embodiments, the depth or height of the sample well 5-210 may be between about 50 nm and about 500 nm. In some implementations, the depth or height of the sample well 5-210 may be between about 80 nm and about 250 nm.

A sample well 5-210 having a sub-wavelength, transverse dimension can improve operation of a pixel 5-100 of an integrated device in at least two ways. For example, excitation energy incident on the sample well from a side opposite the specimen may couple into the excitation region 5-215 with an exponentially decreasing power, and not propagate through the sample well to the specimen. As a result, excitation energy is increased in the excitation region where it excites a sample of interest, and is reduced in the specimen where it would excite other samples that would contribute to background noise. Also, emission from a sample retained at a base of the well (e.g., nearer to the sensor 5-260) is preferably directed toward the sensor, since emission propagating up through the sample well is highly suppressed. Both of these effects can improve signal-to-noise ratio at the pixel. The inventors have recognized several aspects of the sample well that can be improved to further boost signal-to-noise levels at the pixel. These aspects relate to sample well shape and structure, and also to adjacent optical and plasmonic structures (described below) that aid in coupling excitation energy to the sample well and emitted radiation from the sample well.

According to some embodiments, a sample well 5-210 may be formed as a nanoaperture configured to not support a propagating mode for particular wavelengths of interest. In some instances, the nanoaperture is configured where all modes are below a threshold wavelength and the aperture maa sub-cutoff nanoaperture (SCN). For example, the sample well 5-210 may comprise a cylindrically-shaped hole or bore in a conductive layer. The cross-section of a sample well need not be round, and may be elliptical, square, rectangular, or polygonal in some embodiments. Excitation energy 5-247 (e.g., visible or near infrared radiation) may enter the sample well through an entrance aperture 5-212 that may be defined by walls 5-214 of the sample well at a first end of the well, as depicted in FIG. 5-2. When formed as a SCN, the excitation energy may decay exponentially along a length of the nanoaperture (e.g. in the direction of the specimen). In some implementations, the waveguide may comprise a SCN for emitted radiation from the sample, but may not be a SCN for excitation energy. For example, the aperture and waveguide formed by the sample well may be large enough to support a propagating mode for the excitation energy, since it may have a shorter wavelength than the emitted radiation. The emission, at a longer wavelength, may be beyond a cut-off wavelength for a propagating mode in the waveguide. According to some embodiments, the sample well 5-210 may comprise a SCN for the excitation energy, such that the greatest intensity of excitation energy is localized to an excitation region 5-215 of the sample well at an entrance to the sample well 5-210 (e.g., localized near the interface between layer 5-235 and layer 5-230 as depicted in the drawing). Such localization of the excitation energy can improve localization of emission energy from the sample, and limit the observed emission that emitted from a single sample (e.g., a single molecule).

An example of excitation localization near an entrance of a SCN is depicted in FIG. 5-3. A numerical simulation was carried out to determine intensity of excitation radiation within and near a sample well 5-210 formed as a SCN. The results show that the intensity of the excitation radiation is about 70% of the incident energy at an entrance aperture of the sample well and drops to about 20% of the incident intensity within about 100 nm in the sample well. For this simulation, the characteristic wavelength of the excitation energy was 633 nm and the diameter of the sample well 5-210 was 140 nm. The sample well 5-210 was formed in a layer of gold metal. Each horizontal division in the graph is 50 nm. As shown by the graph, more than one-half of the excitation energy received in the sample well is localized to about 50 nm within the entrance aperture 5-212 of the sample well.

To improve the intensity of excitation energy that is localized at the sample well, other sample well structures were developed and studied by the inventors. FIG. 5-4 depicts an embodiment of a sample well that includes a cavity or divot 5-216 at an excitation end of the sample well. As can be seen in the simulation results of FIG. 5-3, a region of higher excitation intensity exists just before the entrance aperture 5-212 of the sample well. Adding a divot 5-216 to the sample well allows a sample to move into a region of higher excitation intensity, according to some embodiments. In some implementations, the shape and structure of the divot alters the local excitation field (e.g., because of a difference in refractive index between the layer 5-235 and fluid in the sample well), and can further increase the intensity of the excitation energy in the divot.

The divot may have any suitable shape. The divot may have a transverse shape that is substantially equivalent to a transverse shape of the sample well, e.g., round, elliptical, square, rectangular, polygonal, etc. In some embodiments, the sidewalls of the divot may be substantially straight and vertical, like the walls of the sample well. In some implementations, the sidewalls of the divot may be sloped and/or curved, as depicted in the drawing. The transverse dimension of the divot may be approximately the same size as the transverse dimension of the sample well in some embodiments, may be smaller than the transverse dimension of the sample well in some embodiments, or may be larger than the transverse dimension of the sample well in some embodiments. The divot 5-216 may extend between approximately 10 nm and approximately 200 nm beyond the sample well. In some implementations, the divot may extend between approximately 50 nm and approximately 150 nm beyond the sample well. By forming the divot, the excitation region 5-215 may extend outside the sample well, as depicted in FIG. 5-4.

FIG. 5-5 depicts improvement of excitation energy at the excitation region for a sample well containing a divot (shown in the left simulation image). For comparison, the excitation field is also simulated for a sample well without a divot, shown on the right. The field magnitude has been converted from a color rendering in these plots, and the dark region at the base of the divot represents higher intensity than the light region within the sample well. The dark regions above the sample well represents the lowest intensity. As can be seen, the divot allows a sample 5-101 to move to a region of higher excitation intensity, and the divot also increases the localization of region of highest intensity at an excitation end of the sample well. Note that the region of high intensity is more distributed for the sample well without the divot.

In some embodiments, the divot 5-216 provides an increase in excitation energy at the excitation region by a factor of two or more. In some implementations, an increase of more than a factor of two can be obtained depending on the shape and depth of the divot. In these simulations, the layer containing the sample well includes aluminum and has a thickness of approximately 100 nm, the divot has a depth of approximately 50 nm, and the excitation energy wavelength is 635 nm.

Figures 1, 5:
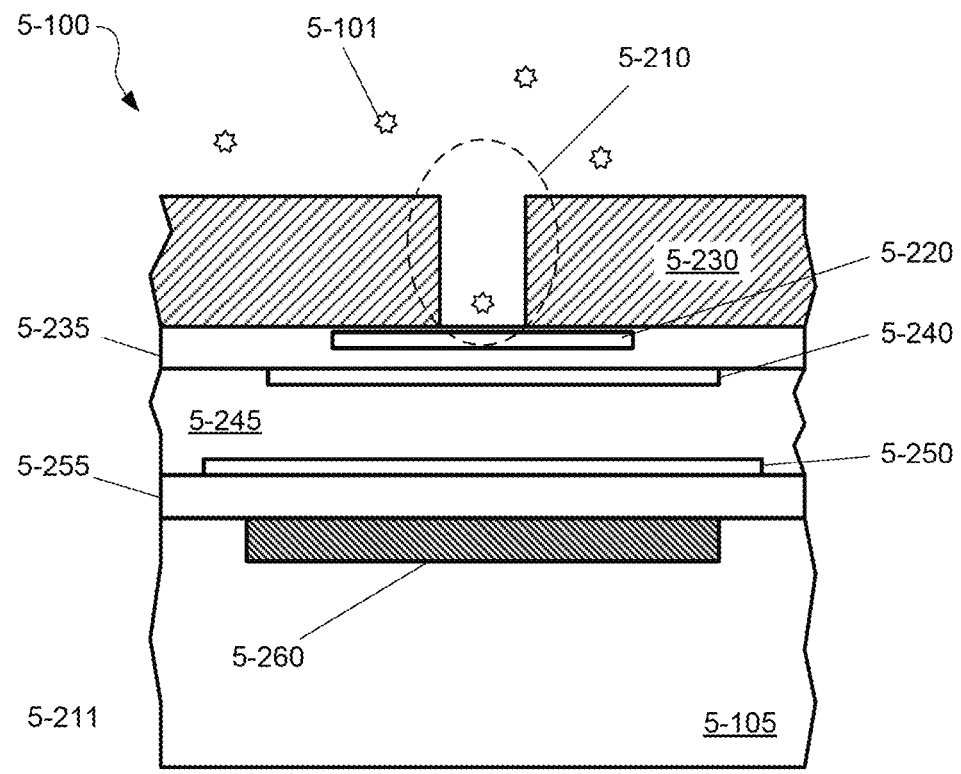
Figures 2, 5:
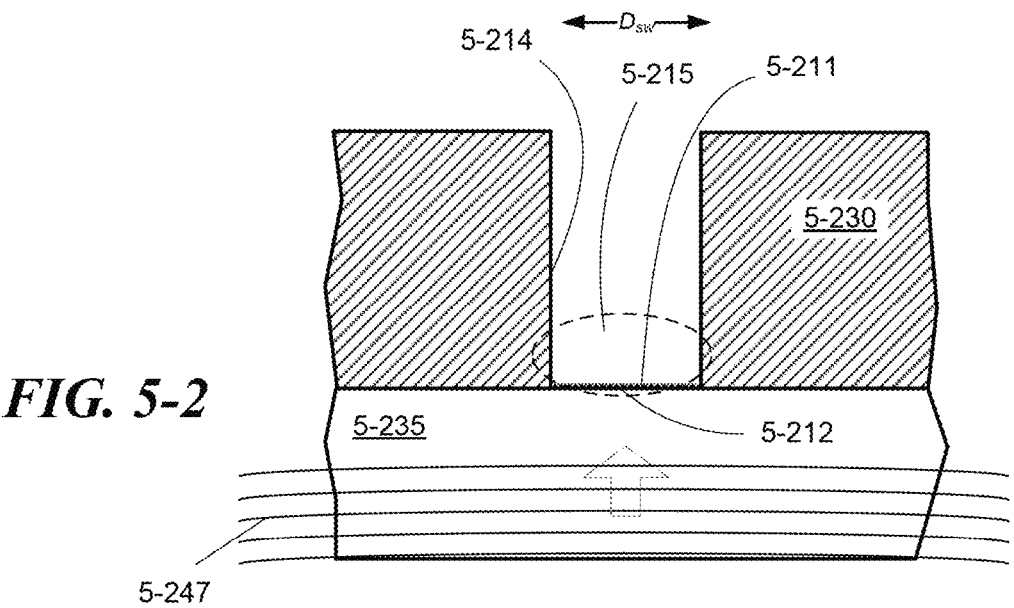
Figures 3, 5:
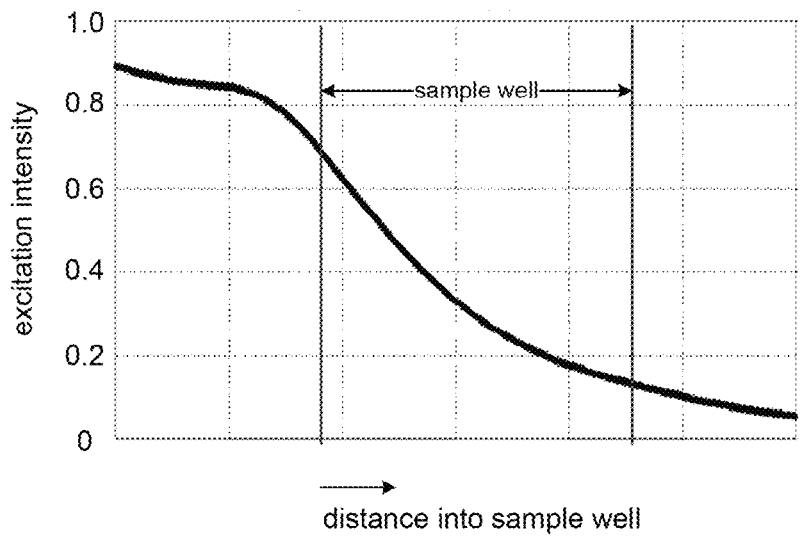
Figures 4, 5:
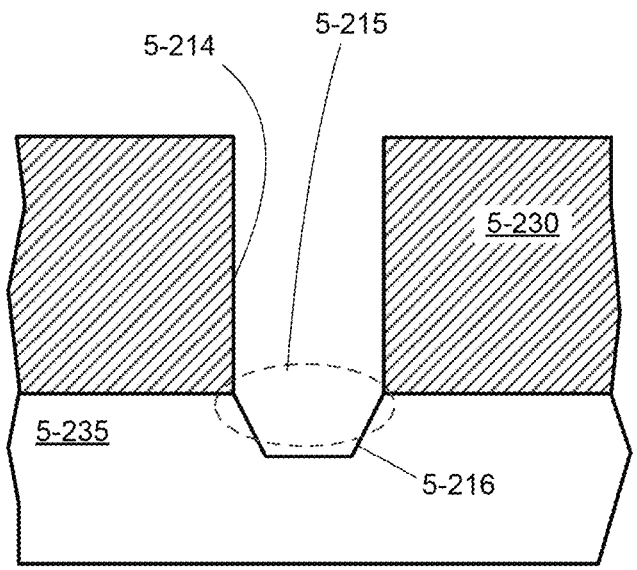
Figure 5:
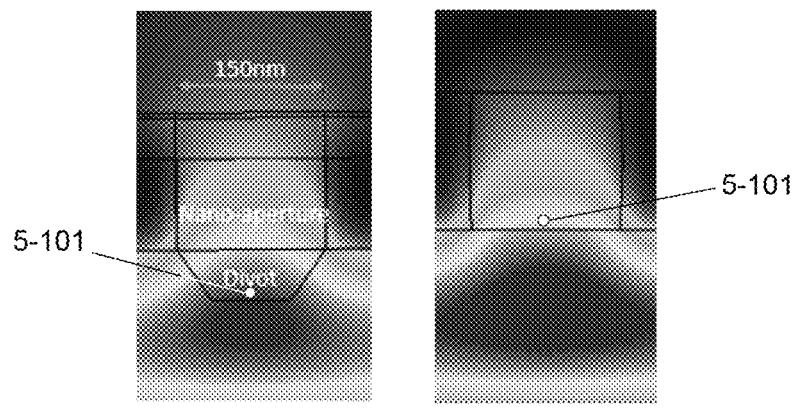
Figures 5, 6:
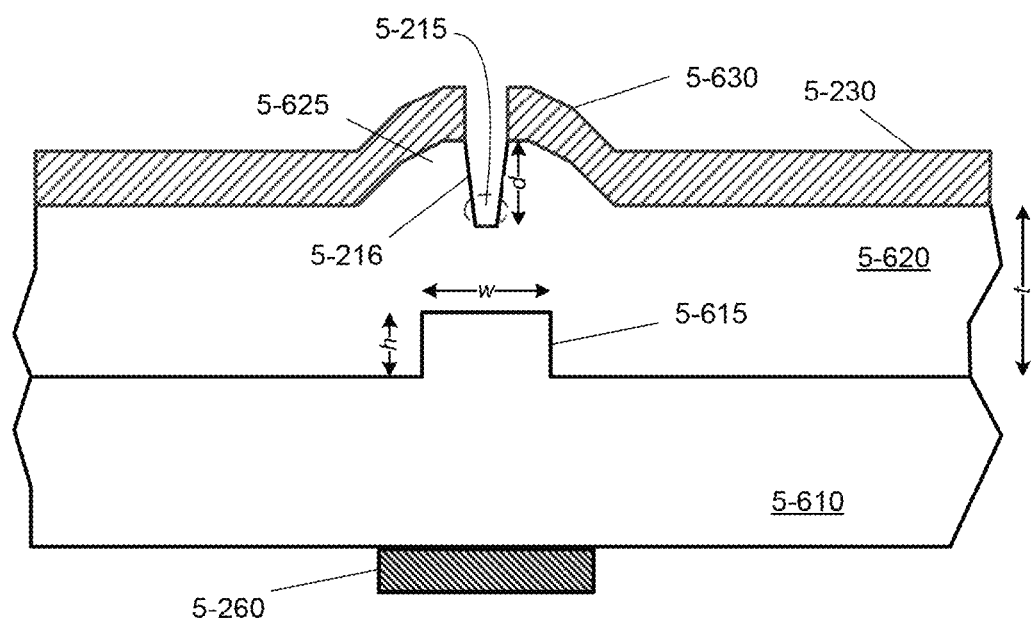

FIG. 5-6 depicts another embodiment of a sample well 5-210 in which the sample well is formed in a protrusion 5-615 at a surface of a substrate. A resulting structure for the sample well may increase the excitation energy at the sample by more than a factor of two compared to a sample well shown in FIG. 5-1, and may condense emission from the sample well to a sensor 5-260. According to some embodiments, a protrusion 5-615 is patterned in a first layer 5-610 of material. In some embodiments, the protrusion comprises a waveguide. The protrusion may be formed as a ridge with a rectangular cross-section in some implementations, and a second layer 5-620 of material may be deposited over the first layer and the protrusion. At the protrusion, the second layer may form a shape above the protrusion that approximates a cylindrical portion 5-625, as depicted. In some embodiments, a conductive layer 5-230 (e.g., a reflective metal) may be deposited over the second layer 5-620 and patterned to form a sample well 5-210 in the conductive layer above the protrusion. A divot 5-216 may then be etched into the second layer. The divot may extend between about 50 nm and about 150 nm below the conductive layer 5-230. According to some embodiments, the first layer 5-610 and second layer 5-620 may be optically transparent, and may or may not be formed of a same material. In some implementations, the first layer 5-610 may be formed from an oxide (e.g., $SiO_2$) or a nitride (e.g., $Si_3N_4$), and the second layer 5-620 may be formed from an oxide or a nitride.

According to some embodiments, the conductive layer 5-230 above the protrusion 5-625 is shaped approximately as a cylindrical reflector 5-630. The shape of the cylindrical portion may be controlled by selection of the protrusion height h, width or transverse dimension w of the protrusion, and a thickness t of the second layer 5-620. The location of the excitation region and position of the sample can be adjusted with respect to an optical focal point of the cylindrical reflector by selection of the divot depth d. It may be appreciated that the cylindrical reflector 5-630 can concentrate excitation energy at the excitation region 5-215, and can also collect radiation emitted from a sample and reflect and concentrate the radiation toward the sensor 5-260.

As noted above, a sample well may be formed in any suitable shape, and is not limited to only cylindrical shapes. In some implementations, a sample well may be conic, tetrahedron, pentahedron, etc. FIG. 5-7A-FIG. 5-7F illustrates some example sample well shapes and structures that may be used in some embodiments. A sample well 5-210 may be formed to have an entrance aperture 5-212 that is larger than an exit aperture 5-218 for the excitation energy, according to some embodiments. The sidewalls of the sample well may be tapered or curved. Forming a sample well in this manner can admit more excitation energy to the excitation region, yet still appreciably attenuate excitation energy that travels toward the specimen. Additionally, emission radiated by a sample may preferentially radiate toward the end of the sample well with the larger aperture, because of favorable energy transfer in that direction.

In some embodiments, a divot 5-216 may have a smaller transverse dimension than the base of the sample well, as depicted in FIG. 5-7B. A smaller divot may be formed by coating sidewalls of the sample well with a sacrificial layer before etching the divot, and subsequently removing the sacrificial layer. A smaller divot may be formed to retain a sample in a region that is more equidistant from the conductive walls of the sample well. Retaining a sample equidistant from the walls of the sample well may reduce undesirable effects of the sample well walls on the radiating sample, e.g., quenching of emission, and/or altering of radiation lifetimes.

FIGS. 5-7C and 5-7D depict another embodiment of a sample well. According to this embodiment, a sample well 5-210 may comprise excitation-energy-enhancing structures 5-711 and an adherent 5-211 formed adjacent the excitation-energy-enhancing structures. The energy-enhancing structures 5-711 may comprise surface plasmon or nano-antenna structures formed in conductive materials on an optically transparent layer 5-235, according to some embodiments. FIG. 5-7C depicts an elevation view of the sample well 5-210 and nearby structure, and FIG. 5-7D depicts a plan view. The excitation-energy-enhancing structures 5-711 may be shaped and arranged to enhance excitation energy in a small localized region. For example, the structures may include pointed conductors having acute angles at the sample well that increase the intensity of the excitation energy within an excitation region 5-215. In the depicted example, the excitation-energy-enhancing structures 5-711 are in the form of a bow-tie. Samples 5-101 diffusing into the region may be retained, temporarily or permanently, by the adherent 5-211 and excited by excitation energy that may be delivered from an excitation source 5-240 located adjacent the sample well 5-210. According to some embodiments, the excitation energy may drive surface-plasmon waves in the energy-enhancing structures 5-711. The resulting surface-plasmon currents may produce high electric fields at the sharp points of the structures 5-711, and these high fields may excite a sample retained in the excitation region 5-215. In some embodiments, a sample well 5-210 depicted in FIG. 5-7C may include a divot 5-216.

Another embodiment of a sample well is depicted in FIG. 5-7E, and shows an excitation-energy-enhancing structure 5-720 formed along interior walls of the sample well 5-210. The excitation-energy-enhancing structure 5-720 may comprise a metal or conductor, and may be formed using an angled (or shadow), directional deposition where the substrate on which the sample well is formed is rotated during the deposition. During the deposition, the base of the sample well 5-210 is obscured by the upper walls of the well, so that the deposited material does not accumulate at the base. The resulting structure 5-720 may form an acute angle 5-722 at the bottom of the structure, and this acute angle of the conductor can enhance excitation energy within the sample well.

In an embodiment as depicted in FIG. 5-7E, the material 5-232 in which the sample well is formed need not be a conductor, and may be any suitable dielectric. According to some implementations, the sample well 5-210 and excitation-energy-enhancing structure 5-720 may be formed at a blind hole etched into a dielectric layer 5-235, and a separate layer 5-232 need not be deposited.

In some implementations, a shadow evaporation may be subsequently performed on the structure shown in FIG. 5-7E to deposit a metallic or conductive energy-enhancing structure, e.g., a trapezoidal structure or pointed cone at the base of the sample well, as depicted by the dashed line. The energy-enhancing structure may enhance the excitation energy within the sample well via surface plasmons. After the shadow evaporation, a planarizing process (e.g., a chemical-mechanical polishing step or a plasma etching process) may be performed to remove or etch back the deposited material at the top of the sample well, while leaving the energy-enhancing structure within the well.

In some embodiments, a sample well 5-210 may be formed from more than a single metal layer. FIG. 5-7F illustrates a sample well formed in a multi-layer structure, where different materials may be used for the different layers. According to some embodiments, a sample well 5-210 may be formed in a first layer 5-232 (which may be a semiconducting or conducting material), a second layer 5-234 (which may be an insulator or dielectric), and a third layer 5-230 (which may be a conductor or semiconductor). In some embodiments, a degeneratively-doped semiconductor or graphene may be used for a layer of the sample well. In some implementations, a sample well may be formed in two layers, and in other implementations a sample well may be formed in four or more layers. In some embodiments, multi-layer materials used for forming a sample well may be selected to increase or suppress interfacial excitons which may be generated by excitation radiation incident on the sample well. In some embodiments, multi-layer materials used for forming a sample well may be selected to increase surface-plasmon generation at a base of the sample well or suppress surface-plasmon radiation at a top of the well. In some embodiments, multi-layer materials used for forming a sample well may be selected to suppress excitation radiation from propagating beyond the sample well and multi-layer structure into the bulk specimen. In some embodiments, multi-layer materials used for forming a sample well may be selected to increase or suppress interfacial excitons which may be generated by excitation radiation incident on the sample well.

Various materials may be used to form sample wells described in the foregoing embodiments. According to some embodiments, a sample well 5-210 may be formed from at least one layer of material 5-230, which may comprise any one of or a combination of a conductive material, a semiconductor, and an insulator. In some embodiments, the sample well 5-210 comprises a highly conductive metallic layer, e.g., gold, silver, aluminum, copper. In some embodiments, the layer 5-230 may comprise a multi-layer stack that includes any one of or a combination of gold, silver, aluminum, copper, titanium, titanium nitride, palladium, platinum, and chromium. In some implementations, other metals may be used additionally or alternatively. According to some embodiments, a sample well may comprise an alloy such as AlCu or AlSi.

In some embodiments, the multiple layers of different metals or alloys may be used to form a sample well. In some implementations, the material in which the sample well 5-210 is formed may comprise alternating layers of metals and non-metals, e.g., alternating layers of metal and one or more oxides. In some embodiments, the non-metal may include a polymer, such as polyvinyl phosphonic acid or a polyethylene glycol (PEG)-thiol.

A layer 5-230 in which a sample well is formed may be deposited on or adjacent to at least one optically transparent layer 5-235, according to some embodiments, so that excitation energy (in the form of optical radiation, such as visible or near-infrared radiation) and emission energy (in the form of optical radiation, such as visible or near-infrared radiation) may travel to and from the sample well 5-210 without significant attenuation. For example, excitation energy from an excitation source 5-240 may pass through the at least one optically transparent layer 5-235 to the excitation region 5-215, and emission from the sample may pass through the same layer or layers to the sensor 5-260.

In some embodiments, at least one surface of the sample well 5-210 may be coated with one or more layers 5-211, 5-280 of material that affect the action of a sample within the sample well, as depicted in FIG. 5-8. For example, a thin dielectric layer 5-280 (e.g., alumina, titanium nitride or silica) may be deposited as a passivating coating on sidewalls of the sample well. Such a coating may be implemented to reduce sample adhesion of a sample outside the excitation region 5-215, or to reduce interaction between a sample and the material 5-230 in which the sample well 5-210 is formed. The thickness of a passivating coating within the sample well may be between about 5 nm and about 50 nm, according to some embodiments.

In some implementations, a material for a coating layer 5-280 may be selected based upon an affinity of a chemical agent for the material, so that the layer 5-280 may be treated with a chemical or biological substance to further inhibit adhesion of a sample species to the layer. For example, a coating layer 5-280 may comprise alumina, which may be passivated with a polyphosphonate passivation layer, according to some embodiments. Additional or alternative coatings and passivating agents may be used in some embodiments.

According to some embodiments, at least a bottom surface of the sample well 5-210 and/or divot 5-216 may be treated with a chemical or biological adherent 5-211 (e.g., biotin) to promote retention of a sample. The sample may be retained permanently or temporarily, e.g., for at least a period of time between about 0.5 milliseconds and about 50 milliseconds. In another embodiment, the adherent may promote temporary retention of a sample 5-101 for longer periods. Any suitable adherent may be used in various embodiments, and is not limited to biotin.

According to some embodiments, the layer of material 5-235 adjacent the sample well may be selected based upon an affinity of an adherent for the material of that layer. In some embodiments, passivation of the sample well's sidewalls may inhibit coating of an adherent on the sidewalls, so that the adherent 5-211 preferentially deposits at the base of the sample well. In some embodiments, an adherent coating may extend up a portion of the sample well's sidewalls. In some implementations, an adherent may be deposited by an anisotropic physical deposition process (e.g., evaporation, sputtering), such that the adherent accumulates at the base of a sample well or divot and does not appreciably form on sidewalls of the sample well.

Various fabrication techniques may be employed to fabricate sample wells 5-210 for an integrated device. A few example processes are described below, but the invention is not limited to only these examples.

The sample well 5-210 may be formed by any suitable micro- or nano-fabrication process, which may include, but is not limited to, processing steps associated with photolithography, deep-ultraviolet photolithography, immersion photolithography, near-field optical contact photolithography, EUV lithography, x-ray lithography, nanoimprint lithography, interferometric lithography, step-and-flash lithography, direct-write electron beam lithography, ion beam lithography, ion beam milling, lift-off processing, reactive-ion etching, etc. According to some embodiments, a sample well 5-210 may be formed using photolithography and lift-off processing. Example fabrication steps associated with lift-off processing of a sample well are depicted in FIG. 5-9. Although fabrication of only a single sample well or structure at a pixel is typically depicted in the drawings, it will be understood that a large number of sample wells or structures may be fabricated on a substrate (e.g., at each pixel) in parallel.

According to some embodiments, a layer 5-235 (e.g., an oxide layer) on a substrate may be covered with an anti-reflection (ARC) layer 5-910 and photoresist 5-920, as depicted in FIG. 5-9A. The photoresist may be exposed and patterned using photolithography and development of the resist. The resist may be developed to remove exposed portions or unexposed portions (depending on the resist type), leaving a pillar 5-922 that has a diameter approximately equal to a desired diameter for the sample well, as depicted in FIG. 5-9B. The height of the pillar may be substantially different than a desired depth of the sample well. For example, the height of the pillar may be substantially greater than a desired depth of the sample well.

The pattern of the pillar 5-922 may be transferred to the ARC layer 5-910 via anisotropic, reactive ion etching (RIE), for example as shown in FIG. 5-9C. The region may then be coated with at least one material 5-230, e.g., a conductor or metal, that is desired to form the sample well. A portion of the deposited material, or materials, forms a cap 5-232 over the pillar 5-922, as depicted in FIG. 5-9D. The resist and ARC may then be stripped from the substrate, using a selective removal process (e.g., using a chemical bath with or without agitation which dissolves at least the resist and releases or "lifts off" the cap). If the ARC remains, it may be stripped from the substrate using a selective etch, leaving the sample well 5-210 as shown in FIG. 5-9E. According to some embodiments, the sidewalls 5-214 of the sample well may be sloped due to the nature of the deposition of the at least one material 5-230.

As used herein, a "selective etch" means an etching process in which an etchant selectively etches one material that is desired to be removed or etched at a higher rate (e.g., at least twice the rate) than the etchant etches other materials which are not intended to be removed.

Because the resist and ARC are typically polymer based, they are considered soft materials which may not be suitable for forming sample wells having high aspect ratios (e.g., aspect ratios greater than about 2:1 with respect to height-to-width). For sample wells having higher aspect ratios, a hard material may be included in the lift-off process. For example, before depositing the ARC and photoresist, a layer of a hard (e.g., an inorganic material) may be deposited. In some embodiments, a layer of titanium or silicon nitride may be deposited. The layer of hard material should exhibit preferential etching over the material, or materials, 5-230 in which the sample well is formed. After the photoresist is patterned, a pattern of the pillar may be transferred into the ARC and the underlying hard material 5-930 yielding a structure as depicted in FIG. 5-9F. The photoresist and ARC may be then stripped, the material(s) 5-230 deposited, and a lift-off step performed to form the sample well.

According to some embodiments, a lift-off process may be used to form a sample well comprising energy-enhancing structures 5-711, as depicted in FIG. 5-7C and FIG. 5-7D.

An alternative process for forming a sample well is depicted in FIG. 5-10. In this process, the sample well may be directly etched into at least one material 5-230. For example, at least one material 5-230 in which a sample well is to be formed may be deposited on a substrate. The layer may be covered by an ARC layer 5-910 and a photoresist 5-920, as illustrated in FIG. 5-10A. The photoresist may be patterned to form a hole having a diameter approximately equal to a desired diameter of the sample well, as depicted in FIG. 5-10B. The pattern of the hole may be transferred to the ARC and through the layer 5-230 using an anisotropic, reactive ion etch, as shown in FIG. 5-10C for example. The resist and ARC may be stripped, yielding a sample well as depicted in FIG. 5-10D. According to some embodiments, the sidewalls of a sample well formed by etching into the layer of material 5-230 may be more vertical than sidewalls resulting from a lift-off process.

In some embodiments, the photoresist and ARC may be used to pattern a hard mask (e.g., a silicon nitride or oxide layer, not shown) over the material 5-230. The patterned hole may then be transferred to the hard mask, which is then used to transfer the pattern into the layer of material 5-230. A hard mask may allow greater etching depths into the layer of material 5-230, so as to form sample wells of higher aspect ratio.

It will be appreciated that lift-off processes and direct etching fabrication techniques described above may be used to form a sample well when multiple layers of different materials are used to form a stack of material 5-230 in which the sample well is formed. An example stack is shown in FIG. 5-11. According to some embodiments, a stack of material may be used to form a sample well to improve coupling of excitation energy to the excitation region of a sample well, or to reduce transmission or re-radiation of excitation energy into the bulk specimen. For example, an absorbing layer 5-942 may be deposited over a first layer 5-940. The first layer may comprise a metal or metal alloy, and the absorbing layer may comprise a material that inhibits surface plasmons, e.g., amorphous silicon, TaN, TiN or Cr. In some implementations, a surface layer 5-944 may also be deposited to passivate the surface surrounding the sample well (e.g., inhibit adhesion of molecules).

Formation of a sample well including a divot 5-216 may be done in any suitable manner. In some embodiments, a divot may be formed by etching further into an adjacent layer 5-235, and/or any intervening layer or layers, adjacent the sample well. For example, after forming a sample well in a layer of material 5-230, that layer 5-230 may be used as an etch mask for patterning a divot, as depicted in FIG. 5-12. For example, the substrate may be subjected to a selective, anisotropic reactive ion etch so that a divot 5-216 may be etched into adjacent layer 5-235. For example, in an embodiment where the material 5-230 is metallic and the adjacent layer 5-235 silicon oxide, a reactive-ion plasma etch having a feed gas comprising $CHF_3$ or $CF_4$ may be used to preferentially remove exposed silicon oxide below the sample well and form the divot 5-216. As used herein, "silicon oxide" generally refers to $SiO_x$ and may include silicon dioxide, for example.

In some embodiments, conditions within the plasma (e.g., bias to the substrate and pressure) during an etch may be controlled to determine the etch profile of the divot. For example, at low pressure (e.g., less than about 100 mTorr) and high DC bias (e.g., greater than about 20V), the etching may be highly anisotropic and form substantially straight and vertical sidewalls of the divot, as depicted in the drawing. At higher pressures and lower bias, the etching may be more isotropic yielding tapered and/or curved sidewalls of the divot. In some implementations, a wet etch may be used to form the divot, which may be substantially isotropic and form an approximately spherical divot that may extend laterally under the material 5-230, up to or beyond the sidewalls of the sample well.

FIG. 5-13A through FIG. 5-13C depict process steps that may be used to form a divot 5-216 having a smaller transverse dimension than the sample well 5-210 (for example, a divot like that depicted in FIG. 5-7B). In some implementations, after forming a sample well, a conformal sacrificial layer 5-960 may be deposited over a region including the sample well. According to some embodiments, the sacrificial layer 5-960 may be deposited by a vapor deposition process, e.g., chemical vapor deposition (CVD), plasma-enhanced CVD, or atomic layer deposition (ALD). The sacrificial layer may then be etched back using a first anisotropic etch that is selective to the sacrificial layer 5-960, removes the layer from horizontal surfaces, leaves side wall coatings 5-962 on walls of the sample well, as depicted in FIG. 5-13B. The etch back may be selective and stop on the material 5-230 and adjacent layer 5-235 in some embodiments, or may be a non-selective, timed etch in some embodiments.

A second anisotropic etch that is selective to the adjacent layer 5-235 may be executed to etch a divot 5-216 into the adjacent layer as depicted in FIG. 5-13C. The sacrificial side wall coatings 5-962 may then optionally be removed by a selective wet or dry etch. The removal of the sidewall coatings open up the sample well to have a larger transverse dimension than the divot 5-216.

According to some embodiments, the sacrificial layer 5-960 may comprise the same material as the adjacent layer 5-235. In such embodiments, the second etch may remove at least some of the side wall coating 5-962 as the divot is etched into the adjacent layer 5-235. This etch back of the side wall coating can form tapered sidewalls of the divot in some embodiments.

In some implementations, the sacrificial layer 5-960 may be formed from, or include a layer of, a material that is used to passivate the sidewalls of the sample well (e.g., reduce adhesion of samples at the sidewalls of the sample well). At least some of the layer 5-960 may then be left on the walls of the sample well after formation of the divot.

According to some embodiments, the formation of the sidewall coatings 5-962 occurs after the formation of the divot. In such embodiments, the layer 5-960 coats the sidewalls of the divot. Such a process may be used to passivate the sidewalls of the divot and localize the sample at the within a center region of the divot.

Process steps associated with depositing an adherent 5-211 at a base of a sample well 5-210, and a passivation layer 5-280 are depicted in FIG. 5-15. According to some embodiments, a sample well may include a first passivation layer 5-280 on walls of the sample well. The first passivation layer may be formed, for example, as described above in connection with FIG. 5-13B or FIG. 5-8. In some embodiments, a first passivation layer 5-280 may be formed by any suitable deposition process and etch back. In some embodiments, a first passivation layer may be formed by oxidizing the material 5-230 in which the sample well is formed. For example, the sample well may be formed of aluminum, which may be oxidized to create a coating of alumina on sidewalls of the sample well.

An adherent 5-980 or an adherent precursor (e.g., a material which preferentially binds an adherent) may be deposited on the substrate using an anisotropic physical deposition process, e.g., an evaporative deposition, as depicted in FIG. 5-14A. The adherent or adherent precursor may form an adherent layer 5-211 at the base of the sample well, as depicted in FIG. 5-14B, and may coat an upper surface of the material 5-230 in which the sample well is formed. A subsequent angled, directional deposition depicted in FIG. 5-14C (sometimes referred to as a shadow deposition or shadow evaporation process) may be used to deposit a second passivation layer 5-280 over an upper surface of the material 5-230 without covering the adherent layer 5-211. During the shadow deposition process, the substrate may be rotated around an axis normal to the substrate, so that the second passivation layer 5-280 deposits more uniformly around an upper rim of the sample well. A resulting structure is depicted in FIG. 5-14D, according to some embodiments. As an alternative to depositing the second passivation layer, a planarizing etch (e.g., a CMP step) may be used to remove adherent from an upper surface of the material 5-230.

According to some implementations, an adherent layer 5-211 may be deposited centrally at the base of a tapered sample well, as depicted in FIG. 5-15. For example, an adherent, or adherent precursor, may be directionally deposited, as depicted in FIG. 5-14A, in a tapered sample well, formed as described above. Walls of the sample well may be passivated by an oxidation process before or after deposition of the adherent layer 5-211. Adherent or precursor remaining on a surface of the material 5-230 may be passivated as described in connection with FIG. 5-14D. In some embodiments, an adherent on an upper surface of the material 5-230 may be removed by a chemical-mechanical polishing step. By forming an adherent layer, or an adherent layer precursor, centrally at the base of a sample well, deleterious effects on emission from a sample (e.g., suppression or quenching of sample radiation from sample walls, unfavorable radiation distribution from a sample because it is not located centrally with respect to energy coupling structures formed around a sample well, adverse effects on luminescent lifetime for a sample) may be reduced.

In some embodiments, lift-off patterning, etching, and deposition processes used to form the sample well and divot may be compatible with CMOS processes that are used to form integrated CMOS circuits on an integrated device. Accordingly, an integrated device may be fabricated using conventional CMOS facilities and fabrication techniques, though custom or specialized fabrication facilities may be used in some implementations.

Variations of the process steps described above may be used to form alternative embodiments of sample wells. For example, a tapered sample well such as depicted in FIG. 5-7A or FIG. 5-7B may be formed using an angled deposition process depicted in FIG. 5-14C. For the sample well of FIG. 5-7B, the angle of deposition may be changed during the deposition process. For such embodiments, a sample well having substantially straight and vertical sidewalls may first be formed, and then additional material 5-230 deposited by an angled deposition to taper the sidewalls of the sample well.

In some embodiments, a sample well 5-210 may be formed at a pixel after an excitation source is formed. For example, an excitation source for a pixel may be formed at another region and/or at another level on the integrated device, within or outside a pixel. The type of excitation source may place processing constraints on the steps used to fabricate the sample well 5-210. For example, if the excitation source comprises an organic light-emitting diode (OLED), then processing steps used to fabricate the sample well 5-210 may not exceed temperatures greater than about 100° C. Further, the processing steps may not subject the OLED to harsh chemical environments or oxidizing environments.

D. Coupling Excitation Energy to Sample Well

Coupling of excitation energy to one or more sample wells of the integrated device may occur through one or more techniques. As previously discussed, in some embodiments, a waveguide is positioned to couple with an excitation source to one or more sample wells. As excitation energy propagates along the waveguide, a portion of the excitation energy may be couple to one or more sample wells through a variety of light coupling techniques. For example, the waveguide may guide excitation energy substantially in one direction, and an evanescent wave or tail may form perpendicular to this one direction and, in some instances, be located outside the waveguide structure. Such an evanescent tail may direct a portion of excitation energy towards one or more sample wells. In some embodiments, the sample well layer may be designed and configured to direct excitation energy to a localized region within the sample well. The sample well may be configured to retain a sample within the localized region of the sample well such that excitation energy is directed towards the sample.

Figures 4, 5, 5B:
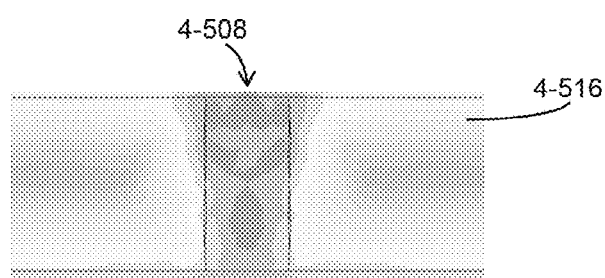

FIGS. 4-5A and 4-5B are cross-sectional views of an integrated device and provide an exemplary illustration of using a waveguide to couple excitation energy into a sample well. FIG. 4-5A is a cross-sectional schematic showing a waveguide 4-5A positioned in proximity to a sample well 4-508 in a sample well layer 4-516. Excitation energy propagates along the waveguide in a direction perpendicular to the field of view of FIG. 4-5A. Proximity of a sample well to the waveguide may allow excitation energy to couple into the sample well. Excitation energy FIG. 4-5B illustrates a closer view of the region of the sample well 4-508 and the sample well layer 4-516 and shows excitation energy located within sample well 4-508.

Additionally components may be formed in the integrated device to improve or enhance coupling excitation energy into one or more sample wells. These additional components may be formed in each pixel that couples excitation energy from a waveguide into the pixel and towards the sample well. One or more components located in a pixel may act to tap a portion of the excitation energy from a waveguide into the pixel. Such components may include optical structures such as, grating structures, scattering structures, and/or nano-antennas. Features or configurations of one or more of these components may be selected for coupling a certain amount of excitation energy to each sample well within a row of sample wells. A waveguide configured to provide excitation energy to a row of pixels may couple to a component in each pixel in order to provide a portion of the excitation energy to each pixel in the row of pixels. When a waveguide is configured to direct excitation energy from an excitation source towards one or more pixels, the waveguide may be referred to as a bus waveguide.

In some embodiments, one or more pixels include at least one waveguide located within the pixel region. Such a pixel waveguide may be configured to direct excitation energy towards the sample well of the pixel. A pixel waveguide may be configured to couple to a bus waveguide and to the sample well in the pixel. When excitation energy propagates along the bus waveguide, a portion of the excitation energy may be directed towards the pixel and/or sample well via the pixel waveguide. A bus waveguide may couple to a pixel waveguide using any suitable coupler, such as an evanescent waveguide coupler. In some embodiments, multiple couplers may be used to couple one or more wavelengths of excitation light to a pixel waveguide. A portion of the pixel waveguide may be configured to act as a coupler to a bus waveguide. In some embodiments, a coupler or portion of the pixel waveguide may be designed to couple specific excitation energies, wavelengths, and/or spectral ranges. By configuring a coupling portion of a pixel waveguide to certain wavelengths of light, the directionality of the coupling between a bus waveguide and the pixel waveguide may be controlled and/or tuned. For example, a first coupler or portion of a pixel waveguide may couple to a portion of the excitation light having a first wavelength propagating through a bus waveguide, while a second coupler or portion of a pixel waveguide may couple to a portion of the excitation light having a second wavelength to the pixel waveguide. The first coupler or portion of a pixel waveguide may couple a negligible amount of the excitation light at the second wavelength from the pixel waveguide to the bus waveguide. Such a configuration may allow excitation light at the second wavelength to remain in the pixel waveguide. Similarly, the second coupler or portion of a pixel waveguide may couple a negligible amount of excitation light at the first wavelength from the pixel waveguide to the bus waveguide such that excitation light at the first wavelength may remain in the pixel waveguide.

Additionally, one or more resonant structures may be formed within a pixel region to couple excitation energy towards a sample well. A first waveguide acting as an optical bus, may allow excitation energy to couple to the resonant structure through a second waveguide. A resonant structure may be configured to receive excitation energy by coupling to a bus waveguide and/or a pixel waveguide. The resonant structure may direct and/or enhance excitation energy into an excitation region of the sample well. A resonant structure may concentrate excitation energy in a localized region and by positioning a sample well in proximity to the localized region the resonant structure may act to enhance an amount of excitation energy that couples to the sample well. By forming a resonant structure, excitation energy may have multiple opportunities to interact with a sample in a sample well. The overall configuration of a resonant structure may be configured for a specific field enhancement within the resonant structure and/or quality factor. The waveguides and the resonator are made of a dielectric material with an index of refraction higher than the surrounding dielectric material in which they are embedded. For example, the waveguides and/or resonator may be made of silicon nitride, silicon oxide, silicon carbide, or any combinations thereof. The waveguides and/or resonator may be designed to propagate excitation wavelengths within the visible and/or infrared spectral ranges.

A resonant structure may be located within a pixel waveguide and/or in the vicinity of a pixel waveguide. A waveguide directing excitation energy towards a pixel, such as a bus waveguide, may couple with a resonant structure through a pixel waveguide and the resonant structure may direct excitation energy to a sample well in the pixel. A sample well may be located above the resonant structure at a height that may be adjusted to control the interaction between the resonant structure and the sample well. In some embodiments, multiple excitation energies may be provided to one or more pixels and couple with the resonant structure which resonates at the multiple excitation energies or wavelengths. Any suitable resonant structure may be used, such as a waveguide ring resonator, a photonic crystal cavity resonator, and a waveguide linear resonator. An example of a waveguide linear resonator includes a pair of Bragg reflectors in a pixel waveguide that form a resonant cavity between the pair of reflectors. In some embodiments, a resonant structure may be a plasmonic resonant structure, such as a plasmonic ring resonator or a photonic crystal cavity.

In some embodiments, a resonant structure may be included in a pixel waveguide associated with a pixel of the integrated device. Such a resonant structure may comprise a plurality of reflectors within the pixel waveguide and allow excitation energy to resonate within a localized region of the pixel waveguide. By positioning a sample well in proximity to the localized region formed by the resonant structure, excitation energy may be directed into the sample well. In some embodiments, a layer may separate the resonant structure from the sample well. For example, a dielectric layer may be formed in the integrated device between the sample well layer and the resonant structure. Additionally or alternatively, a ring resonator may be formed in proximity to the pixel waveguide and excitation energy from a bus waveguide may couple to the ring resonator through the pixel waveguide. A sample well may be positioned in the vicinity of the ring resonator such that excitation energy from the ring resonator couples to the sample well. In some embodiments, a waveguide ring resonator is configured near the sample well such that the concentrated excitation energy is positioned directly adjacent the base of the sample well.

Examples of resonant structures are illustrated in FIGS. 6-1 to 6-4. An example of a linear waveguide resonator is illustrated in FIG. 6-1 where a waveguide 6-104 is configured to propagate excitation light and reflectors are positioned to create a region of the waveguide that forms a resonant cavity 6-136. The reflectors are positioned in one or more pairs, such as reflectors 6-132 and 6-134, such that the resonant cavity 6-136 forms between the one or more pairs. FIG. 6-1 illustrates an exemplary location of a sample well 6-108 with respect to the resonant cavity 6-136. The sample well may be positioned in another layer separate from the layer containing the waveguide 6-104 and reflectors 6-132 and 6-134. An example of a ring resonator is shown with reference to FIG. 6-2 where a waveguide 6-204 is positioned in proximity to a ring resonator 6-226. As excitation energy propagates through the waveguide 6-204, as indicated by the arrow shown in FIG. 6-2, a portion of excitation energy may be received by the ring resonator 6-226. The distance between the waveguide and the ring resonator may be designed to couple a specific excitation wavelength into the ring resonator and/or a certain amount of excitation energy. A sample well may be positioned with respect to the ring resonator such that the ring resonator couples to the sample well to provide excitation energy into an excitation region of the sample well. FIG. 6-2 illustrates an exemplary position of a sample well at region 6-208 where the sample well is located in a separate layer of an integrated device. In some embodiments, plasmonic ring resonators may be formed in an integrated device to couple excitation energy to one or more sample wells. Such plasmonic ring resonators may be positioned to couple with a bus waveguide and/or pixel waveguide. A sample well may be positioned directly over a portion of a plasmonic ring resonator or in a location adjacent to a plasmonic ring resonator. Non-limiting examples of plasmonic ring resonators are shown with respect to FIGS. 6-3A-F. An exemplary position of a sample well 6-308 adjacent to the plasmonic ring resonator structure shown is FIG. 6-3C. In some embodiments, a resonator structure may include a cavity in a photonic crystal. FIG. 6-4 illustrates an exemplary photonic crystal 6-400 with a cavity such that the cavity acts as a resonator for excitation energy. A sample well may be positioned, such as at location 6-408, with respect to the cavity in a photonic crystal and receive excitation energy.

Figures 5, 6, 7, 7A:
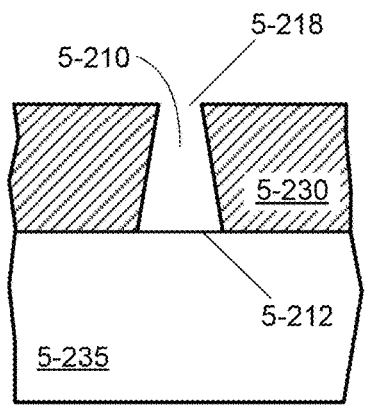

An exemplary portion of a pixel is illustrated in the cross-sectional view of integrated device 7-102 shown in FIG. 7-1A. Integrated device 7-102 includes a sample well layer 7-116 containing at least one sample well 7-108 and a waveguide layer 7-114. The sample well layer may be formed of a metal, a semiconductor, a highly degeneratively-doped semiconductor, an insulator, or graphene. The waveguide layer may include structures formed out of a higher index of refraction than a surrounding material. As an example, waveguide structures may consist of a nitride material and the surrounding material may consist of a dielectric or oxide material. Optionally, a layer 7-118 between the sample well layer 7-116 and the waveguide layer 7-114 may be formed. For example, layer 7-118 may be formed of a dielectric material or oxide material or nitride material. The waveguide layer may contain both a bus waveguide and a pixel waveguide. The pixel waveguide may be formed adjacent to the bus waveguide and be configured to receive excitation energy from the bus waveguide. FIG. 7-1B illustrates an exemplary planar view of a pixel 7-112b along the line A-A' in FIG. 7-1A showing a bus waveguide 7-104b and a pixel waveguide 7-120b. The bus waveguide may be configured to receive and direct one or more excitation energies. In the example configuration shown in FIG. 7-1B, bus waveguide 7-104b is configured to receive excitation energy of a first wavelength, $\lambda_1$, at one end and receive excitation energy of a second wavelength, $\lambda_2$, at another end.

The pixel waveguide 7-120b may include portions or couplers 7-128b and 7-130b configured to couple with bus waveguide 7-104b and receive excitation energy. A sample well located in a sample well layer may be positioned in proximity to the resonant structure 7-126b in order to receive excitation energy from the pixel waveguide 7-120b. The sample well may be located above the linear resonator at a height that may be adjusted to control the interaction between the linear resonator and the sample well. For example, FIG. 7-1B illustrates a sample well position at 7-108b in a sample well layer with respect to the features in the waveguide layer. As excitation light propagates along the bus waveguide 7-104b, a portion of the excitation energy may couple to pixel waveguide 7-120b. In some instances, a coupler may be configured for a particular wavelength of excitation light. When two excitation energies are used, each coupler may be configured to couple with one of the two excitation energies. As an example, in the embodiment shown in FIG. 7-1B, each of the two couplers located on the pixel waveguide may be configured to receive a different excitation light wavelength where coupler 7-128b substantially receives excitation energy of a first wavelength, $\lambda_1$, while coupler 7-130b substantially receives excitation energy of a second wavelength, $\lambda_2$.

A resonant structure may be located within the pixel waveguide, such as resonant structure 7-126b in pixel waveguide 7-120b. Such a resonant structure may comprise a plurality of spatially separated reflectors configured to reflect one or more wavelengths. The reflectors may act to enhance the intensity of excitation energy within a region between at least two reflectors. For example, the reflectors may act as a waveguide linear resonator which includes one or more pairs of distributed Bragg reflectors in a waveguide as illustrated in FIG. 7-1. A pair of reflectors may form a resonant cavity between the pair of reflectors which define the boundaries of the resonant cavity for the linear resonator. In embodiments, where two excitation wavelengths are used, the resonant structure 7-126b may resonant at both wavelengths of excitation energy, a combination of both wavelengths, and/or a multiple of either wavelength. For example, resonant structure 7-126b may be configured to resonant at both wavelengths $\lambda_1$ and $\lambda_2$. The excitation energy at wavelengths $\lambda_1$ and $\lambda_2$ may transfer to the sample well.

Beam dumps 7-122b and 7-124b are positioned with respect to the pixel waveguide 7-120b to absorb excitation light and/or redirect excitation light away from pixel 7-112b, one or more sensors, and/or the integrated device. Beam blockers may be configured to reduce excitation energy of one or more wavelengths from propagating to the sensors in order to enhance detection of emission energy received by the sensors. A non-limiting example of a beam dump is an amorphous siliconplug configured to absorb light that is transmitted through an end of the pixel waveguide. Any suitable material that absorbs excitation light may be used as a beam blocker. There may be at least one beam blocker placed at each end of a waveguide located in a pixel to absorb excitation light from the waveguide. In some embodiments, a beam dump may be configured to redirect or absorb excitation light of a particular wavelength. When two excitation energies are used, one beam dump may be configured to absorb and/or redirect excitation energy of one wavelength while the other beam dump absorbs and/or redirects excitation energy of the other wavelength. In the example shown in FIG. 7-1B, beam dump 7-122b may be configured to substantially absorb or redirect excitation light of the first wavelength, $\lambda_1$, while beam dump 7-124b substantially absorbs or redirects excitation light of the second wavelength, $\lambda_2$.

In some embodiments, the resonant structure is separate from the pixel waveguide and is configured to couple with the pixel waveguide. An example of such a resonant structure may include a ring resonator located within the waveguide layer and separate from the pixel waveguide. A ring resonator is positioned next to a pixel waveguide which is positioned close to the bus waveguide. The pixel waveguide, which may be referred to as a waveguide coupler, couples excitation energy to the ring resonator. The ring resonator resonates one or more wavelengths and transfers the excitation energy at these wavelengths to the sample well. A sample well may be positioned within the sample well layer and in proximity to the ring resonator such that the ring resonator can couple excitation energy into the sample well. The sample well may be formed directly above and on top of the ring resonator at a height adjusted to control the interaction between the resonator and the sample well.

Figures 1A, 7:
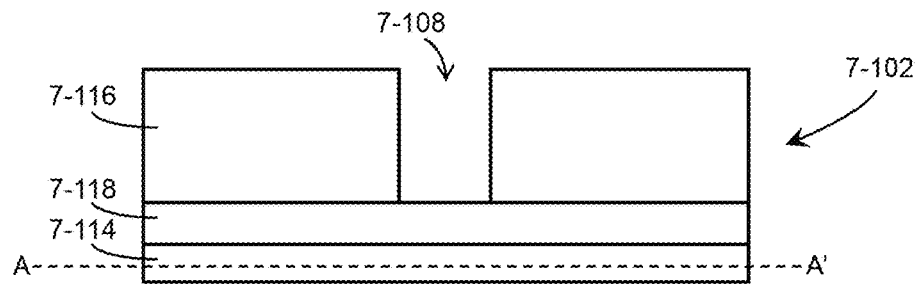
Figures 1B, 7:
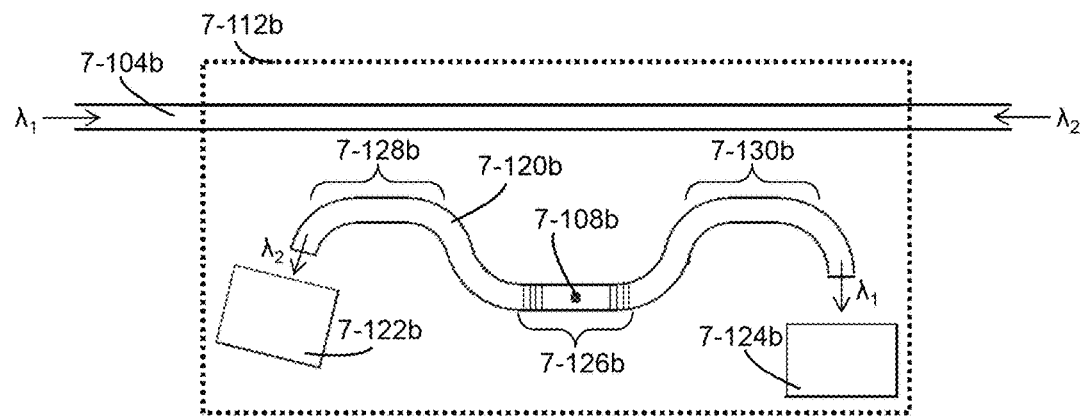
Figures 1C, 7:
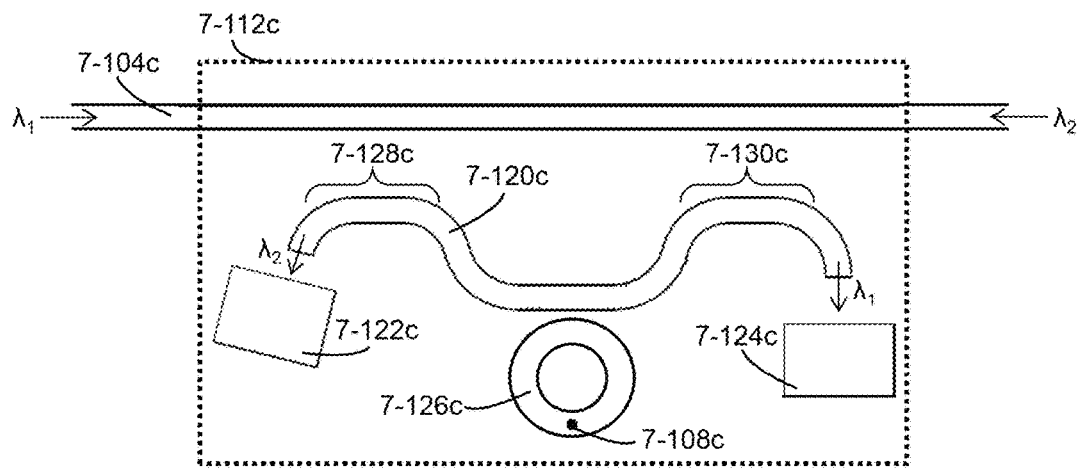

FIG. 7-1C illustrates an exemplary embodiment of a pixel 7-112c having a pixel waveguide 7-120c and a ring resonator 7-126c. Pixel waveguide 7-120c has two portions 7-128c and 7-130c that act as couplers to bus waveguide 7-104c. As excitation light propagates along the bus waveguide 7-104c, a portion of the excitation energy may couple to pixel waveguide 7-120c and the ring resonator couples to the pixel waveguide to receive excitation energy. A sample well located in a sample well layer and positioned at location 7-108c with respect to other features in the waveguide layer may be configured to receive excitation energy from the ring resonator 7-126c. Beam dumps configured to absorb and/or redirect excitation light may be located at the ends of the pixel waveguide. For example, pixel 7-112c includes beam dumps 7-122c and 7-124c on either end of pixel waveguide 7-120c. In some embodiments, the bus waveguide 7-104c may be configured to receive excitation light of one wavelength, $\lambda_1$, at one end and receive excitation energy of a second wavelength, $\lambda_2$, at another end. Coupler 7-128c may be configured to couple excitation energy of the first wavelength, $\lambda_1$, while coupler 7-130c is configured to couple excitation of the second wavelength, $\lambda_2$. The two excitation energies may couple to ring resonator 7-126c. The ring resonator may be configured to resonate at both excitation wavelengths, a combination of the two wavelengths, and or a multiple of either wavelength.

Figures 1D, 7:
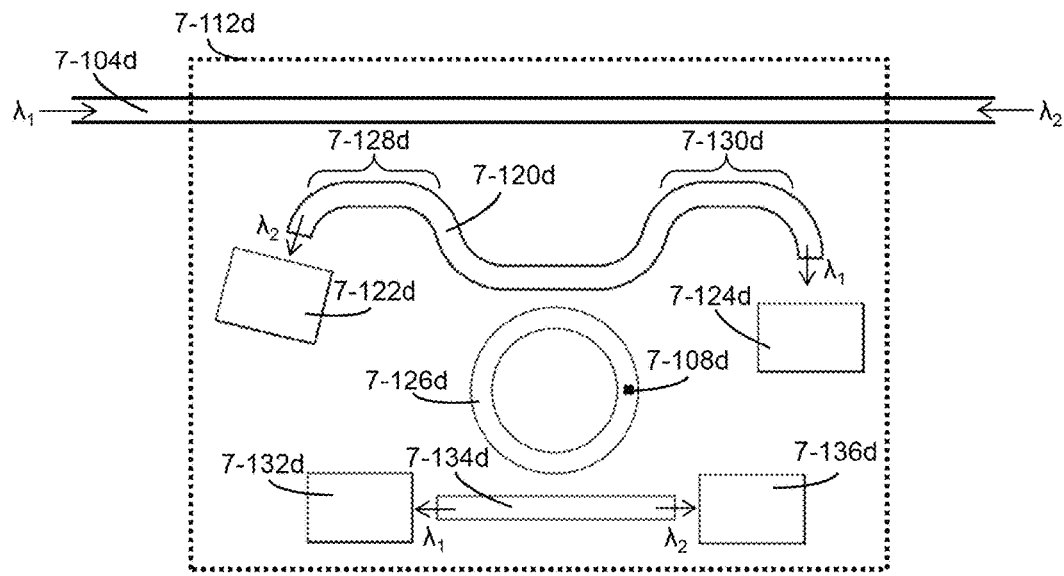
Figures 2A, 7:
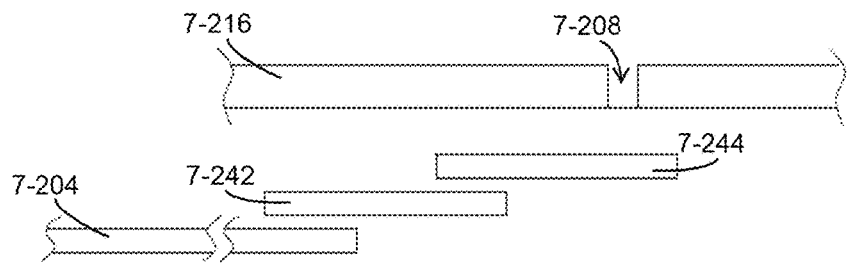
Figures 2B, 7:
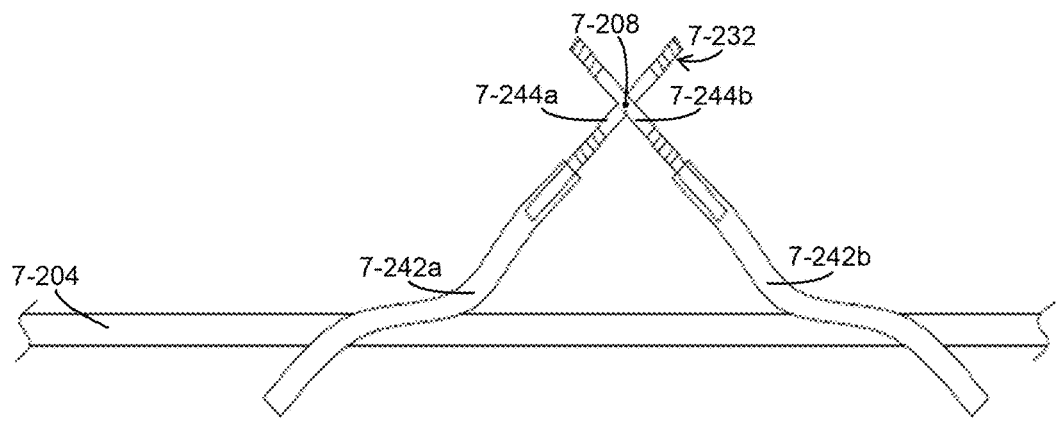
Figures 1A, 8:
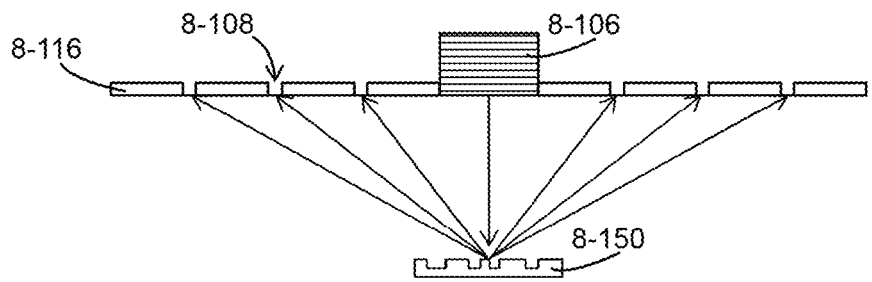
Figures 1B, 8:
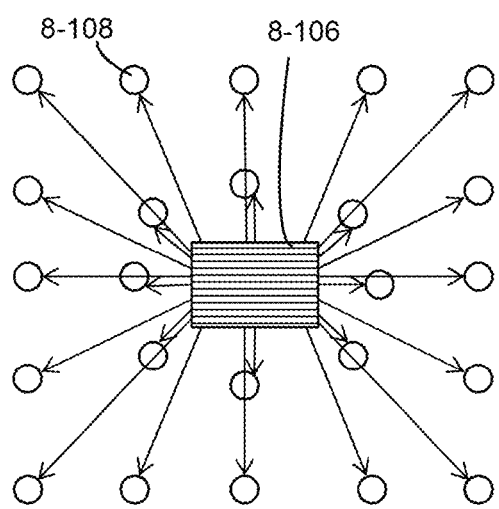

In some embodiments, an additional waveguide may be located within a pixel region to allow a pathway for excitation light that is not directed to a sample well to be redirected to the sample well. The additional waveguide is positioned to couple with a ring resonator and may be capable of propagating multiple excitation wavelengths. In such embodiments, a sample well may be positioned above the ring resonator between the waveguide that couples to the bus waveguide and the additional waveguide. At least one beam blocker is positioned on either end of this additional waveguide in order to absorb excitation energy from being directed to other areas of the integrated device, such as the sensors. Such a waveguide may be made of any suitable material as the other waveguide and resonator structures. FIG. 7-1D illustrates an exemplary arrangement of a pixel region 7-112d having a second waveguide 7-134d that couples to a ring resonator 7-126d. Excitation energy is delivered to the pixel region 7-112d by propagating along bus waveguide 7-104d and couples to pixel waveguide 7-120d. Ring resonator 7-126d receives excitation energy from pixel waveguide 7-120d and a sample well is located in a sample well layer at position 7-108d to receive excitation energy from the ring resonator 7-126d. A portion of excitation energy may remain in the ring resonator and couple to waveguide 7-134d which is configured to redirect the excitation energy towards the ring resonator. The waveguide 7-134d may transfer excitation energy away from the pixel by directed the excitation energy towards one or more beam dumps. In the example shown in FIG. 7-1D, beam dumps 7-132d and 7-136d are located on each side of waveguide 7-134d and are configured to absorb and/or redirect excitation energy.

An integrated device may include a plurality of waveguides at different levels within the integrated device. The plurality of waveguides at different levels within the integrated device may be configured to direct excitation light of one or more wavelengths to the vicinity of a sample well located in a pixel. A first waveguide may couple with an excitation source and act as a bus waveguide, carrying excitation light to a plurality of pixels. One or more waveguides located within a pixel region may couple with the first waveguide and direct a portion of excitation energy towards a sample well in the pixel. Waveguides may couple evanescently with one another or through other coupling techniques, such as by using a multimode interference coupler. A portion of excitation energy from the first waveguide may be directed to a pixel through an additional waveguide while excitation energy within the first waveguide may propagate along the first waveguide to couple with other components in other pixels.

A portion of the excitation light from the first waveguide may couple to a second waveguide located within a pixel. The second waveguide may be located in a separate layer than the first waveguide. For example, the second waveguide may be located between the first waveguide and a sample well layer containing one or more sample wells. In some embodiments, a third waveguide located within the pixel may couple with the second waveguide to direct a portion of the excitation energy from the second waveguide towards the sample well in a pixel. A configuration with multiple waveguides in several layers may provide flexibility in the waveguide profile for each element and isolation of the separate layers. Coupling between waveguides may occur through evanescent couplers where waveguides overlap at non-orthogonal, non-parallel angles. The positioning of the waveguides and overlap between waveguides may provide tolerance in the coupling between the waveguide when there are slight shifts or deviations from the positioning of the waveguides.

An example of a multiple layer waveguide configuration is illustrated in the cross-sectional view shown in FIG. 7-2A. Sample well layer 7-216 includes a sample well 7-208. A first waveguide or optical bus 7-204 is configured to deliver excitation energy towards the pixel region containing sample well 7-208. A second waveguide 7-242 located between the first waveguide 7-204 and the sample well layer 7-216 is positioned to couple a portion of the excitation energy from the first waveguide 7-204 to the second waveguide 7-242 and act to direct the excitation energy towards the sample well 7-208. Additionally, a third waveguide, such as 7-244 in FIG. 7-2A, positioned between the second waveguide 7-242 and the sample well layer 7-216 may couple excitation energy towards the sample well 7-208.

In some embodiments, a multiple layer waveguide configuration may include a resonator, such as a linear waveguide resonator on one or more of the waveguides located within a pixel region. As shown in the planar view of FIG. 7-2B, a linear waveguide resonator may be included in one of the waveguides that directs excitation energy from a bus waveguide 7-204 to a sample well located above position 7-208. In such an example, waveguides 7-242a and 7-242b couple excitation energy from bus waveguide 7-204 to waveguides 7-244a and 7-244b, where waveguide 7-242a couples to waveguide 7-244a and waveguide 7-242b couples to waveguide 7-244b. Both waveguides 7-244a and 7-244b have a linear waveguide resonator comprised of at least one pair of reflectors, such as reflectors 7-232 of waveguide 7-244a. The linear waveguide resonators of waveguides 7-244a and 7-244b overlap. In some embodiments, the two linear waveguide resonators may overlap orthogonally and form a dual-resonator that allows spatially orthogonal resonances. Such a dual-resonator may form a dual-resonant cavity with an enhanced field of excitation energy in the region of overlap between the two waveguides that limits the size of the cavity. The position of the sample well 7-208 located in a separate sample well layer is located between the two linear resonators where excitation energy may be localized in order to couple excitation energy from the dual-resonator to the sample well.

In some embodiments, a diffractive optical element may be used to direct excitation light from an excitation source to a sub-array of sample wells, each sample well associated with a pixel in the sub-array. In this way, excitation sources may be located periodically throughout the array of pixels. For example, a "unit cell" of the array of pixels may include one excitation source, a diffractive optical element and a plurality of sample wells. The unit cell may be tiled to form the pixelated array. In some embodiments, the excitation source may emit excitation light in the direction of one or more sensors and the diffractive optical element may reflectively diffract the excitation light back towards the excitation source, but with different lateral trajectories. In this way, the excitation light is converted into a plurality of excitation light beams, each of the plurality of excitation light beams being associated with a respective sample well.

Figures 5, 6, 7, 7B:
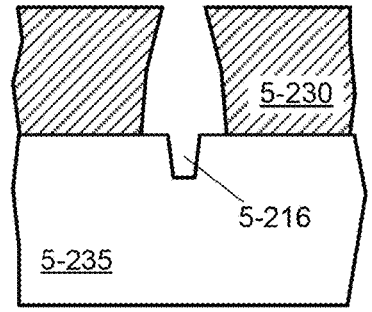
Figures 5, 6, 7, 7C:
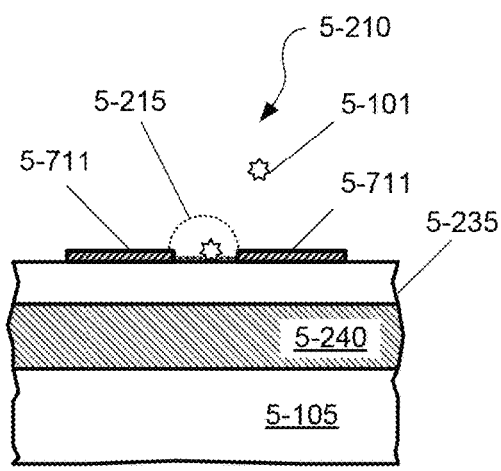
Figures 5, 6, 7, 7D:
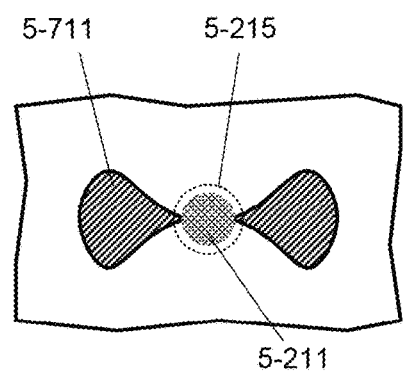
Figures 5, 6, 7, 7E:
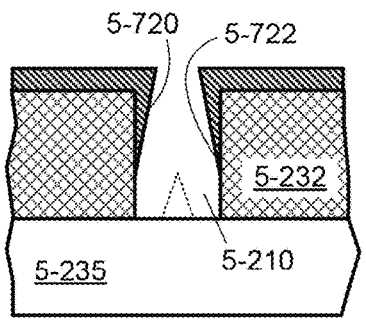
Figures 5, 6, 7, 7F:
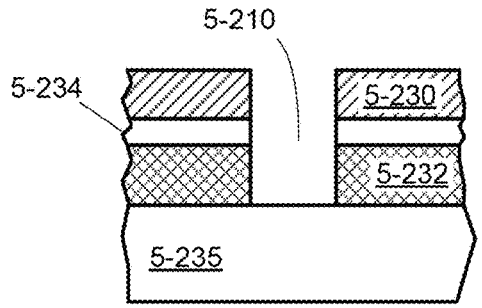
Figures 5, 6, 7, 8:
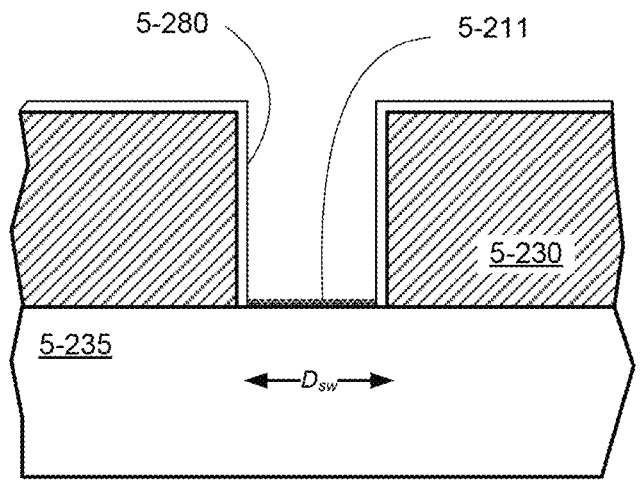

FIGS. 8-1A and 8-1B illustrate a non-limiting exemplary implementation of using a diffractive optical element to direct excitation light towards a plurality of sample wells. FIG. 8-1A is a cross-sectional schematic showing an excitation source 8-106 that provides excitation light to a plurality of pixels in a unit cell. Sample wells, such as sample well 8-108, are located in sample well layer 8-116. A diffractive optical element 8-150 is configured to receive excitation light from excitation source and redirect excitation light to the sample wells in the unit cell, as indicated by the arrows. FIG. 8-1B shows a top planar view to show how the sample wells in the unit cell, including sample well 8-108 that are positioned to receive the excitation light from the excitation source 8-106 that has been redirected by the diffractive optical element located beneath the excitation source 8-106.

Coupling of energy from an excitation source to a sample well may be improved or affected by forming excitation-coupling structures within and/or adjacent a sample well. Excitation-coupling structures may comprise micro- or nano-scale structures fabricated around a sample well in some embodiments, or may comprise structures or particles formed at a sample well in some embodiments. Excitation-coupling structures may affect radiative excitation of a sample in some implementations, and may affect non-radiative excitation of a sample in some implementations. In various embodiments, radiative excitation-coupling structures may increase an intensity of excitation energy within an excitation region of a sample well. Non-radiative excitation-coupling structures may improve and/or alter non-radiative energy-transfer pathways from an excitation source (which may be radiative or non-radiative) to a sample.

E. Radiative Plasmonic Excitation-Coupling Structures

There are a number of different types of radiative, excitation-coupling structures that may be used to affect coupling of excitation energy from an excitation source to an excitation region within a sample well. Some radiative coupling structures may be formed of a conductor (e.g., include a metal layer), and support surface plasmon oscillations that locally affect the excitation energy (e.g., locally alter an electromagnetic field). In some cases, surface-plasmon structures may enhance the excitation energy within an excitation region of the sample well by a factor of two or more. Some radiative coupling structures may alter the phase and/or amplitude of an excitation field to enhance excitation energy within a sample well. Various embodiments of radiative excitation-coupling structures are described in this section.

Figures 5, 6, 7, 8, 9, 9A:
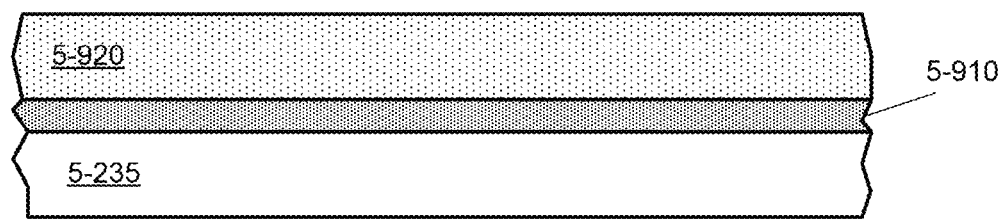

FIG. 9-1A depicts just one example of a surface-plasmon structure 9-120 that may be used to enhance coupling of excitation energy into a sample well. The drawing depicts a plan view of a region around a surface-plasmon structure 9-120, and represents results of a numerical simulation of electric field intensity around the structure. The drawing depicts a surface-plasmon structure comprising three triangular features having sharp apexes that are located in close proximity to a sample well (not shown). According to some embodiments, a surface-plasmon structure may comprise a metal or conductor (e.g., a patterned thin film of any one or combination of the following metals or metal alloys: Al, Au, Ag, Ti, TiN). A thickness of the film may be between approximately 10 nm and approximately 100 nm in some embodiments, though other thicknesses may be used in other embodiments. A surface-plasmon structure, in some embodiments, may include sharp features 9-110 located in close proximity to a sample well (e.g., within about 100 nm).

FIG. 9-1B depicts a cross-section, elevation view of the surface-plasmon structure of FIG. 9-1A, taken at the dashed line. The simulation shows a localized, high-intensity region 5-505 of the excitation energy adjacent an apex of a triangle of the surface-plasmon structure. For this simulation, the surface-plasmon structure 9-120 was located on a dielectric layer 9-135 (silicon dioxide) above a waveguide 9-130. The surface-plasmon structure taps energy from an evanescent field of the waveguide, and enhances the intensity at the sample well.

In some embodiments, enhancement of excitation energy by a surface-plasmon structure may be localized to an extent that a sample well 5-215 is not needed. For example, if a high-intensity region 5-505 is formed having a diameter of approximately 100 nm with a peak intensity value greater than about 80% of the intensity outside the region, then a deep sample well may not be needed. Only samples within the high-intensity region 5-505 would contribute appreciable emission for purposes of detection.

When an incident electromagnetic field interacts with a surface-plasmon structure, surface-wave currents are generated in the structure. The shape of the structure can affect the intensity and distribution of these surface-plasmons. These localized currents can interact with and significantly alter and intensify the incident electromagnetic field in the immediate vicinity of the surface-plasmon structure, e.g., as depicted by the high-intensity region 5-505 in FIG. 9-1B. In some embodiments, an emitter (e.g., a fluorescing tag) that emits radiation near a surface-plasmon structure can have its emission altered by the structure, so as to alter a far-field radiation pattern from the emitter.

Another embodiment of a surface-plasmon structure 9-122 is depicted in the plan view of FIG. 9-1C. The illustrated bow-tie structure comprises two triangular metallic structures located adjacent a sample well 5-210. The structures may be patterned below a sample well, for example, and/or adjacent an excitation region of the sample well. There may be a gap 9-127 between the sample well and sharp features 9-125 of the surface-plasmon structure, in some implementations. The gap 9-127 may be between approximately 10 nm and approximately 200 nm, according to some embodiments. In some implementations, the gap 9-127 may be between approximately 10 nm and approximately 100 nm. The sharp features 9-125 may comprise a point or sharp bend in an edge of the surface-plasmon structure, as depicted in the drawing. The sharp features may have any suitable shape. In some embodiments a bend radius of a sharp feature 9-125 may be less than approximately five wavelengths associated with the incident excitation energy. In some embodiments a bend radius of a sharp feature 9-125 may be less than approximately two wavelengths associated with the incident excitation energy. In some embodiments a bend radius of a sharp feature 9-125 may be less than approximately five wavelengths associated with a surface-plasmon wave that is excited by the incident excitation energy. In some embodiments a bend radius of a sharp feature 9-125 may be less than approximately two wavelengths associated with a surface-plasmon wave that is excited by the incident excitation energy.

Figures 1A, 9:
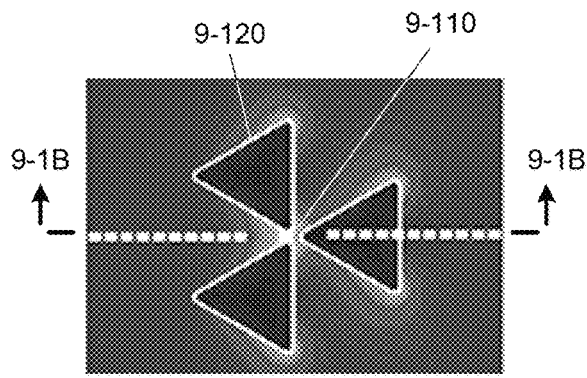
Figures 1B, 9:
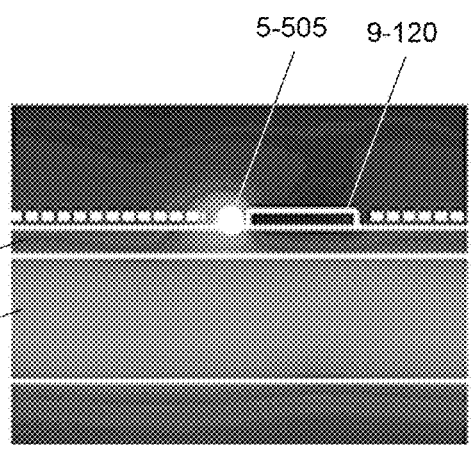
Figures 1C, 9:
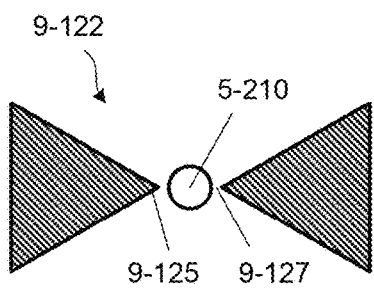
Figures 1D, 9:
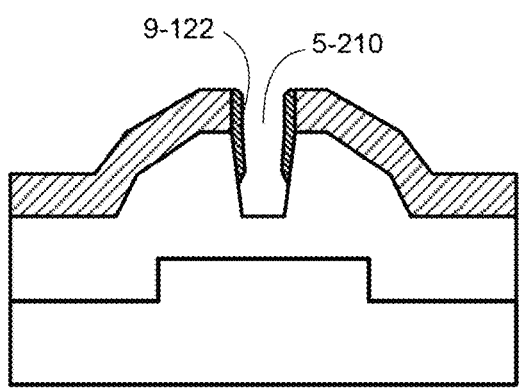
Figures 1E, 9:
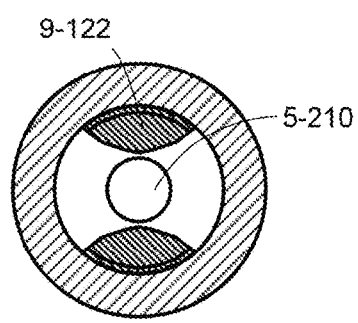
Figures 2A, 9:
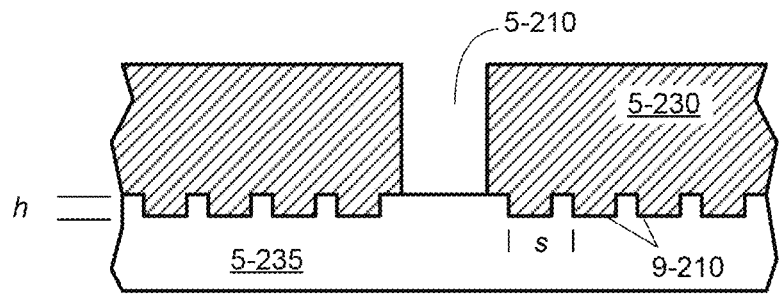
Figures 2B, 9:
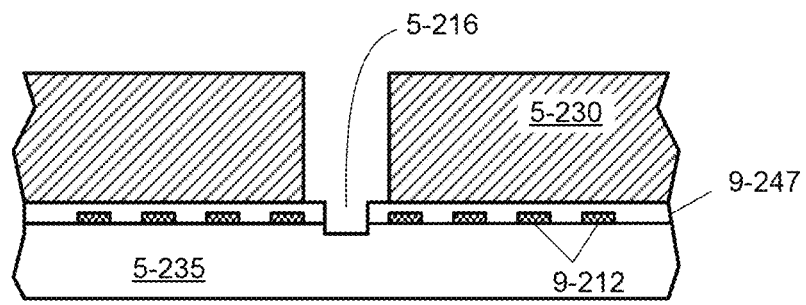

According to some embodiments, surface-plasmon structures 9-122 may be patterned within a sample well 5-210 as illustrated in the elevation view of FIG. 9-1D. In some embodiments, a surface-plasmon structure within a sample well may comprise one or more fingers (e.g., metallic fingers) patterned onto sidewalls of the sample well, as depicted in the drawing. FIG. 9-1E depicts a plan view of the sample well 5-210 showing the surface-plasmon structures 9-122 formed on sidewalls within the sample well. In some embodiments, the lower ends of these surface-plasmon structures 9-122 form sharp features or bends where the electromagnetic field will be enhanced. The surface-plasmon structures 9-122 may, or may not, extend to a base of the sample well.

In some embodiments, the surface-plasmon structures 9-122 may be arranged to affect the polarization of the excitation energy and/or emitted radiation from the sample well. For example, a pattern as depicted in FIG. 9-1E may be used to affect a preferred orientation of linear or elliptical excitation polarization and/or a preferred orientation of linear or elliptical polarization from an emitter within the sample well.

Surface-plasmon structures may be patterned as shapes other than those depicted in FIG. 9-1A through FIG. 9-1E. For example, surface-plasmon structures may be patterned as regular or periodic structures, as depicted in FIG. 9-2A, according to some embodiments. For example, a surface-plasmon structure may be patterned as an array of protruding features 9-210 on a lower surface of a material 5-230 in which the sample well 5-210 is formed. Periodic surface-plasmon structures may be formed in a regular array, for example, a grating, a grid, a lattice, a circular grating, a spiral grating, an elliptical grating, or any other suitable structure. In some implementations, there may be a substantially uniform spacing s between the protrusions 9-210 of a surface-plasmon structure. In some implementations, the spacing s may have any value between approximately 40 nm and approximately 250 nm. According to some embodiments, the protrusions may have a height h between approximately 20 nm and approximately 100 nm. In some implementations, the spacing s may be non-uniform or may be chirped (having a decreasing value at larger radial distances). In some embodiments, the protrusions 9-210 of a surface-plasmon structure may be patterned as a Fresnel zone plate. According to some embodiments, a surface-plasmon structure of 9-210 may be formed adjacent a transparent layer and/or dielectric layer 5-245.

In some implementations, a surface-plasmon structure 9-212 may be spaced from a material 5-230 in which the sample well is formed as depicted in FIG. 9-2B. For example, there may be an intervening dielectric layer 9-247 between the surface-plasmon structure 9-212 and the material 5-230. According to some embodiments, a surface plasmons structure 9-212 may be located adjacent a divot 5-216 of a sample well, as depicted in the drawing. For example, a surface-plasmon structure 9-212 may be located adjacent sidewalls of a divot 5-216, as depicted in FIG. 9-2B.

Figures 2C, 9:
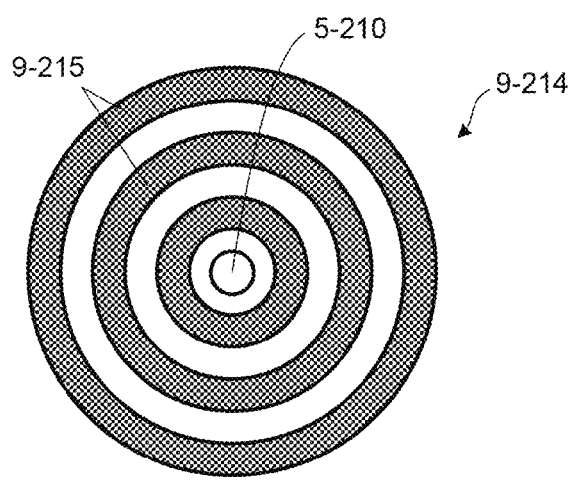

FIG. 9-2C illustrates a surface-plasmon structure 9-214 that is formed as a concentric, circular grating. The structure 9-214 may comprise concentric conducting rings 9-215, according to some embodiments. The rings may be separated by a regular spacing s and have a height h, as described in connection with FIG. 9-2A. According to some embodiments, a sample well 5-210 with an optional divot may be located at a center of the rings. The circular grating may be patterned adjacent a base of the sample well.

A periodicity of a surface-plasmon structure may be selected to form a resonant structure according to some embodiments. For example a spacing s of a surface-plasmon structure may be selected to be approximately one-half wavelength of a surface-plasmon wave that is generated in the structure by the excitation energy. When formed as a resonant structure, a surface-plasmon structure may accumulate and resonate excitation energy along the direction of the periodic surface-plasmon structure. Such a resonant behaviour can intensify electromagnetic energy within a sample well, or adjacent a sample well, as depicted in FIG. 9-2D.

Figures 1A, 13:
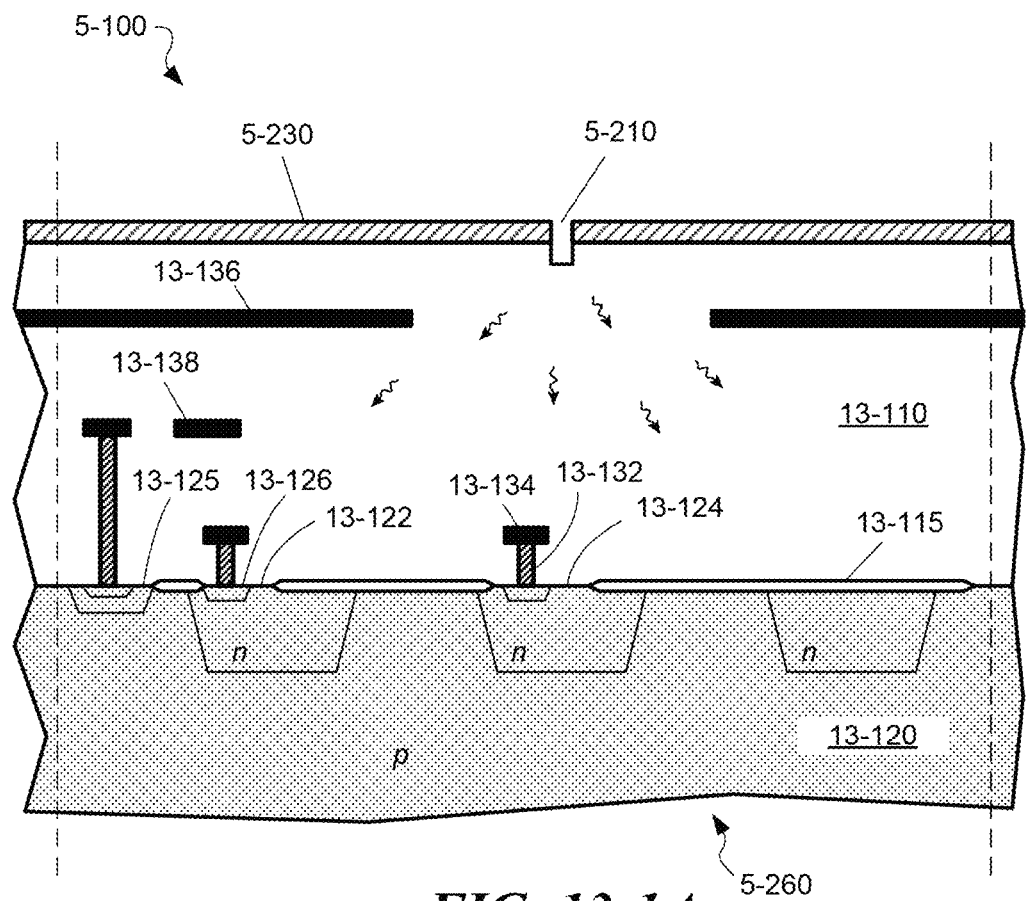
Figures 1B, 13:
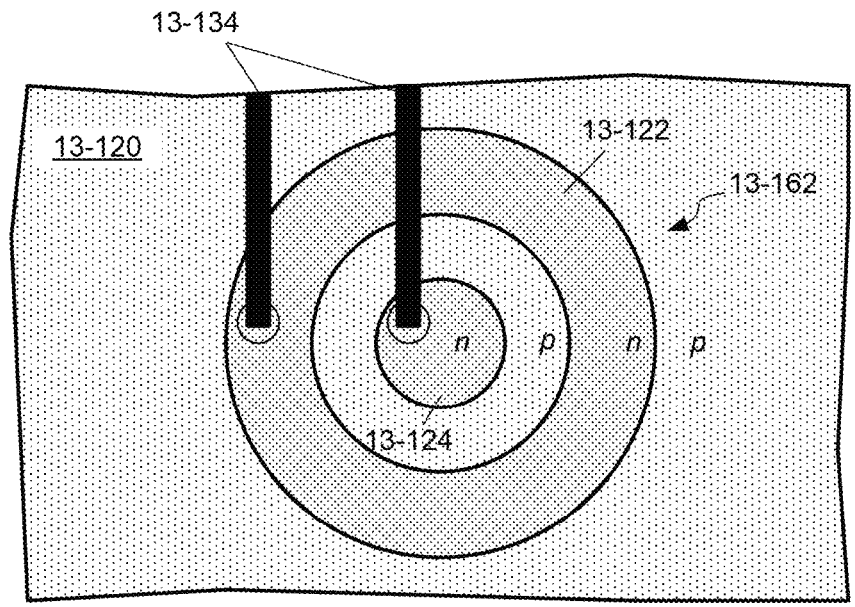
Figures 1C, 13:
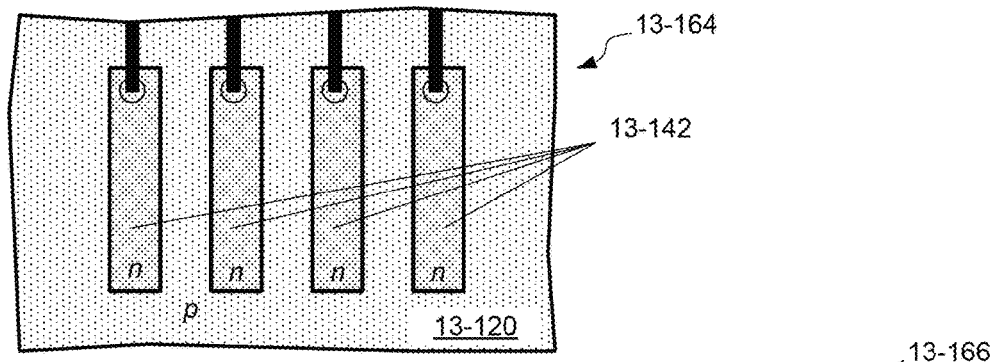
Figures 1D, 13:
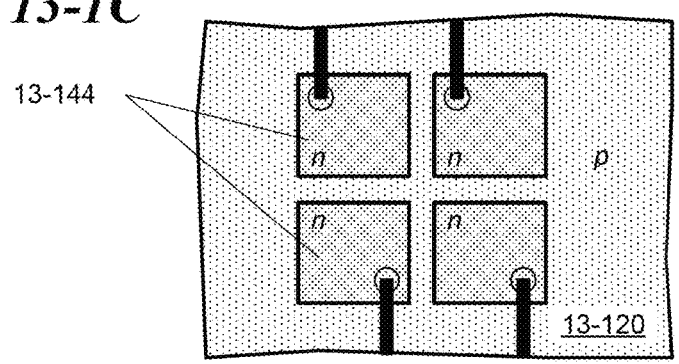
Figures 1E, 13:
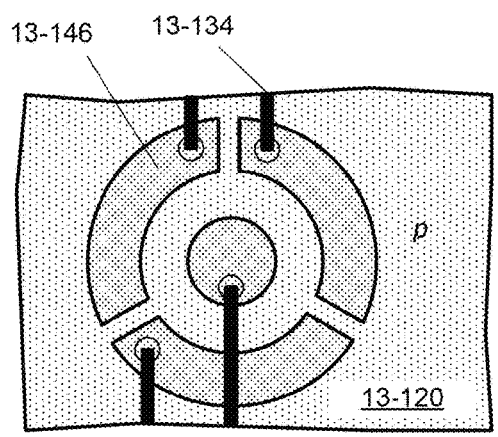
Figures 1F, 13:
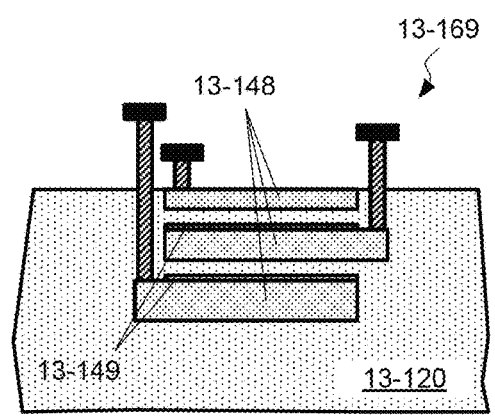
Figures 2A, 13:
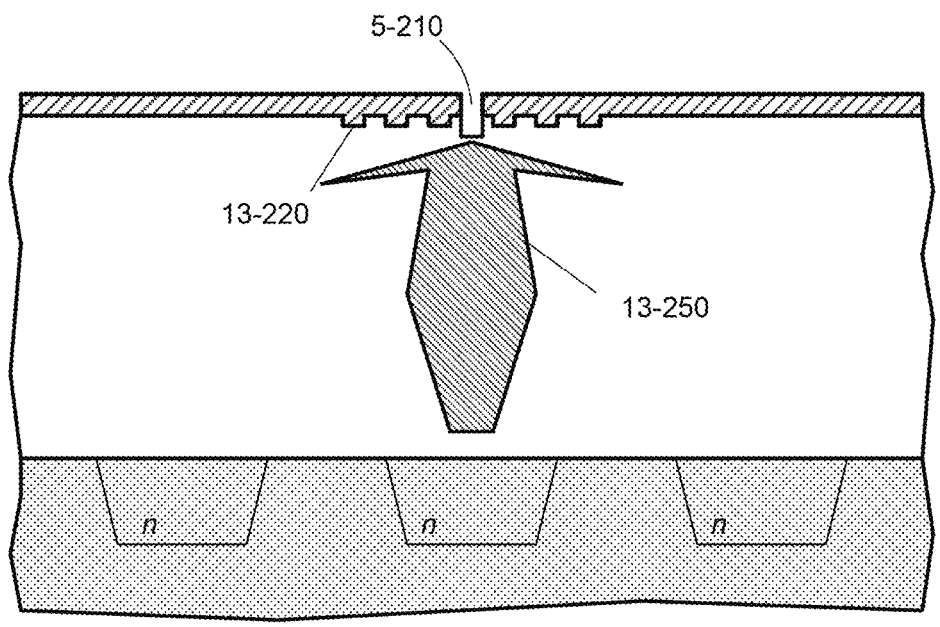
Figures 2B, 13:
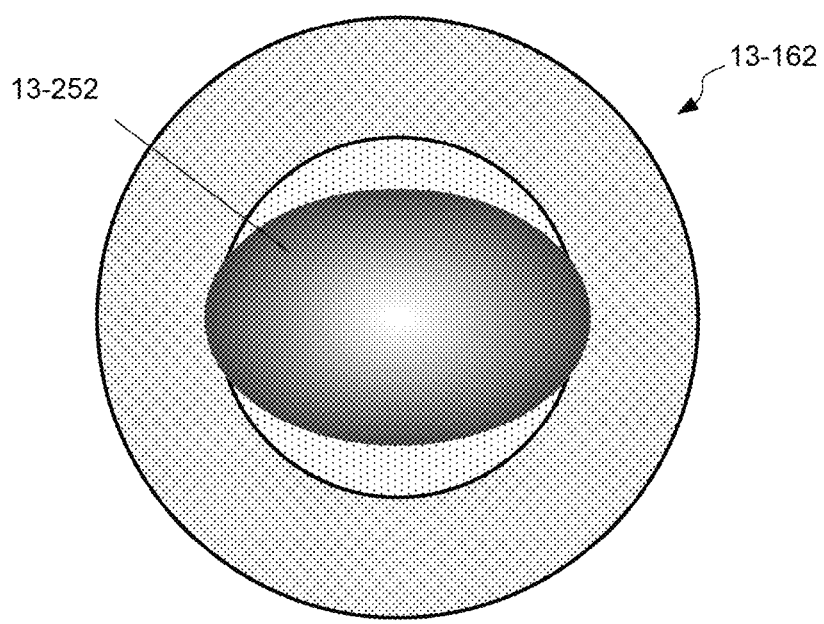
Figures 2C, 13:
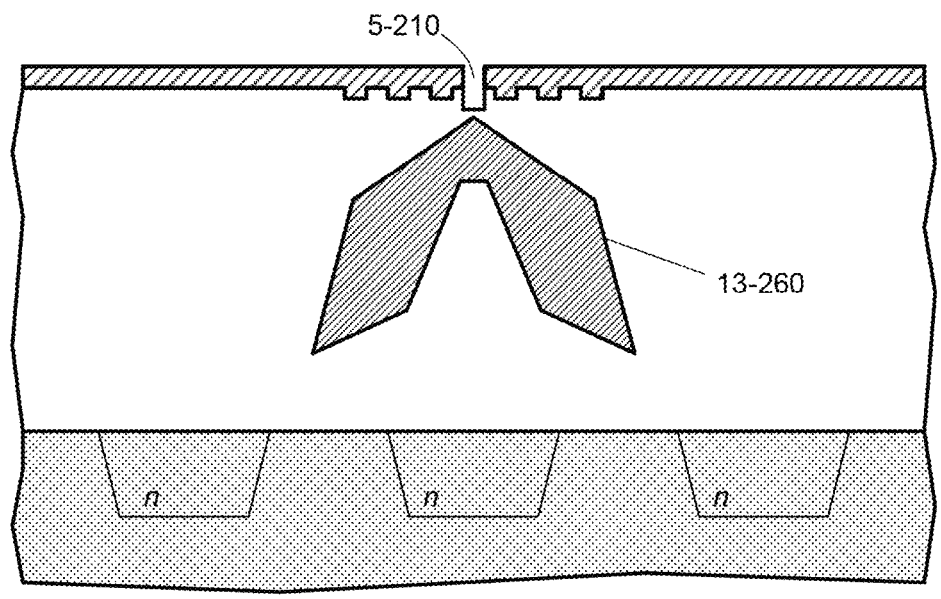
Figures 2D, 13:
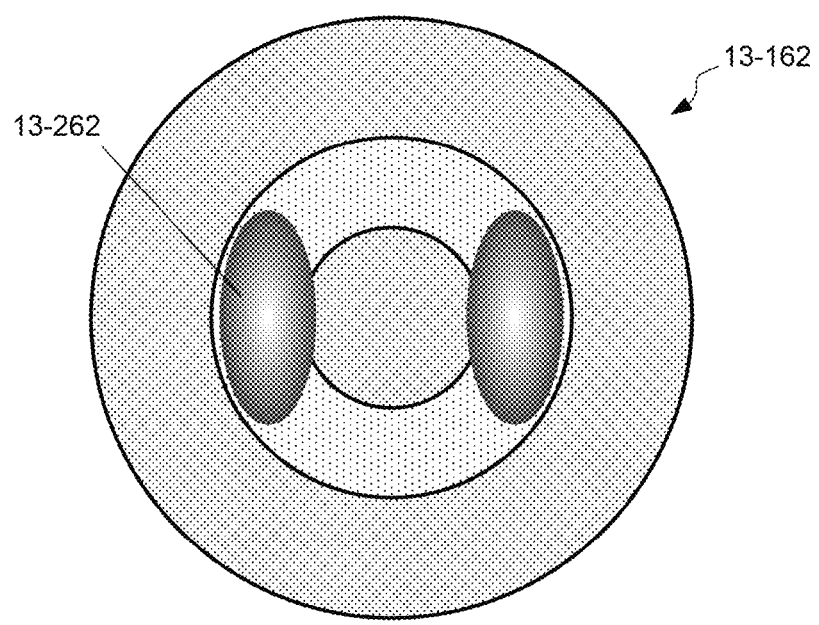

FIG. 9-2D represents numerically simulated electromagnetic field results at the base of the sample well and around a periodic surface-plasmon structure. The surface-plasmon structure 9-216 is located adjacent the material 5-230 in which the sample well is formed, and is adjacent a base of a sample well 5-210. The surface-plasmon structure may be in the form of a grating or circular grating that repeats at regular spacing intervals in regions away from the sample well and outside the simulated region. For example, there may be between three and 50 repeated grating protrusions of the surface-plasmon structure 9-216. A region of high intensity 9-240 can be seen at the base of the sample well 5-210. The intensity within this region has been enhanced by more than a factor of 2 over the surrounding region just below the surface-plasmon structure.

Figures 2E, 13:
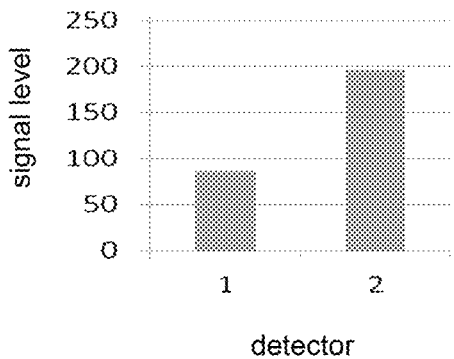
Figures 2F, 13:
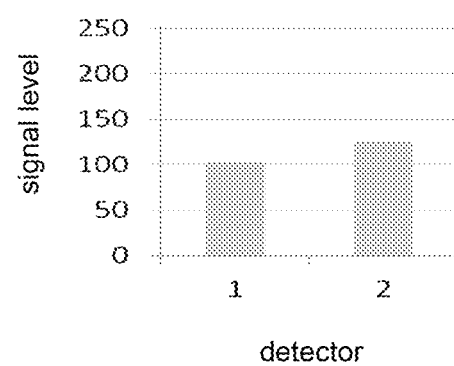
Figures 2G, 13:
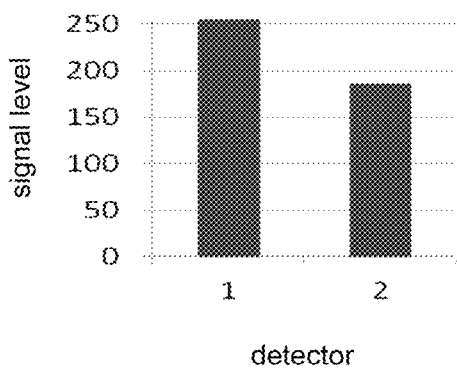
Figures 2H, 13:
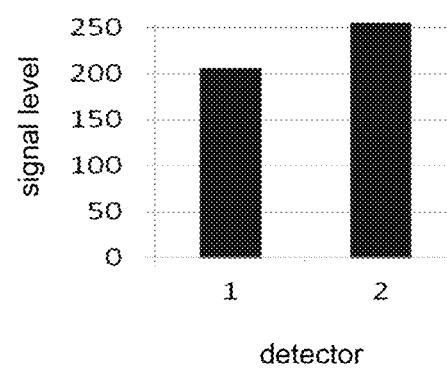
Figures 2I, 13:
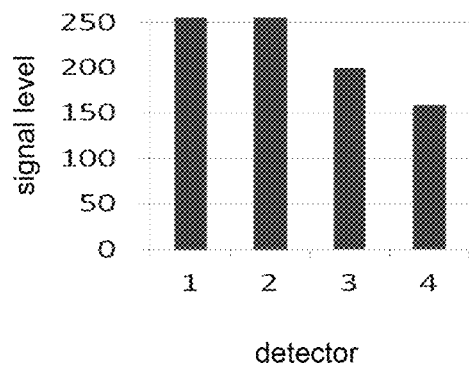

FIG. 9-2E depicts, in elevation view, an alternative embodiment of a resonant surface-plasmon structure 9-218. According to some embodiments, a surface-plasmon structure may be formed as periodic grating or grid patterns, and may be patterned in multiple layers 9-247. A sample well 5-210 may be patterned through the multiple layers 9-247 and within the resonant surface-plasmon structure 9-218, according to some embodiments. In some implementations, a resonant surface-plasmon structure may comprise discrete conductive elements 9-222 is depicted in the plan view of FIG. 9-2F. In some implementations, a resonant surface-plasmon structure may comprise a continuous lattice pattern 9-250, as depicted in FIG. 9-2G. A dielectric filler 9-252 may be located in voids of the conductive material 9-250, and a sample well 5-210 may be located with a void.

Figures 2H, 9:
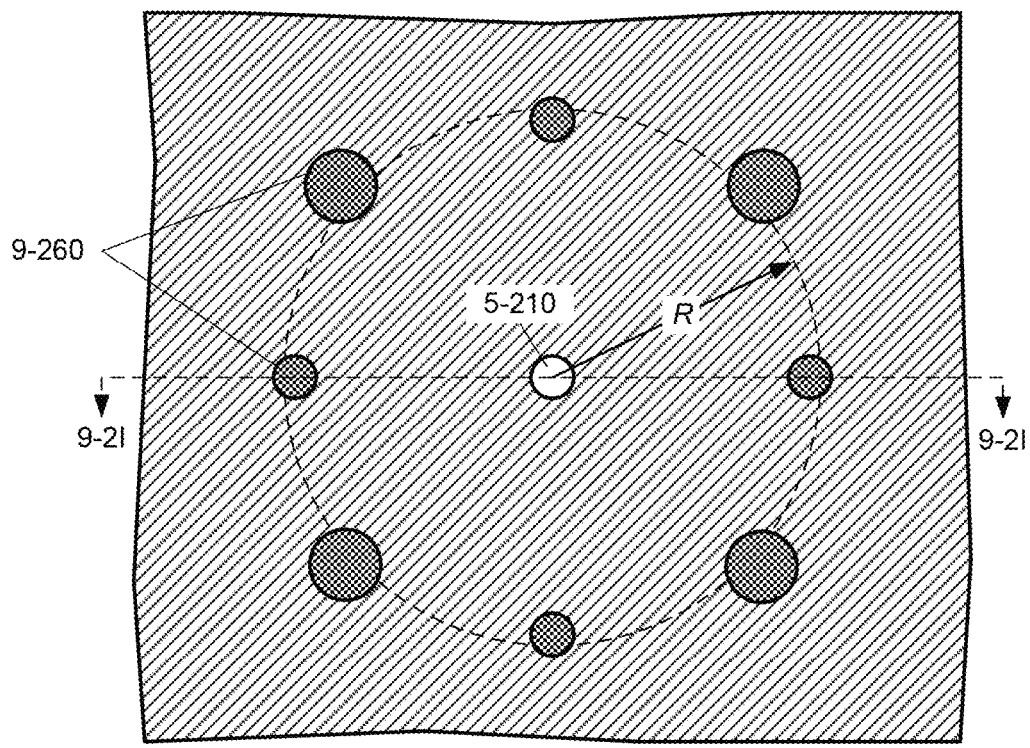
Figures 2I, 9:
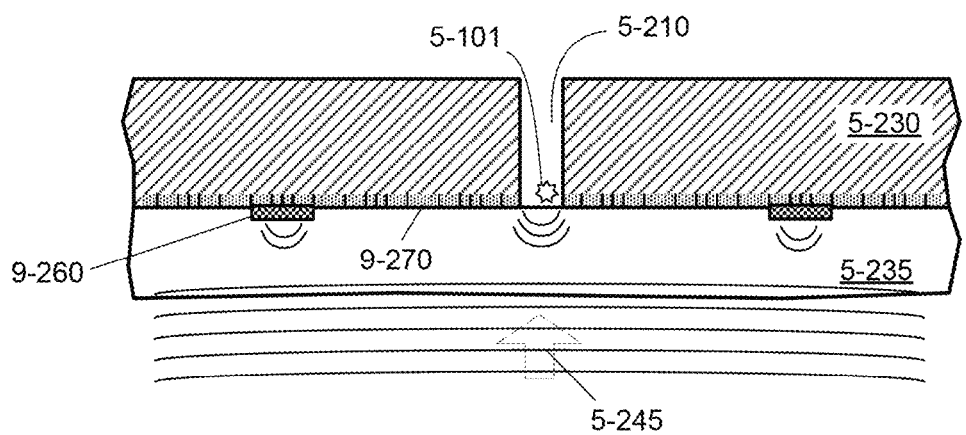
Figures 3A, 9:
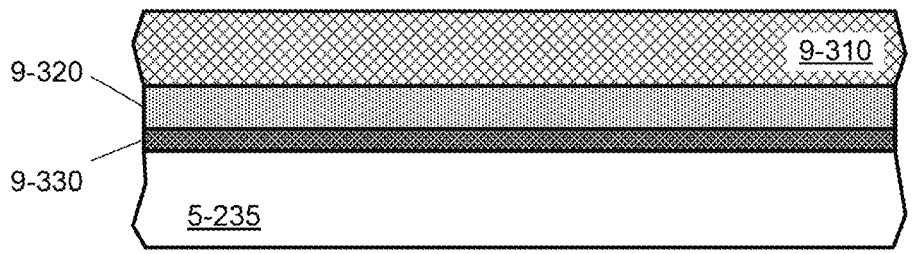
Figures 3B, 9:
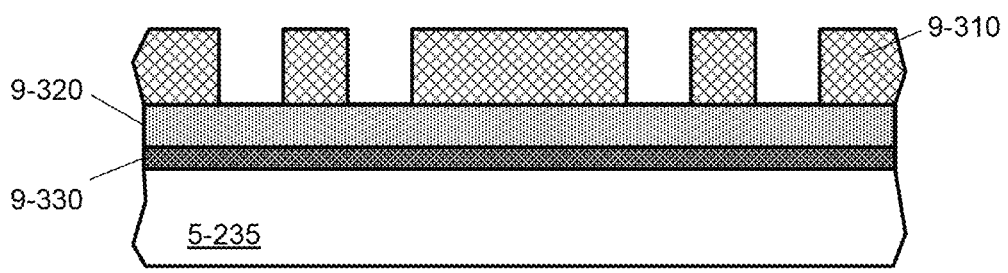
Figures 3C, 9:
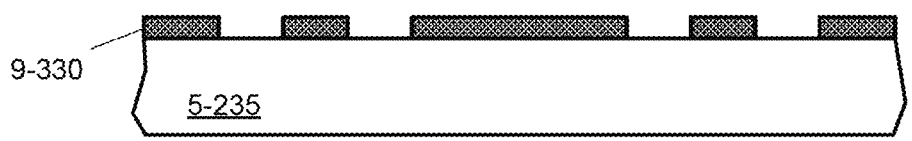
Figures 3D, 9:
Figures 3E, 9:
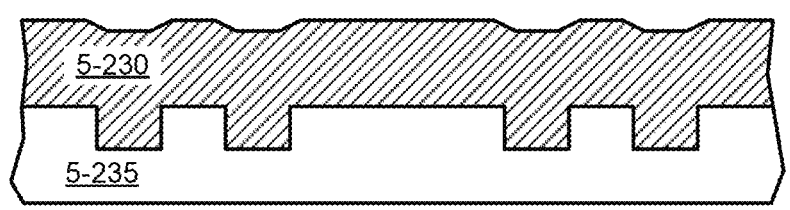

There are a variety of different surface-plasmon structures that may be used to enhance coupling into a sample well or to affect emission from a sample within the sample well. FIG. 9-2H depicts, in plan view, yet an alternative embodiment of the surface-plasmon structure. An elevation view of the structure is depicted in FIG. 9-2I. According to some implementations, a surface-plasmon structure may comprise an array of discs distributed around a sample well 5-210. In some implementations, instead of using conductive discs 9-260, a surface-plasmon structure may comprise a conductive layer through which a distributed pattern of holes is formed. Such a structure may be referred to as a "nano-antenna."

F. Fabrication of Plasmonic Excitation-Coupling Structures

A variety of different processes may be used to pattern surface-plasmon structures adjacent a sample well. FIG. 9-3A through FIG. 9-5E depict structures associated with process steps that may be used to form surface-plasmon structures adjacent to a sample well, according to some embodiments. Referring now to FIG. 9-3A, a process for forming a surface-plasmon structure may comprise forming a resist layer 9-310 on an anti-reflective coating (ARC) 9-320 on a masking layer 9-330. The layers may be disposed on a transparent dielectric layer 5-245, according to some implementations. The resist layer 9-310 may comprise a photoresist or an electron- or ion-beam resist that may be lithographically patterned. The masking layer 9-330 may comprise a hard mask formed of an inorganic material (e.g., silicon or silica nitride, or any other suitable material), according to some embodiments.

Figures 1, 6:
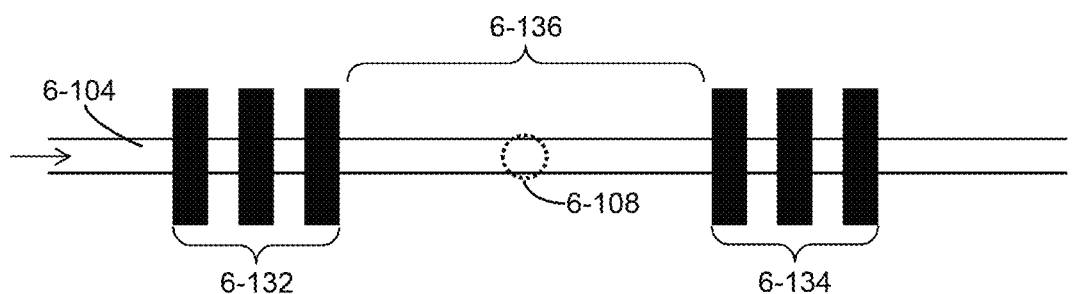
Figures 2, 6:
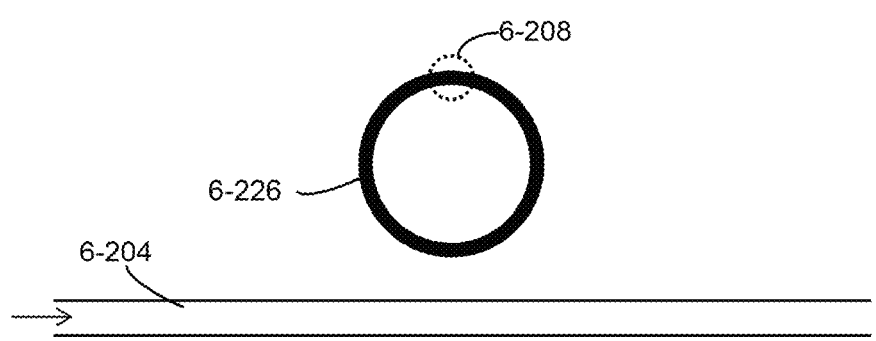
Figures 3A, 6:
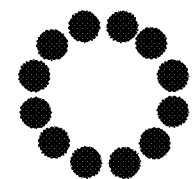
Figures 3B, 6:
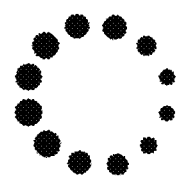
Figures 3C, 6:
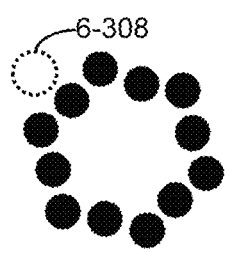
Figures 3D, 6:
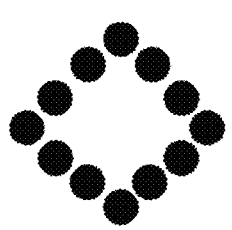

In some implementations, a photolithographic process may be used to pattern the resist 9-310 as depicted in FIG. 9-3B. The selected pattern may comprise a layout of protrusions or holes that will be used to form a desired surface-plasmon structure. After development of the resist 9-310, regions of the ARC will be exposed, and the pattern may be etched into the ARC layer 9-320 and then into the masking layer 9-330. The resist and ARC may be stripped from the substrate, and a resulting structure may appear as shown in FIG. 9-3C. The masking layer 9-330 may then be used as an etch mask, so that the pattern may be transferred into the underlying dielectric layer 5-235 via a selective anisotropic etch, as depicted in FIG. 9-3D.

Figures 3E, 6:
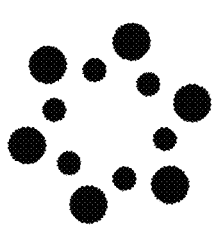
Figures 3F, 6:
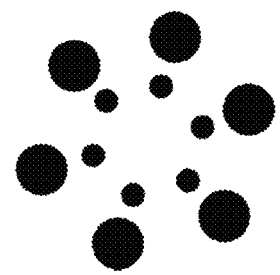
Figures 4, 6:
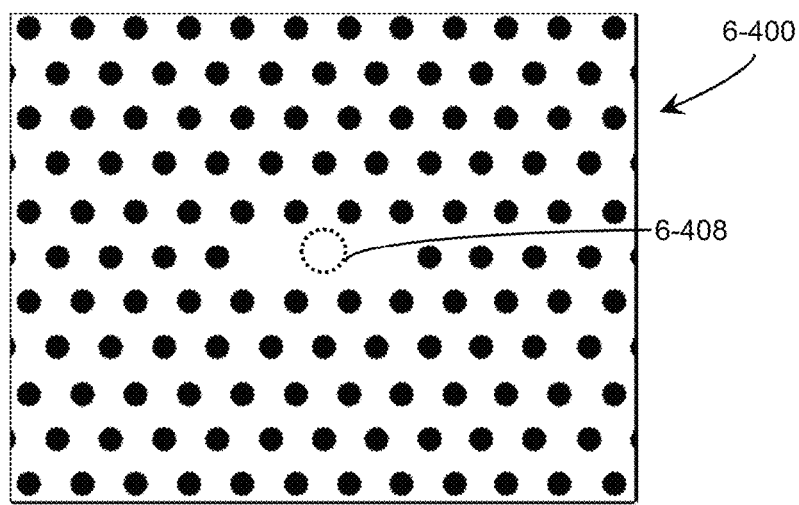

A conductive material 5-230, or a layer of materials comprising a conductor, may then be deposited over the region, as illustrated in FIG. 9-3E. Any suitable conductive material may be used for forming a surface plasmon structure, whether or not it is deposited as a separate layer from the material 5-230. For example, in some cases, a first conductive material may be deposited as a base layer of material 5-230 in which a surface-plasmon structure is formed. Examples of materials that may be used for forming a surface-plasmon structure include, but are not limited to, Au, Al, Ti, TiN, Ag, Cu, and alloys or combination layers thereof.

The material 5-230, or layer of materials, may be deposited by any suitable deposition process, including but not limited to a physical deposition process or a chemical vapor deposition process. In some embodiments, the material 5-230 may have a thickness between approximately 80 nm and approximately 300 nm. In some implementations, the material 5-230 may be planarized (e.g., using a CMP process), though planarization is not necessary. A sample well may be formed in the material 5-230 using any suitable process described herein in connection with fabricating a sample well.

The inventors have recognized that forming a surface-plasmon structure according to the steps shown in FIG. 9-3A through FIG. 9-3E may require accurate alignment of the sample well to the surface-plasmon structure. For example, a surface-plasmon structure comprising a concentric grating, as depicted in FIG. 9-2C, would require accurate alignment of the sample well 5-210 to the center of the surface-plasmon structure 9-214. To avoid fabrication difficulties associated with such accurate alignment, the inventors have developed self-alignment processes that are depicted in FIG. 9-4A through FIG. 9-5E.

Figures 4A, 9:

Referring now to FIG. 9-4A, a process for forming a surface-plasmon structure and sample well that is self-aligned to the surface-plasmon structure may comprise forming a masking layer 9-410 on a transparent dielectric layer 5-235. The masking layer may comprise a hard mask formed of an inorganic material, such as silicon or silica nitride, according to some embodiments. A thickness of the masking layer 9-410 may be approximately equal to a desired height of a sample well 5-210. For example, the thickness of the masking layer may be between approximately 50 nm and approximately 200 nm, according to some embodiments, though other thicknesses may be used in other embodiments.

Figures 4B, 9:
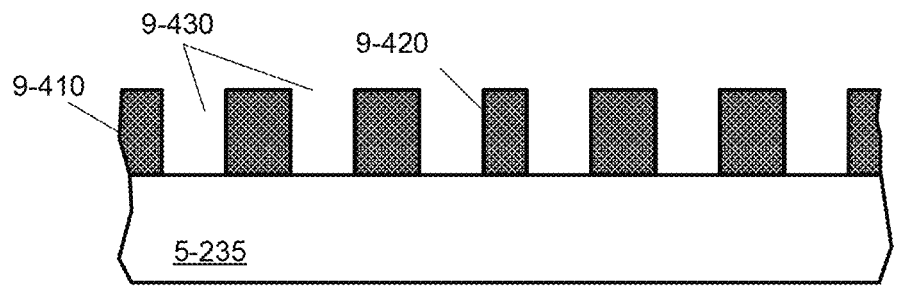

The masking layer 9-410 may be patterned to create voids 9-430 having the desired pattern of a surface-plasmon structure that will be patterned in the dielectric layer 5-235. The patterning of the masking layer 9-410 may be done with any suitable lithography process (e.g., photolithography, electron-beam lithography, ion-beam lithography, EUV lithography, x-ray lithography). The resulting structure may appear as shown in FIG. 9-4B. The structure may include a central pillar 9-420, which will be used subsequently to form the self-aligned sample well.

Figures 4C, 9:
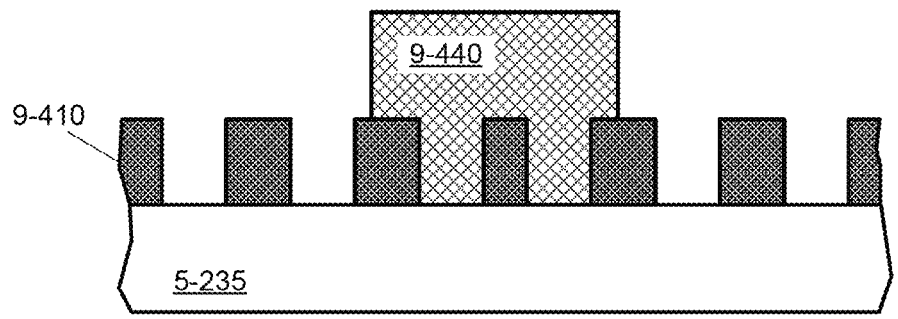

A resist 9-440 (e.g., a photoresist) may then be patterned over the patterned masking layer 9-410, as depicted in FIG. 9-4C. Alignment for patterning the resist 9-440 (e.g., mask to substrate alignment) need not be highly accurate, and only requires the resist 9-440 to cover a central pillar 9-420 and not cover voids 9-430 that will be used to form the surface-plasmon structure.

Figures 4D, 9:
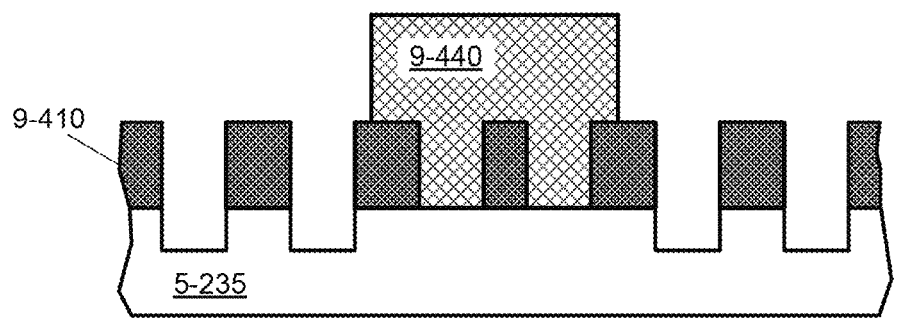
Figures 4E, 9:
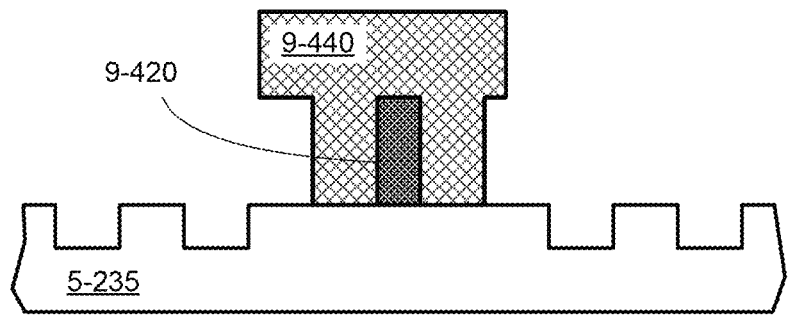
Figures 4F, 9:
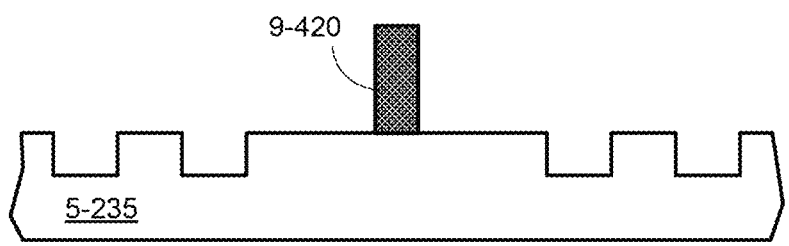

A selective anisotropic etch may then be used to etch the dielectric layer 5-235 and transfer the pattern of the surface-plasmon structure into the dielectric, as depicted in FIG. 9-4D according to some embodiments. A selective isotropic etch may then be used to remove the exposed portions of the masking layer 9-410. The isotropic etch may be a wet etch, for example, though an isotropic dry etch may be used in some embodiments. Because the resist 9-440 covers the central pillar 9-420, the central pillar will not be etched and remain on the substrate, as depicted in FIG. 9-4E. The resist 9-440 may then be stripped from the substrate exposing the pillar 9-420, as depicted in FIG. 9-4F.

Figures 4G, 9:
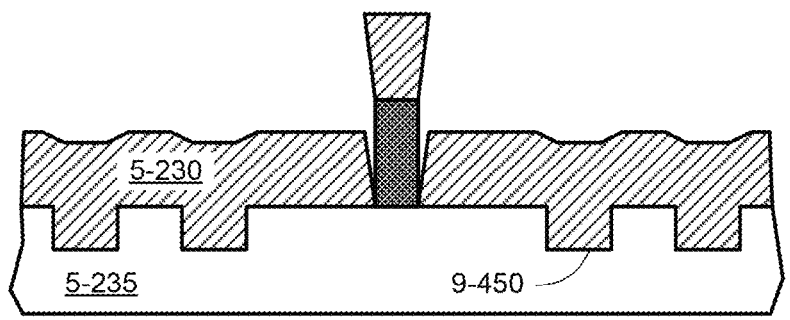
Figures 5A, 9:
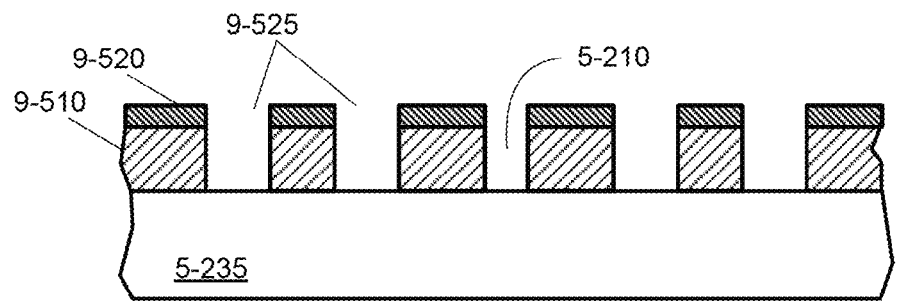
Figures 5B, 9:
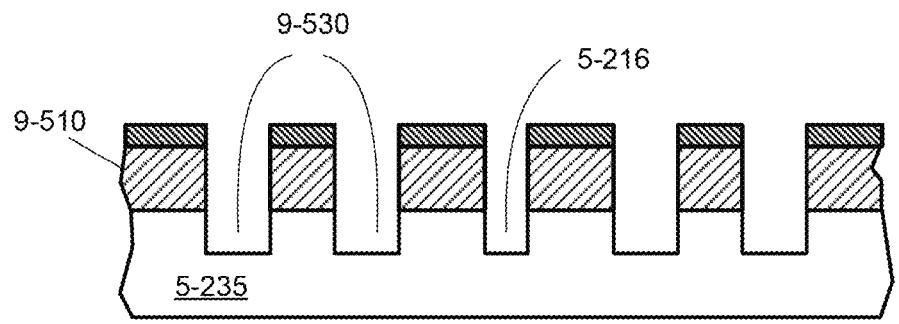

According to some embodiments, a metal conductive material 5-230, or a stack of materials including a conductive material, may then be deposited over the region as illustrated in FIG. 9-4G. The central pillar 9-420 and a cap of deposited material over the pillar may then be removed by a selective wet etch of the pillar, lifting off the cap. The removal of the central pillar leaves a sample well that is self-aligned to the underlying surface-plasmon structure 9-450.

An alternative process may be used to form a sample well that is self-aligned to a surface-plasmon structure, and is depicted in FIG. 9-5A through FIG. 9-5E. According to some embodiments, one or more conductive layers 9-510, 9-520 may be patterned on a transparent dielectric layer 5-235 using any suitable lithography process, as depicted in FIG. 9-5A. In some implementations, a first layer 9-510 may comprise aluminum, and a second layer 9-520 may comprise titanium nitride, though other material combinations may be used in various embodiments. A total thickness of the one or more layers may be approximately equivalent to a desired height of the sample well, according to some embodiments. The patterning may form a sample well 5-210, and voids 9-525 adjacent the sample well in the one or more metal layers. The voids may be arranged in the pattern of a desired surface-plasmon structure.

Figures 5C, 9:
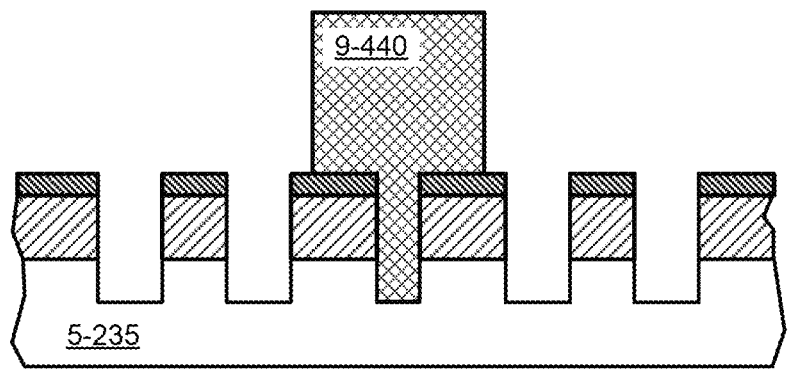

In some implementations, the dielectric layer 5-235 may be etched to transfer the pattern of the surface-plasmon structure and sample well 5-210 into the dielectric layer, as depicted in FIG. 9-5B. The etch depth into the dielectric may be between approximately 20 nm and approximately 150 nm, according to some embodiments. A resist 9-440 may be patterned to cover the sample well, as depicted in FIG. 9-5C. Alignment for patterning the resist need not be highly accurate, and only need cover the sample well without covering adjacent etched regions of the dielectric layer 5-235 that will be used to form the surface-plasmon structure.

Figures 5D, 9:
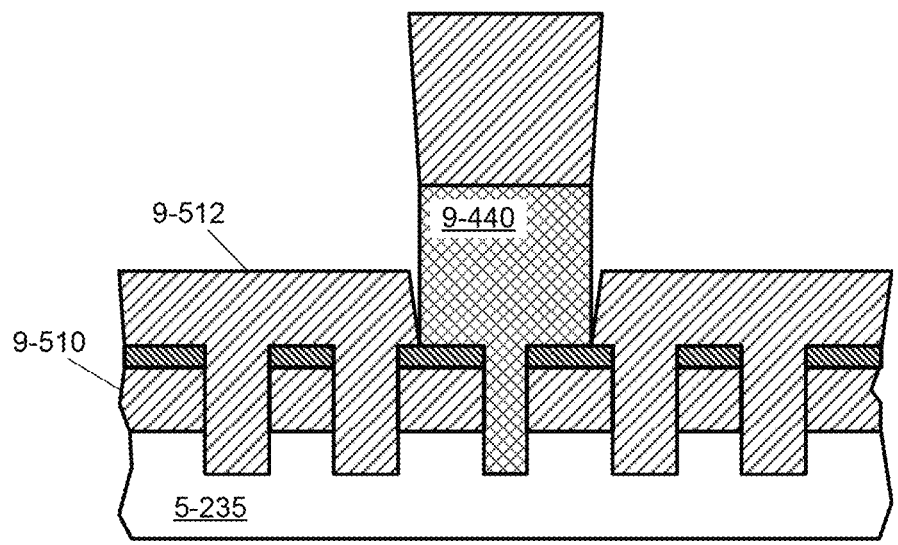
Figures 5E, 9:
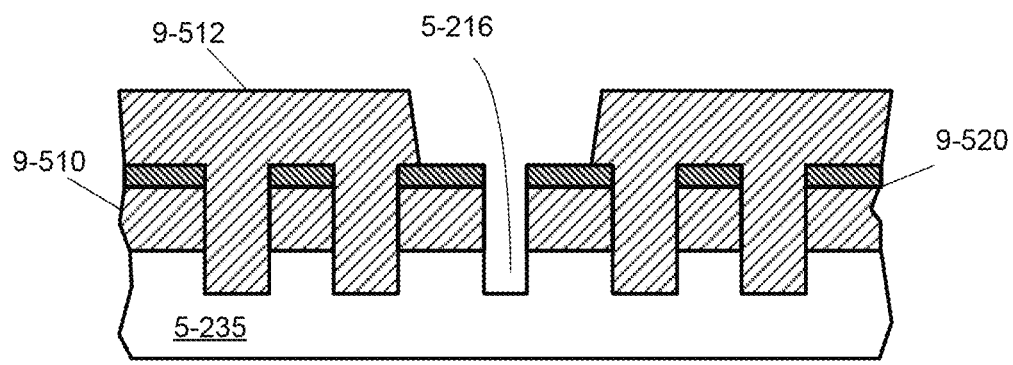

As illustrated in FIG. 9-5D, a conductive material 9-512, or layers of materials including a conductor, may be deposited over the region using any suitable deposition process. The material 9-512 may fill the etched regions of the dielectric layer, and may extend above the one or more layers 9-510, 9-520. The resist 9-440 and the material covering the resist may then be removed according to a lift-off process. The resulting structure, shown in FIG. 9-5E, leaves a sample well that is self-aligned to the surrounding surface-plasmon structure. The sample well includes a divot 5-216.

In some embodiments the process depicted in FIG. 9-5A through FIG. 9-5E may be used to form a sample well that does not have a divot 5-216. For example, the resist 9-440 may be patterned over the sample well 5-210 before the dielectric layer 5-235 is etched. The dielectric layer 5-235 may then be etched, which will transfer the pattern of the surface-plasmon structure to the dielectric layer but not form a divot. The process may then proceed as illustrated in FIG. 9-5D and FIG. 9-5 E to create a self-aligned sample well having no divot.

G. Amplitude/Phase Excitation-Coupling Structures

Figures 6A, 9:
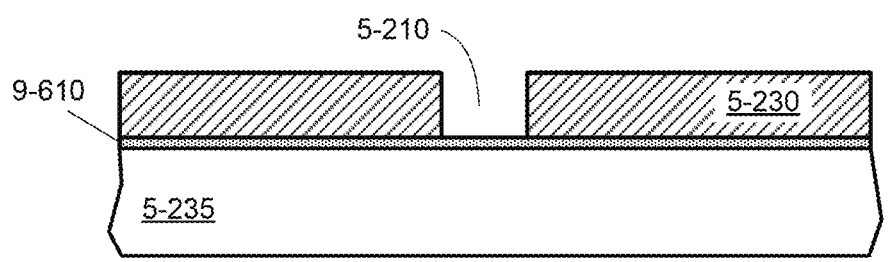

Other structures, in addition to or as an alternative to surface-plasmon structures, may be patterned in the vicinity of the sample well 5-210 to increase the excitation energy within the sample well. For example some structures may alter the phase and/or the amplitude of the incident excitation field so as to increase the intensity of the excitation energy within the sample well. FIG. 9-6A depicts a thin lossy film 9-610 that may be used to alter the phase and amplitude of incident excitation radiation and increase the intensity of electromagnetic radiation within the sample well.

Figures 6B, 9:
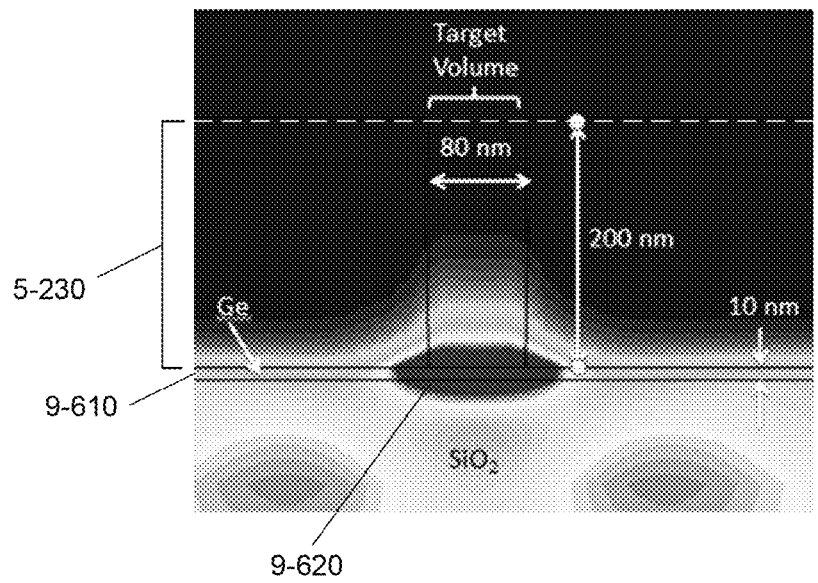

According to some embodiments, a thin lossy film may create constructive interference of the excitation radiation, resulting in field enhancement within an excitation region of the sample well. FIG. 9-6B depicts a numerical simulation of excitation radiation incident upon a sample well where a thin lossy film 9-610 has been formed immediately adjacent the sample well. For the simulation, the sample well has a diameter of approximately 80 nm and is formed in a metallic layer of gold approximately 200 nm thick. The sample well may comprises a SCN, and suppresses propagation of excitation radiation through the sample well. The thin lossy film 9-610 is approximately 10 nm thick, is formed from germanium, and covers an underlying transparent dielectric comprising silicon dioxide. The thin lossy film extends across an entrance aperture of the sample well. The simulation shows that the intensity of the excitation radiation is a highest value at the entrance aperture of the sample well. The intensity of the excitation radiation in this bright region 9-620 is more than twice the value of the intensity to the left and right of the sample well.

A thin lossy film may be made from any suitable material. For example, a thin lossy film may be made from a material where the index of refraction n is approximately the same order of magnitude as the extinction coefficient k for the material. In some embodiments, a thin lossy film may be made from a material where the index of refraction n is within about two orders of magnitude difference from the value of the extinction coefficient k of the material. Non-limiting examples of such materials at visible wavelengths are germanium and silicon.

A thin lossy film may be any suitable thickness, which may depend upon a characteristic wavelength, or wavelengths, associated with the excitation source, or sources. In some embodiments, a thin lossy film may be between approximately 1 nm and approximately 45 nm thick. In other embodiments, a thin lossy film may be between approximately 15 nm and approximately 45 nm thick. In still other embodiments, a thin lossy film may be between approximately 1 nm and approximately 20 nm thick.

Figures 6C, 9:
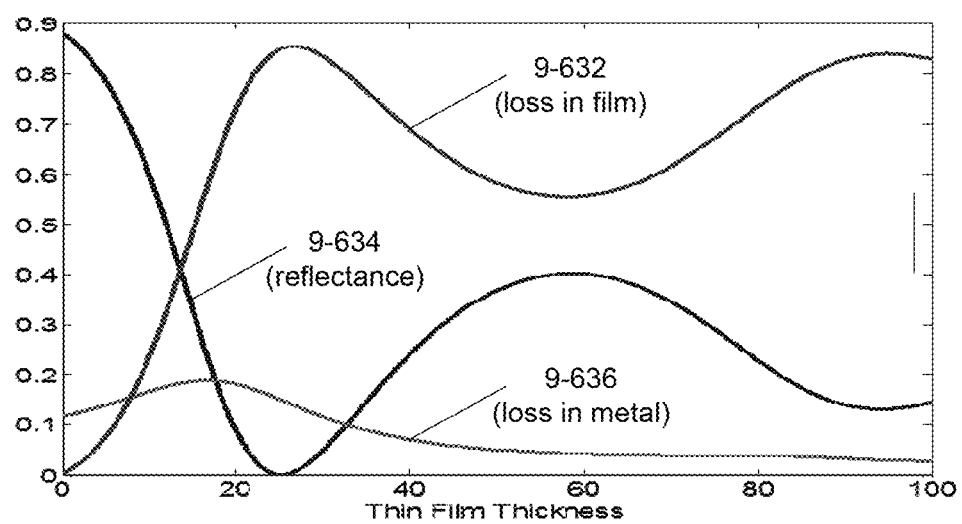

Effects of a thin lossy film on reflectance from the material 5-230 in which a sample well is formed, excitation energy loss within the thin lossy film, and excitation energy loss within the material 5-230 are shown in the graph of FIG. 9-6C. One curve plotted in the graph represents a reflectance curve 9-634, and shows how reflectance from the material 5-230 and the thin lossy film 9-610 vary as the thickness of the thin lossy film changes from 0 nm to 100 nm. The reflectance reaches a minimum value at about 25 nm, according to the simulated embodiment. The reflectance minimum will occur at different thicknesses depending on a characteristic wavelength of the excitation energy and materials used for the thin lossy film and material 5-230. In some implementations a thickness of thin lossy film is selected such that the reflectance is approximately at its minimal value.

Figures 6D, 9:
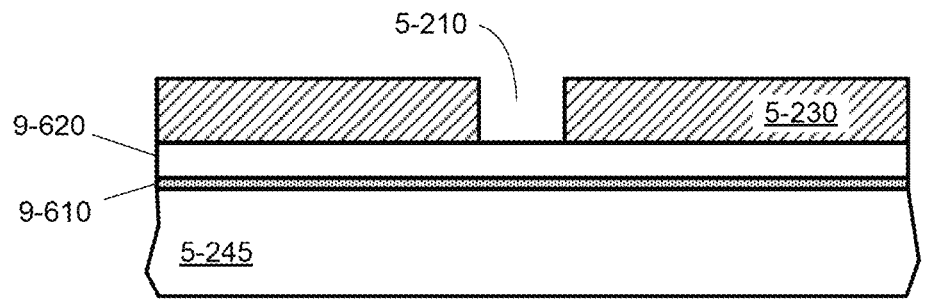

In some embodiments, a thin lossy film 9-610 may be spaced from a sample well 5-210 and material 5-230, as depicted in FIG. 9-6D. For example, a thin dielectric layer 9-620 (e.g., a silicon oxide SiOx) may be formed over a thin lossy film, and a sample well 5-210 may be formed adjacent the dielectric layer 9-620. A thickness of the dielectric layer 9-620 may be between approximately 10 nm and approximately 150 nm according to some embodiments, though other thicknesses may be used in some embodiments.

Figures 6E, 9:
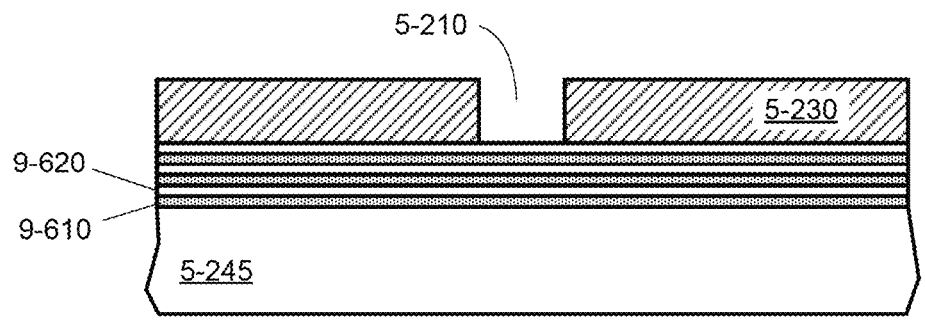
Figures 7A, 9:
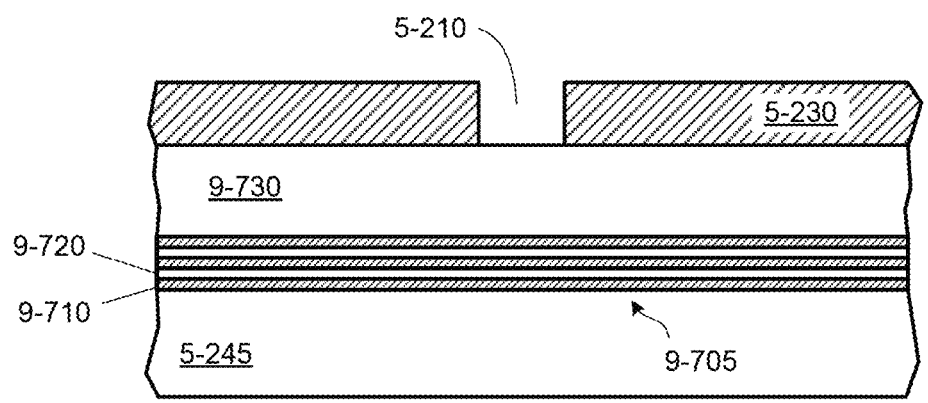
Figures 7B, 9:
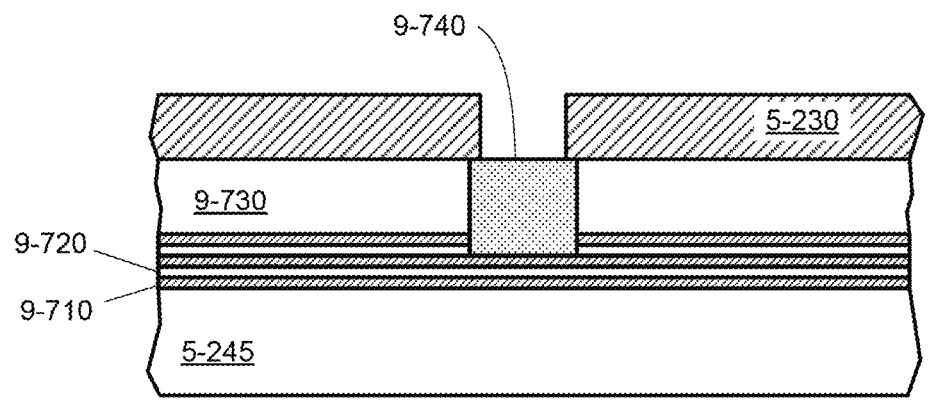
Figures 7C, 9:
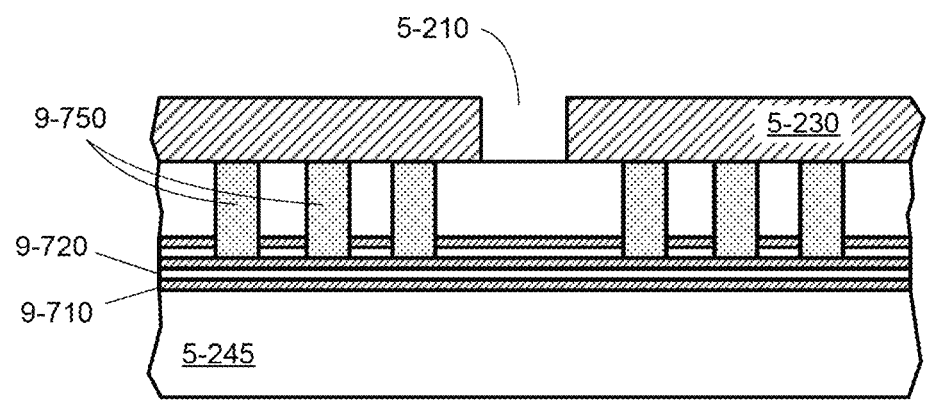
Figures 7D, 9:
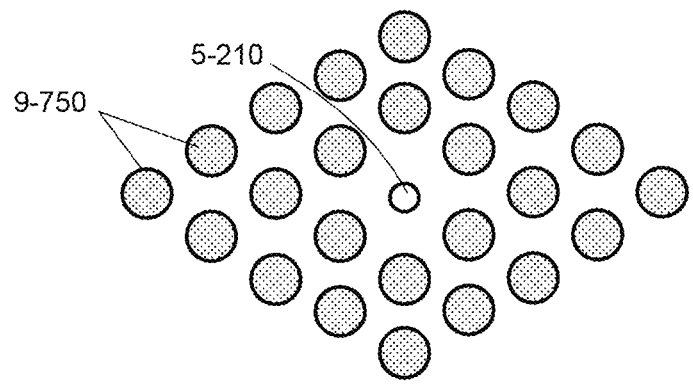

Although depicted as a single layer, a thin lossy film may comprise multiple layers of two or more materials. In some implementations, a multilayer stack comprising alternating layers of a thin lossy film 9-610 and a dielectric layer 9-620 may be formed adjacent a sample well 5-210, as depicted in FIG. 9-6E. A thickness of a thin lossy film 9-610 in a stack of layers may be between approximately 5 nm and approximately 100 nm, and a thickness of a dielectric layer 9-620 within the stack may be between approximately 5 nm and approximately 100 nm, according to some embodiments. In some implementations, the multilayer stack may comprise a layer of silicon dioxide having a thickness between approximately 2 nm and approximately 8 nm, a layer of silicon having a thickness between approximately 5 nm and approximately 20 nm, and a layer of germanium having a thickness between approximately 2 nm and approximately 12 nm, though other thicknesses may be used in other embodiments. In some implementations, the multilayer stack may comprise a layer of silicon dioxide (approximately 4.2 nm thick), a layer of silicon (approximately 14.4 nm thick), and a layer of germanium (approximately 6.5 nm thick), though other thicknesses may be used in other embodiments.

A thin lossy film may be fabricated from any suitable material that exhibits at least some loss to the incident radiation. In some embodiments, a thin lossy film may comprise a semiconductor material, for example silicon and germanium, though other materials may be used. In some implementations, a thin lossy film may comprise inorganic material or a metal. In some embodiments, a thin lossy film may comprise an alloy or compound semiconductor. For example, a thin lossy film may comprise an alloy including Si (57.4% by weight), Ge (25.8% by weight), and SiO2 (16.8% by weight), though other ratios and compositions may be used in other embodiments.

According to some embodiments, a thin lossy film may be formed on the substrate using any suitable blanket deposition process, for example, a physical deposition process, a chemical vapor deposition process, a spin on process, or a combination thereof. In some embodiments, a thin lossy film may be treated after deposition, e.g., baked, annealed and/or subjected to ion implantation.

Other phase/amplitude altering structures may be used additionally or alternatively to enhance excitation energy within the sample well. According to some implementations and as shown in FIG. 9-7A, a reflective stack 9-705 may be spaced from a sample well 5-210. In some embodiments, a reflective stack may comprise a dielectric stack of materials having alternating indices of refraction. For example a first dielectric layer 9-710 may have a first index of refraction, and a second dielectric layer 9-720 may have a second index of refraction different than the first index of refraction. The reflective stack 9-705 may exhibit a high reflectivity for excitation radiation in some embodiments, and exhibit a low reflectivity for radiative emission from an emitter within the sample well. For example, a reflective stack 9-705 may exhibit a reflectivity greater than approximately 80% for excitation radiation and a reflectivity lower than approximately 40% for emission from a sample, though other reflectivity values may be used in some embodiments. A dielectric layer 9-730 that transmits the excitation energy may be located between the reflective stack and the sample well.

According to some implementations, a reflective stack 9-705 depicted in FIG. 9-7A may form a resonator with the material 5-230 in which the sample well 5-210 is formed. For example, the reflective stack may be spaced from the material 5-230 by a distance that is approximately equal to one-half the wavelength of the excitation radiation within the dielectric material 9-730, or an integral multiple thereof. By forming a resonator, excitation energy may pass through the reflective stack, resonate, and build up in the space between the material 5-230 and the reflective stack 9-705. This can increase excitation intensity within the sample well 5-210. For example, the intensity may increase within the resonant structure by more than a factor of 2 in some embodiments, and more than a factor of 5 in some embodiments, and yet more than a factor of 10 in some embodiments.

A resonant cavity formed at the sample well may comprise a Gires-Tournois resonator, according to some embodiments. In some implementations, a resonant structure may comprise a linear resonant cavity or ring resonator. In some implementations, a resonant structure may comprise a distributed Bragg reflector formed adjacent the sample well. The distributed Bragg reflector may comprise alternating layers of material having different indices of refraction. In some implementations, a resonant cavity may comprise a microcavity. The microcavity may have microscale dimensions. In some aspects, a microcavity may have a size that is approximately equal to one-half the characteristic wavelength of an excitation source or a multiple thereof (as modified by the refractive index n of the resonant cavity). For example, the dimension of a microcavity may be $M\lambda/2n$, where M is an integer.

Additional structures may be added in the vicinity of the sample well, as depicted in FIG. 9-7B and FIG. 9-7C. According to some embodiments, a dielectric plug 9-740 having a first index of refraction that is higher than a second index of refraction of the dielectric layer 9-730 may be formed adjacent the sample well 5-210, as depicted in FIG. 9-7B. The plug may be in the shape of a cylinder having a diameter approximately equal to that of the sample well, though other shapes and sizes may be used. Because of its higher refractive index, the dielectric plug 9-740 may condense and guide excitation radiation toward the sample well.

A dielectric structure, such as the plug 9-740, may be used with or without a reflective stack 9-705, according to some embodiments. Such a dielectric structure may be referred to as a dielectric resonant antenna. The dielectric resonant antenna may have any suitable shape, for example, cylindrical, rectangular, square, polygon old, trapezoidal, or pyramid.

FIG. 9-7C and FIG. 9-7D depict a photonic bandgap (PBG) structure that may be formed in the vicinity of a sample well 5-210, according to some embodiments. A photonic bandgap structure may comprise a regular array or lattice of optical contrast structures 9-750. The optical contrast structures may comprise dielectric material having a refractive index that is different from a refractive index of the surrounding dielectric material, according to some embodiments. In some implementations, the optical contrast structures 9-750 may have a loss value that is different from the surrounding medium. In some implementations, a sample well 5-210 may be located at a defect in the lattice as depicted in FIG. 9-7D. According to various embodiments, the defect in the photonic lattice may confine photons within the region of the defect can enhance the intensity of the excitation energy at the sample well. The confinement due to the photonic bandgap structure may be substantially in two dimensions transverse to a surface of the substrate. When combined with the reflective stack 9-705, confinement may be in three dimensions at the sample well. In some embodiments, a photonic bandgap structure may be used without a reflective stack.

Various methods have been contemplated for fabricating the excitation-coupling structures depicted in FIG. 9-6A through FIG. 9-7D. Structures that require thin planar films (e.g., dielectric films of alternating refractive index) may be formed by planar deposition processes, according to some embodiments. Planar deposition processes may comprise physical deposition (for example, electron beam evaporation or sputtering) or chemical vapor deposition processes. Structures that require discrete embedded dielectrics formed in three-dimensional shapes, such as a dielectric resonant antenna 9-740 shown in FIG. 9-7B or the optical contrast structures 9-750 shown in FIG. 9-7C, may be formed using lithographic patterning and etching processes to etch the pattern into the substrate, and using subsequent deposition of a dielectric layer, and a planarization of the substrate, for example. Also contemplated are self-alignment processing techniques for forming dielectric resonant antennas as well as photonic bandgap structures in the vicinity of the sample well 5-210.

H. Fabrication of Amplitude/Phase Excitation-Coupling Structures

Figures 8A, 9:
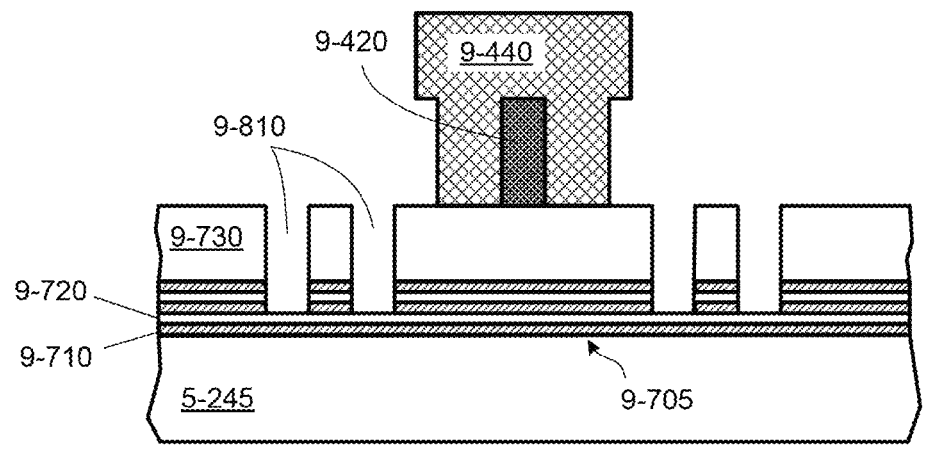
Figures 8B, 9:
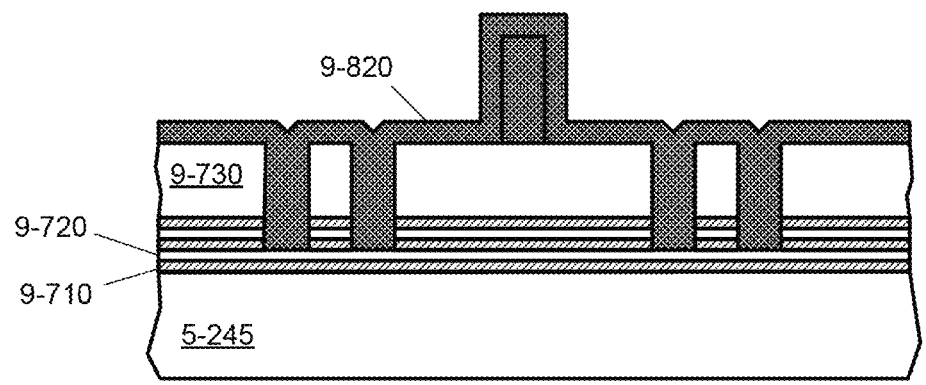
Figures 8C, 9:
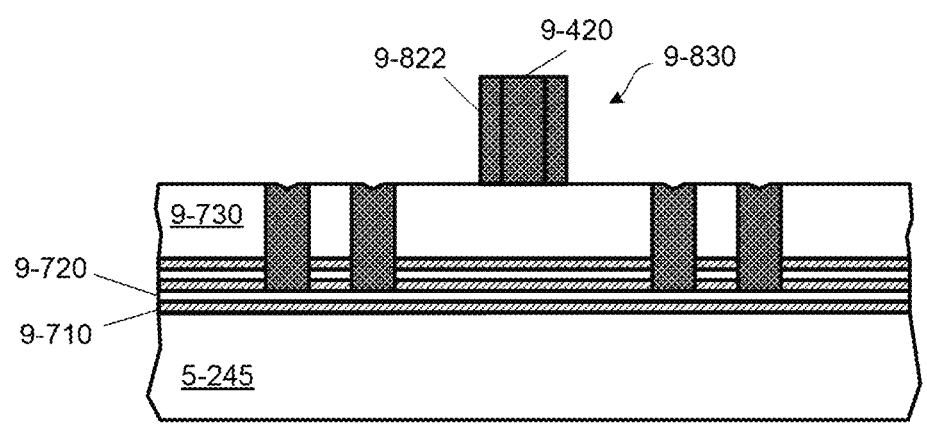
Figures 8D, 9:
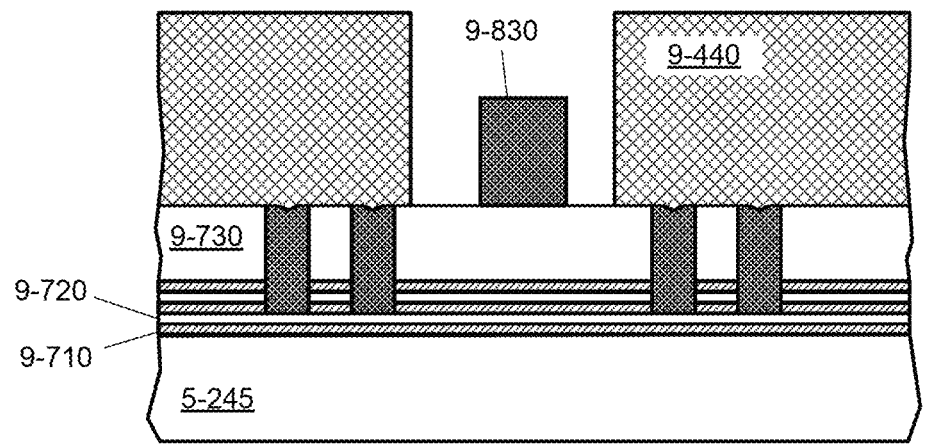
Figures 8E, 9:
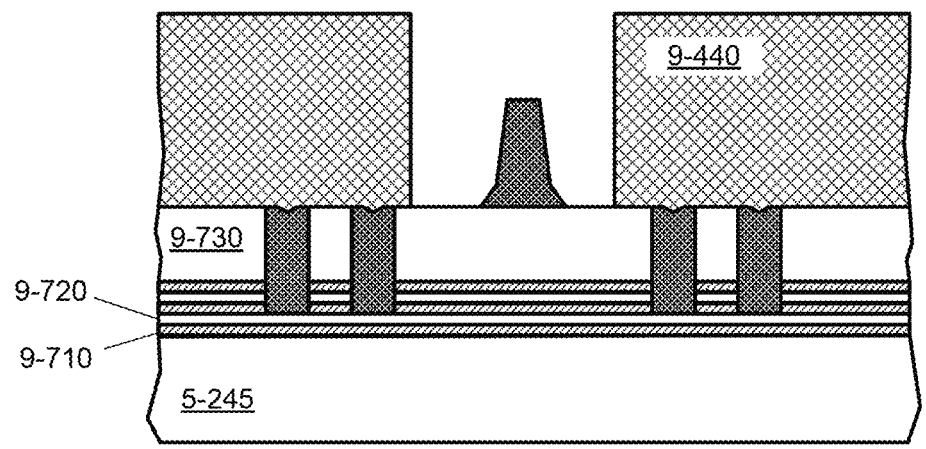
Figures 8F, 9:
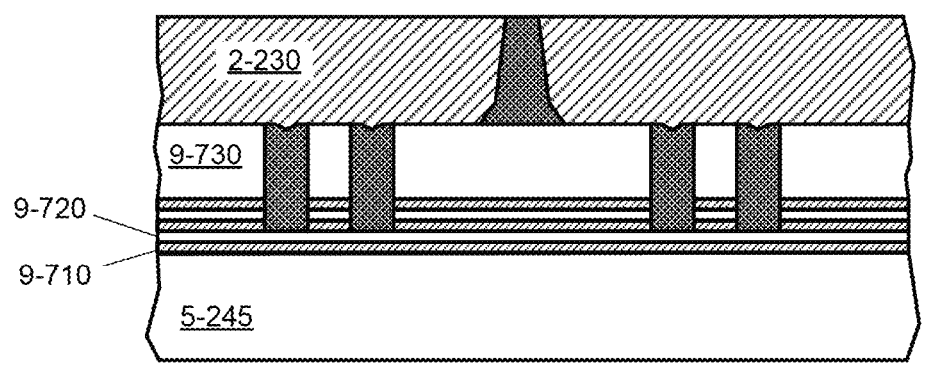
Figures 8G, 9:
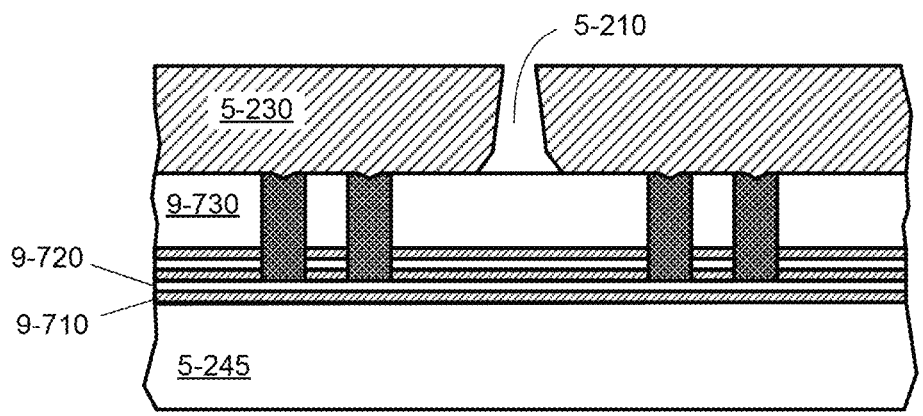
Figures 9, 9A:
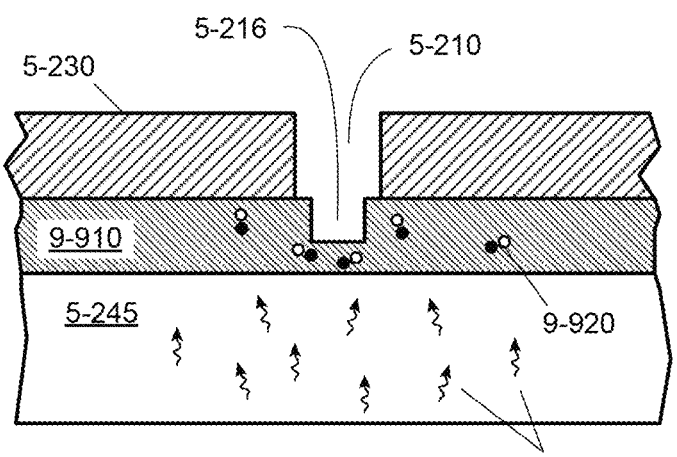
Figures 9, 9B:
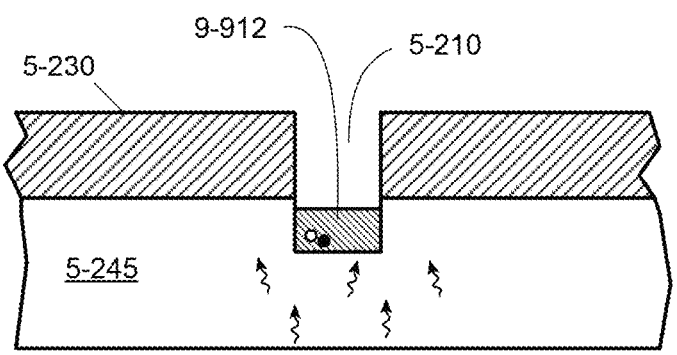
Figures 9, 9C:
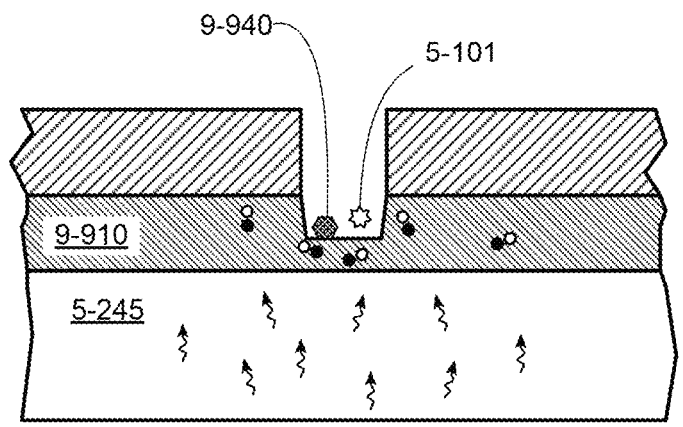
Figures 9, 9D:
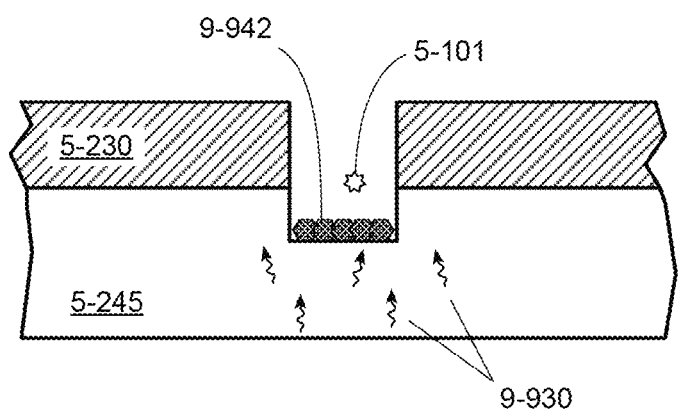
Figures 9, 9E:
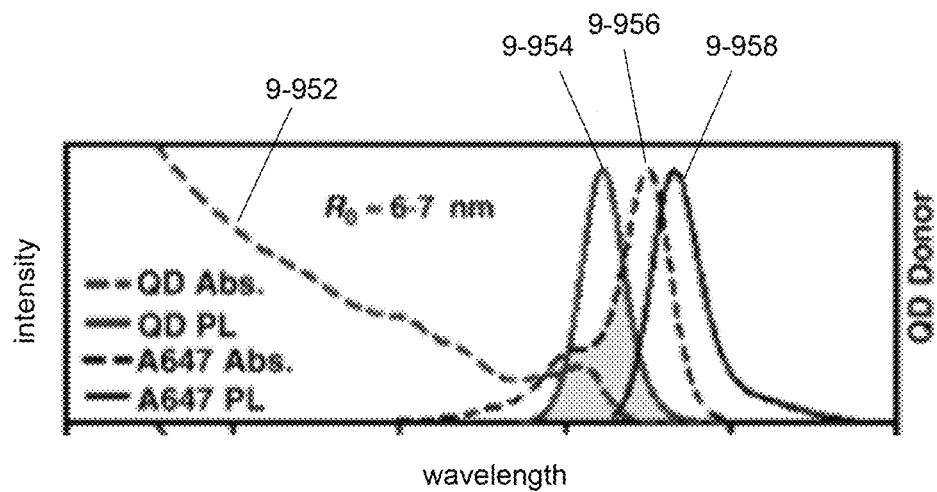
Figures 9, 9F:
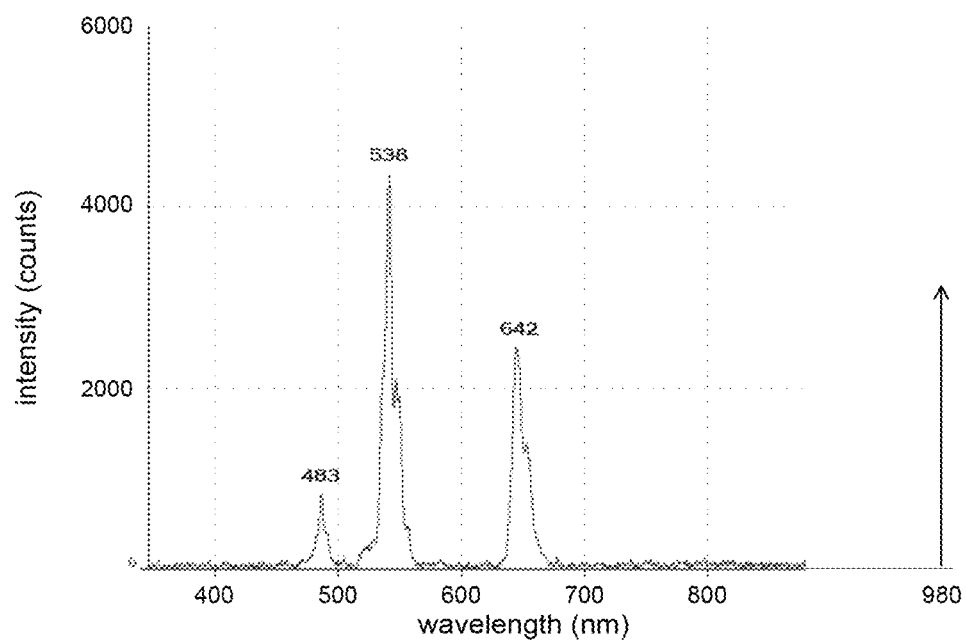
Figures 1A, 11:
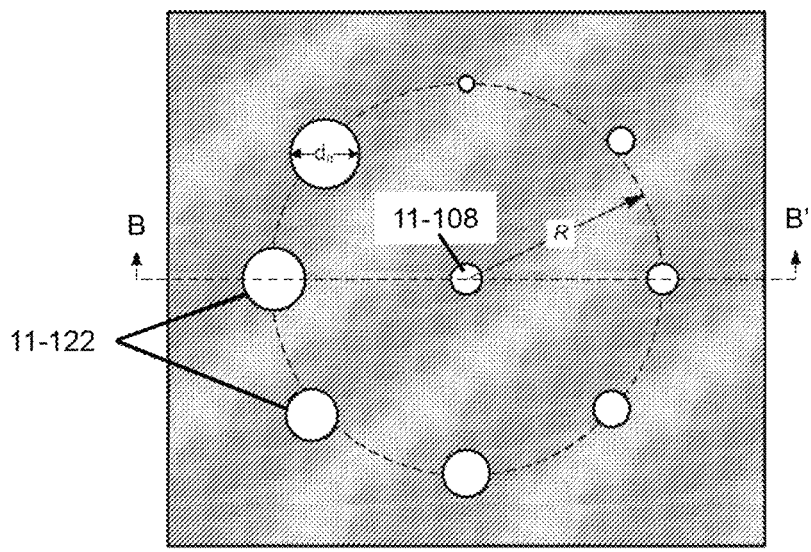
Figures 1B, 11:
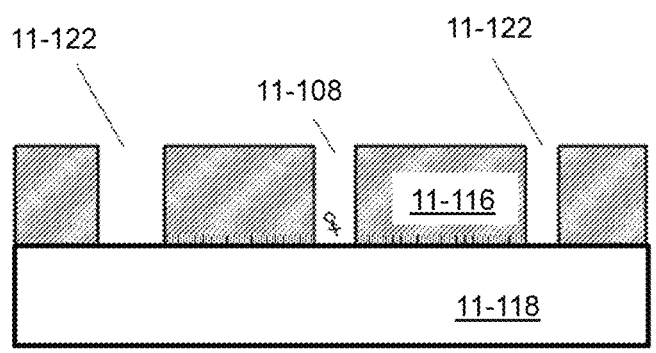
Figures 2A, 11:
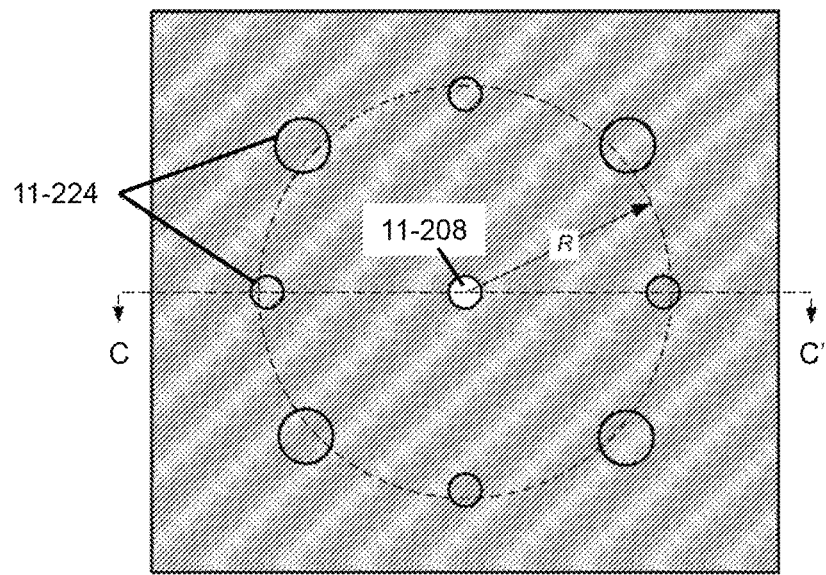
Figures 2B, 11:
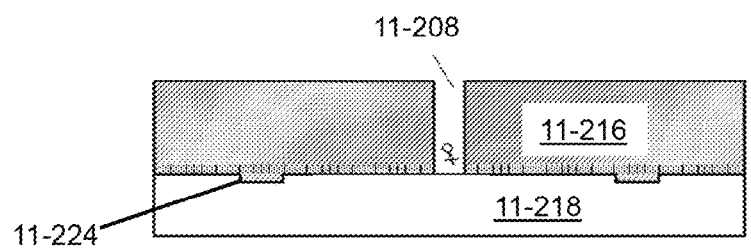
Figures 3, 11:
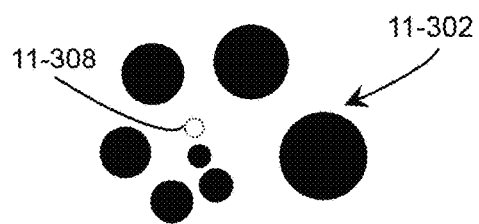
Figures 4, 11:
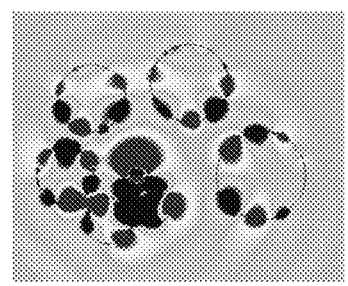
Figures 5, 11:
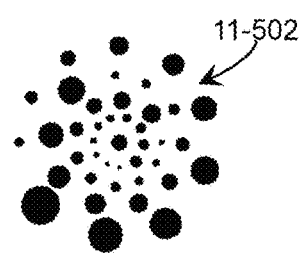
Figures 6, 11:
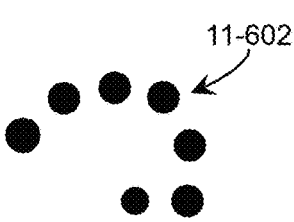
Figures 7, 11:
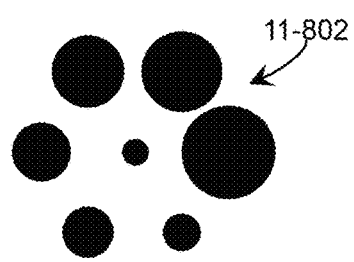
Figures 8, 11:
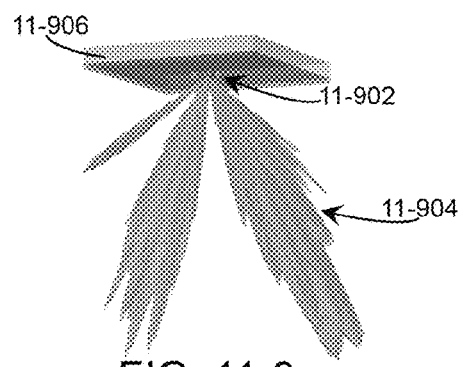
Figures 9, 11:
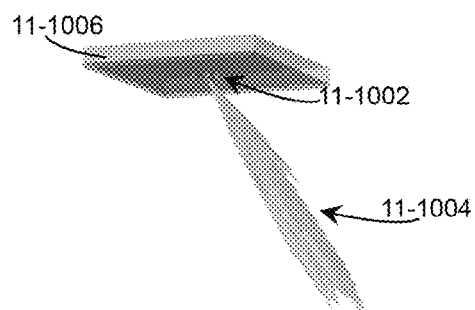
Figures 10, 11:
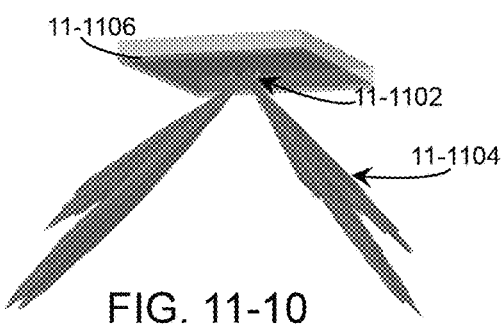
Figure 11:
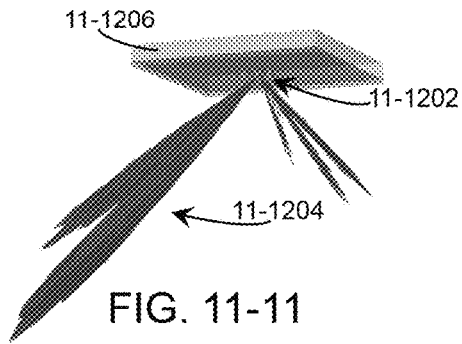
Figures 1A, 12:
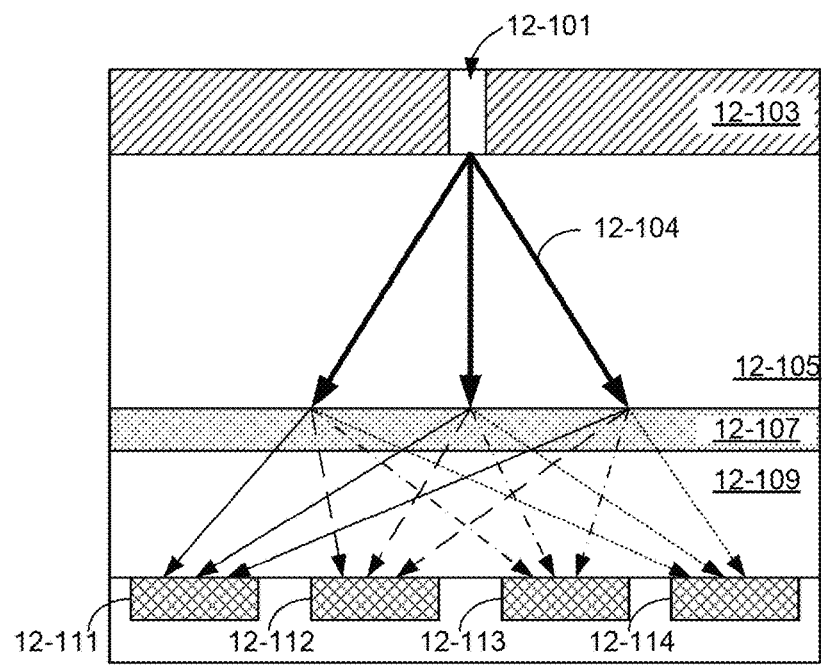
Figures 1B, 12:
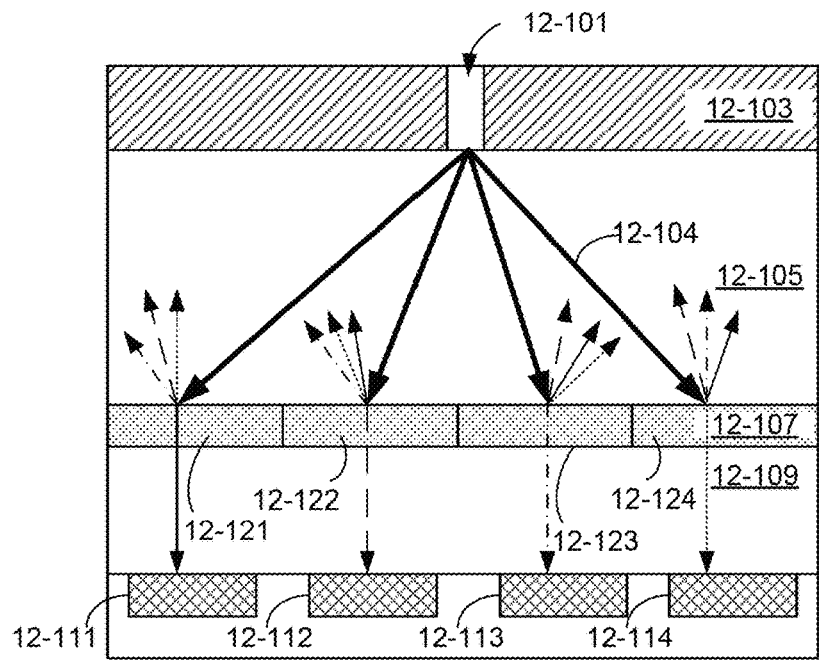
Figures 2A, 12:
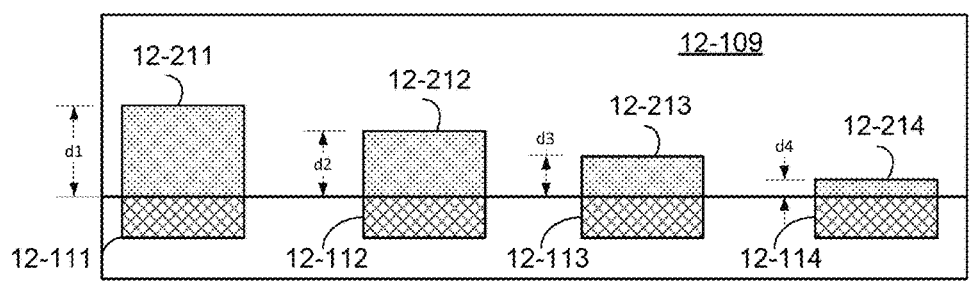
Figures 2B, 12:
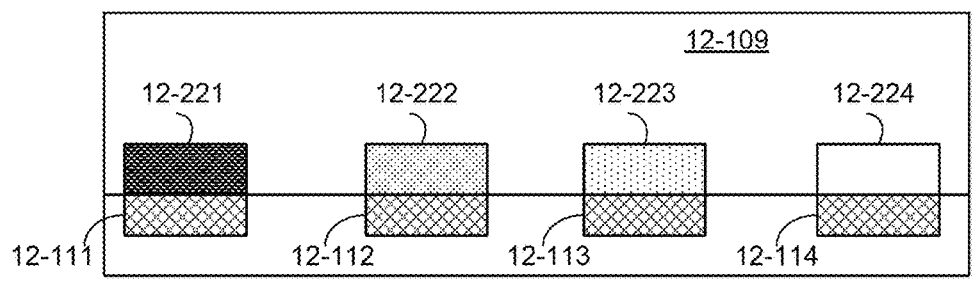

FIG. 9-8A through FIG. 9-8G depict structures associated with process steps for just one self-alignment process that may be used to form a photonic bandgap structure and a self-aligned sample well as illustrated in FIG. 9-7C. According to some embodiments, a reflective stack 9-705 may be first formed on a substrate above a dielectric layer 5-245, as illustrated in FIG. 9-8A. A second dielectric layer 9-730 may then be deposited over the reflective stack. The thickness of the dielectric layer 9-730 may be approximately equal to about one-half a wavelength of the excitation radiation in the material, or an integral multiple thereof. Process steps described in connection with FIG. 9-4A through FIG. 9-4E may then be carried out to form a pillar 9-420 above the dielectric layer 9-730 and a pattern of etched features 9-810 for the photonic bandgap structure. The etched features may extend into the dielectric layer 9-730 and optionally into the reflective stack 9-705. The resulting structure may appear as shown in FIG. 9-8A.

A resist 9-440 covering the pillar 9-420 may be stripped from the substrate and a conformal deposition performed to fill the etched features with a filling material 9-820, as depicted in FIG. 9-8B. The filling material 9-820 may be the same material that is used to form the pillar 9-420, according to some embodiments. For example the filling material 9-820 and the pillar 9-420 may be formed of silicon nitride and the dielectric layer 9-730 may comprise an oxide, e.g., SiO2.

An anisotropic etch may then be carried out to etch back the filling material 9-820. The filling material may be etched back to expose a surface of the dielectric layer 9-730, according to some embodiments, resulting in a structure as depicted in FIG. 9-8C. The etch may leave a pillar 9-830 comprising the original pillar 9-420 and sidewalls 9-822 that remain from the filling material 9-820.

A resist 9-440 may then be patterned over the substrate as depicted in FIG. 9-8D. For example, the resist may be coated onto the substrate, a hole patterned in the resist, and the resist developed to open up a region in the resist around the pillar 9-830. Alignment of the hole to the pillar need not be highly accurate, and only need expose the pillar 9-830 without exposing the underlying photonic bandgap structures embedded in the dielectric layer 9-730.

After the pillar 9-830 is exposed, and isotropic etch may be used to reduce the transverse dimension of the pillar. According to some embodiments, the resulting pillar shape may appear as depicted in FIG. 9-8E. The resist 9-440 may then be stripped from the substrate and a material 5-230, or layers of materials, may be deposited over the region. In some embodiments, the material 5-230 may be etched back using a CMP process to planarize the region as depicted in FIG. 9-8F. Subsequently, a selective dry or wet etch may be used to remove the remaining pillar structure leaving a sample well 5-210, as illustrated in FIG. 9-8G. As indicated by the drawings, the sample well 5-210 is self-aligned to the photonic bandgap structure patterned in the dielectric layer 9-730.

As an alternative process, the filling material 9-820 may comprise a different material than the material used to form the pillar 9-420. In this process, the steps associated with FIG. 9-8D and FIG. 9-8E may be omitted. After deposition of material 5-230 and planarization, as depicted in FIG. 9-8F, a selective etch may be performed to remove the pillar 9-420. This may leave sidewalls of the filling material 9-820 lining the sample well 5-210.

I. Non-Radiative Excitation-coupling Structures and Fabrication

Structures for non-radiative coupling of excitation energy to a sample within the sample well have also been contemplated by the inventors. Just one embodiment of a non-radiative coupling structure is depicted in FIG. 9-9A. According to some embodiments, a non-radiative coupling structure may comprise a semiconductor layer 9-910 formed immediately adjacent a sample well 5-210. The semiconductor layer 9-910 may be an organic semiconductor in some embodiments, or an inorganic semiconductor in some embodiments. In some implementations, a divot 5-216 may, or may not, be formed in the semiconductor layer. The semiconductor layer 9-910 may have a thickness between approximately 5 nm and approximately 100 nm according to some embodiments, though other thicknesses may be used in some embodiments. According to some implementations, excitation radiation or photons 9-930 from an excitation source may impinge upon the semiconductor layer 9-910 and produce excitons 9-920. The excitons may diffuse to a surface of the sample well where they may non-radiatively recombine and transfer energy to a sample adjacent the walls of the sample well.

Figures 5, 6, 7, 8, 9, 9B:
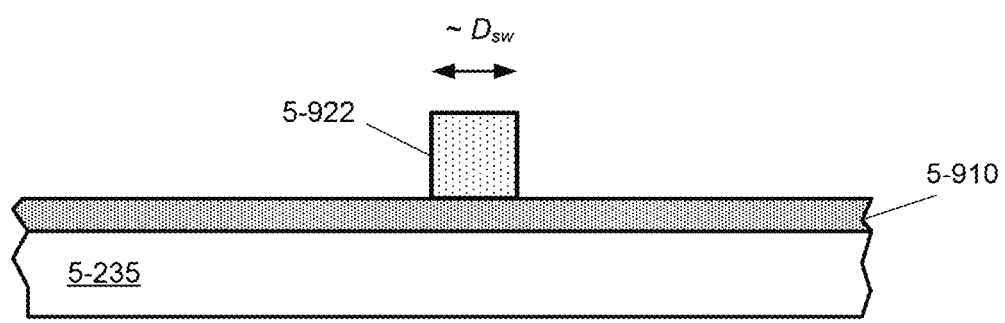

FIG. 9-9B depicts another embodiment in which a semiconductor layer 9-912 may be used to non-radiatively transfer energy from excitation energy to a sample. In some embodiments, a semiconductor layer 9-912 may be formed at the bottom of a sample well or in a divot of the sample well 5-210, as depicted in the drawing. The semiconductor layer 9-912 may be formed in a sample well by using a directional deposition process as described herein in connection with process steps for depositing an adherent at the base of the sample well, according to some embodiments. The semiconductor layer 9-912 may have a thickness between approximately 5 nm and approximately 100 nm according to some embodiments, though other thicknesses may be used in other embodiments. Incident radiation may generate excitons within the semiconductor layer, which may then diffuse to the a bottom surface of the sample well 5-210. The excitons may then non-radiatively transfer energy to a sample within the sample well.

Figures 5, 6, 7, 8, 9, 9C:
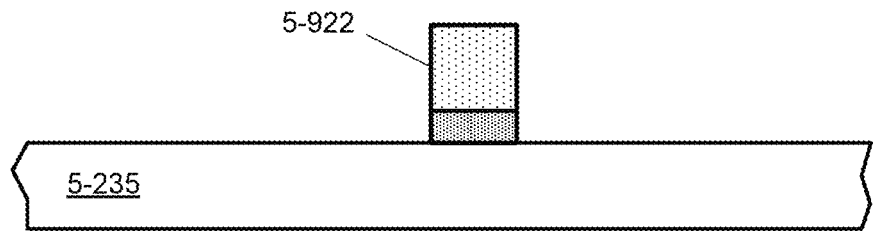

Multiple non-radiative pathways for transferring excitation energy to a sample have also been contemplated by the inventors. According to some embodiments, and as depicted in FIG. 9-9C, an energy-transfer particle 9-940 may be deposited within a sample well. The energy-transfer particle may comprise a quantum dot in some embodiments, or may comprise a molecule in some embodiments. In some implementations, the energy-transfer particle 9-940 may be functionalized to a surface of the sample well through a linking molecule. A thin semiconductor layer 9-910 may be formed adjacent the sample well, or within the sample well, and excitons may be generated within the semiconductor layer from the excitation radiation incident upon the semiconductor layer, as depicted in the drawing. The excitons may diffuse to the surface of the sample well, and non-radiatively transfer energy to the energy-transfer particle 9-940. The energy-transfer particle 9-940 may then non-radiatively transfer energy to a sample 5-101 within the sample well.

According to some implementations, there may be more than one energy-transfer particle 9-940 within a sample well. For example, a layer of energy-transfer particles 9-942 may be deposited within a sample well, such as the sample well depicted in FIG. 9-9C.

Figures 5, 6, 7, 8, 9, 9D:
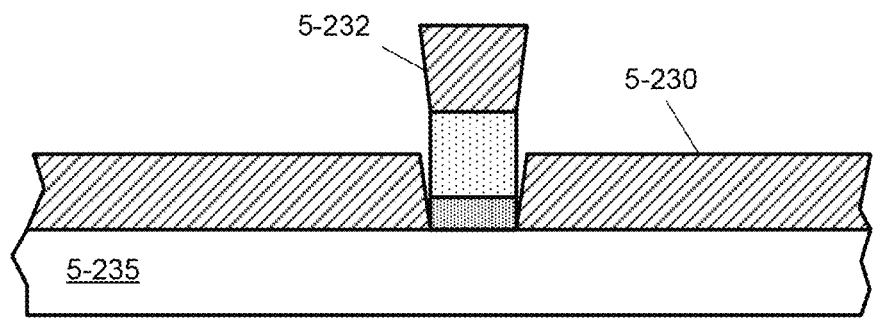
Figures 5, 6, 7, 8, 9, 9E:
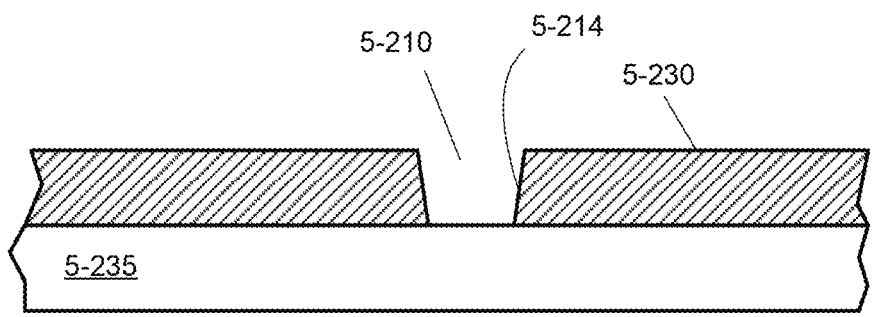

In some implementations, energy-transfer particles 9-942, or a single energy-transfer particle 9-940, may be deposited at a base of a sample well, as depicted in FIG. 9-9D. The energy-transfer particle, or particles, may radiatively or non-radiatively transfer excitation energy to a sample 5-101 within the well. For example, an energy-transfer particle may absorb incident radiation to form an excited state of the energy-transfer particle, and then radiatively or non-radiatively transfer energy to the sample 5-101.

Figures 5, 6, 7, 8, 9, 9F:
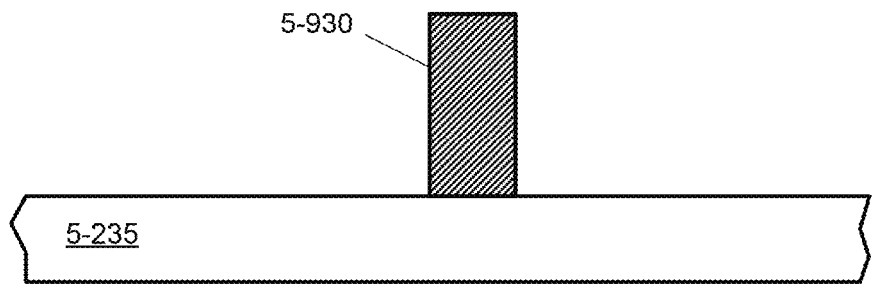

In some implementations, an energy-transfer particle may absorb incident excitation energy, and then re-emit radiative energy at a wavelength that is different than the wavelength of the absorbed excitation energy. The re-emitted energy may then be used to excite a sample within the sample well. FIG. 9-9F represents spectral graphs associated with a down-converting energy-transfer particle. According to some embodiments, a down-converting energy-transfer particle comprises a quantum dot that may absorb short wavelength radiation (higher energy), and emit one or more longer wavelength radiations (lower energy). An example absorption curve 9-952 is depicted in the graph as a dashed line for a quantum dot having a radius between 6 to 7 nm. The quantum dot may emit a first band of radiation illustrated by the curve 9-954, a second band of radiation illustrated by the curve 9-956, and a third band of radiation illustrated by the curve 9-958.

In some implementations an energy-transfer particle may up convert energy from an excitation source. FIG. 9-9F depicts spectra associated with up conversion from an energy-transfer particle. According to some embodiments, a quantum dot may be excited with radiation at approximately 980 nm, and then re-emit into one of three spectral bands as illustrated in the graph. A first band may be centered at approximately 483 nm, a second band may be centered at approximately 538 nm, and a third band may be centered at approximately 642 nm. The re-emitted photons from the quantum dot are more energetic than the photons of the radiation used to excite the quantum dot. Accordingly, energy from the excitation source is up-converted. One or more of the emitted spectral bands may be used to excite one or more one or more samples within the sample well.

J. Directing Emission Energy to Sensor

One or more components may be formed between a sample well and corresponding sensors in a pixel to improve collection of emission energy by the sensors from a sample in the sample well. Such components may improve the signal-to-noise ratio of the emission energy signal to a background signal in order to improve detection of a marker for identifying the sample within a specimen. Such components may be designed to spatially direct and/or spatially separate emission energies of different characteristic wavelengths. Such components may direct excitation energy from a sample well to one or more corresponding sensors in a pixel. In some embodiments, the location of the sample well with respect to the structure is selected so as to direct the emission energy from the sample well in a particular way toward one or more sensors. When identifying one or more markers based on emission energy, an element may be configured to direct emission energy into a radiation distribution pattern that depends on the characteristic wavelength emitted by the marker. Multiple markers, each emitting within different spectral ranges, may be distinguishable by the radiation pattern that forms when the emission energy couples to an emission directing component within the integrated device. Other components, such as filters, may reduce excitation energy and other energy not associated with the sample in a pixel from reaching the corresponding one or more sensors of the pixel.

1. Surface Optics

Components within a pixel located near the sample well of the pixel may be configured to couple with the emission energy emitted by a sample when located within the sample well. Such components may be formed at the interface between two layers of the integrated device. For example, some emission energy coupling elements may be formed at the interface between a sample well layer and the layer adjacent to the sample well layer opposite to where the sample wells are formed. In some instances, the layer underneath the sample well layer is a dielectric layer and the emission energy coupling elements may support surface plasmons. In other embodiments, the sample well layer may be a conductive material adjacent to an optically-transparent material. Surface-energy coupling elements may be surface optical structures that are excited by and interact with radiative emission from the sample well. The surface optical structures may be configured to form different spatial radiation patterns for emission energies of different characteristic wavelengths. The term "characteristic wavelength" or "characteristic energy" may be used to refer to a central or predominant wavelength within a limited bandwidth of radiation emitted from a source. Examples of characteristic wavelengths of fluorophores are 563 nm, 595 nm, 662 nm, and 687 nm.

A characteristic dimension of a surface optical structure such as a grating period, feature size, or distance from the sample well may be selected to maximally couple a parallel component of an emission energy momentum vector into a surface wave momentum vector for a surface plasmon. For example, the parallel component of the emission energy momentum vector may be matched to the surface wave momentum vector for a surface plasmon supported by the structure, according to some embodiments. In some embodiments, a distance d from the sample well to an edge or characteristic feature of a surface optical structure may be selected so as to direct emission energy from the sample well in a selected direction, such as normal to the surface or inclined at an angle θ from normal to the surface. For example, the distance, d, may be an integral number of surface-plasmon wavelengths for directing emission normal to the surface. In some embodiments, distance, d, may be selected to be a fractional surface-plasmon wavelength, or wavelength modular thereof, for directing emission at an angle θ from normal to the surface.

In operation, a surface energy-coupling component and sample well may be configured to increase the amount of emission energy that is radiated from the sample well toward one or more sensors in the pixel containing the sample well. Without surface energy-coupling, an excited sample may emit radiation isotropically and the presence of sample well that acts as a zero mode waveguide may restrict most emission to a half-shell or Lambertian distribution since the radiation may not propagate through the nanoaperture. The addition of surface energy-coupling components may create a highly anisotropic emission distribution.

According to some embodiments, the surface optical structures may couple radiative emission energy from a sample well at a first characteristic wavelength in a first direction and/or in a first characteristic spatial pattern. The coupled energy may be directed in the first direction in a narrowed, anisotropic radiation pattern. In some embodiments, the surface optical structures may further couple radiative emission energy from the same sample well at a second characteristic wavelength in a second direction and/or second characteristic spatial pattern that is different from the first direction and/or in a first characteristic spatial pattern. The second emission may also be direction in a narrowed, anisotropic radiation pattern. In some embodiments, radiation with a first characteristic wavelength is directed in a narrowed lobe normal to the surface at which the surface optical structure is formed, and radiation of a second characteristic wavelength is directed in annular lobes at an angle from normal to the surface.

An example of a surface optical structure is a concentric grating. A concentric grating structure may be formed in a pixel of the integrated device to direct emission energy towards one or more sensors of the pixel. The concentric grating rings, or bullseye, structure may be formed around a sample well. The concentric grating structure may couple with the sample well to improve propagation of emission energy out of the sample well. Additionally, the concentric grating structure may direct emission energy emitted by a sample in the sample will into a radiation pattern where the radiation pattern that forms depends on a characteristic wavelength of the emission energy.

Figures 5, 6, 7, 8, 9, 10, 10A:
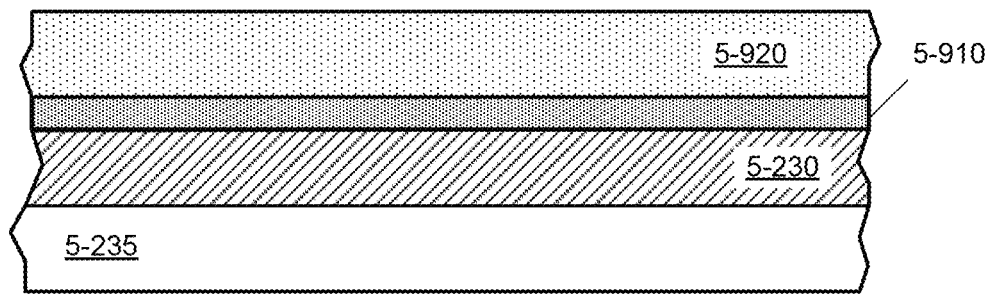
Figures 5, 6, 7, 8, 9, 10, 10B:
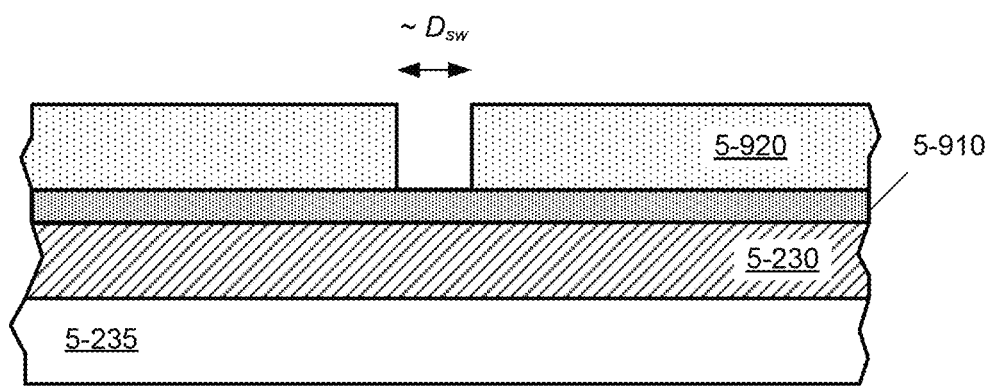
Figures 5, 6, 7, 8, 9, 10, 10C:
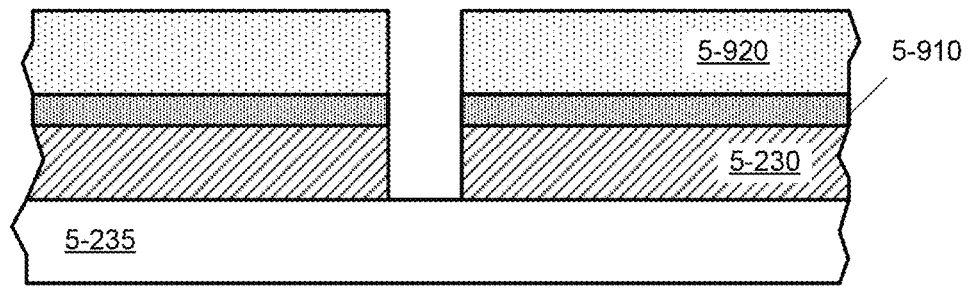
Figures 5, 6, 7, 8, 9, 10, 10D:
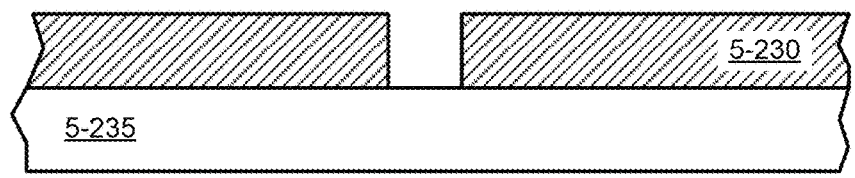

An example of a concentric circular grating surface 10-102 as a surface plasmon structure is depicted in FIG. 10-1. The circular grating may comprise any suitable number of rings and the number of rings shown in FIG. 10-1 is a non-limiting example. The circular grating may comprise protruding rings from a surface of a conductive film. For example, the circular grating may be formed at the interface of the sample well layer and a dielectric layer formed underneath the sample well layer. The sample well layer may be a conductive material and the concentric grating may be formed by patterning the grating structure at the interface between the conductive material and the dielectric. The rings of the circular grating may be on a regular periodic spacing, or may have irregular or aperiodic spacings between the rings. The sample well may be located at or near the center of the circular grating. In some embodiments, the sample well may be located off-center to the circular grating and may be positioned a certain distance from the center of the grating. In some embodiments, a grating-type surface energy-coupling component may comprise a spiral grating. An example of a spiral grating 10-202 is depicted in FIG. 10-2. The spiral grating 10-202 may comprise a spiral aperture in a conductive film. Any suitable dimensions of the spiral grating may be used to form the spiral grating.

A grating structure may be formed near a sample well such that emission energy may couple with the grating structure. The grating structure may be configured to form a spatial distribution pattern of the emission energy based on a characteristic wavelength of the emission energy. Different spatial distribution patterns may form for different characteristic wavelengths. Examples of possible spatial distribution patterns that form as a result of having a concentric grating positioned underneath a sample well is depicted in FIGS. 10-3 to 10-6. For example, a layer 10-306 of an integrated device may contain a sample well with a concentric grating structure 10-302 positioned underneath the sample well. When emission energy having a first characteristic wavelength is emitted by a sample in the sample well, the emission energy couples with the concentric grating and forms a first spatial distribution pattern 10-304 illustrated in FIG. 10-3. Additionally, when emission energy having a second characteristic wavelength is emitted by a sample in the sample well, a second distribution pattern may form, such as the distribution pattern 10-404 shown in FIG. 10-4. Similarly, FIG. 10-5 illustrates a third spatial distribution pattern 10-504 for emission energy having a third characteristic wavelength and FIG. 10-6 illustrates a fourth spatial distribution pattern 10-604 having a fourth characteristic wavelength. The different spatial distribution patterns may be detected by spatially separated sensors within the pixel to differentiate among the first, second, third, and fourth characteristic wavelengths.

Another example of a surface optic or surface plasmon structure is a nano-antenna structure. A nano-antenna structure may be designed to spatially direct and/or spatially separate emission energies of different characteristic wavelengths. In some embodiments, the location of the sample well with respect to the nano-antenna structure is selected so as to direct the emission energy from the sample well in a particular way toward one or more sensors. Nano-antennas may comprise nano-scale dipole antenna structures that are designed to produce a directional radiation pattern when excited by emission energy. The nano-antennas may be distributed around a sample well. The directional radiation pattern may result from a summation of the antennas' electromagnetic fields. In some embodiments, the directional radiation pattern may result from a summation of the antennas' electromagnetic fields with the field emitted directly from the sample. In some implementations, the field emitted directly from the sample may be mediated by a surface plasmon between the sample well and nano-antenna structure.

The dimensions of the individual nano-antennas that form the nano-antenna structure may be selected for the combined ability of the overall nano-antenna structure to produce specific distribution patterns of one or more emission energies. For example, the diameters of the individual nano-antennas may vary within a nano-antenna structure. However, in some instances, the diameters may be the same within a set of nano-antennas. In other implementations, a few selected diameters may be used throughout the overall nano-antenna structure. Some nano-antennas may be distributed on a circle of radius R and some may be shifted in a radial direction from the circle. Some nano-antennas may be equally spaced around a circle of radius R (e.g., centered on equivalent polar-angle increments), and some may be shifted from equal spacing around the circle. In some embodiments, the nano-antennas may be arranged in a spiral configuration around a sample well. Additionally or alternatively, other configurations of nano-antennas are possible, such as a matrix array around the sample well, a cross distribution, and star distributions. Individual nano-antennas may be shapes other than a circle, such as square, rectangular, cross, triangle, bow-tie, annular ring, pentagon, hexagon, polygons, etc. In some embodiments, the circumference of an aperture or disc may be approximately an integer multiple of a fractional wavelength, e.g., $(N/2)\lambda$.

A nano-antenna array may direct emission energy from a sample into concentrated radiation lobes that have a spatial pattern dependent upon a characteristic wavelength of the emission energy. When a sample emits energy, it may excite surface plasmons that propagate from the sample well to the nano-antennas distributed around the sample well. The surface plasmons may then excite radiation modes or dipole emitters at the nano-antennas that emit radiation perpendicular to the surface of the sample well layer. The phase of an excited mode or dipole at a nano-antenna will depend upon the distance of the nano-antenna from the sample well. Selecting the distance between the sample well and an individual nano-antenna controls the phase of radiation emitted from the nano-antenna. The spatial radiation mode excited at a nano-antenna will depend upon the geometry and/or size of the nano-antenna. Selecting the size and/or geometry of an individual nano-antenna controls the spatial radiation mode emitted from the nano-antenna. Contributions from all nano-antennas in the array and, in some instances the sample well, may determine an overall radiation lobe or lobes that form the radiation pattern. As may be appreciated, phase and spatial radiation mode emitted from an individual nano-antenna may depend upon wavelength, so that the overall radiation lobe or lobes that form the radiation pattern will also be dependent upon wavelength. Numerical simulations of the electromagnetic fields may be employed to determine overall radiation lobe patterns for emission energies of different characteristic wavelengths.

The nano-antenna may comprise an array of holes or apertures in a conductive film. For example, the nano-antenna structure may be formed at the interface between a conductive sample well layer and an underlying dielectric layer. The holes may comprise sets of holes distributed in concentric circles surrounding a central point. In some embodiments, a sample well is located at the central point of the array, while in other embodiments the sample well may be off-center. Each circularly-distributed set of holes may comprise a collection of different diameters arranged smallest to largest around the circular distribution. The hole diameters may be different between the sets (e.g., a smallest hole in one set may be larger than a smallest hole in another set), and the location of the smallest hole may be oriented at a different polar angle for each set of circles. In some embodiments, there may be one to seven sets of the circularly-distributed holes in a nano-antenna. In other embodiments, there may be more than seven sets. In some embodiments, the holes may not be circular, but may be any suitable shape. For example, the holes may be ellipses, triangles, rectangles, etc. In other embodiments, the distribution of holes may not be circular, but may create a spiral shape.

Figures 5, 6, 7, 8, 9, 10, 11:
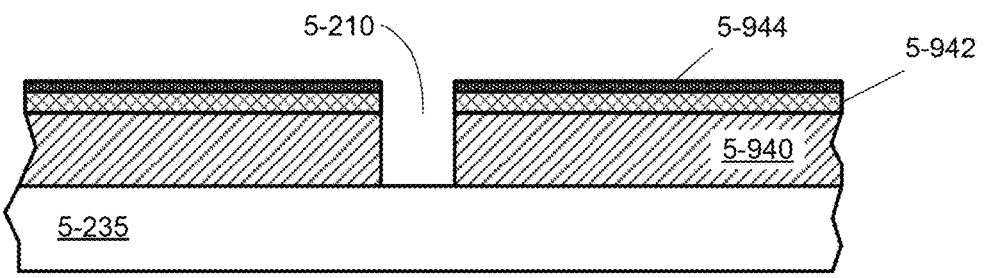

FIGS. 11-1A and 11-1B illustrate an exemplary nano-antenna structure comprised of holes or apertures in a conductive layer. FIG. 11-1A shows a top planar view of the surface of an integrated device with a sample well 11-108 surrounded by holes 11-122. The nano-antenna holes are distributed approximately around a circle of radius R. In this non-limiting example, the hole diameters vary by incrementally increasing around the circumference of the circle of holes. FIG. 11-1B shows a schematic of a cross-sectional view of the integrated device shown in FIG. 11-1A along line B-B'. The sample well layer 11-116 that includes sample well 11-108 and apertures 11-122 that are part of the nano-antenna structure. Layer 11-118 of the integrated device lies underneath sample well layer 11-116. Layer 11-118 may be a dielectric material and/or an optically transparent material.

In some embodiments, the nano-antenna structure may comprise a plurality of disks. The disks of the nano-antenna structure may be formed as conductive disks protruding from a surface of a conductive material. The conductive material may be adjacent an optically-transparent material. In some embodiments, the nano-antennas may be distributed around a sample well. In some instances, the nano-antennas may be distributed approximately around a sample well at a circle of radius R. A nano-antenna array may comprise multiple sets of nano-antennas distributed approximately on additional circles of different radii around a sample well.

FIGS. 11-2A and 11-2B illustrate an exemplary embodiment of a nano-antenna structure comprising disks protruding from a conductive layer. FIG. 11-2A shows a top planar view schematic of the surface of an integrated device with a sample well 11-208 surrounded by disks 11-224. The nano-antenna disks are distributed approximately around a circle of radius R. In this non-limiting example, two diameters are used for the disks and the disks alternate between these two diameters around the circumference of the circle of nano-antenna. FIG. 11-2B shows a schematic of a cross-sectional view of the integrated device shown in FIG. 11-2A along line C-C'. The sample well layer 11-216 that includes sample well 11-208 and disks 11-224 that are part of the nano-antenna structure. The disks 11-224 protrude from the sample well layer 11-216 by a certain distance. In some embodiments, the distance the disks extend from the sample well layer may vary within a nano-antenna structure. Layer 11-218 of the integrated device lies underneath sample well layer 11-216. Layer 11-18 may be a dielectric material and/or an optically transparent material. The sample well layer 11-216 and the protruding disks may be a conductive material.

The holes and/or disks that form a nano-antenna structure may be any suitable pattern or distribution such that emission energy from sample well couples with one or more of the nano-antennas of the nano-antenna structure. Another example of a nano-antenna structure is illustrated in FIG. 11-3. A sample well may be located within a sample well layer at position 11-308 with respect to nano-antenna structure 11-302. Surface plasmons may form in the area of the nano-antenna structure when emission energy is emitted from the sample well. FIG. 11-4 illustrates an exemplary schematic of the propagation of surface plasmons within the nano-antenna structure. Other exemplary patterns and distributions of nano-antennas that form a nano-antenna structure within a pixel are shown in FIGS. 11-5, 11-6, and 11-7.

A nano-antenna structure may be used to distinguish emissions at different characteristic wavelengths. The nano-antenna aperture structure may produce radiation lobes that extend from the sample well in different directions for emission energy of different characteristic wavelengths. The radiation lobes form a spatial distribution pattern that differs depending on the characteristic wavelength of the emission energy. Examples of possible spatial distribution patterns that form as a result of having a nano-antenna structure positioned underneath a sample well is depicted in FIGS. 11-8, 11-9, 11-10, and 11-11. For example, a layer 11-806 of an integrated device may contain a sample well with a nano-aperture structure 11-802 positioned underneath the sample well. When emission energy having a first characteristic wavelength is emitted by a sample in the sample well, the emission energy couples with the nano-antennas in the nano-antenna structure which directs the emission energy into a first spatial distribution pattern 11-904 illustrated in FIG. 11-8. Additionally, when emission energy having a second characteristic wavelength is emitted by a sample in the sample well, a second distribution pattern may form, such as the distribution pattern 11-1004 shown in FIG. 11-9. Similarly, FIG. 11-10 illustrates a third spatial distribution pattern 11-1104 for emission energy having a third characteristic wavelength and FIG. 11-11 illustrates a fourth spatial distribution pattern 11-1204 having a fourth characteristic wavelength. The different spatial distribution patterns may be detected by spatially separated sensors within the pixel to differentiate among the first, second, third, and fourth characteristic wavelengths.

2. Far Field Optics

Emission energy emitted from a sample in the sample well may be transmitted to the sensor of a pixel in a variety of ways, some examples of which are described in detail below. Some embodiments may use optical and/or plasmonic components to increase the likelihood that light of a particular wavelength is directed to an area or portion of the sensor that is dedicated to detecting light of that particular wavelength. The sensor may include multiple sub-sensors for simultaneously detecting emission energy of different wavelengths.

Figures 5, 6, 7, 8, 9, 10, 11, 12:
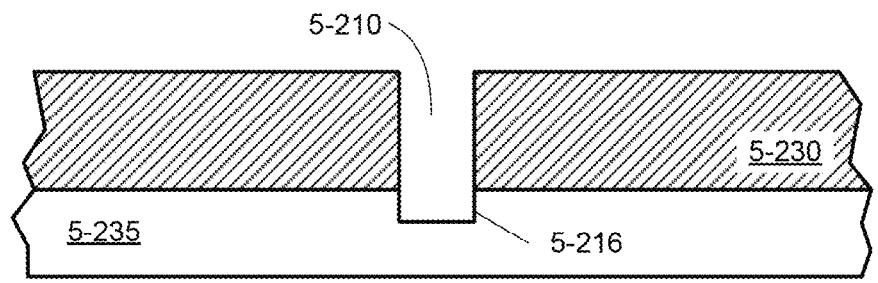

FIG. 12-1a is a schematic diagram of a single pixel of the integrated device according to some embodiments where at least one sorting element is used to direct emission energy of a particular wavelength to a respective sub-sensor. A sample well 12-101 formed in a conductive material 12-103 receives a sample and may emit emission energy 12-104. For clarity, details of the sample well and any near field optical and plasmonic components are not shown. The emission energy 12-104 travels through a dielectric material 12-105 until it reaches a sorting element 12-107. The sorting element 12-107 couples the wavelength of the emission energy 12-104 to a spatial degree of freedom, thereby separating the emission energy into its constituent wavelength components, referred to as sorted emission energy. FIG. 12-1a illustrates schematically the emission energy 12-104 being split into four sorted emission energy paths through a dielectric material 12-109, each of the four paths associated with a sub-sensor 12-111 through 12-114 of the pixel. In this way, each sub-sensor is associated with a different portion of the spectrum, forming a spectrometer for each pixel of the integrated device.

Any suitable sorting element 12-107 may be used to separate the different wavelengths of the emission energy. Embodiments may use optical or plasmonic elements. Examples of optical sorting elements include, but are not limited to, holographic gratings, phase mask gratings, amplitude mask gratings, and offset Fresnel lenses. Examples of plasmonic sorting elements include, but are not limited to phased nano-antenna arrays, and plasmonic quasi-crystals.

FIG. 12-1b is a schematic diagram of a single pixel of the integrated device according to some embodiments where at least one filtering element is used to direct emission energy of a particular wavelength to a respective sub-sensor and prevent emission energy of other wavelengths from reaching the sub-sensor. Where the components of FIG. 12-1b are similar to those of FIG. 12-1a the same reference numerals are used. A sample well 12-101 formed in a conductive material 12-103 receives a sample and may emit emission energy 12-104. For clarity, details of the sample well and any near field optical and plasmonic components are not shown. The emission energy 12-104 travels through a dielectric material 12-105 until it reaches one of the filtering elements 12-121 through 12-124. The filtering elements 12-121 through 12-124, each associated with a particular sub-sensor 12-111 through 12-114, are each configured to transmit emission energy of a respective wavelength and reject emission energy of other wavelengths by absorbing the emission energy (not illustrated in FIG. 12-1b) and/or reflecting the emission energy. After passing through a respective filtering element, the filtered emission energy travels through a dielectric material 12-109 and impinges on a corresponding sub-sensor 12-111 through 12-114 of the pixel. In this way, each sub-sensor is associated with a different portion of the spectrum, forming a spectrometer for each pixel of the integrated device.

Any suitable filtering elements may be used to separate the different wavelengths of the emission energy. Embodiments may use optical or plasmonic filtering elements. Examples of optical sorting elements include, but are not limited to, reflective multilayer dielectric filters or absorptive filters. Examples of plasmonic sorting elements include, but are not limited to frequency selective surfaces designed to transmit energy at a particular wavelength and photonic band-gap crystals.

Alternatively, or in addition to the above mentioned sorting elements and filtering elements, additional filtering elements may be place adjacent to each sub-sensor 12-11 through 12-114. The additional filtering elements may include a thin lossy film configured to create constructive interference for emission energy of a particular wavelength. The thin lossy film may be a single or multi-layer film. The thin lossy film may be made from any suitable material. For example, the thin lossy film may be made from a material where the index of refraction n is approximately the same order of magnitude as the extinction coefficient k. In other embodiments, the thin lossy film may be made from a material where the index of refraction n is within about two orders of magnitude difference from the value of the extinction coefficient k of the material. Non-limiting examples of such materials at visible wavelengths are germanium and silicon.

The thin lossy film may be any suitable thickness. In some embodiments, the thin lossy film may be 1-45 nm thick. In other embodiments, the thin lossy film may be 15-45 nm thick. In still other embodiments, the thin lossy film may be 1-20 nm thick. FIG. 12-2a illustrates an embodiment where the thin lossy films 12-211 through 12-214 each have a different thickness determined at least in part by the wavelength that is associated with each sub-sensor 12-11 through 12-114. The thickness of the film determines, at least in part, a distinct wavelength that will selectively pass through the thin lossy film to the sub-sensor. As illustrated in FIG. 12-211, thin lossy film 12-211 has a thickness d1, thin lossy film 12-212 has a thickness d2, thin lossy film 12-213 has a thickness d3, and thin lossy film 12-214 has a thickness d4. The thickness of each subsequent thin lossy film is less than the previous thin lossy film such that d1>d2>d3>d4.

Additionally, or alternatively, the thin lossy films may be formed of a different material with different properties such that emission energy of different wavelengths constructively interferes at each respective sub-sensor. For example, the index of refraction n and/or the extinction coefficient k may be selected to optimize transmission of emission energy of a particular wavelength. FIG. 12-2b illustrates thin lossy films 12-221 through 12-224 with the same thickness but each thin lossy film is formed from a different material. In some embodiments, both the material of the thin lossy films and the thickness of the thin lossy films may be selected such that emission energy of a desired wavelength constructively interferes and is transmitted through the film.

In some embodiments, a photonic crystal resonator structure may be used. In such embodiments, the symmetry of the photonic crystal structure may cause destructive interference of the excitation light at the sensor, thereby reducing the amount of background light that reaches the sensor originating from the excitation light.

K. Sensors

Figures 5, 6, 7, 8, 9, 10, 11, 12, 13, 13A:
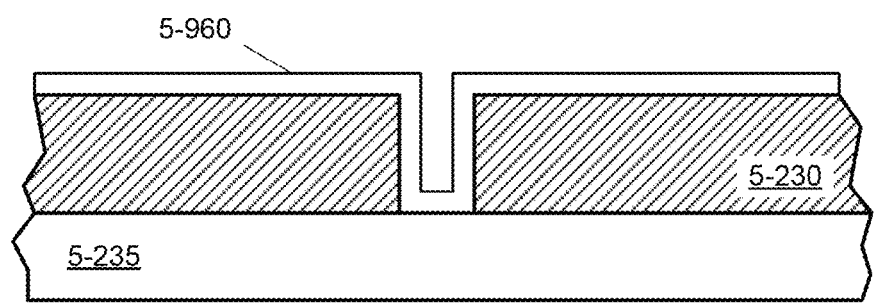
Figures 5, 6, 7, 8, 9, 10, 11, 12, 13, 13B:
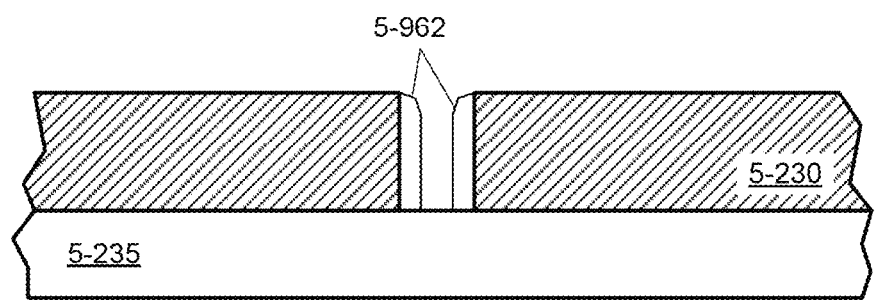
Figures 5, 6, 7, 8, 9, 10, 11, 12, 13, 13C:
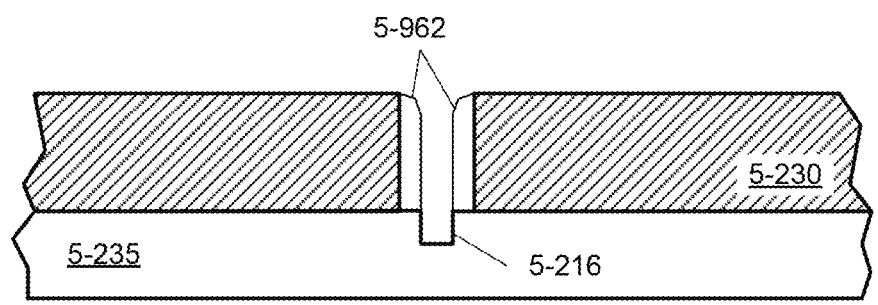

Various embodiments of sensors, sensor operation, and signal processing methods have been contemplated by the inventors. According to some embodiments, a sensor 5-260 at a pixel may comprise any suitable sensor capable of receiving emission energy from one or more tags in the sample well, and producing one or more (e.g., at least 2, 3, or 4) electrical signals representative of the received emissions. In some embodiments, a sensor may comprise at least one, two, three, or four photodetectors. Each photodetector may comprise a p-n junction formed in a semiconductor substrate. FIG. 13-1A depicts just one embodiment of a sensor that may be fabricated within a pixel 5-100 of an integrated device.

According to some embodiments, a sensor 5-260 may be formed at each active pixel 5-100 of an integrated device. The sensor may be centered about a sample well 5-210, and spaced from the sample well by a distance between approximately 1 micron and approximately 20 microns. There may be one or more transparent layers 13-110 between the sample well and the sensor, so that emission from the sample well may travel to the sensor without significant attenuation. The sensor 5-260 may be formed in a semiconductor substrate 13-120 at a base of the pixel, according to some embodiments, and be located on a same side of the sample well as the excitation source (not shown).

The sensor may comprise one or more semiconductor junction photodetector segments. Each semiconductor junction may comprise a well of a first conductivity type. For example, each semiconductor junction may comprise an n-type well formed in a p-type substrate, as depicted in the drawing. According to some embodiments, a sensor 5-260 may be arranged as a bulls-eye detector 13-162, as depicted in the plan view of FIG. 13-1B. A first photodetector 13-124 may be located at a center of the sensor, and a second annular photodetector 13-122 may surround the center photodetector. Electrical contacts to the wells may be made through conductive traces 13-134 formed at a first or subsequent metallization level and through conductive vias 13-132. There may be a region of highly doped semiconductor material 13-126 at contact regions of the vias. In some embodiments, a field oxide 13-115 may be formed at surfaces between the photodetectors and or may cover a portion of each photodetector. In some implementations, there may be additional semiconductor devices 13-125 (e.g., transistors, amplifiers, etc.) formed within the pixel adjacent to the sensor 5-260. There may be additional metallization levels 13-138, 13-136 within the pixel.

In some implementations, a metallization levels 13-136 may extend across a majority of the pixel and have an opening below the sample well 5-210, so that emission from the sample well can reach the sensor. In some cases, a metallization level 13-136 may serve as a reference potential or a ground plane, and additionally serve as an optical block to prevent at least some background radiation (e.g., radiation from an excitation source or from the ambient environment) from reaching the sensor 5-260.

As depicted in FIG. 13-1A and FIG. 13-1B, a sensor 5-260 may be subdivided into a plurality of photodetector segments 13-122, 13-124 that are spatially and electrically separated from each other. In some embodiments, segments of a sensor 5-260 may comprise regions of oppositely-doped semiconductor material. For example, a first charge accumulation well 13-124 for a first sensor segment may be formed by doping a first region of a substrate to have a first conductivity type (e.g., n-type) within the first well. The substrate may be p-type. A second charge accumulation well 13-122 for a second sensor segment may be formed by doping a second region of the substrate to have the first conductivity type within the second well. The first and second wells may be separated by a p-type region of the substrate.

The plurality of segments of the sensor 5-260 may be arranged in any suitable way other than a bulls-eye layout, and there may be more than two segments in a sensor. For example, in some embodiments, a plurality of photodetector segments 13-142 may be laterally separated from one another to form a stripe sensor 13-164, as depicted in FIG. 13-1C. In some embodiments, a quad (or quadrant) sensor 13-166 may be formed by arranging the segments 13-144 in a quad pattern, as depicted in FIG. 13-1D. In some implementations, arc segments 13-146 may be formed in combination with a bulls-eye pattern, as depicted in FIG. 13-1E, to form an arc-segmented sensor 13-168. Another sensor configuration may comprise pie-piece sections, which may include individual sensors arranged in separate sections of a circle. In some cases, sensor segments may be arranged symmetrically around a sample well 5-210 or asymmetrically around a sample well. The arrangement of sensor segments is not limited to only the foregoing arrangements, and any suitable distribution of sensor segments may be used.

The inventors have found that a quadrant sensor 13-166, pie-sector sensor, or similar sector sensor can scale to smaller pixel sizes more favorably than other sensor designs. Quadrant and sector detectors may consume less pixel area for a number of wavelengths detected and active sensor area. Quadrant and sector detectors may be used in combination with nano-antenna arrays or surface-plasmon structures to produce distinct spatial distribution patterns that are discernable by the detectors. Sensors may be arranged in various geometric configurations. In some examples, sensors are arranged in a square configuration or hexagonal configuration.

Sensors of the present disclosure may be independently (or individually) addressable. An individually addressable sensor is capable of detecting emission from a corresponding sample well and providing output signals independent of other sensors. An individually addressable sensor may be individually readable.

In some embodiments, a stacked sensor 13-169 may be formed by fabricating a plurality of separated sensor segments 13-148 in a vertical stack, as depicted in FIG. 13-1F. For example, the segments may be located one above the other, and there may, or may not, be insulating layers between the stacked segments. Each vertical layer may be configured to absorb emission energy of a particular energy, and pass emission at different energies. For example, a first detector may absorb and detect shorter-wavelength radiation (e.g., blue-wavelength radiation below about 500 nm from a sample). The first detector may pass green- and red-wavelength emissions from a sample. A second detector may absorb and detect green-wavelength radiation (e.g., between about 500 nm and about 600 nm) and pass red emissions. A third detector may absorb and detect the red emissions. Reflective films 13-149 may be incorporated in the stack, in some embodiments, to reflect light of a selected wavelength band back through a segment. For example, a film may reflect green-wavelength radiation that has not been absorbed by the second segment back through the second segment to increase its detection efficiency.

In some embodiments with vertically-stacked sensor segments, emission-coupling components may not be included at the sample well to produce distinct spatial distribution patterns of sample emission that are dependent on emission wavelength. Discernment of spectrally different emissions may be achieved with a vertically-stacked sensor 13-169 by analyzing the ratio of signals from is stacked segment, according to some embodiments.

In some embodiments, segments of a sensor 5-260 are formed from silicon, though any suitable semiconductor (e.g., Ge, GaAs, SiGe, InP, etc.) may be used. In some embodiments, a sensor segment may comprise an organic photoconductive film. In other embodiments, quantum dot photodetectors may be used for sensor segments. Quantum dot photodetectors may respond to different emission energies based on the size of the quantum dot. In some embodiments, a plurality of quantum dots of varying sizes may be used to discriminate between different emission energies or wavelengths received from the sample well. For example, a first segment may be formed from quantum dots having a first size, and a second segment may be formed from quantum dots having a second size. In various embodiments, sensors 5-260 may be formed using conventional CMOS processes.

As described above, emission-coupling components may be fabricated adjacent the sample well in some embodiments. The emission-coupling components can alter emission from a sample within the sample well 5-210 to produce distinct spatial distribution patterns of sample emission that are dependent on emission wavelength. FIG. 13-2A depicts an example of a first spatial distribution pattern 13-250 that may be produced from a first sample at a first wavelength. The first spatial distribution pattern 13-250 may have a prominent central lobe directed toward a central segment of a bulls-eye sensor 13-162, for example. As just one example, such a pattern 13-250 may be produced from a sample well surrounded by a circular grating 13-220 emission-coupling structure, where the sample emits at a wavelength of about 663 nm. A projected pattern 13-252 incident on the sensor may appear as illustrated in FIG. 13-2B.

FIG. 13-2C depicts a spatial distribution pattern 13-260 that may be produced from a second sample emitting at a second wavelength from the same sample well, according to some embodiments. The second spatial distribution pattern 13-260 may comprise two lobes of radiation and differ from the first spatial distribution pattern 13-250. A projected pattern 13-262 of the second spatial distribution pattern 13-260 may appear as depicted in FIG. 13-2D, according to some embodiments. As just one example, a second spatial distribution pattern 13-260 may be produced from the same sample well surrounded by the circular grating 13-220 emission-coupling structure, where the sample emits at a wavelength of about 687 nm.

The segments of a sensor 5-260 may be arranged to detect particular emission energies, according to some embodiments. For example, emission-coupling structures adjacent the sample well and segments of a sensor may be designed in combination to increase signal differentiation between particular emission energies. The emission energies may correspond to selected tags that will be used with the integrated device. As an example, a bulls-eye sensor 13-162 could have its segments sized and/or located to better match the projected patterns 13-260, 13-262 from a sample, so that regions of higher intensity fall more centrally within active segments of the sensor. Alternatively or additionally, emission-coupling structures may be designed to alter the projected patterns 13-260, 13-262 so that intense regions fall more centrally within segments of the sensor.

Although a sensor 5-260 may comprise two segments, it is possible in some embodiments to discern more than two spectrally-distinct emission bands from a sample. For example, each emission band may produce a distinct projected pattern on the sensor segments and yield a distinct combination of signals from the sensor segments. The combination of signals may be analyzed to discern an identify the emission band. FIG. 13-2E through FIG. 13-2H represent results from numerical simulations of signals from a two-segment sensor 5-260 exposed to four distinct emission patterns. The emission patterns were simulated as being produced at four wavelengths (565 nm, 595 nm, 663 nm, 687 nm) from a sample well having a circular grating formed adjacent the sample well. As can be seen, each combination of signals from the two sensor segments is distinct, and can be used to discriminate between emitters at the four wavelengths. For the simulation, because the outer detector segment of the bulls-eye sensor 13-162 had a larger area, more signal was integrated for that detector. Additionally, light that impinged on an area between the detectors generated carriers that may drift towards either detector segment and contribute to signals from both segments.

In some embodiments, there may be N photodetector segments per pixel, where N may be any integer value. In some embodiments, N may be greater than or equal to 1 and less than or equal to 10. In other embodiments, N may be greater than or equal to 2 and less than or equal to 5. The number M of discernible sample emissions (e.g., distinct emission wavelengths from different luminescent tags) that may be detected by the N detectors may be equal to or greater than N. The discernment of M sample emissions may be achieved by evaluating the ratio of signals from each sensor segment, according to some embodiments. In some implementations, the ratio, sum and/or amplitudes of the received signals may be measured and analyzed to determine a characteristic wavelength of emission from the sample well.

In some embodiments, more than one emitter may emit at different characteristic wavelengths in a given time window within a sample well 5-210. A sensor 5-260 may simultaneously detect signals from multiple emissions at different wavelengths and provide the summed signal for data processing. In some implementations, multi-wavelength emission may be distinguishable as another set of signal values from the sensor segments (e.g., signal values different from those shown in FIG. 13-2E through FIG. 13-2H). The signal values may be analyzed to discern that multi-wavelength emission has occurred and to identify a particular combination of emitters associated with the emissions.

Figures 2J, 13:
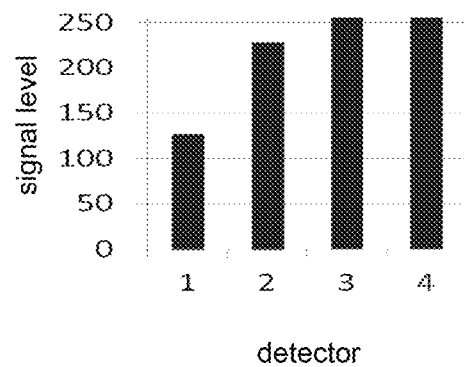
Figures 3A, 13:
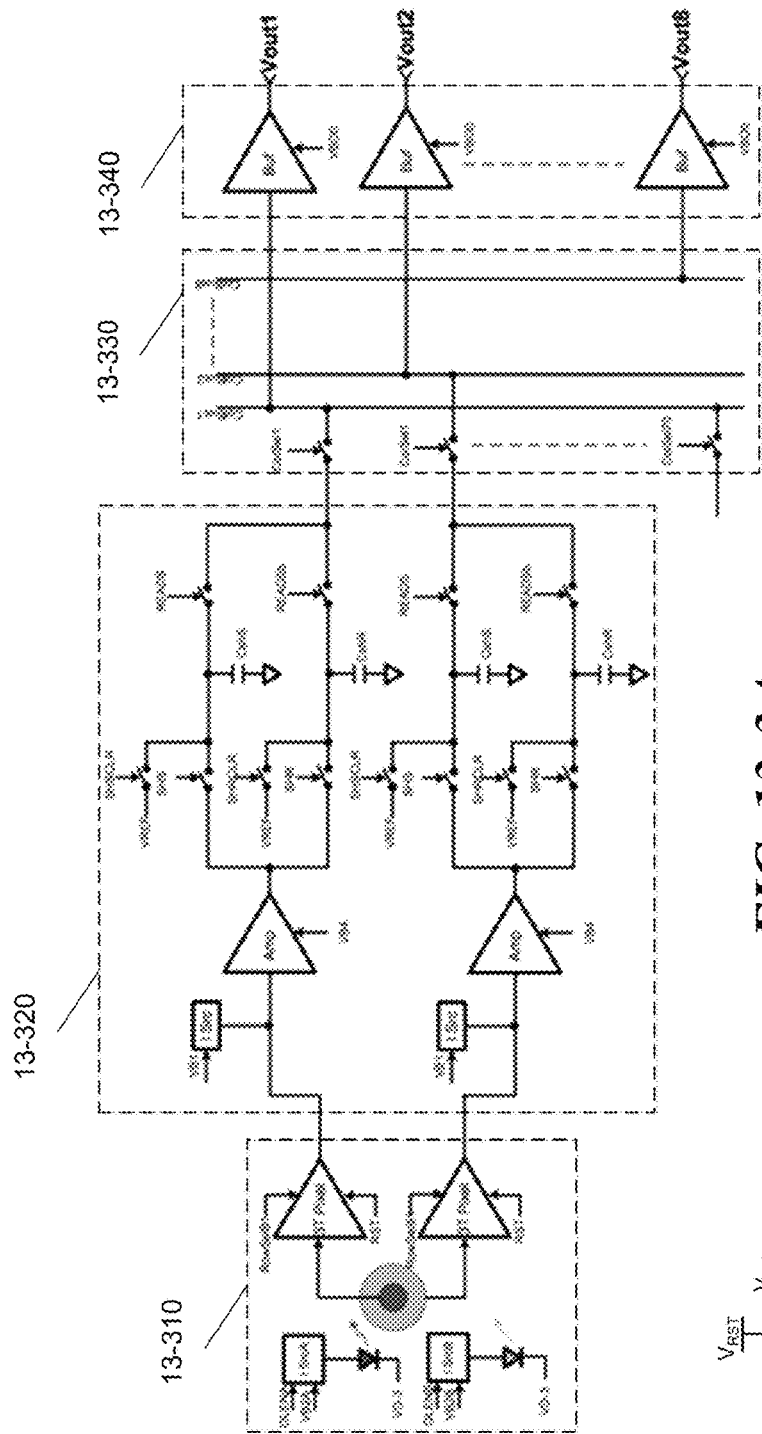
Figures 3B, 13:
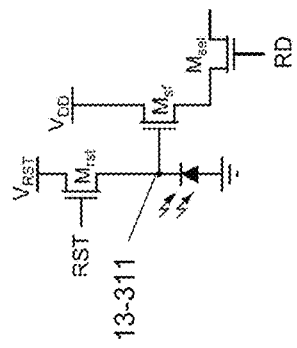
Figures 3C, 13:
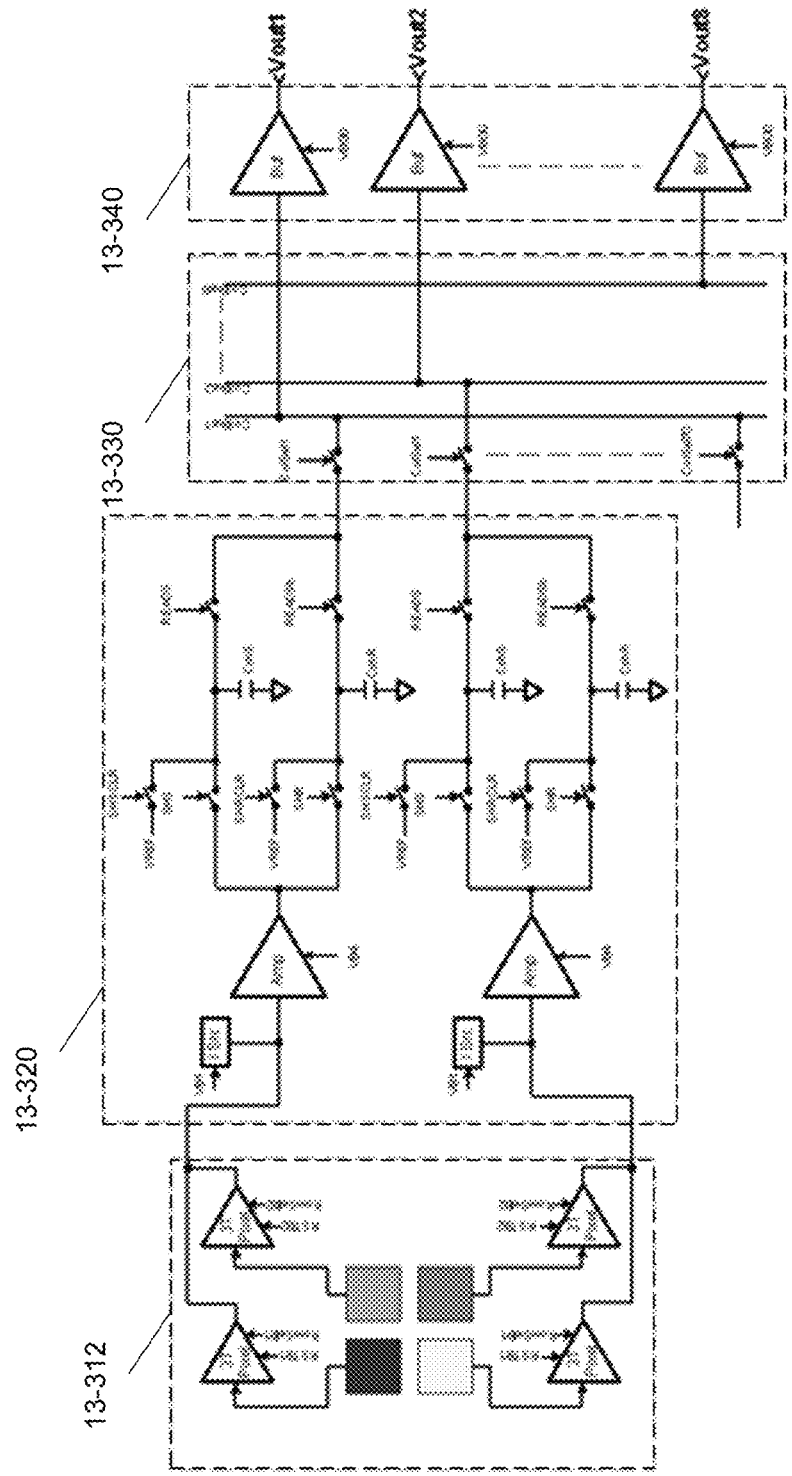
Figures 4A, 13:
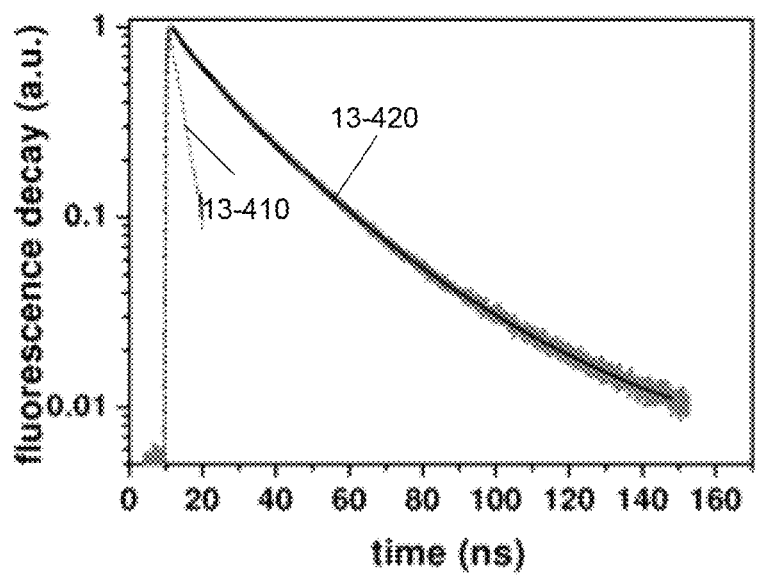
Figures 4B, 13:
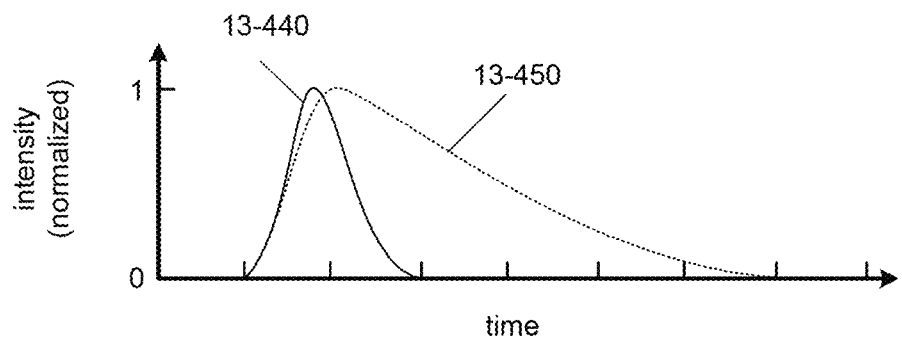
Figures 4C, 13:
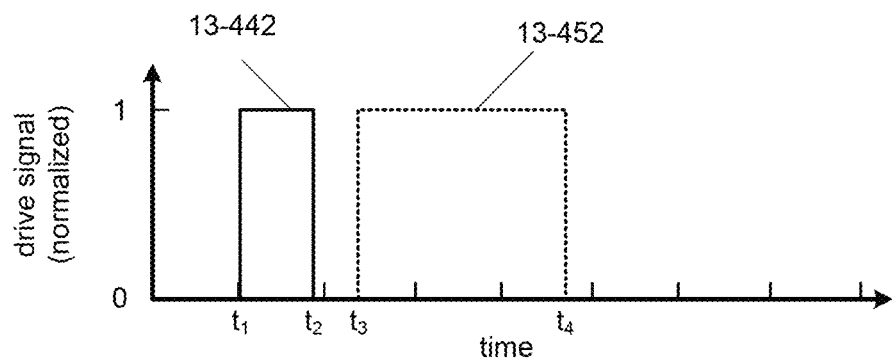
Figures 1, 14:
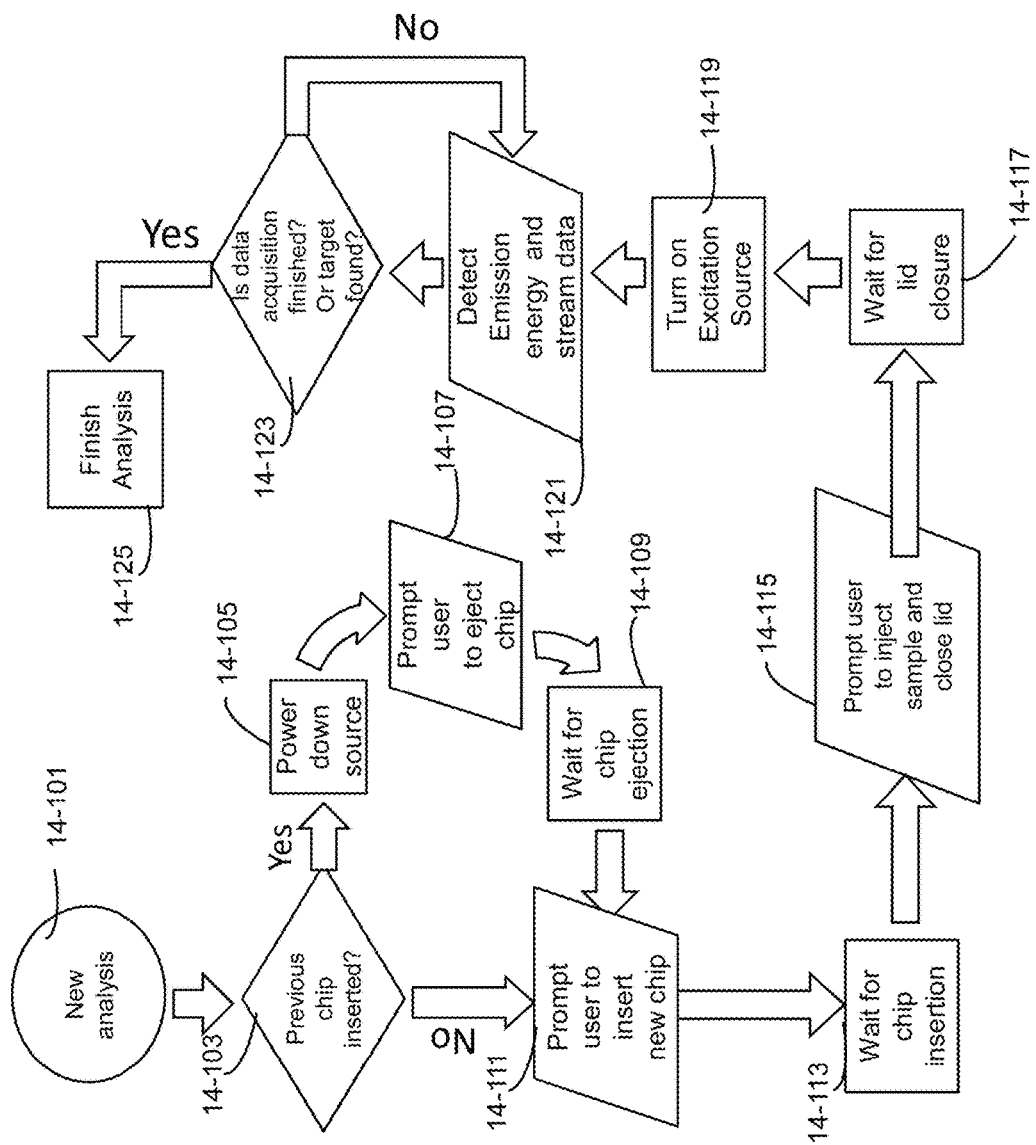
Figures 2, 14:
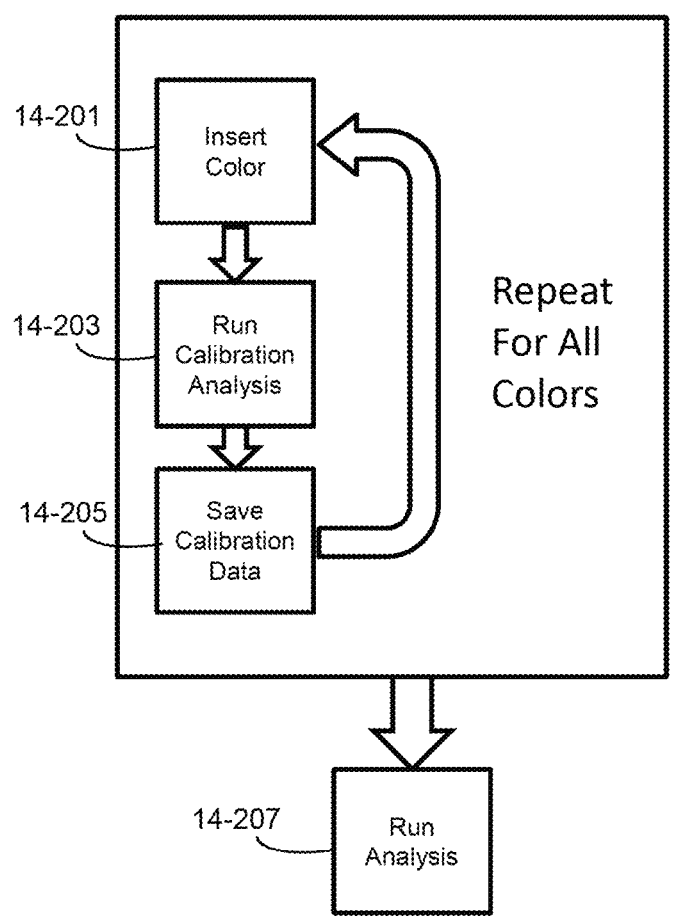
Figures 3, 14:
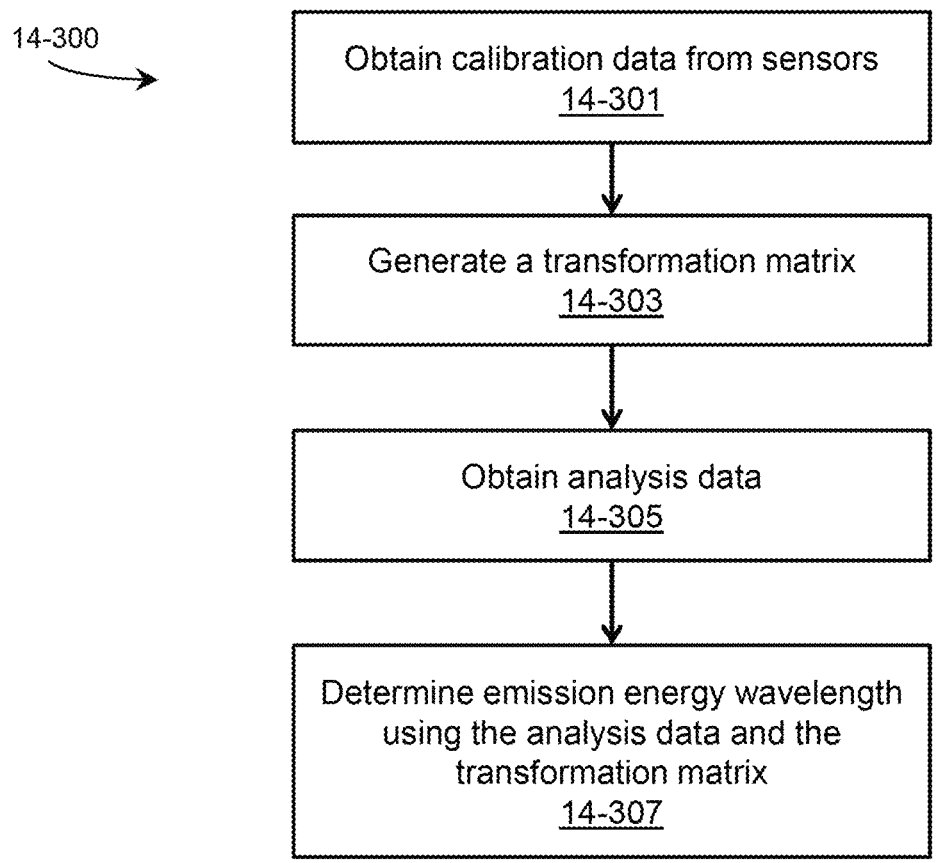
Figures 1, 15:
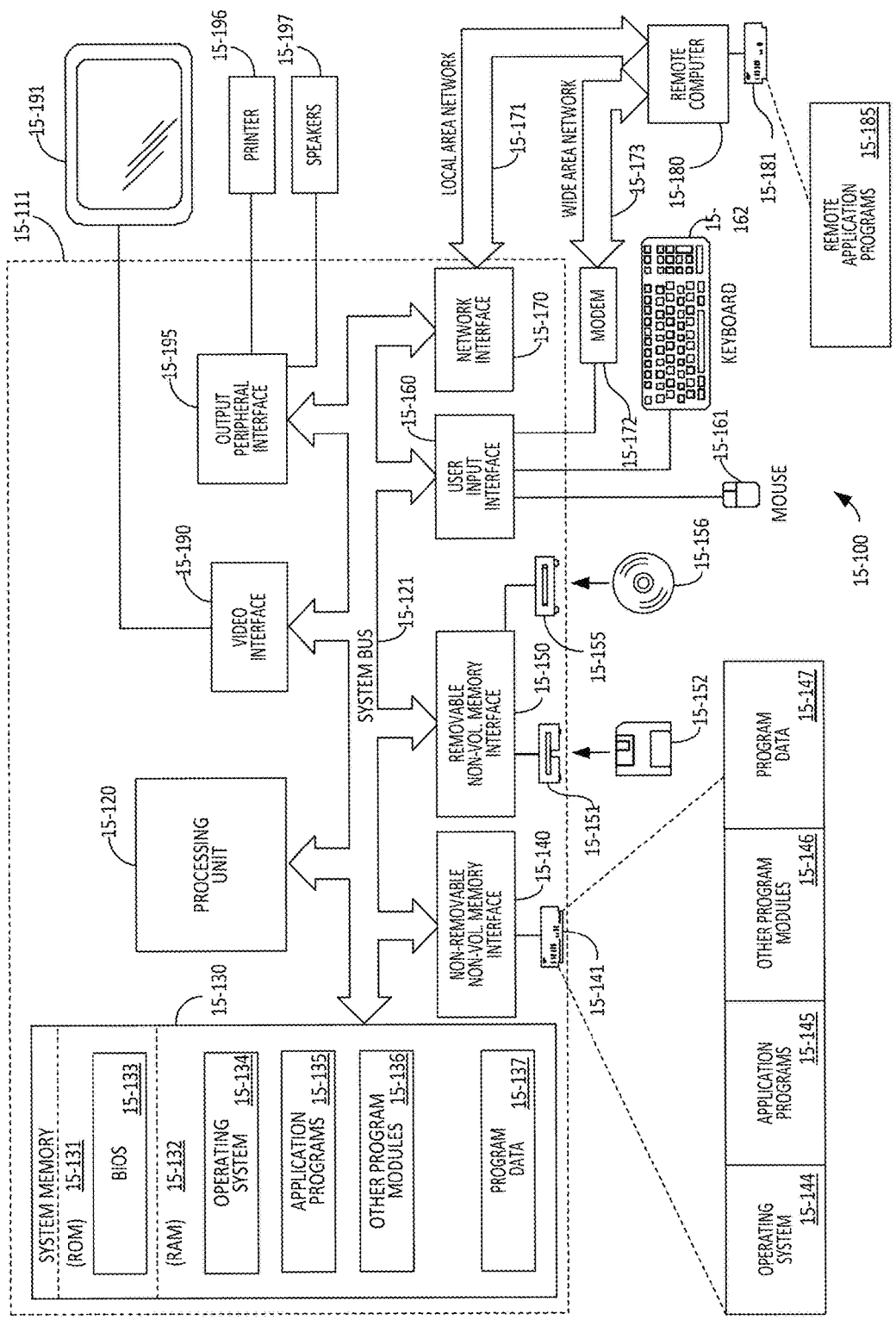

The inventors have also contemplated and analyzed a bulls-eye sensor having at least two, three, or four concentric segments. Signals from the segments are plotted in FIG. 13-2I and FIG. 13-2J for the same emission conditions associated with FIG. 13-2G and FIG. 13-2H, respectively. The four-segment bulls-eye sensor also shows discernable signals that may be analyzed to identify a particular emitter within the sample well.

When wavelength filtering is used at each sensor segment, or the spectral separation is high, each segment of a sensor may detect substantially only a selected emission band. For example, a first wavelength may be detected by a first segment, a second wavelength may be detected by a second segment, and a third wavelength may be detected by a third segment.

Referring again to FIG. 13-1A, there may be additional electronic circuitry 13-125 within a pixel 2-205 that may be used to collect and readout signals from each segment of a sensor 5-260. FIG. 13-3A and FIG. 13-3D depict circuitry that may be used in combination with a multi-segment sensor, according to some embodiments. As an example, signal collection circuitry 13-310 may comprise three transistors for each sensor segment. An arrangement of the three transistors is depicted in FIG. 13-3B, according to some implementations. A signal level at a charge accumulation node 13-311 associated with each segment may be reset by a reset transistor RST prior to a charge-accumulation period, and a signal level for the segment (determined by the amount of charge at the charge accumulation node) may be read out with a read transistor RD during and/or at the conclusion of a charge-accumulation period. Signals may be provided to a processor (not shown) for analysis to discern the detection of M different emission wavelengths from the sample detected by N spatially-separated detectors, as described above.

The pixel circuitry may further include amplification and correlated double-sampling circuitry 13-320, according to some embodiments. The amplification and double-sampling circuitry may comprise transistors configured to amplify signals from the sensor segments as well as transistors configured to reset the voltage level at the charge-accumulation node and to read a background, or "reset", signal at the node when no emission radiation is present on the sensor (e.g., prior to application of excitation energy at the sample well) and to read a subsequent emission signal, for example.

According to some embodiments, correlated double sampling is employed to reduce background noise by subtracting a background or reset signal level from the detected emission signal level. The collected emission signal and background signal associated with each segment of the sensor may be read out onto column lines 13-330. In some embodiments, an emission signal level and background signal are time-multiplexed onto a common column line. There may be a separate column line for each sensor segment. Signals from the column lines may be buffered and/or amplified with amplification circuitry 13-340 (which may be located outside of an active pixel array), and provided for further processing and analysis. In some embodiments the subtraction of the double-sampled signals is calculated off-chip, e.g., by a system processor. In other embodiments, the subtraction may be performed on chip or in circuitry of the base instrument.

Some embodiments of correlated double sampling may operate by selecting a row to sample, wherein the sensors associated with the row have integrated signal charges over a sampling period and contain signal levels. The signal levels may be simultaneously read out onto the columns lines. After sampling the integrated signal levels, all the pixels in the selected row may be reset and immediately sampled. This reset level may be correlated to the next integrated signal that starts accumulating after the reset is released, and finishes integrating a frame time later when the same row is selected again. In some embodiments, the reset values of the frame may be stored off-chip so that when the signals have finished integrating and have been sampled, the stored correlated reset values can be subtracted.

In some embodiments, a sensor 5-260 with more than two segments may require additional circuitry. FIG. 13-3C depicts signal-collection, amplification, and double-sampling circuitry associated with a quad sensor. According to some embodiments, signals from two or more segments may be time-multiplexed onto a common signal channel at the pixel, as depicted in the drawing. The time-multiplexed signals may include sampled background signals for each segment for noise cancellation. Additionally, the signals from two or more segments may be time-multiplexed onto a common column line.

According to some embodiments, temporal signal-acquisition techniques may be used to reduce background signal levels from an excitation source or sources, and/or discern different emissions from different emitters associated with a sample. FIG. 13-4A depicts fluorescent emission and decay from two different emitters that may be used to tag a sample, according to some embodiments. The two emissions have appreciably different time-decay characteristics. A first time-decay curve 13-410 from a first emitter may correspond to a common fluorescent molecule such as rhodamine. A second time-decay curve 13-420 may be characteristic of a second emitter, such as a quantum dot or a phosphorescent emitter. Both emitters exhibit an emission-decay tail that extends for some time after initial excitation of the emitter. In some embodiments, signal-collection techniques applied during the emission-decay tail may be timed to reduce a background signal from an excitation source, in some embodiments, and to distinguish between the emitters, in some embodiments.

According to some implementations, time-delayed sampling may be employed during the emission-decay tail to reduce a background signal due to radiation from an excitation source. FIG. 13-4B and FIG. 13-4C illustrate time-delay sampling, according to some embodiments. FIG. 13-4B depicts the temporal evolution of an excitation pulse 13-440 of excitation radiation from an excitation source, and a subsequent emission pulse 13-450 that may follow from a sample that is excited within the sample well. The excitation pulse 13-440 may result from driving the excitation source with a drive signal 13-442 for a brief period of time, as depicted in FIG. 13-4C. For example, the drive signal may begin at a first time $t_1$ and end at a second time $t_2$. The duration of the drive signal $(t_2-t_1)$ may be between about 1 picosecond and about 50 nanoseconds, according to some embodiments, though shorter durations may be used in some implementations.

At a time $t_3$ following termination of the drive signal for the excitation source, a sensor 5-260 (or sensor segment) at the pixel may be gated to accumulate charge at a charge accumulation node 13-312 during a second time interval extending from a time $t_3$ to a time $t_4$. The second time interval may be between about 1 nanosecond and about 50 microseconds, according to some embodiments, though other durations may be used in some implementations. As can be seen in reference to FIG. 13-4B, a charge accumulation node will collect more signal charges due to the emitting sample then due to the excitation source. Accordingly, an improved signal-to-noise ratio may be obtained.

Referring again to FIG. 13-4A, because of the different temporal emission characteristics of the emitters, corresponding signals at a sensor may peak at different times. In some implementations, signal-acquisition techniques applied during the emission-decay tail may be used to discern different emitters. In some embodiments, temporal detection techniques may be used in combination with spatial and spectral techniques (as described above in connection with FIG. 13-2, for example) to discern different emitters.

FIG. 13-4D through FIG. 13-4H illustrate how double-sampling at a sensor, or sensor segment, can be used to distinguish between two emitters having different temporal emission characteristics. FIG. 13-4D depicts emission curves 13-470, 13-475 associated with a first emitter and second emitter, respectively. As an example, the first emitter may be a common fluorophore such as rhodamine, and the second emitter may be a quantum dot or phosphorescent emitter.

FIG. 13-4E represents dynamic voltage levels at a charge accumulation node 13-312 that may occur in response to the two different emission characteristics of FIG. 13-4D. In the example, a first voltage curve 13-472 corresponding to the fluorescent emitter may change more rapidly, because of the shorter emission span, and reach its maximum (or minimum, depending on the polarity of the node) at a first time $t_1$. The second voltage curve 13-477 may change more slowly due to the longer emission characteristics of the second emitter, and reach its maximum (or minimum) at a second time $t_2$.

In some embodiments, sampling of the charge-accumulation node may be done at two times $t_3$, $t_4$ after the sample excitation, as depicted in FIG. 13-4F. For example, a first read signal 13-481 may be applied to read out a first voltage value from the charge-accumulation node at a first time $t_3$. Subsequently, a second read signal 13-482 may be applied to read out a second voltage value from the charge-accumulation node at a second time $t_4$ without resetting the charge-accumulation node between the first read and second read. An analysis of the two sampled signal values may then be used to identify which of the two emitters provided the detected signal levels.

FIG. 13-4G depicts an example of two signals from the first read and second read that may be obtained for the first emitter having an emission curve 13-470 as depicted in FIG. 13-4D. FIG. 13-4H depicts an example of two signals from the first read and second read that may be obtained for the second emitter having an emission curve 13-475 as depicted in FIG. 13-4D. For example the sampling sequence shown in FIG. 13-4F for the first emitter will sample the curve 13-472 and obtain approximately the same values at the two read times. In the case of the second emitter, the sampling sequence depicted in FIG. 13-4F samples two different values of the curve 13-477 at the two read times. The resulting pairs of signals from the two read times distinguish between the two emitters, and can be analyzed to identify each emitter. According to some embodiments, double sampling for background subtraction may also be executed to subtract a background signal from the first and second read signals.

According to some embodiments, a sensor may comprise a semiconductor junction formed adjacent the sample well 5-210. In some implementations, the semiconductor junction may be formed as a multilayer structure, and the sample well may be formed in the multilayer structure, as depicted in FIG. 5-7F, for example. In some embodiments, an excited sample may non-radiatively transfer emission energy to a semiconductor junction formed adjacent the sample well via FRET or DET, creating excitons at the semiconductor junction. The semiconductor junction may comprise a p-n or p-i-n junction that converts the received energy to an electrical signal that is detected by CMOS circuitry associated with the sample well. In some implementations, a quantum dot or molecule may be attached to the semiconductor junction via a linker and may participate in non-radiative energy transfer from an excited sample to the semiconductor junction.

In operation, sensors 5-260 of an integrated device may be subjected to a wavelength calibration procedure prior to data collection from a specimen to be analyzed. The wavelength calibration procedure may include subjecting the sensors to different known energies having characteristic wavelengths that may, or may not, correspond to fluorophore wavelengths that may be used with an integrated device. The different energies may be applied in a sequence so calibration signals can be recorded from the sensors for each energy. The calibration signals may then be stored as reference signals, that may be used to process real data acquisition and to determine what emission wavelength or wavelengths are detected by the sensors.

IV. Instrument Operation, Method of Use and User Interface

The instrument 2-104 may be controlled using software and/or hardware. For example, the instrument may be controlled using a processing device 2-122, such as an ASIC, an FPGA and/or a general purpose processor executing software.

Figures 5, 6, 7, 8, 9, 10, 11, 12, 13, 14, 14A:
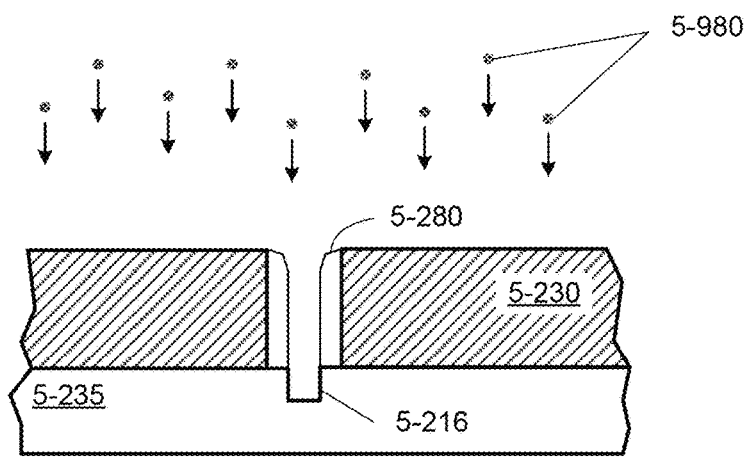
Figures 5, 6, 7, 8, 9, 10, 11, 12, 13, 14, 14B:
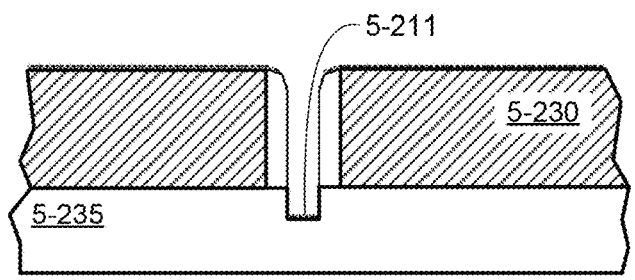
Figures 5, 6, 7, 8, 9, 10, 11, 12, 13, 14, 14C:
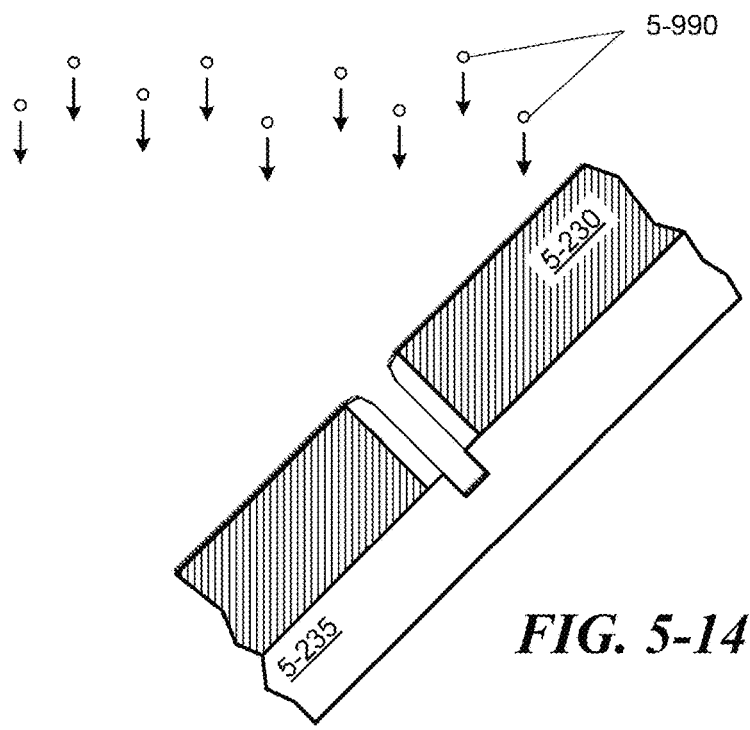
Figures 5, 6, 7, 8, 9, 10, 11, 12, 13, 14, 14D:
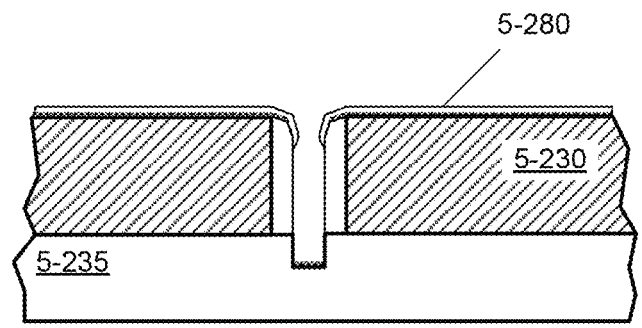

FIG. 14-1 illustrates a flowchart of operation of the instrument 2-104 according to some embodiments. After a user has acquired a specimen to analyze, the user begins a new analysis at act 14-101. This may be done by providing an indication to the instrument 2-104 via the user interface 2-116 by, e.g., pressing a button. At act 14-103, the instrument 2-104 checks whether the integrated device 2-102 (also referred herein as a "chip") from a previously performed analysis is still inserted in the instrument 2-104. If it is determined that an old chip is present, then the power to excitation source may be turned off at act 14-105, the user is prompted at act 14-107 to eject the previous chip using an indicator of the user interface 2-116 and the instrument 2-104 waits for the old chip to be ejected at act 14-109.

When the previous chip is ejected by the user, or if the instrument 2-104 determined at act 14-103 that the previous chip was already removed, the user is prompted to insert a new integrated device 2-102 for the new analysis at act 14-111. The instrument 2-104 then waits for the new integrated device 2-102 to be inserted at act 14-113. When the user inserts the new chip, the user is prompted at act 14-115 by an indicator of the user interface 2-116 to place the specimen to be analyzed onto the exposed top surface of the integrated device 2-102 and also prompted to close the lid on the instrument 2-104. The instrument 2-104 then waits for the lid to be closed at act 14-117. When the lid is closed by the user, at act 14-119 the excitation source may be driven to produce excitation energy for exciting the sample portions of the specimen present in the sample wells of the integrated device 2-102. At act 14-121, the emission energy from the samples is detected by the sensor 2-110 and data from the sensor 2-110 is streamed to the processing device 2-122 for analysis. In some embodiments, the data may be streamed to external computing device 2-120. At act 14-123, the instrument 2-104 checks whether the data acquisition is complete. The data acquisition may be complete after a particular length of time, a particular number of excitation pulses from the excitation source or one a particular target has been identified. When the data acquisition is completed, the data analysis is finished at 14-125.

FIG. 14-2 illustrates an example self-calibration routine according to some embodiments. The calibration routine may be executed at any suitable time prior to the analysis of a specimen. For example, it may be done once by the manufacturer for each instrument prior to shipment to the end user. Alternatively, the end user may perform a calibration at any suitable time. As discussed above, the instrument 2-104 is capable of distinguishing between emission energy having different wavelengths emitted from different samples. The instrument 2-104 and/or computing device 2-120 may be calibrated with calibration associated with each particular color of light associated with, for example, a luminescent tag used to tag molecules of a specimen being analyzed. In this way, the precise output signal associated with a particular color may be determined.

To calibrate the device, a calibration specimen associated with a single luminescent tag is provided to the instrument 2-104 one at a time. The self-calibration begins at act 14-201 when a user places a specimen comprising luminescent tags that emit emission energy of a single wavelength on an integrated device 2-102 and inserts the integrated device 2-102 into the instrument 2-104. Using the user interface 2-116, the user instructs the instrument 2-104 to begin the self-calibration. In response, at act 14-203, the instrument 2-104 runs the calibration analysis by illuminating the integrated device 2-102 with excitation energy and measuring the single wavelength emission energy from the calibration specimen. The instrument 2-104 may then, at act 14-205, save the detection pattern measured on the array of sub-sensors of the sensor 2-110 for each pixel of the sensor array. The detection pattern for each luminescent tag may be considered a detection signature associated with the luminescent tag. In this way, the signatures may be used as a training data set used to analyze the data received from unknown samples analyzed in subsequent analysis runs.

The above calibration routine may then be executed for every calibration specimen associated with a single luminescent tag. In this way, each sensor 2-110 of the array of pixels is associated with calibration data that may be used to determine the luminescent tag present in a sample well during a subsequent analysis implemented at act 14-207 after the competition of the calibration routine.

FIG. 14-3 further illustrates how the calibration data may be acquired and used to analyze the data according to some embodiments. At act 14-301 calibration data is obtained from the sensors. This may be done using the aforementioned self-calibration routine. At act 14-303, a transformation matrix is generated based on the calibration data. The transformation matrix maps sensor data to the emission wavelength of a sample and is a m×n matrix, where m is the number of luminescent tags with different emission wavelengths and n is the number of sub-sensors used to detect the emission energy per pixel. Thus, each column of the transformation matrix represents the calibration values for the sensor. For example, if there are four sub-sensors per pixel and five different luminescent tags, then the transformation matrix is a 4×5 matrix (i.e., four rows and five columns) and each column is associated with a different luminescent tag, the values in the column corresponding to the measured values obtained from the sub-sensors during the self-calibration routine. In some embodiments, each pixel may have its own transformation matrix. In other embodiments, the calibration data from at least some of the pixels may be averaged and all the pixels may then use the same transformation matrix based on the averaged data.

At act 14-305, the analysis data associated with a bioassay is obtained from the sensors. This may be done in any of the ways described above. At act 14-307, the wavelength of the emission energy and/or the identity of the luminescent tag may be determined using the transformation matrix and the analysis data. This may be done in any suitable way. In some embodiments, the analysis data is multiplied by the pseudo-inverse of the transformation matrix, resulting in a m×1 vector. The luminescent tag associated with the vector component with the maximum value may then be identified as the luminescent tag present in the sample well. Embodiments are not limited to this technique. In some embodiments, to prevent possible pathologies that may arise when the inverse of a matrix with small values is taken, a constrained optimization routine, such as a least square method or a maximum likelihood technique, may be performed to determine the luminescent tag present in the sample well.

The foregoing method of using the calibration data to analyze data from the sensors may be implement by any suitable processor. For example, processing device 2-122 of the instrument 2-104 may perform the analysis, or computing device 2-120 may perform the analysis.

FIG. 14-2 illustrates the base instrument control of the aforementioned correlated double sampling of the pixels of the integrated device 2-102 according to some embodiments. At the start of a new frame of data acquisition, a row shift register is reset. The pixel reset value from the previous frame is read by incrementing the column register. Simultaneously the current frames pixel sample levels are stored within the reading element on the chip. Once the desired number of columns to be measured is reached, the column register is reset. Then the pixel sample levels from the current frame are read by incrementing the column register and outputting the sample values eight pixels at a time to a buffer, in some embodiments the first frame of sample levels can be discarded. The buffer can be located off chip in memory or in some embodiments it can be stored locally on the chip. Once the number of columns to be measured is met the row register is incremented. This processes is repeated until a frame is completed. Upon finishing a frame of data the processes is started again with the change that the frames sample levels are subtracted from the previous frames reset levels.

V. Computing Device

Figures 5, 6, 7, 8, 9, 10, 11, 12, 13, 14, 15:
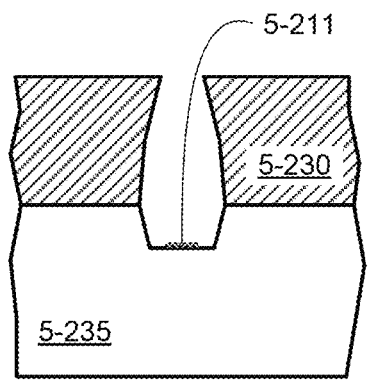

FIG. 15-1 illustrates an example of a suitable computing system environment 15-100 on which embodiments may be implemented. For example, computing device 2-120 of FIG. 2-1B may be implemented according to the computing system environment 15-100. Additionally, the computing system environment 15-100 may act as a control system that is programmed to control the instrument to perform an assay. For example, the control system may control the excitation source to emit and direct light towards the sample wells of the integrated device; control the sensors to allow detection of emission light from one or more samples in the sample wells; and analyze signals from the sensors to identify, e.g., by analyzing the spatial distribution of the emission energy, the sample present in a sample well. The computing system environment 15-100 is only one example of a suitable computing environment and is not intended to suggest any limitation as to the scope of use or functionality of the invention. Neither should the computing environment 15-100 be interpreted as having any dependency or requirement relating to any one or combination of components illustrated in the exemplary operating environment 15-100.

Embodiments are operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 15-1, an exemplary system for implementing the invention includes a general purpose computing device in the form of a computer 15-110. Components of computer 15-110 may include, but are not limited to, a processing unit 15-120, a system memory 15-130, and a system bus 15-121 that couples various system components including the system memory to the processing unit 15-120. The system bus 15-121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 15-110 typically includes a variety of computer readable media. Computer readable media can be any available media that can be accessed by computer 15-110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 15-110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 15-130 includes computer storage media in the form of volatile and/or nonvolatile memory such as read only memory (ROM) 15-131 and random access memory (RAM) 15-132. A basic input/output system 15-133 (BIOS), containing the basic routines that help to transfer information between elements within computer 15-110, such as during start-up, is typically stored in ROM 15-131. RAM 15-132 typically contains data and/or program modules that are immediately accessible to and/or presently being operated on by processing unit 15-120. By way of example, and not limitation, FIG. 15-1 illustrates operating system 15-134, application programs 15-135, other program modules 15-136, and program data 15-137.

The computer 15-110 may also include other removable/non-removable, volatile/nonvolatile computer storage media. By way of example only, FIG. 15-1 illustrates a hard disk drive 15-141 that reads from or writes to non-removable, nonvolatile magnetic media, a magnetic disk drive 15-151 that reads from or writes to a removable, nonvolatile magnetic disk 15-152, and an optical disk drive 15-155 that reads from or writes to a removable, nonvolatile optical disk 15-156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 15-141 is typically connected to the system bus 15-121 through an non-removable memory interface such as interface 15-140, and magnetic disk drive 15-151 and optical disk drive 15-155 are typically connected to the system bus 15-121 by a removable memory interface, such as interface 15-150.

The drives and their associated computer storage media discussed above and illustrated in FIG. 15-1, provide storage of computer readable instructions, data structures, program modules and other data for the computer 15-110. In FIG. 15-1, for example, hard disk drive 15-141 is illustrated as storing operating system 15-144, application programs 15-145, other program modules 15-146, and program data 15-147. Note that these components can either be the same as or different from operating system 15-134, application programs 15-135, other program modules 15-136, and program data 15-137. Operating system 15-144, application programs 15-145, other program modules 15-146, and program data 15-147 are given different numbers here to illustrate that, at a minimum, they are different copies. A user may enter commands and information into the computer 15-110 through input devices such as a keyboard 15-162 and pointing device 15-161, commonly referred to as a mouse, trackball or touch pad. Other input devices (not shown) may include a microphone, joystick, game pad, satellite dish, scanner, or the like. These and other input devices are often connected to the processing unit 15-120 through a user input interface 15-160 that is coupled to the system bus, but may be connected by other interface and bus structures, such as a parallel port, game port or a universal serial bus (USB). A monitor 15-191 or other type of display device is also connected to the system bus 15-121 via an interface, such as a video interface 15-190. In addition to the monitor, computers may also include other peripheral output devices such as speakers 15-197 and printer 15-196, which may be connected through a output peripheral interface 15-195.

The computer 15-110 may operate in a networked environment using logical connections to one or more remote computers, such as a remote computer 15-180. The remote computer 15-180 may be a personal computer, a server, a router, a network PC, a peer device or other common network node, and typically includes many or all of the elements described above relative to the computer 15-110, although only a memory storage device 15-181 has been illustrated in FIG. 15-1. The logical connections depicted in FIG. 15-1 include a local area network (LAN) 15-171 and a wide area network (WAN) 15-173, but may also include other networks. Such networking environments are commonplace in offices, enterprise-wide computer networks, intranets and the Internet.

When used in a LAN networking environment, the computer 15-110 is connected to the LAN 15-171 through a network interface or adapter 15-170. When used in a WAN networking environment, the computer 15-110 typically includes a modem 15-172 or other means for establishing communications over the WAN 15-173, such as the Internet. The modem 15-172, which may be internal or external, may be connected to the system bus 15-121 via the user input interface 15-160, or other appropriate mechanism. In a networked environment, program modules depicted relative to the computer 15-110, or portions thereof, may be stored in the remote memory storage device. By way of example, and not limitation, FIG. 15-1 illustrates remote application programs 15-185 as residing on memory device 15-181. It will be appreciated that the network connections shown are exemplary and other means of establishing a communications link between the computers may be used.

VI. Conclusion

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An integrated device comprising:
   a pixel region comprising:
      a plurality of pixels, each pixel of the plurality of pixels having:
         a sample well on a surface of the integrated device, wherein the sample well is configured to receive a sample; and
         at least one excitation-coupling structure configured to direct excitation energy to a vicinity of the sample well; and
      at least one waveguide configured to optically couple excitation energy to multiple pixels of the plurality of pixels, and wherein the at least one excitation-coupling structure of each pixel of the multiple pixels is positioned to optically couple with the at least one waveguide.

2. The integrated device of claim 1, wherein the at least one waveguide is configured to provide excitation energy to an excitation region within the sample well and a sample located within the excitation region emits emission energy in response to excitation energy illuminating the excitation region.

3. The integrated device of claim 1, wherein the at least one waveguide is configured to receive excitation energy from at least one excitation source.

4. The integrated device of claim 3, wherein the at least one excitation source is external to the integrated device.

5. The integrated device of claim 4, further comprising an excitation source coupling region having a grating coupler configured to receive excitation energy from the at least one excitation source and couple the excitation energy to the at least one waveguide.

6. The integrated device of claim 3, wherein the at least one excitation source is located on the surface of the integrated device in a region separate from the pixel region.

7. The integrated device of claim 1, wherein the at least one waveguide is configured to optically couple excitation energy to a vicinity of a sample well for each pixel of the multiple pixels.

8. The integrated device of claim 1, wherein the at least one excitation-coupling structure includes at least one pixel waveguide.

9. The integrated device of claim 8, wherein the at least one excitation-coupling structure includes at least one resonant structure.

10. The integrated device of claim 9, wherein the sample well is positioned in proximity to a localized region formed by the at least one resonant structure.

11. The integrated device of claim 1, wherein each pixel of the plurality of pixels further includes at least one surface-energy coupling element configured to couple with emission energy emitted by a sample located within the sample well.

12. The integrated device of claim 11, wherein the sample is labeled with one of a plurality of markers and the at least one surface-energy coupling element generates a radiation pattern based on a spectral range of emission energy from each of the plurality of markers.

13. The integrated device of claim 11, wherein the at least one surface-energy coupling element is a concentric grating structure formed around the sample well.

14. The integrated device of claim 11, wherein the at least one surface-energy coupling element is a nano-antenna structure.

15. The integrated device of claim 11, wherein the at least one surface-energy coupling element is located adjacent to the sample well and is configured to direct emitted radiations from the sample well into a plurality of different spatial distributions that are dependent upon wavelengths of the emitted radiations.

16. The integrated device of claim 15, wherein each pixel of the plurality of pixels further comprises a plurality of sensors configured to detect a spatial distribution of at least a portion of the radiation pattern for each of the plurality of markers.

17. The integrated device of claim 16, wherein at least one sorting element is located between the sample well and the plurality of sensors and is configured to direct emission energy of a particular wavelength to one sensor of the plurality of sensors.

18. The integrated device of claim 1, wherein the at least one excitation-coupling structure is positioned between the at least one waveguide and the surface of the integrated device.

19. The integrated device of claim 1, wherein each pixel of the plurality of pixels further comprises:
   at least one component configured to generate a radiation pattern based on emission energy emitted from the sample in the sample well in response to the excitation energy; and
   at least one sensor configured to detect a spatial distribution of at least a portion of the radiation pattern.

20. A system comprising:
   an instrument having
      an excitation energy source configured to emit at least one excitation energy;
      at least one alignment component configured to align an integrated device to the instrument;
   the integrated device having:
      a pixel region having a plurality of pixels, each pixel having:
         a sample well configured to receive a sample; and
         at least one excitation-coupling structure configured to direct excitation energy to a vicinity of the sample well; and
      at least one waveguide configured to optically couple excitation energy to multiple pixels of the plurality of pixels, and wherein the at least one excitation-coupling structure of each pixel of the multiple pixels is positioned to optically couple with the at least one waveguide; and an excitation source coupling region for receiving excitation energy from the excitation energy source and coupling the excitation energy into the at least one waveguide.

21. The system of claim 20, wherein the integrated device further comprises at least one element for generating a radiation pattern based on a spectral range of emission energy emitted by the sample and at least one sensor configured to detect a spatial distribution of at least a portion of the radiation pattern, wherein the at least one element is selected from the group consisting of a refractive element, a diffractive element, a plasmonic element, and a resonator.

22. The system of claim 20, wherein the excitation source coupling region includes a grating coupler configured to receive excitation energy and couple excitation energy to the at least one waveguide.

* * * * *